United States Patent
Travins et al.

(10) Patent No.: US 11,905,285 B2
(45) Date of Patent: *Feb. 20, 2024

(54) INHIBITORS OF PLASMA KALLIKREIN AND USES THEREOF

(71) Applicant: Takeda Pharmaceutical Company Limited, Osaka (JP)

(72) Inventors: Jeremy Travins, Burlington, MA (US); Thomas Miller, Wakefield, MA (US); Nikolaos Papaioannou, Newton, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 146 days.

This patent is subject to a terminal disclaimer.

(21) Appl. No.: 17/519,013

(22) Filed: Nov. 4, 2021

(65) Prior Publication Data

US 2022/0056028 A1 Feb. 24, 2022

Related U.S. Application Data

(63) Continuation of application No. 16/636,518, filed as application No. PCT/US2018/045183 on Aug. 3, 2018, now Pat. No. 11,168,083.

(60) Provisional application No. 62/541,403, filed on Aug. 4, 2017.

(51) Int. Cl.
*C07D 471/04* (2006.01)
*C07D 417/04* (2006.01)
*C07D 417/14* (2006.01)

(52) U.S. Cl.
CPC ......... *C07D 471/04* (2013.01); *C07D 417/04* (2013.01); *C07D 417/14* (2013.01)

(58) Field of Classification Search
CPC .......................... C07D 417/04; C07D 417/14
See application file for complete search history.

(56) References Cited

U.S. PATENT DOCUMENTS

| | | | |
|---|---|---|---|
| 11,168,083 B2 | 11/2021 | Travins et al. | |
| 2007/0149460 A1 | 6/2007 | Larsen et al. | |
| 2012/0009141 A1 | 1/2012 | Laurent et al. | |
| 2012/0178752 A1* | 7/2012 | Ginn ....................... | A61P 19/02 514/254.02 |
| 2015/0005283 A1 | 1/2015 | Cheung et al. | |
| 2015/0152048 A1 | 6/2015 | Imagawa et al. | |
| 2018/0298110 A1 | 10/2018 | Chyung et al. | |
| 2019/0263818 A1 | 8/2019 | McDonald et al. | |
| 2019/0284182 A1 | 9/2019 | Papaioannou et al. | |
| 2020/0317667 A1 | 10/2020 | Papaioannou et al. | |
| 2021/0078999 A1 | 3/2021 | Papaioannou et al. | |
| 2021/0079022 A1 | 3/2021 | Papaioannou et al. | |
| 2023/0167132 A1* | 6/2023 | Tipparaju .............. | C07C 309/04 514/300 |

FOREIGN PATENT DOCUMENTS

| | | |
|---|---|---|
| JP | 2015120685 A | 7/2015 |
| WO | WO 00/00477 A1 | 1/2000 |
| WO | WO 2010/015090 A1 | 2/2010 |
| WO | WO 2013/111108 A1 | 8/2013 |
| WO | WO 2016/138532 A1 | 9/2016 |
| WO | WO 2016/160926 A1 | 10/2016 |
| WO | WO 2017/001936 A2 | 1/2017 |
| WO | WO 2017/059178 A1 | 4/2017 |

OTHER PUBLICATIONS

International Search Report and Written Opinion in connection with Application No. PCT/US2018/045183 dated Oct. 8, 2018.
International Preliminary Report on Patentability in connection with Application No. PCT/US2018/045183 dated Feb. 13, 2020.
[No Author Listed], PubChem Compound Summary for CID 87694443.. National Center for Biotechnology Information. PubChem. Feb. 12, 2015. https://pubchem.ncbi.nlm.nih.gov/compound/87694443. Accessed Nov. 5, 2020.
Farkas et al., Ecallantide is a novel treatment for attacks of hereditary angioedema due to C1 inhibitor deficiency. Clin Cosmet Investig Dermatol. 2011;4:61-8. doi: 10.2147/CCID.S10322. Epub May 31, 2011.
Gardelli et al., Discovery and synthesis of HIV integrase inhibitors: development of potent and orally bioavailable N-methyl pyrimidones. J Med Chem. Oct. 4, 2007;50(20):4953-75. doi: 10.1021/jm0704705. Epub Sep. 8, 2007.
Govers-Riemslag et al., The plasma kallikrein-kinin system and risk of cardiovascular disease in men. J Thromb Haemost. Sep. 2007;5(9):1896-903. doi: 10.1111/j.1538-7836.2007.02687.x.
Xie et al., Discovery and development of plasma kallikrein inhibitors for multiple diseases. Eur J Med Chem. Mar. 15, 2020;190:112137. doi: 10.1016/j.ejmech.2020.112137. Epub Feb. 10, 2020.

* cited by examiner

*Primary Examiner* — Daniel R Carcanague
(74) *Attorney, Agent, or Firm* — Wolf, Greenfield & Sacks, P.C.

(57) ABSTRACT

Provided herein are compounds that inhibit pKal, a serine protease whose activity is responsible for proteolytically cleaving kininogen and generating the potent vasodilator and pro-inflammatory peptide bradykinin, which can lead to painful and debilitating inflammatory attacks (e.g., edema). Also provided are pharmaceutical compositions and kits comprising the compounds, and methods of treating pKal-related diseases and disorders (e.g., edema) with the compounds in a subject, by administering the compounds and/or compositions described herein.

20 Claims, No Drawings

INHIBITORS OF PLASMA KALLIKREIN AND USES THEREOF

RELATED APPLICATIONS

This application is a continuation of and claims benefit under 35 U.S.C. § 120 to U.S. patent application U.S. Ser. No. 16/636,518, filed Feb. 4, 2020, which is a national stage filing under 35 U.S.C. § 371 of International PCT Application, PCT/US2018/045183, filed Aug. 3, 2018, which claims priority under 35 U.S.C. § 119(e) to U.S. Provisional Application, U.S. Ser. No. 62/541,403, filed Aug. 4, 2017. The entire content of each is incorporated by reference herein.

FIELD OF THE INVENTION

The present invention relates generally to compounds that inhibit the trypsin-like serine protease Plasma Kallikrein (pKal) and uses of the compounds in the treatment of pKal-related diseases or disorders (e.g., edema such as hereditary angioedema).

BACKGROUND OF THE INVENTION

Plasma Kallikrein (pKal) is a serine protease zymogen in blood that is converted to its catalytically active form by coagulation factor XIIa, and contributes to the innate inflammatory response and intrinsic cascade of blood coagulation. The mechanisms that lead to the activation of this pathway in vivo include interactions with polyphosphates released from activated platelets and deficiency of C1 inhibitor (C1-INH), the primary physiological inhibitor of pKal. pKal-mediated cleavage of high-molecular weight kininogen generates the potent vasodilator and pro-inflammatory nonapeptide bradykinin (BK), which activates the bradykinin 2 receptor.

Subsequent cleavage of BK by carboxypeptidases generates des-Arg9-BK, which activates the B1 receptor. Both B1 and B2 receptors are expressed by vascular, glial, and neuronal cell types, with the highest levels of retinal expression detected in the ganglion cell layer and inner and outer nuclear layers. Activation of B1 and B2 receptors causes vasodilation and increases vascular permeability.

pKal is also associated with a number of disorders, such as Hereditary Angioedema (HAE), an autosomal dominant disease characterized by painful, unpredictable, recurrent attacks of inflammation affecting the hands, feet, face, abdomen, urogenital tract, and the larynx. Prevalence for HAE is uncertain but is estimated to be approximately 1 case per 50,000 persons without known differences among ethnic groups. HAE is caused by deficient (Type I) or dysfunctional (Type II) levels of C1-INH, which inhibits pKal, bradykinin, and other serine proteases in the blood. Individuals with hereditary angioedema (HAE) are deficient in C1-INH and consequently undergo excessive bradykinin generation, which in turn cause painful, debilitating, and potentially fatal swelling attacks. If left untreated, HAE can result in a mortality rate as high as 40% primarily due to upper airway obstruction.

SUMMARY OF THE INVENTION

The present disclosure is based on, at least in part, the development of a number of small molecule compounds, which bind to plasma kallikrein and effectively inhibit its activity. Accordingly, provided herein are pKal inhibitory compounds and uses thereof for targeting pKal and/or treating pKal-mediated diseases and disorders.

In one aspect, provided herein are compounds of Formula I:

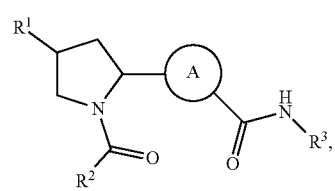

or pharmaceutically acceptable salts, co-crystals, tautomers, stereoisomers, solvates, hydrates, polymorphs, isotopically enriched derivatives, or prodrugs thereof, wherein:
A is substituted or unsubstituted heteroarylene, or substituted or unsubstituted heterocyclylene;
$R^1$ is $-N(R^A)_2$;
$R^2$ is substituted or unsubstituted aryl, substituted or unsubstituted aralkyl, substituted or unsubstituted heteroaryl, substituted or unsubstituted heteroaralkyl, substituted or unsubstituted alkyl, substituted or unsubstituted heteroalkyl, substituted or unsubstituted alkenyl, substituted or unsubstituted alkynyl, $-OR^A$, or $-N(R^A)_2$;
$R^3$ is substituted or unsubstituted alkyl, substituted or unsubstituted heteroalkyl, substituted or unsubstituted acyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted aralkyl, substituted or unsubstituted heteroaryl, or substituted or unsubstituted heteroaralkyl, wherein any carbon of $R^3$, valence permitting, is optionally replaced with $-O-$, $-NR^A-$, $-C(O)-$, $-C(=NR^A)-$, $-S-$, $-S(O)-$, or $-S(O)_2-$; and
each occurrence of $R^A$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, or an oxygen protecting group when attached to an oxygen atom, or two $R^A$ groups are joined to form a substituted or unsubstituted heterocyclic ring.

In certain embodiments, compounds of Formula I include compounds of Formula I-a:

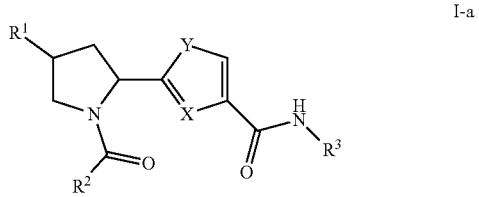

or pharmaceutically acceptable salts, co-crystals, tautomers, stereoisomers, solvates, hydrates, polymorphs, isotopically enriched derivatives, or prodrugs thereof; wherein X is N or CR^y; Y is O, S, or NR^x; and R^x and R^y are, independently, hydrogen or substituted or unsubstituted alkyl.

In certain embodiments, compounds of Formula I include compounds of Formula I-b:

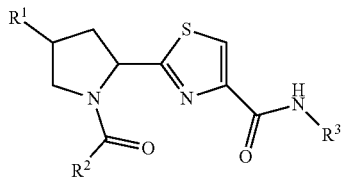

I-b or pharmaceutically acceptable salts, co-crystals, tautomers, stereoisomers, solvates, hydrates, polymorphs, isotopically enriched derivatives, or prodrugs thereof.

In certain embodiments, compounds of Formula I include compounds of Formula I-c:

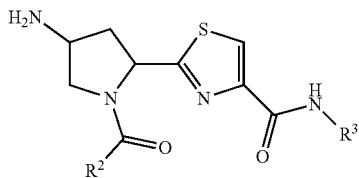

I-c or pharmaceutically acceptable salts, co-crystals, tautomers, stereoisomers, solvates, hydrates, polymorphs, isotopically enriched derivatives, or prodrugs thereof.

In certain embodiments, compounds of Formula I include compounds of Formula I-d:

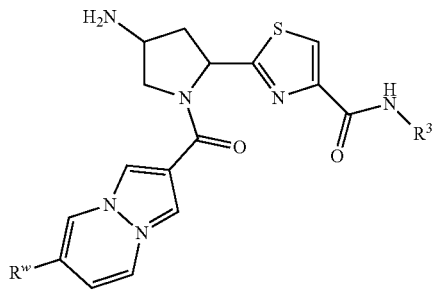

I-d or pharmaceutically acceptable salts, co-crystals, tautomers, stereoisomers, solvates, hydrates, polymorphs, isotopically enriched derivatives, or prodrugs thereof; wherein R^w is hydrogen, halogen, alkoxy, alkoxyalkyl, haloalkoxy, or haloalkyl.

Exemplary compounds of Formula I include, but are not limited to:

2-((2R,4R)-4-amino-1-(6-chloroimidazo[1,2-a]pyridine-2-carbonyl)pyrrolidin-2-yl)-N—((S)-6-guanidino-1-(methylamino)-1-oxohexan-2-yl)thiazole-4-carboxamide (1);

2-((2R,4R)-4-amino-1-(6-chloroimidazo[1,2-a]pyridine-2-carbonyl)pyrrolidin-2-yl)-N—((R)-6-guanidino-1-(methylamino)-1-oxohexan-2-yl)thiazole-4-carboxamide (2);

2-((2R,4R)-4-acetamido-1-(6-chloroimidazo[1,2-a]pyridine-2-carbonyl)pyrrolidin-2-yl)-N—((S)-6-guanidino-1-(methylamino)-1-oxohexan-2-yl)thiazole-4-carboxamide (5);

2-((2R,4S)-4-amino-1-(6-chloroimidazo[1,2-a]pyridine-2-carbonyl)pyrrolidin-2-yl)-N—((S)-6-guanidino-1-(methylamino)-1-oxohexan-2-yl)thiazole-4-carboxamide (6);

2-((2S,4R)-4-amino-1-(6-chloroimidazo[1,2-a]pyridine-2-carbonyl)pyrrolidin-2-yl)-N—((S)-6-guanidino-1-(methylamino)-1-oxohexan-2-yl)thiazole-4-carboxamide (11);

2-((2S,4R)-4-amino-1-(6-chloroimidazo[1,2-a]pyridine-2-carbonyl)pyrrolidin-2-yl)-N—((R)-6-guanidino-1-(methylamino)-1-oxohexan-2-yl)thiazole-4-carboxamide (12);

2-((2S,4R)-4-amino-1-(imidazo[1,2-a]pyridine-2-carbonyl)pyrrolidin-2-yl)-N—((S)-6-guanidino-1-(methylamino)-1-oxohexan-2-yl)thiazole-4-carboxamide (13);

2-((2S,4R)-4-amino-1-(1,2-dimethyl-1H-imidazole-4-carbonyl)pyrrolidin-2-yl)-N—((S)-6-guanidino-1-(methylamino)-1-oxohexan-2-yl)thiazole-4-carboxamide (14);

2-((2S,4R)-4-amino-1-benzoylpyrrolidin-2-yl)-N—((S)-6-guanidino-1-(methylamino)-1-oxohexan-2-yl)thiazole-4-carboxamide (15);

3-chlorobenzyl (2S,4R)-4-amino-2-(4-(((S)-6-guanidino-1-(methylamino)-1-oxohexan-2-yl)carbamoyl)thiazol-2-yl)pyrrolidine-1-carboxylate (16);

2-((2S,4R)-4-amino-1-(cyclohexanecarbonyl)pyrrolidin-2-yl)-N—((S)-6-guanidino-1-(methylamino)-1-oxohexan-2-yl)thiazole-4-carboxamide (17);

2-((2S,4R)-4-amino-1-isobutyrylpyrrolidin-2-yl)-N—((S)-6-guanidino-1-(methylamino)-1-oxohexan-2-yl)thiazole-4-carboxamide (18);

2-((2S,4R)-4-amino-1-(6-(trifluoromethyl)imidazo[1,2-a]pyridine-2-carbonyl)pyrrolidin-2-yl)-N—((S)-6-guanidino-1-(methylamino)-1-oxohexan-2-yl)thiazole-4-carboxamide (19);

2-((2S,4R)-4-amino-1-(6-methoxyimidazo[1,2-a]pyridine-2-carbonyl)pyrrolidin-2-yl)-N—((S)-6-guanidino-1-(methylamino)-1-oxohexan-2-yl)thiazole-4-carboxamide (20);

2-((2S,4R)-4-amino-1-(6-iodoimidazo[1,2-a]pyridine-2-carbonyl)pyrrolidin-2-yl)-N—((S)-6-guanidino-1-(methylamino)-1-oxohexan-2-yl)thiazole-4-carboxamide (21);

2-((2S,4R)-4-amino-1-(6-chloroimidazo[1,2-a]pyridine-2-carbonyl)pyrrolidin-2-yl)-N—((S)-1-amino-6-guanidino-1-oxohexan-2-yl)thiazole-4-carboxamide (22);

N^2-(2-((2S,4R)-4-amino-1-(6-chloroimidazo[1,2-a]pyridine-2-carbonyl)pyrrolidin-2-yl)thiazole-4-carbonyl)-N6-carbamimidoyl-L-lysine (23);

2-((2S,4R)-4-amino-1-(6-chloroimidazo[1,2-a]pyridine-2-carbonyl)pyrrolidin-2-yl)-N—((S)-1-(dimethylamino)-6-guanidino-1-oxohexan-2-yl)thiazole-4-carboxamide (24);

2-((2S,4R)-4-amino-1-(6-chloroimidazo[1,2-a]pyridine-2-carbonyl)pyrrolidin-2-yl)-N—((S)-6-amino-1-(methylamino)-1-oxohexan-2-yl)thiazole-4-carboxamide (25);

N—((S)-6-acetamido-1-(methylamino)-1-oxohexan-2-yl)-2-((2S,4R)-4-amino-1-(6-chloroimidazo[1,2-a]pyridine-2-carbonyl)pyrrolidin-2-yl)thiazole-4-carboxamide (26);

2-((2S,4R)-4-amino-1-(6-chloroimidazo[1,2-a]pyridine-2-carbonyl)pyrrolidin-2-yl)-N—((S)-1-(methylamino)-1-oxo-6-ureidohexan-2-yl)thiazole-4-carboxamide (27);

2-((2S,4R)-4-amino-1-(6-chloroimidazo[1,2-a]pyridine-2-carbonyl)pyrrolidin-2-yl)-N—((S)-5-guanidino-1-(methylamino)-1-oxopentan-2-yl)thiazole-4-carboxamide (28);

(S)-2-(2-((2S,4R)-4-amino-1-(6-chloroimidazo[1,2-a]pyridine-2-carbonyl)pyrrolidin-2-yl)thiazole-4-carboxamido)-N1-methylpentanediamide (29);

N—((S)-3-(1H-imidazol-4-yl)-1-(methylamino)-1-oxopropan-2-yl)-2-((2S,4R)-4-amino-1-(6-chloroimidazo[1,2-a]pyridine-2-carbonyl)pyrrolidin-2-yl)thiazole-4-carboxamide (30);

N—((S)-3-(1H-indol-3-yl)-1-(methylamino)-1-oxopropan-2-yl)-2-((2S,4R)-4-amino-1-(6-chloroimidazo[1,2-a]pyridine-2-carbonyl)pyrrolidin-2-yl)thiazole-4-carboxamide (31);

2-((2S,4R)-4-amino-1-(6-chloroimidazo[1,2-a]pyridine-2-carbonyl)pyrrolidin-2-yl)-N—((S)-3-(4-hydroxyphenyl)-1-(methylamino)-1-oxopropan-2-yl)thiazole-4-carboxamide (3²);

2-((2S,4R)-4-acetamido-1-(6-chloroimidazo[1,2-a]pyridine-2-carbonyl)pyrrolidin-2-yl)-N—((S)-6-guanidino-1-(methylamino)-1-oxohexan-2-yl)thiazole-4-carboxamide (35);

2-((2S,4S)-4-amino-1-(6-chloroimidazo[1,2-a]pyridine-2-carbonyl)pyrrolidin-2-yl)-N—((S)-6-guanidino-1-(methylamino)-1-oxohexan-2-yl)thiazole-4-carboxamide (36);

2-((2S,4R)-1-(2-naphthoyl)-4-aminopyrrolidin-2-yl)-N—((S)-6-guanidino-1-(methylamino)-1-oxohexan-2-yl)thiazole-4-carboxamide (40);

2-((2S,4R)-4-amino-1-(3-chloroquinoline-6-carbonyl)pyrrolidin-2-yl)-N—((S)-6-guanidino-1-(methylamino)-1-oxohexan-2-yl)thiazole-4-carboxamide (41);

2-((2S,4R)-4-amino-1-(6-chloroquinoline-2-carbonyl)pyrrolidin-2-yl)-N—((S)-6-guanidino-1-(methylamino)-1-oxohexan-2-yl)thiazole-4-carboxamide (42);

2-((2S,4R)-4-amino-1-(3-chlorobenzo[b]thiophene-6-carbonyl)pyrrolidin-2-yl)-N—((S)-6-guanidino-1-(methylamino)-1-oxohexan-2-yl)thiazole-4-carboxamide (43);

2-((2S,4R)-4-amino-1-(5-chlorobenzo[b]thiophene-2-carbonyl)pyrrolidin-2-yl)-N—((S)-6-guanidino-1-(methylamino)-1-oxohexan-2-yl)thiazole-4-carboxamide (44);

2-((2S,4R)-4-amino-1-(5-chlorobenzo[d]thiazole-2-carbonyl)pyrrolidin-2-yl)-N—((S)-6-guanidino-1-(methylamino)-1-oxohexan-2-yl)thiazole-4-carboxamide (45);

2-((2S,4R)-4-amino-1-(6-chloroimidazo[1,2-a]pyridine-2-carbonyl)pyrrolidin-2-yl)-N-(5-guanidinopentyl)thiazole-4-carboxamide (46);

2-((2S,4R)-4-amino-1-(6-chloroimidazo[1,2-a]pyridine-2-carbonyl)pyrrolidin-2-yl)-N-(4-carbamimidoylbenzyl)thiazole-4-carboxamide (47);

2-((2S,4R)-4-amino-1-(6-chloroimidazo[1,2-a]pyridine-2-carbonyl)pyrrolidin-2-yl)-N-((6-amino-2,4-dimethylpyridin-3-yl)methyl)thiazole-4-carboxamide (48);

2-((2S,4R)-4-amino-1-(6-chloroimidazo[1,2-a]pyridine-2-carbonyl)pyrrolidin-2-yl)-N-((1-aminoisoquinolin-6-yl)methyl)thiazole-4-carboxamide (49);

2-((2S,4R)-4-amino-1-(6-chloroimidazo[1,2-a]pyridine-2-carbonyl)pyrrolidin-2-yl)-N-(4-(aminomethyl)benzyl)thiazole-4-carboxamide (50);

2-((2S,4R)-4-amino-1-(6-chloroimidazo[1,2-a]pyridine-2-carbonyl)pyrrolidin-2-yl)-N-(4-carbamimidoylphenethyl)thiazole-4-carboxamide (51);

2-((2S,4R)-4-amino-1-(6-chloroimidazo[1,2-a]pyridine-2-carbonyl)pyrrolidin-2-yl)-N-(2-(6-amino-2,4-dimethylpyridin-3-yl)ethyl)thiazole-4-carboxamide (52);

2-((2S,4R)-4-amino-1-(6-chloroimidazo[1,2-a]pyridine-2-carbonyl)pyrrolidin-2-yl)-N-(2-(1-aminoisoquinolin-6-yl)ethyl)thiazole-4-carboxamide (53);

2-((2S,4R)-4-amino-1-(6-chloroimidazo[1,2-a]pyridine-2-carbonyl)pyrrolidin-2-yl)-N-(4-(aminomethyl)phenethyl)thiazole-4-carboxamide (54);

2-((2S,4R)-4-amino-1-(6-chloroimidazo[1,2-a]pyridine-2-carbonyl)pyrrolidin-2-yl)-N-((7-chloroimidazo[1,5-a]pyridin-1-yl)methyl)thiazole-4-carboxamide (55);

2-((2S,4R)-4-amino-1-(6-chloroimidazo[1,2-a]pyridine-2-carbonyl)pyrrolidin-2-yl)-N-((6-chloronaphthalen-2-yl)methyl)thiazole-4-carboxamide (56);

2-((2S,4R)-4-amino-1-(5-chlorobenzo[b]thiophene-2-carbonyl)pyrrolidin-2-yl)-N—((R)-6-guanidino-1-(methylamino)-1-oxohexan-2-yl)thiazole-4-carboxamide (57);

2-((2S,4R)-4-amino-1-(6-chloroimidazo[1,2-a]pyridine-2-carbonyl)pyrrolidin-2-yl)-N-((5-chloro-1H-indazol-3-yl)methyl)thiazole-4-carboxamide (58);

2-((2S,4R)-4-amino-1-(6-chloroimidazo[1,2-a]pyridine-2-carbonyl)pyrrolidin-2-yl)-N-((6-chloro-1H-indazol-3-yl)methyl)thiazole-4-carboxamide (59);

2-((2S,4R)-4-amino-1-(6-chloroimidazo[1,2-a]pyridine-2-carbonyl)pyrrolidin-2-yl)-N-((1-amino-5,7-dimethylisoquinolin-6-yl)methyl)thiazole-4-carboxamide (60);

2-((2S,4R)-4-amino-1-(5,6-dichlorobenzo[b]thiophene-2-carbonyl)pyrrolidin-2-yl)-N—((S)-6-guanidino-1-(methylamino)-1-oxohexan-2-yl)thiazole-4-carboxamide (61);

2-((2S,4R)-4-amino-1-(6-chlorobenzo[b]thiophene-2-carbonyl)pyrrolidin-2-yl)-N—((S)-6-guanidino-1-(methylamino)-1-oxohexan-2-yl)thiazole-4-carboxamide (62);

2-((2S,4R)-4-amino-1-(4-chlorobenzo[b]thiophene-2-carbonyl)pyrrolidin-2-yl)-N—((S)-6-guanidino-1-(methylamino)-1-oxohexan-2-yl)thiazole-4-carboxamide (63);

2-((2S,4R)-4-amino-1-(5-(trifluoromethyl)benzo[b]thiophene-2-carbonyl)pyrrolidin-2-yl)-N—((S)-6-guanidino-1-(methylamino)-1-oxohexan-2-yl)thiazole-4-carboxamide (64);

2-((2S,4R)-4-amino-1-(6-methylbenzo[b]thiophene-2-carbonyl)pyrrolidin-2-yl)-N—((S)-6-guanidino-1-(methylamino)-1-oxohexan-2-yl)thiazole-4-carboxamide (65);

2-((2S,4R)-4-amino-1-(6-chloroquinoline-3-carbonyl)pyrrolidin-2-yl)-N—((S)-6-guanidino-1-(methylamino)-1-oxohexan-2-yl)thiazole-4-carboxamide (66);

2-((2S,4R)-4-amino-1-(2-chloroquinoline-6-carbonyl)pyrrolidin-2-yl)-N—((S)-6-guanidino-1-(methylamino)-1-oxohexan-2-yl)thiazole-4-carboxamide (67);

and pharmaceutically acceptable salts thereof.

In another aspect, provided are pharmaceutical compositions comprising any of the compounds of Formula I as described herein, or a pharmaceutically acceptable salt thereof, and optionally a pharmaceutically acceptable excipient.

In another aspect, provided are methods of inhibiting the activity of pKal, the method comprising contacting a compound of Formula I, or a pharmaceutically acceptable salt thereof, with pKal. In certain embodiments, the pKal is in a cell (e.g., a human cell).

In another aspect, provided are methods of treating a pKal-mediated disease or condition in a subject in need thereof (e.g., a human patient), the method comprising administering a compound of Formula I, or a pharmaceutically acceptable salt thereof, or a pharmaceutical composition comprising such to the subject. In certain embodiments, the pKal-mediated disease or condition is edema. In one example, the edema is hereditary angioedema. In certain embodiments, the pKal-mediated disease or condition is an ocular disease. In some examples, the ocular disease is DME, age-related macular degeneration (AMD), including both wet AMD and dry AMD, or diabetic retinopathy. In certain embodiments, the pKal-mediated disease or condition is an ischemic reperfusion injury, which may be associated with a surgical procedure.

In another aspect, provided are kits comprising a compound of Formula I, or a pharmaceutically acceptable salt thereof, or a pharmaceutical composition comprising such. In certain embodiments, the kits further comprise instructions for administration (e.g., human administration).

Also within the scope of the present disclosure are pharmaceutical compositions comprising any of the compounds of Formula I described herein or a pharmaceutically acceptable salt, and a pharmaceutically acceptable carrier for use in treating a pKal-mediated disease (e.g., edema such as HAE), as well as uses of any of the compounds of Formula I or a pharmaceutically acceptable salt thereof for manufacturing a medicament for use in treating any of the target diseases.

The details of certain embodiments of the invention are set forth in the Detailed Description of Certain Embodiments, as described below. Other features, objects, and advantages of the invention will be apparent from the Definitions, Examples, and Claims.

DEFINITIONS

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, E. L. Stereochemistry of Carbon Compounds (McGraw-Hill, N Y, 1962); and Wilen, S. H., Tables of Resolving Agents and Optical Resolutions p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

In a formula, ～ is a single bond where the stereochemistry of the moieties immediately attached thereto is not specified, --- is absent or a single bond, and ═ or ═ is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of $^{12}$C with $^{13}$C or $^{14}$C are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —$CHF_2$, —$CH_2F$, —$CF_3$, —$CH_2CF_3$, —$CF_2CF_3$, —$CF_2CF_2CF_3$, —$CCl_3$, —$CFCl_2$, —$CF_2Cl$, and the like.

The term "hydroxyalkyl" is a substituted alkyl group, wherein one or more of the hydrogen atoms are independently replaced by a hydroxyl. In some embodiments, the hydroxyalkyl moiety has 1 to 8 carbon atoms ("$C_{1-8}$ hydroxyalkyl"). In some embodiments, the hydroxyalkyl moiety has 1 to 6 carbon atoms ("$C_{1-6}$ hydroxyalkyl"). In some embodiments, the hydroxyalkyl moiety has 1 to 4 carbon atoms ("$C_{1-4}$ hydroxyalkyl"). In some embodiments, the hydroxyalkyl moiety has 1 to 3 carbon atoms ("$C_{1-3}$ hydroxyalkyl"). In some embodiments, the hydroxyalkyl moiety has 1 to 2 carbon atoms ("$C_{1-2}$ hydroxyalkyl").

The term "alkoxy" refers to an alkyl group, as defined herein, appended to the parent molecular moiety through an oxygen atom. In some embodiments, the alkoxy moiety has 1 to 8 carbon atoms ("$C_{1-8}$ alkoxy"). In some embodiments, the alkoxy moiety has 1 to 6 carbon atoms ("$C_{1-6}$ alkoxy"). In some embodiments, the alkoxy moiety has 1 to 4 carbon atoms ("$C_{1-4}$ alkoxy"). In some embodiments, the alkoxy moiety has 1 to 3 carbon atoms ("$C_{1-3}$ alkoxy"). In some embodiments, the alkoxy moiety has 1 to 2 carbon atoms ("$C_{1-2}$ alkoxy"). Representative examples of alkoxy include, but are not limited to, methoxy, ethoxy, propoxy, 2-propoxy, butoxy and tert-butoxy.

The term "haloalkoxy" refers to a haloalkyl group, as defined herein, appended to the parent molecular moiety through an oxygen atom. In some embodiments, the alkoxy moiety has 1 to 8 carbon atoms ("$C_{1-8}$ haloalkoxy"). In some embodiments, the alkoxy moiety has 1 to 6 carbon atoms ("$C_{1-6}$ haloalkoxy"). In some embodiments, the alkoxy moiety has 1 to 4 carbon atoms ("$C_{1-4}$ haloalkoxy"). In some embodiments, the alkoxy moiety has 1 to 3 carbon atoms ("$C_{1-3}$ haloalkoxy"). In some embodiments, the alkoxy moiety has 1 to 2 carbon atoms ("$C_{1-2}$ haloalkoxy"). Representative examples of haloalkoxy include, but are not limited to, difluoromethoxy, trifluoromethoxy, and 2,2,2-trifluoroethoxy.

The term "alkoxyalkyl" is a substituted alkyl group, wherein one or more of the hydrogen atoms are independently replaced by an alkoxy group, as defined herein. In some embodiments, the alkoxyalkyl moiety has 1 to 8 carbon atoms ("$C_{1-8}$ alkoxyalkyl"). In some embodiments, the alkoxyalkyl moiety has 1 to 6 carbon atoms ("$C_{1-6}$ alkoxyalkyl"). In some embodiments, the alkoxyalkyl moiety has 1 to 4 carbon atoms ("$C_{1-4}$ alkoxyalkyl"). In some embodiments, the alkoxyalkyl moiety has 1 to 3 carbon atoms ("$C_{1-3}$ alkoxyalkyl"). In some embodiments, the alkoxyalkyl moiety has 1 to 2 carbon atoms ("$C_{1-2}$ alkoxyalkyl").

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 20 carbon atoms and 1 or more heteroatoms within the parent chain ("heteroC$_{1-20}$ alkyl"). In some embodiments, a heteroalkyl group is a saturated group having 1 to 18 carbon atoms and 1 or more heteroatoms within the parent chain ("heteroC$_{1-18}$ alkyl"). In some embodiments, a heteroalkyl group is a saturated group having 1 to 16 carbon atoms and 1 or more heteroatoms within the parent chain ("heteroC$_{1-16}$ alkyl"). In some embodiments, a heteroalkyl group is a saturated group having 1 to 14 carbon atoms and 1 or more heteroatoms within the parent chain ("heteroC$_{1-14}$ alkyl"). In some embodiments, a heteroalkyl group is a saturated group having 1 to 12 carbon atoms and 1 or more heteroatoms within the parent chain ("heteroC$_{1-12}$ alkyl"). In some embodiments, a heteroalkyl group is a saturated group having 1 to 10 carbon atoms and 1 or more heteroatoms within the parent chain ("heteroC$_{1-10}$ alkyl"). In some embodiments, a heteroalkyl group is a saturated group having 1 to 8 carbon atoms and 1 or more heteroatoms within the parent chain ("heteroC$_{1-8}$alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 4 carbon atoms and 1 or 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_{1-3}$ alkyl"). In some embodiments, the heteroalkyl group defined herein is a partially unsaturated group having 1 or more heteroatoms within the parent chain and at least one unsaturated carbon, such as a carbonyl group. For example, a heteroalkyl group may comprise an amide or ester functionality in its parent chain such that one or more carbon atoms are unsaturated carbonyl groups. Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-20}$ alkyl. In certain embodiments, the heteroalkyl group is an unsubstituted heteroC$_{1-10}$ alkyl. In certain embodiments, the heteroalkyl group is a substituted heteroC$_{1-20}$ alkyl. In certain embodiments, the heteroalkyl group is an unsubstituted heteroC$_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C=C double bond for which the stereochemistry is not specified (e.g., —CH=CHCH$_3$ or

)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, aziridinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl, and phenazinyl.

"Heteroaralkyl" is a subset of "alkyl" and refers to an alkyl group substituted by a heteroaryl group, wherein the point of attachment is on the alkyl moiety.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_3$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(=NH)NH(C$_{1-6}$ alkyl), —OC(=NH)NH$_2$, —NHC(=NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$(C$_{1-6}$ alkyl), —SO$_2$O(C$_{1-6}$ alkyl), —OSO$_2$(C$_{1-6}$ alkyl), —SO(C$_{1-6}$ alkyl), —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

The term "halo" or "halogen" refers to fluorine (fluoro, —F), chlorine (chloro, —C$_1$), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O) SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(=O)(R$^{aa}$)$_2$, —OP(=O)(OR$^{cc}$)$_2$, and —OP(=O)(N(R$^{bb}$)$_2$)$_2$, wherein $X^-$, $R^{aa}$, $R^{bb}$, and $R^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(N(R$^{bb}$)$_2$)$_2$, wherein $R^{aa}$, $R^{bb}$ and $R^{cc}$ are as defined herein, and wherein $R^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(N(R$^{bb}$)$_2$)$_2$, wherein $R^{aa}$, $R^{bb}$, and $R^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3^+$X$^-$, wherein $R^{bb}$ and $X^-$ are as defined herein.

The term "sulfonyl" refers to a group selected from —SO$_2$N(R$^{bb}$)$_2$, —SO$_2$R$^{aa}$, and —SO$_2$OR$^{aa}$, wherein $R^{aa}$ and $R^{bb}$ are as defined herein.

The term "sulfinyl" refers to the group —S(=O)R$^{aa}$, wherein $R^{aa}$ is as defined herein.

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, —C(=S)O(R$^{X1}$), —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers a group wherein the carbon directly attached to the parent molecule is sp$^2$ hybridized, and is substituted with an oxygen, nitrogen or sulfur atom, e.g., a group selected from ketones (e.g., —C(=O)R$^{aa}$), carboxylic acids (e.g., —CO$_2$H), aldehydes (—CHO), esters (e.g., —CO$_2$R$^{aa}$, —C(=O)SR$^{aa}$, —C(=S)SR$^{aa}$), amides (e.g., —C(=O)N(R$^{bb}$)$_2$, —C(=O)NR$^{bb}$SO$_2$R$^{aa}$, —C(=S)N(R$^{bb}$)$_2$), and imines (e.g., —C(=NR$^{bb}$)R$^{aa}$, —C(=NR$^{bb}$)OR$^{aa}$), —C(=NR$^{bb}$)N(R$^{bb}$)$_2$), wherein R$^{aa}$ and R$^{bb}$ are as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)

benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In certain embodiments, a nitrogen protecting group is benzyl (Bn), tert-butyloxycarbonyl (BOC), carbobenzyloxy (Cbz), 9-flurenylmethyloxycarbonyl (Fmoc), trifluoroacetyl, triphenylmethyl, acetyl (Ac), benzoyl (Bz), p-methoxybenzyl (PMB), 3,4-dimethoxybenzyl (DMPM), p-methoxyphenyl (PMP), 2,2,2-trichloroethyloxycarbonyl (Troc), triphenylmethyl (Tr), tosyl (Ts), brosyl (Bs), nosyl (Ns), mesyl (Ms), triflyl (Tf), or dansyl (Ds).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). In certain embodiments, an oxygen protecting group is silyl. In certain embodiments, an oxygen protecting group is t-butyldiphenylsilyl (TBDPS), t-butyldimethylsilyl (TBDMS), triisoproylsilyl (TIPS), triphenylsilyl (TPS), triethylsilyl (TES), trimethylsilyl (TMS), triisopropylsiloxymethyl (TOM), acetyl (Ac), benzoyl (Bz), allyl carbonate, 2,2,2-trichloroethyl carbonate (Troc), 2-trimethylsilylethyl carbonate, methoxymethyl (MOM), 1-ethoxyethyl (EE), 2-methyoxy-2-propyl (MOP), 2,2,2-trichloroethoxyethyl, 2-methoxyethoxymethyl (MEM), 2-trimethylsilylethoxymethyl (SEM), methylthiomethyl (MTM), tetrahydropyranyl (THP), tetrahydrofuranyl (THF), p-methoxyphenyl (PMP), triphenylmethyl (Tr), methoxytrityl (MMT), dimethoxytrityl (DMT), allyl, p-methoxybenzyl (PMB), t-butyl, benzyl (Bn), allyl, or pivaloyl (Piv).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)(OR^{cc})_2$, and —$P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, $3^{rd}$ edition, John Wiley & Sons, 1999, incorporated herein by reference. In certain embodiments, a sulfur protecting group is acetamidomethyl, t-Bu, 3-nitro-2-pyridine sulfenyl, 2-pyridine-sulfenyl, or triphenylmethyl.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6S)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

The term "leaving group" is given its ordinary meaning in the art of synthetic organic chemistry and refers to an atom or a group capable of being displaced by a nucleophile. See, for example, Smith, *March's Advanced Organic Chemistry* 6th ed. (501-502). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), —$OS(=O)_2(CF_2)_3CF_3$ (nonaflate, —ONf), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties. Further exemplary leaving groups include, but are not limited to, halo (e.g., chloro, bromo, iodo) and activated substituted hydroxyl groups (e.g., —$OC(=O)SR^{aa}$, —$OC(=O)R^{aa}$, —$OCO_2R^{aa}$, —$OC(=O)N(R^{bb})_2$, —$OC(=NR^{bb})R^{aa}$, —$OC(=NR^{bb})OR^{aa}$, —$OC(=NR^{bb})N(R^{bb})_2$, —$OS(=O)R^{aa}$, —$OSO_2R^{aa}$, —$OP(R^{cc})_2$, —$OP(R^{cc})_3$, —$OP(=O)_2R^{aa}$, —$OP(=O)(R^{aa})_2$, —$OP(=O)(OR^{cc})_2$, —$OP(=O)_2N(R^{bb})_2$, and —$OP(=O)(NR^{bb})_2$, wherein $R^{aa}$, $R^{bb}$, and $R^{cc}$ are as defined herein).

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

These and other exemplary substituents are described in more detail in the Detailed Description, Examples, and claims. The invention is not intended to be limited in any manner by the above exemplary listing of substituents.

Other Definitions

The following definitions are more general terms used throughout the present disclosure.

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and N+($C_{1-4}$ alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, which are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R·x H$_2$O, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R·0.5H$_2$O)), and polyhydrates (x is a number greater than 1, e.g., dihydrates (R·2H$_2$O) and hexahydrates (R·6H$_2$O)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-8 alkyl, $C_{2-8}$ alkenyl, $C_{2-8}$ alkynyl, aryl, $C_7$-12 substituted aryl, and $C_{7-12}$ arylalkyl esters of the compounds described herein may be preferred.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. The term "patient" refers to a human subject in need of treatment of a disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The term "target tissue" refers to any biological tissue of a subject (including a group of cells, a body part, or an organ) or a part thereof, including blood and/or lymph vessels, which is the object to which a compound, particle, and/or composition of the invention is delivered. A target tissue may be an abnormal or unhealthy tissue, which may need to be treated. A target tissue may also be a normal or healthy tissue that is under a higher than normal risk of becoming abnormal or unhealthy, which may need to be prevented. In certain embodiments, the target tissue is the liver. In certain embodiments, the target tissue is the lung. A "non-target tissue" is any biological tissue of a subject (including a group of cells, a body part, or an organ) or a part thereof, including blood and/or lymph vessels, which is not a target tissue.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is an amount sufficient for pKal inhibition. In certain embodiments, a therapeutically effective amount is an amount sufficient for treating edema (e.g., HAE or DME). In certain embodiments, a therapeutically effective amount is an amount sufficient for pKal inhibition and treating edema (e.g., HAE or DME).

A "prophylactically effective amount" of a compound described herein is an amount sufficient to prevent a condition, or one or more signs or symptoms associated with the condition, or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is an amount sufficient for pKal inhibition. In certain embodiments, a prophylactically effective amount is an amount sufficient for treating edema (e.g., HAE). In certain embodiments, a prophylactically effective amount is an amount sufficient for pKal inhibition and treating edema (e.g., HAE).

As used herein, the term "inhibit" or "inhibition" in the context of enzymes, for example, in the context of pKal, refers to a reduction in the activity of the enzyme. In some embodiments, the term refers to a reduction of the level of enzyme activity, e.g., pKal activity, to a level that is statistically significantly lower than an initial level, which may, for example, be a baseline level of enzyme activity. In some embodiments, the term refers to a reduction of the level of enzyme activity, e.g., pKal activity, to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of enzyme activity.

The terms "biologic," "biologic drug," and "biological product" refer to a wide range of products such as vaccines, blood and blood components, allergenics, somatic cells, gene therapy, tissues, nucleic acids, and proteins. Biologics may include sugars, proteins, or nucleic acids, or complex combinations of these substances, or may be living entities, such as cells and tissues. Biologics may be isolated from a variety of natural sources (e.g., human, animal, microorganism) and may be produced by biotechnological methods and other technologies.

The term "small molecule" or "small molecule therapeutic" refers to molecules, whether naturally occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

The term "therapeutic agent" refers to any substance having therapeutic properties that produce a desired, usually beneficial, effect. For example, therapeutic agents may treat, ameliorate, and/or prevent disease. Therapeutic agents, as disclosed herein, may be biologics or small molecule therapeutics.

DETAILED DESCRIPTION OF CERTAIN EMBODIMENTS

Several biologic therapies have been developed to treat plasma kallikrein-related inflammation both acutely and prophylactically, including $C_1$-esterase inhibitor replacement (human and recombinant), peptide and antibody inhibitors of pKal, and bradykinin antagonists. However, an orally bioavailable small molecule inhibitor of pKal has yet to be realized. The present disclosure stems from the recognition that, by targeting pKal activity via small molecule therapy, new compounds, compositions, and methods are provided that are useful for the inhibition of pKal and its role in the excessive generation of bradykinin, and thus the treatment of related diseases (e.g., edemas such as HAE or DME).

Provided herein are inhibitors of plasma kallikrein, for example, inhibitors of the active form of plasma kallikrein. In one aspect, the disclosure provides compounds of Formula I, and pharmaceutically acceptable salts, solvates, hydrates, polymorphs, co-crystals, tautomers, stereoisomers, isotopically labeled derivatives, prodrugs, and pharmaceutical compositions thereof. The compounds are useful for inhibiting pKal activities in a subject, thereby being beneficial in treating diseases mediated by pKal such as edema.

Compounds

The compounds described herein interact with pKal. As described herein, the therapeutic effect may be a result of inhibition, modulation, binding, and/or modification of pKal by the compounds described herein. In certain embodiments, the compounds inhibit, modulate, and/or modify pKal by binding to an active site of pKal. The compounds may be provided for use in any composition, kit, or method described herein as a pharmaceutically acceptable salt, co-crystal, tautomer, stereoisomer, solvate, hydrate, polymorph, isotopically enriched derivative, or prodrug thereof.

Provided is a compound of Formula I:

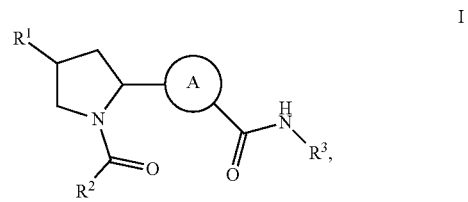

or a pharmaceutically acceptable salt, co-crystal, tautomer, stereoisomer, solvate, hydrate, polymorph, isotopically enriched derivative, or prodrug thereof, wherein:

A is substituted or unsubstituted heteroarylene, or substituted or unsubstituted heterocyclylene;

$R^1$ is —N($R^A$)$_2$;

$R^2$ is substituted or unsubstituted aryl, substituted or unsubstituted aralkyl, substituted or unsubstituted heteroaryl, substituted or unsubstituted heteroaralkyl, substituted or unsubstituted alkyl, substituted or unsubstituted heteroalkyl, substituted or unsubstituted alkenyl, substituted or unsubstituted alkynyl, —OR$^A$, or —N(R$^A$)$_2$;

$R^3$ is substituted or unsubstituted alkyl, substituted or unsubstituted heteroalkyl, substituted or unsubstituted acyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted aralkyl, substituted or unsubstituted heteroaryl, or substituted or unsubstituted heteroaralkyl, wherein any carbon of $R^3$, valence permitting, is optionally replaced with —O—, —NR$^A$—, —C(O)—, —C(═NR$^A$)—, —S—, —S(O)—, or —S(O)$_2$—; and each occurrence of $R^A$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^A$ groups are joined to form a substituted or unsubstituted heterocyclic ring.

Group A

In certain embodiments, A is substituted or unsubstituted heteroarylene, or substituted or unsubstituted heterocyclylene. In certain embodiments, A is substituted or unsubstituted heteroarylene. In certain embodiments, A is substituted or unsubstituted 5-6 membered heteroarylene. In certain embodiments, A is unsubstituted 5-6 membered heteroarylene. In certain embodiments, A is substituted or unsubstituted 6-membered heteroarylene. In certain embodiments, A is unsubstituted 6-membered heteroarylene. In certain embodiments, A is substituted or unsubstituted 5-membered heteroarylene. In certain embodiments, A is unsubstituted 5-membered heteroarylene.

In certain embodiments, A is substituted or unsubstituted 3-14 membered heterocyclylene. In certain embodiments, A is 3-8 membered substituted or unsubstituted monocyclic heterocyclylene. In certain embodiments, A is substituted or unsubstituted 6-14 membered bicyclic heterocyclylene. In certain embodiments, A is substituted or unsubstituted 6-14 membered tricyclic heterocyclylene. In certain embodiments, A is substituted or unsubstituted 5-10 membered heterocyclylene comprising 1-4 ring heteroatoms, wherein each heteroatom is independently selected from nitrogen, oxygen, and sulfur. In certain embodiments, A is substituted or unsubstituted 5-8 membered heterocyclylene comprising 1-4 ring heteroatoms, wherein each heteroatom is independently selected from nitrogen, oxygen, and sulfur. In certain embodiments, A is substituted or unsubstituted 5-6 membered heterocyclylene comprising 1-4 ring heteroatoms, wherein each heteroatom is independently selected from nitrogen, oxygen, and sulfur. In certain embodiments, A is substituted or unsubstituted 5-6 membered heterocyclylene comprising 1-3 ring heteroatoms, wherein each heteroatom is independently selected from nitrogen, oxygen, and sulfur. In certain embodiments, A is substituted or unsubstituted 5-6 membered heterocyclylene comprising 1-2 ring heteroatoms, wherein each heteroatom is independently selected from nitrogen, oxygen, and sulfur. In certain embodiments, A is substituted or unsubstituted 5-6 membered heterocyclylene comprising 1 ring heteroatom selected from nitrogen, oxygen, and sulfur.

In certain embodiments, A is substituted or unsubstituted aziridinylene, oxiranylene, thiiranylene, azetidinylene, oxetanylene, thietanylene, tetrahydrofuranylene, dihydrofuranylene, tetrahydrothiophenylene, dihydrothiophenylene, pyrrolidinylene, dihydropyrrolylene, pyrrolylene-2,5-dione, dioxolanylene, oxathiolanylene, dithiolanylene, triazolinylene, oxadiazolinylene, thiadiazolinylene, piperidinylene, tetrahydropyranylene, dihydropyridinylene, thianylene, piperazinylene, morpholinylene, dithianylene, dioxanylene, triazinylene, azepanylene, oxepanylene, thiepanylene, azocanylene, oxecanylene, thiocanylene, indolinylene, isoindolinylene, dihydrobenzofuranylene, dihydrobenzothienylene, tetrahydrobenzothienylene, tetrahydrobenzofuranylene, tetrahydroindolylene, tetrahydroquinolinylene, tetrahydroisoquinolinylene, decahydroquinolinylene, decahydroisoquinolinylene, octahydrochromenylene, octahydroisochromenylene, decahydronaphthyridinylene, decahydro-1,8-naphthyridinylene, octahydropyrrolo[3,2-b]pyrrole, indolinylene, phthalimidylene, naphthalimidylene, chromanylene, chromenylene, 1H-benzo[e][1,4]diazepinylene, 1,4,5,7-tetrahydropyrano[3,4-b]pyrrolylene, 5,6-dihydro-4H-furo[3,2-b]pyrrolylene, 6,7-dihydro-5H-furo-[3,2-b]pyranylene, 5,7-dihydro-4H-thieno[2,3-c]pyranylene, 2,3-dihydro-1H-pyrrolo[2,3-b]pyridinylene, 2,3-dihydrofuro[2,3-b]pyridinylene, 4,5,6,7-tetrahydro-1H-pyrrolo[2,3-b]pyridinylene, 4,5,6,7-tetrahydrofuro[3,2-c]pyridinylene, 4,5,6,7-tetrahydrothieno[3,2-b]pyridinylene, or 1,2,3,4-tetrahydro-1,6-naphthyridinylene.

In certain embodiments, A is substituted or unsubstituted 5-14 membered heteroarylene. In certain embodiments, A is substituted or unsubstituted 5-8 membered monocyclic heteroarylene. In certain embodiments, A is substituted or unsubstituted 8-14 membered bicyclic heteroarylene (e.g., fused bicyclic heteroarylene). In certain embodiments, A is substituted or unsubstituted 10-14 membered tricyclic heteroarylene (e.g., fused tricyclic heteroarylene). In certain embodiments, A is substituted or unsubstituted 5-10 membered heteroarylene comprising 1-4 ring heteroatoms, wherein each heteroatom is independently selected from nitrogen, oxygen, and sulfur. In certain embodiments, A is substituted or unsubstituted 5-8 membered heteroarylene comprising 1-4 ring heteroatoms, wherein each heteroatom is independently selected from nitrogen, oxygen, and sulfur. In certain embodiments, A is substituted or unsubstituted 5-6 membered heteroarylene comprising 1-4 ring heteroatoms, wherein each heteroatom is independently selected from nitrogen, oxygen, and sulfur. In certain embodiments, A is substituted or unsubstituted 5-membered heteroarylene comprising 1-4 ring heteroatoms, wherein each heteroatom is independently selected from nitrogen, oxygen, and sulfur. In certain embodiments, A is substituted or unsubstituted 5-6 membered heteroarylene comprising 1-3 ring heteroatoms, wherein each heteroatom is independently selected from nitrogen, oxygen, and sulfur. In certain embodiments, A is substituted or unsubstituted 5-membered heteroarylene comprising 1-3 ring heteroatoms, wherein each heteroatom is independently selected from nitrogen, oxygen, and sulfur. In certain embodiments, A is substituted or unsubstituted 5-6 membered heteroarylene comprising 1-2 ring heteroatoms, wherein each heteroatom is independently selected from nitrogen, oxygen, and sulfur. In certain embodiments, A is substituted or unsubstituted 5-membered heteroarylene comprising 1-2 ring heteroatoms, wherein each heteroatom is independently selected from nitrogen, oxygen, and sulfur. In certain embodiments, A is substituted or unsubstituted 5-6 membered heteroarylene comprising 1 ring heteroatom selected from nitrogen, oxygen, and sulfur. In certain embodiments, A is substituted or unsubstituted 5-membered heteroarylene comprising 1 ring heteroatom selected from nitrogen, oxygen, and sulfur.

In certain embodiments, A is substituted or unsubstituted pyrrolylene, furanylene, thiophenylene, imidazolylene, pyrazolylene, oxazolylene, isoxazolylene, thiazolylene, isothiazolylene, triazolylene, oxadiazolylene, thiadiazolylene, tetrazolylene, pyridinylene, pyridazinylene, pyrimidinylene, pyrazinylene, triazinylene, tetrazinylene, azepinylene, oxepinylene, thiepinylene, indolylene, isoindolylene, indazolylene, benzotriazolylene, benzothiophenylene, isobenzothiophenylene, benzofuranylene, benzoisofuranylene, benzimidazolylene, benzoxazolylene, benzisoxazolylene, benzoxadiazolylene, benzthiazolylene, benzisothiazolylene, benzthiadiazolylene, imidazopyridinylene, indolizinylene, purinylene, naphthyridinylene, pteridinylene, quinolinylene, isoquinolinylene, cinnolinylene, quinoxalinylene, phthalazinylene, quinazolinylene, phenanthridinylene, dibenzofuranylene, carbazolylene, acridinylene, phenothiazinylene, phenoxazinylene, or phenazinylene.

In certain embodiments, A is of the formula:

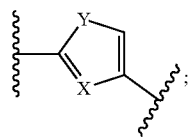

wherein:
X is N or CR$^y$;
Y is O, S, or NR$^x$; and
R$^x$ and R$^y$ are, independently, hydrogen or substituted or unsubstituted alkyl.
In certain embodiments, A is of the formula:

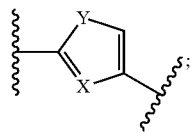

wherein:
X is CR$^y$;
Y is O, S, or NR$^x$; and
R$^x$ and R$^y$ are, independently, hydrogen or substituted or unsubstituted alkyl.
In certain embodiments, A is of the formula:

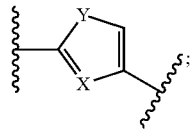

wherein:
X is N;
Y is O, S, or NR$^x$; and
R$^x$ is hydrogen or substituted or unsubstituted alkyl.
In certain embodiments, A is of the formula:

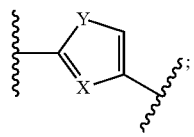

wherein:
X is N; and
Y is O or S.
In certain embodiments, A is of the formula:

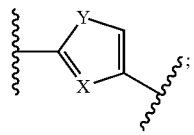

wherein:
X is N; and
Y is S.
In certain embodiments, A is of the formula:

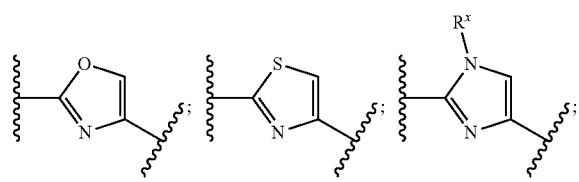

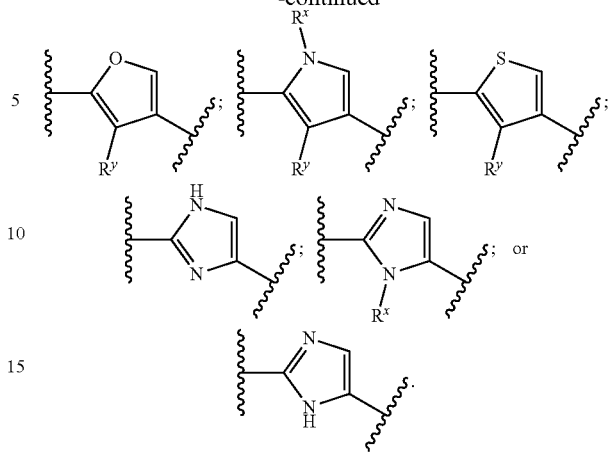

In certain embodiments, A is of the formula:

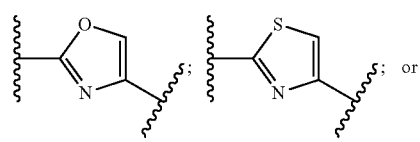

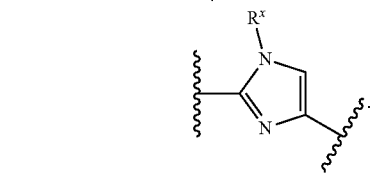

In certain embodiments, A is of the formula:

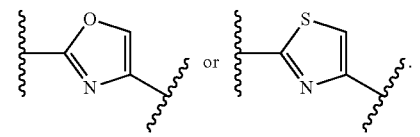 [SMILES: *c1coc(*)n1 ; *c1csc(*)n1]

In certain embodiments, A is of the formula:

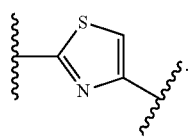 [SMILES: *c1csc(*)n1]

In certain embodiments, R$^1$ is —N(R$^A$)$_2$.
In certain embodiments, R$^1$ is —N(R$^A$)$_2$; and each occurrence of R$^A$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, substituted or unsubstituted aryl, substituted or unsubstituted heteroaryl, or a nitrogen protecting group, or two R$^A$ groups are joined to form a substituted or unsubstituted heterocyclic ring. In certain embodiments, R$^1$ is —NHR$^A$; and R$^A$ is hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, substituted or unsubstituted aryl, substituted or unsubstituted heteroaryl, or a nitrogen protecting group.

In certain embodiments, $R^1$ is $-N(R^A)_2$; and each occurrence of $R^A$ is, independently, hydrogen, substituted or unsubstituted acyl, substituted or unsubstituted alkyl, or a nitrogen protecting group. In certain embodiments, $R^1$ is $-NHR^A$; and $R^A$ is hydrogen, substituted or unsubstituted acyl, substituted or unsubstituted alkyl, or a nitrogen protecting group.

In certain embodiments, $R^1$ is $-N(R^A)_2$; and $R^A$ is hydrogen, substituted or unsubstituted alkyl, or a nitrogen protecting group. In certain embodiments, $R^1$ is $-NHR^A$; and $R^A$ is hydrogen, substituted or unsubstituted alkyl, or a nitrogen protecting group.

In certain embodiments, $R^1$ is $-N(R^A)_2$; and each occurrence of $R^A$ is, independently, hydrogen, substituted or unsubstituted acyl, or substituted or unsubstituted alkyl. In certain embodiments, $R^1$ is $-NHR^A$; and $R^A$ is hydrogen, substituted or unsubstituted acyl, or substituted or unsubstituted alkyl.

In certain embodiments, $R^1$ is $-N(R^A)_2$; and each occurrence of $R^A$ is, independently, hydrogen, or substituted or unsubstituted alkyl. In certain embodiments, $R^1$ is $-NHR^A$; and $R^A$ is hydrogen, or substituted or unsubstituted alkyl.

In certain embodiments, $R^1$ is $-N(R^A)_2$; and each occurrence of $R^A$ is, independently, substituted or unsubstituted alkyl. In certain embodiments, $R^1$ is $-N(R^A)_2$; and each occurrence of $R^A$ is, independently, unsubstituted alkyl.

In certain embodiments, $R^1$ is $-NH_2$.

Group $R^2$

In certain embodiments, $R^2$ is substituted or unsubstituted aryl, substituted or unsubstituted aralkyl, substituted or unsubstituted heteroaryl, substituted or unsubstituted heteroaralkyl, substituted or unsubstituted alkyl, substituted or unsubstituted heteroalkyl, substituted or unsubstituted alkenyl, substituted or unsubstituted alkynyl, $-OR^A$, or $-N(R^A)_2$.

In certain embodiments, $R^2$ is substituted or unsubstituted aryl, substituted or unsubstituted heteroaryl, substituted or unsubstituted alkyl, $-OR^A$, or $-N(R^A)_2$. In certain embodiments, $R^2$ is substituted or unsubstituted aryl, substituted or unsubstituted heteroaryl, substituted or unsubstituted alkyl, $-OR^A$, or $-N(R^A)_2$; and each occurrence of $R^A$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, or an oxygen protecting group when attached to an oxygen atom, or two $R^A$ groups are joined to form a substituted or unsubstituted heterocyclic ring.

In certain embodiments, $R^2$ is substituted or unsubstituted aryl, substituted or unsubstituted heteroaryl, substituted or unsubstituted alkyl, or $-OR^A$; and $R^A$ is substituted or unsubstituted alkyl, substituted or unsubstituted aryl, substituted or unsubstituted heteroaryl, or an oxygen protecting group. In certain embodiments, $R^2$ is substituted or unsubstituted aryl, substituted or unsubstituted heteroaryl, or $-OR^A$; and $R^A$ is substituted or unsubstituted aralkyl, substituted or unsubstituted heteroaralkyl, or an oxygen protecting group.

In certain embodiments, $R^2$ is substituted or unsubstituted aryl. In certain embodiments, $R^2$ is substituted or unsubstituted 6-14 membered aryl. In certain embodiments, $R^2$ is substituted or unsubstituted monocyclic aryl. In certain embodiments, $R^2$ is substituted or unsubstituted bicyclic aryl. In certain embodiments, $R^2$ is substituted or unsubstituted tricyclic aryl. In certain embodiments, $R^2$ is substituted or unsubstituted phenyl, naphthyl, or anthracenyl. In certain embodiments, $R^2$ is substituted or unsubstituted phenyl. In certain embodiments, $R^2$ is substituted phenyl. In certain embodiments, $R^2$ is unsubstituted phenyl. In certain embodiments, $R^2$ is substituted or unsubstituted naphthyl. In certain embodiments, $R^2$ is substituted naphthyl. In certain embodiments, $R^2$ is unsubstituted naphthyl. In certain embodiments, $R^2$ is substituted or unsubstituted anthracenyl. In certain embodiments, $R^2$ is substituted anthracenyl. In certain embodiments, $R^2$ is unsubstituted anthracenyl.

In certain embodiments, $R^2$ is substituted or unsubstituted heteroaryl. In certain embodiments, $R^2$ is substituted or unsubstituted 5-14 membered heteroaryl. In certain embodiments, $R^2$ is substituted or unsubstituted 5-8 membered monocyclic heteroaryl. In certain embodiments, $R^2$ is substituted or unsubstituted 8-14 membered bicyclic heteroaryl (e.g., fused bicyclic heteroaryl). In certain embodiments, $R^2$ is substituted or unsubstituted 10-14 membered tricyclic heteroaryl (e.g., fused tricyclic heteroaryl). In certain embodiments, $R^2$ is substituted or unsubstituted 8-14 membered bicyclic heteroaryl comprising 1-4 ring heteroatoms, wherein each heteroatom is independently selected from nitrogen, oxygen, and sulfur. In certain embodiments, $R^2$ is substituted or unsubstituted 8-10 membered bicyclic heteroaryl comprising 1-4 ring heteroatoms, wherein each heteroatom is independently selected from nitrogen, oxygen, and sulfur. In certain embodiments, $R^2$ is substituted or unsubstituted 8-10 membered fused bicyclic heteroaryl comprising 1-4 ring heteroatoms, wherein each heteroatom is independently selected from nitrogen, oxygen, and sulfur. In certain embodiments, $R^2$ is substituted or unsubstituted 8-10 membered fused bicyclic heteroaryl comprising 1-3 ring heteroatoms, wherein each heteroatom is independently selected from nitrogen, oxygen, and sulfur. In certain embodiments, $R^2$ is substituted or unsubstituted 8-10 membered fused bicyclic heteroaryl comprising 1-2 ring heteroatoms, wherein each heteroatom is independently selected from nitrogen, oxygen, and sulfur.

In certain embodiments, $R^2$ is substituted or unsubstituted pyrrolyl, furanyl, thiophenyl, imidazolyl, pyrazolyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl, triazinyl, tetrazinyl, azepinyl, oxepinyl, thiepinyl, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, imidazopyridinyl, indolizinyl, purinyl, naphthyridinyl, pteridinyl, quinolinyl, isoquinolinyl, cinnolinyl, quinoxalinyl, phthalazinyl, quinazolinyl, phenanthridinyl, dibenzofuranyl, carbazolyl, acridinyl, phenothiazinyl, phenoxazinyl, or phenazinyl.

In certain embodiments, $R^2$ is substituted or unsubstituted fused bicyclic heteroaryl. In certain embodiments, $R^2$ is substituted or unsubstituted imidazopyridinyl, quinolinyl, benzothiophenyl, or benzthiazolyl. In certain embodiments, $R^2$ is substituted imidazopyridinyl, quinolinyl, benzothiophenyl, or benzthiazolyl. In certain embodiments, $R^2$ is substituted imidazopyridinyl.

In certain embodiments, $R^2$ is of the formula:
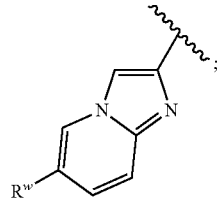
wherein: $R^w$ is hydrogen, halogen, alkoxy, alkoxyalkyl, haloalkoxy, or haloalkyl.
In certain embodiments, $R^2$ is of the formula:
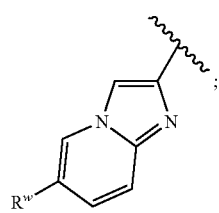
wherein: $R^w$ is halogen, alkoxy, or haloalkyl.
In certain embodiments, $R^2$ is of the formula:
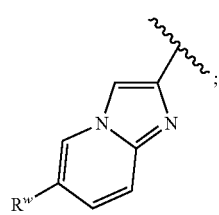
wherein: $R^w$ is halogen or haloalkyl.
In certain embodiments, $R^2$ is of the formula:
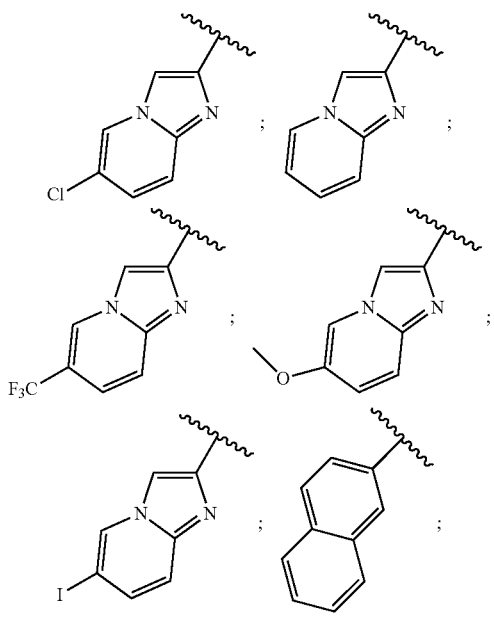
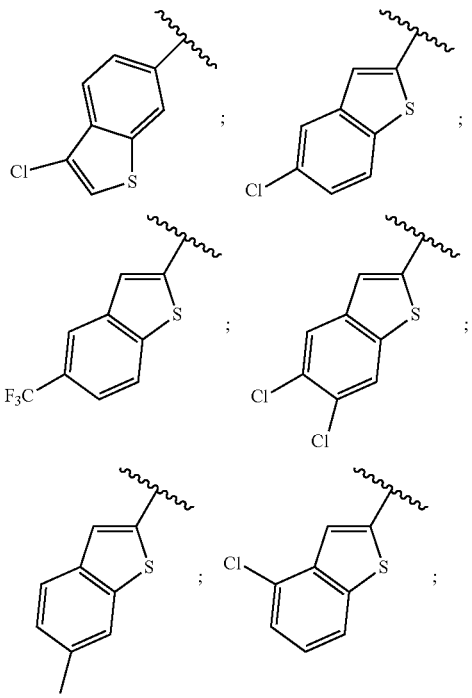
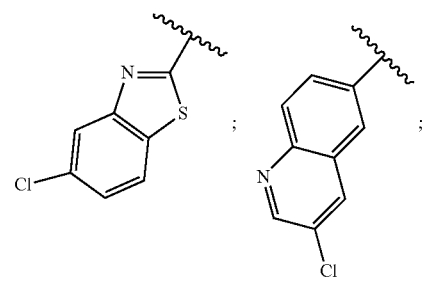
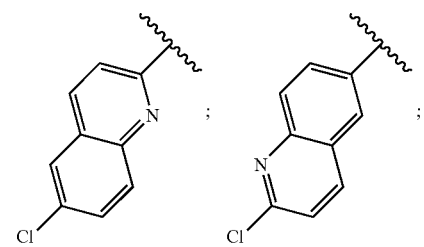
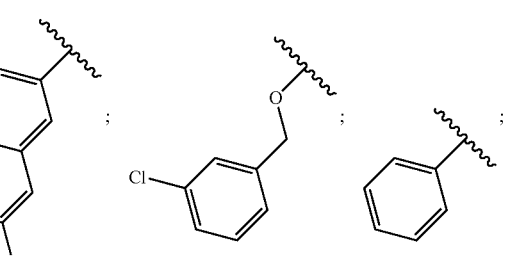
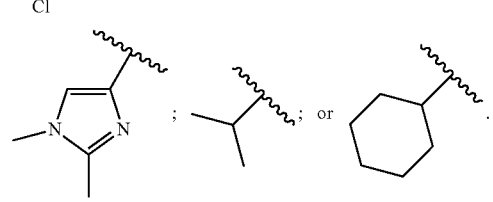

In certain embodiments, R² is of the formula:
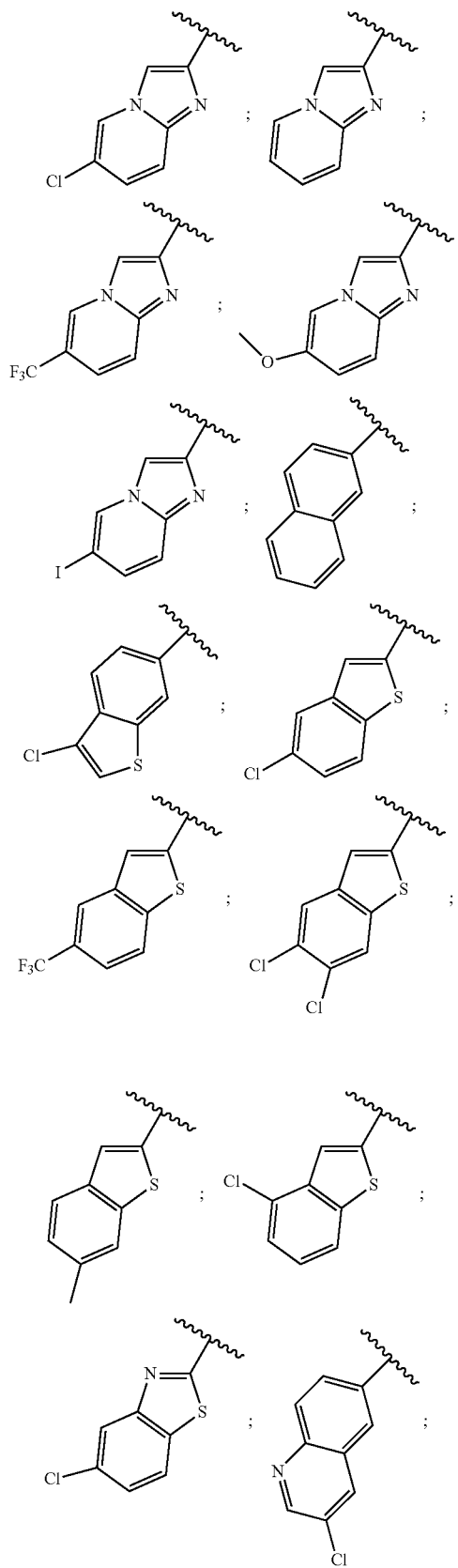
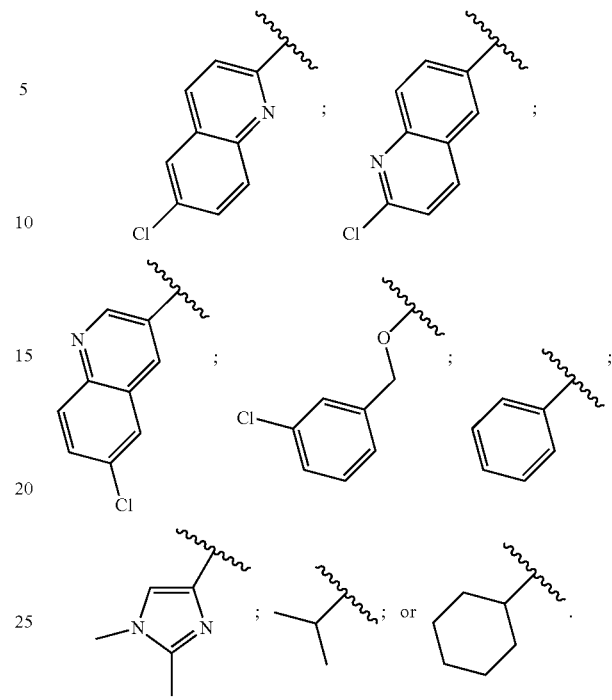
In certain embodiments, R² is of the formula:
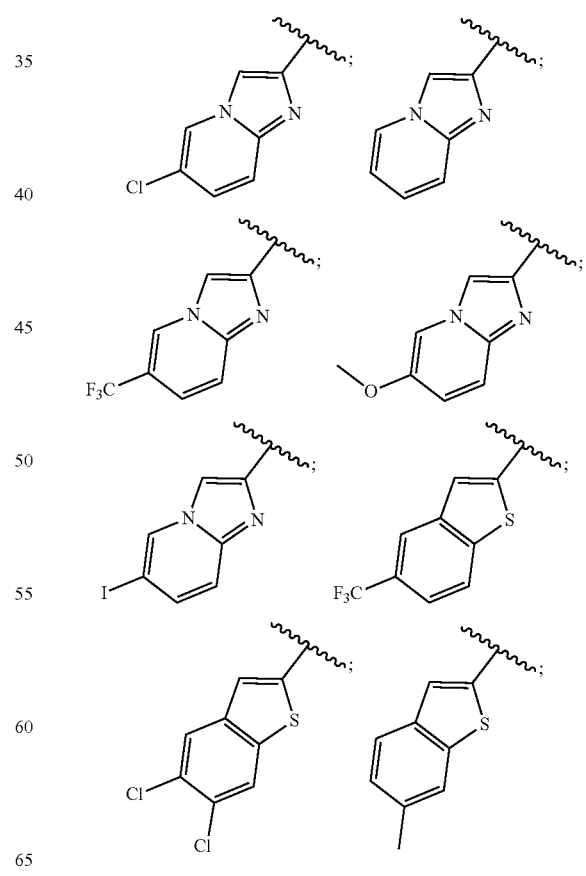

-continued

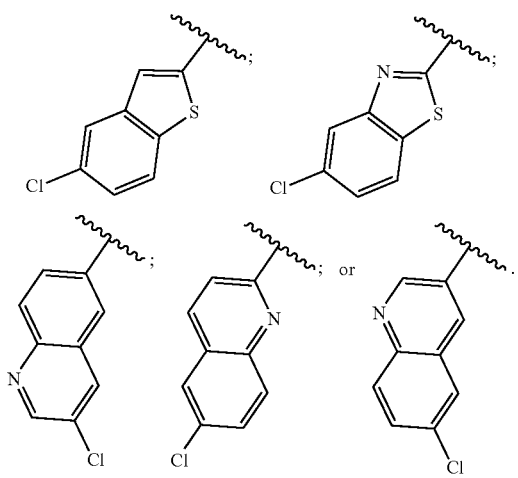

In certain embodiments, R² is of the formula:

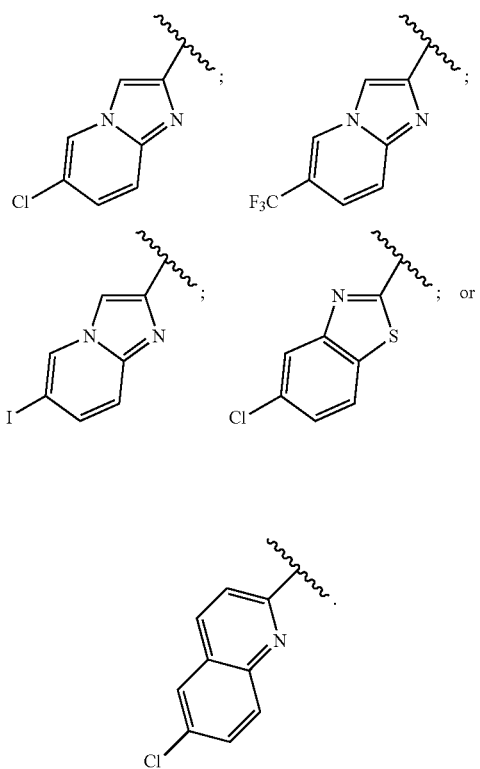

In certain embodiments, R² is of the formula:

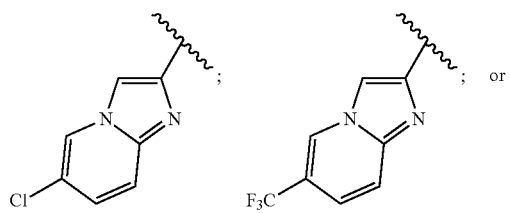

-continued

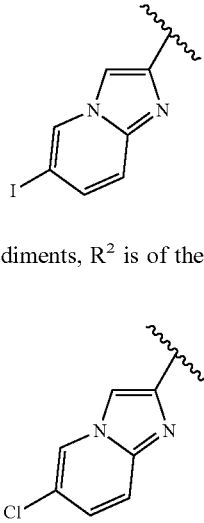

In certain embodiments, R² is of the formula:

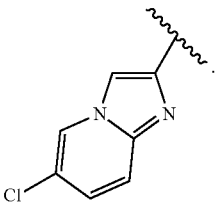 [SMILES: *c1cn2cc(Cl)ccc2n1]

In certain embodiments, R³ is substituted or unsubstituted alkyl, substituted or unsubstituted heteroalkyl, substituted or unsubstituted acyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted aralkyl, substituted or unsubstituted heteroaryl, or substituted or unsubstituted heteroaralkyl, wherein any carbon of R³, valence permitting, is optionally replaced with —O—, —NR$^A$—, —C(O)—, —C(=NR$^A$)—, —S—, —S(O)—, or —S(O)$_2$—. In certain embodiments, R³ is substituted or unsubstituted alkyl, substituted or unsubstituted heteroalkyl, substituted or unsubstituted acyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted aralkyl, substituted or unsubstituted heteroaryl, or substituted or unsubstituted heteroaralkyl, wherein any carbon of R³, valence permitting, is optionally replaced with —O—, —NR$^A$—, —C(O)—, —C(=NR$^A$)—, —S—, —S(O)—, or —S(O)$_2$—; and each occurrence of R$^A$ is, independently, hydrogen or substituted or unsubstituted alkyl.

In certain embodiments, R³ is substituted or unsubstituted alkyl, substituted or unsubstituted heteroalkyl, substituted or unsubstituted acyl, substituted or unsubstituted aralkyl, or substituted or unsubstituted heteroaralkyl, wherein any carbon of R³, valence permitting, is optionally replaced with —O—, —NR$^A$—, —C(O)—, —C(=NR$^A$)—, —S—, —S(O)—, or —S(O)$_2$—. In certain embodiments, R³ is substituted or unsubstituted alkyl, substituted or unsubstituted heteroalkyl, substituted or unsubstituted acyl, substituted or unsubstituted aralkyl, or substituted or unsubstituted heteroaralkyl, wherein any carbon of R³, valence permitting, is optionally replaced with —O—, —NR$^A$—, —C(O)—, —C(=NR$^A$)—, —S—, —S(O)—, or —S(O)$_2$—; and each occurrence of R$^A$ is, independently, hydrogen or substituted or unsubstituted alkyl.

In certain embodiments, R³ is substituted or unsubstituted alkyl, substituted or unsubstituted heteroalkyl, substituted or unsubstituted aralkyl, or substituted or unsubstituted heteroaralkyl, wherein any carbon of R³, valence permitting, is optionally replaced with —O—, —NR$^A$—, —C(O)—, or —C(=NR$^A$)—. In certain embodiments, R³ is substituted or unsubstituted alkyl, substituted or unsubstituted heteroalkyl, substituted or unsubstituted aralkyl, or substituted or unsubstituted heteroaralkyl, wherein any carbon of $R^3$, valence permitting, is optionally replaced with —O—, —$NR^A$—, —C(O)—, or —C(=$NR^A$)—; and each occurrence of $R^A$ is, independently, hydrogen or substituted or unsubstituted alkyl.

In certain embodiments, $R^3$ is substituted or unsubstituted aralkyl, or substituted or unsubstituted heteroaralkyl, wherein any carbon of $R^3$, valence permitting, is optionally replaced with —O—, —$NR^A$—, —C(O)—, or —C(=$NR^A$)—. In certain embodiments, $R^3$ is substituted or unsubstituted aralkyl, or substituted or unsubstituted heteroaralkyl, wherein any carbon of $R^3$, valence permitting, is optionally replaced with —O—, —$NR^A$—, —C(O)—, or —C(=$NR^A$)—; and each occurrence of $R^A$ is, independently, hydrogen or substituted or unsubstituted alkyl.

In certain embodiments, $R^3$ is substituted or unsubstituted alkyl, or substituted or unsubstituted heteroalkyl, wherein any carbon of $R^3$, valence permitting, is optionally replaced with —O—, —$NR^A$—, —C(O)—, or —C(=$NR^A$)—. In certain embodiments, $R^3$ is substituted or unsubstituted alkyl, or substituted or unsubstituted heteroalkyl, wherein any carbon of $R^3$, valence permitting, is optionally replaced with —O—, —$NR^A$—, —C(O)—, or —C(=$NR^A$)—; and each occurrence of $R^A$ is, independently, hydrogen or substituted or unsubstituted alkyl.

In certain embodiments, $R^3$ is substituted or unsubstituted alkyl, wherein any carbon of $R^3$, valence permitting, is optionally replaced with —O—, —$NR^A$—, —C(O)—, or —C(=$NR^A$)—. In certain embodiments, $R^3$ is substituted or unsubstituted alkyl, wherein any carbon of $R^3$, valence permitting, is optionally replaced with —O—, —$NR^A$—, —C(O)—, or —C(=$NR^A$)—; and each occurrence of $R^A$ is, independently, hydrogen or substituted or unsubstituted alkyl.

In certain embodiments, $R^3$ is substituted or unsubstituted heteroalkyl, wherein any carbon of $R^3$, valence permitting, is optionally replaced with —O—, —$NR^A$—, —C(O)—, or —C(=$NR^A$)—. In certain embodiments, $R^3$ is substituted or unsubstituted heteroalkyl, wherein any carbon of $R^3$, valence permitting, is optionally replaced with —O—, —$NR^A$—, —C(O)—, or —C(=$NR^A$)—; and each occurrence of $R^A$ is, independently, hydrogen or substituted or unsubstituted alkyl.

In certain embodiments, $R^3$ is substituted or unsubstituted aralkyl, wherein any carbon of $R^3$, valence permitting, is optionally replaced with —O—, —$NR^A$—, —C(O)—, or —C(=$NR^A$)—. In certain embodiments, $R^3$ is substituted or unsubstituted aralkyl, wherein any carbon of $R^3$, valence permitting, is optionally replaced with —O—, —$NR^A$—, —C(O)—, or —C(=$NR^A$)—; and each occurrence of $R^A$ is, independently, hydrogen or substituted or unsubstituted alkyl.

In certain embodiments, $R^3$ is substituted or unsubstituted heteroaralkyl, wherein any carbon of $R^3$, valence permitting, is optionally replaced with —O—, —$NR^A$—, —C(O)—, or —C(=$NR^A$)—. In certain embodiments, $R^3$ is substituted or unsubstituted heteroaralkyl, wherein any carbon of $R^3$, valence permitting, is optionally replaced with —O—, —$NR^A$—, —C(O)—, or —C(=$NR^A$)—; and each occurrence of $R^A$ is, independently, hydrogen or substituted or unsubstituted alkyl.

In certain embodiments, $R^3$ is of the formula:

$$\begin{array}{c} \xi \\ | \\ \text{C} \\ / \quad \backslash \\ R^c \quad R^d \end{array}$$

wherein:
$R^c$ is hydrogen, substituted or unsubstituted alkyl, substituted or unsubstituted heteroalkyl, substituted or unsubstituted aryl, substituted or unsubstituted heteroaryl, substituted or unsubstituted aralkyl, or substituted or unsubstituted heteroaralkyl, wherein any carbon of $R^c$, valence permitting, is optionally replaced with —$NR^A$—, —C(O)—, or —C(=$NR^A$)—;
$R^d$ is hydrogen, substituted or unsubstituted alkyl, —C(O)N($R^A$)$_2$, or —C(O)O$R^A$; and
each occurrence of $R^A$ is, independently, hydrogen or substituted or unsubstituted alkyl.

In certain embodiments, $R^3$ is of the formula:

$$\begin{array}{c} \xi \\ | \\ \text{C} \\ / \quad \backslash \\ R^c \quad R^d \end{array}$$

wherein:
$R^c$ is hydrogen, substituted or unsubstituted alkyl, substituted or unsubstituted aryl, substituted or unsubstituted heteroaryl, substituted or unsubstituted aralkyl, or substituted or unsubstituted heteroaralkyl, wherein any carbon of $R^c$, valence permitting, is optionally replaced with —$NR^A$—, —C(O)—, or —C(=$NR^A$)—;
$R^d$ is hydrogen, —C(O)N($R^A$)$_2$, or —C(O)O$R^A$; and
each occurrence of $R^A$ is, independently, hydrogen or substituted or unsubstituted alkyl.

In certain embodiments, $R^3$ is of the formula:

$$\begin{array}{c} \xi \\ | \\ R^c \end{array}$$

wherein:
$R^c$ is substituted or unsubstituted aryl, substituted or unsubstituted heteroaryl, substituted or unsubstituted aralkyl, or substituted or unsubstituted heteroaralkyl, wherein any carbon of $R^c$, valence permitting, is optionally replaced with —$NR^A$—, —C(O)—, or —C(=$NR^A$)—; and
each occurrence of $R^A$ is, independently, hydrogen or substituted or unsubstituted alkyl.

In certain embodiments, $R^3$ is of the formula:

$$\begin{array}{c} \xi \\ | \\ R^c \end{array}$$

wherein:
  $R^c$ is substituted or unsubstituted heteroaryl, or substituted or unsubstituted heteroaralkyl, wherein any carbon of $R^c$, valence permitting, is optionally replaced with —$NR^A$—, —C(O)—, or —C(=$NR^A$)—; and
  each occurrence of $R^A$ is, independently, hydrogen or substituted or unsubstituted alkyl.

In certain embodiments, $R^3$ is of the formula:

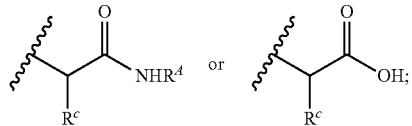

wherein:
  $R^c$ is substituted or unsubstituted alkyl, substituted or unsubstituted aryl, substituted or unsubstituted heteroaryl, substituted or unsubstituted aralkyl, or substituted or unsubstituted heteroaralkyl, wherein any carbon of $R^c$, valence permitting, is optionally replaced with —$NR^A$—, —C(O)—, or —C(=$NR^A$)—; and
  each occurrence of $R^A$ is, independently, hydrogen or substituted or unsubstituted alkyl.

In certain embodiments, $R^3$ is of the formula:

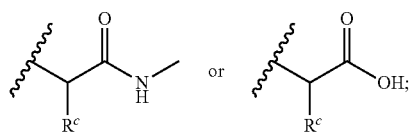

wherein:
  $R^c$ is substituted or unsubstituted alkyl, substituted or unsubstituted aryl, substituted or unsubstituted heteroaryl, substituted or unsubstituted aralkyl, or substituted or unsubstituted heteroaralkyl, wherein any carbon of $R^c$, valence permitting, is optionally replaced with —$NR^A$—, —C(O)—, or —C(=$NR^A$)—; and
  each occurrence of $R^A$ is, independently, hydrogen or substituted or unsubstituted alkyl.

In certain embodiments, $R^3$ is of the formula:

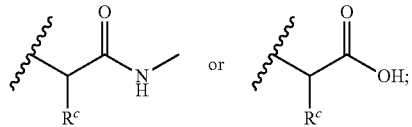

wherein:
  $R^c$ is substituted or unsubstituted alkyl, wherein any carbon of $R^c$, valence permitting, is optionally replaced with —$NR^A$—, —C(O)—, or —C(=$NR^A$)—; and
  each occurrence of $R^A$ is, independently, hydrogen or substituted or unsubstituted alkyl.

In certain embodiments, $R^3$ is of the formula:

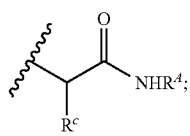

wherein:
  $R^c$ is substituted or unsubstituted alkyl, substituted or unsubstituted aryl, substituted or unsubstituted heteroaryl, substituted or unsubstituted aralkyl, or substituted or unsubstituted heteroaralkyl, wherein any carbon of $R^c$, valence permitting, is optionally replaced with —$NR^A$—, —C(O)—, or —C(=$NR^A$)—; and
  each occurrence of $R^A$ is, independently, hydrogen or substituted or unsubstituted alkyl.

In certain embodiments, $R^3$ is of the formula:

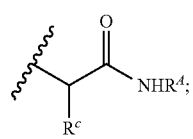

wherein:
  $R^c$ is substituted or unsubstituted alkyl, wherein any carbon of $R^c$, valence permitting, is optionally replaced with —$NR^A$—, —C(O)—, or —C(=$NR^A$)—; and
  each occurrence of $R^A$ is, independently, hydrogen or substituted or unsubstituted alkyl.

In certain embodiments, $R^3$ is of the formula:

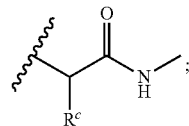

wherein:
  $R^c$ is substituted or unsubstituted alkyl, substituted or unsubstituted aryl, substituted or unsubstituted heteroaryl, substituted or unsubstituted aralkyl, or substituted or unsubstituted heteroaralkyl, wherein any carbon of $R^c$, valence permitting, is optionally replaced with —$NR^A$—, —C(O)—, or —C(=$NR^A$)—; and
  each occurrence of $R^A$ is, independently, hydrogen or substituted or unsubstituted alkyl.

In certain embodiments, $R^3$ is of the formula:

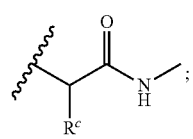

wherein:
  $R^c$ is substituted or unsubstituted alkyl, wherein any carbon of $R^c$, valence permitting, is optionally replaced with —$NR^A$—, —C(O)—, or —C(=$NR^A$)—; and
  each occurrence of $R^A$ is, independently, hydrogen or substituted or unsubstituted alkyl.

In certain embodiments, $R^3$ is of the formula:
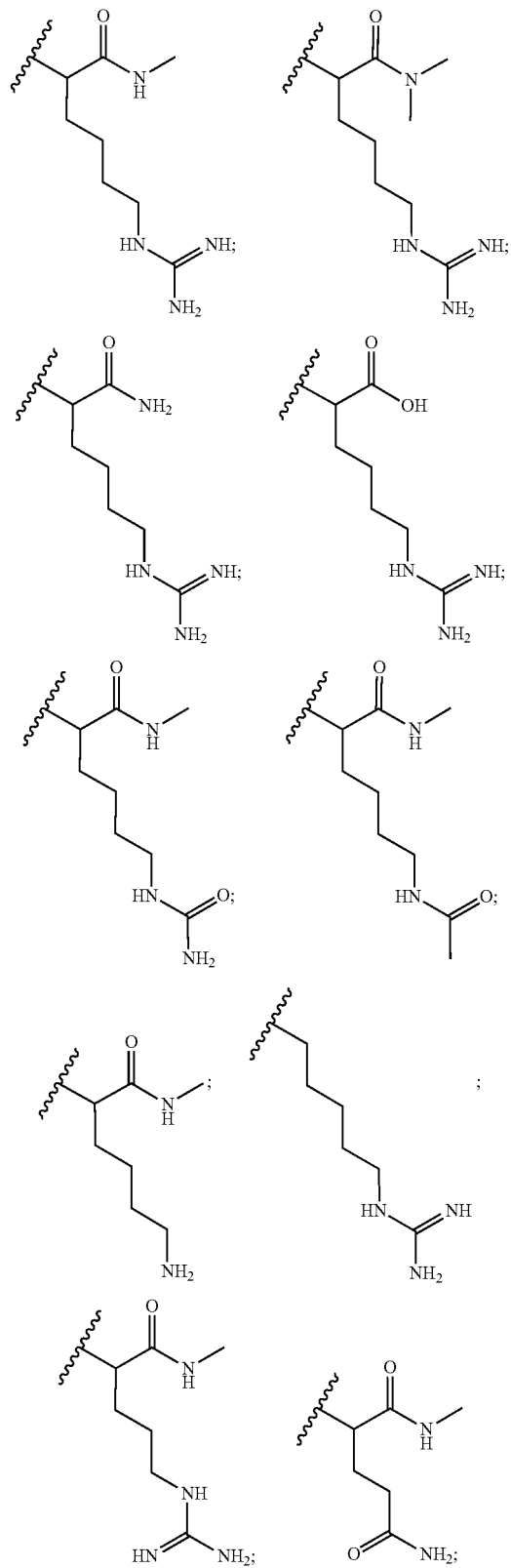
-continued
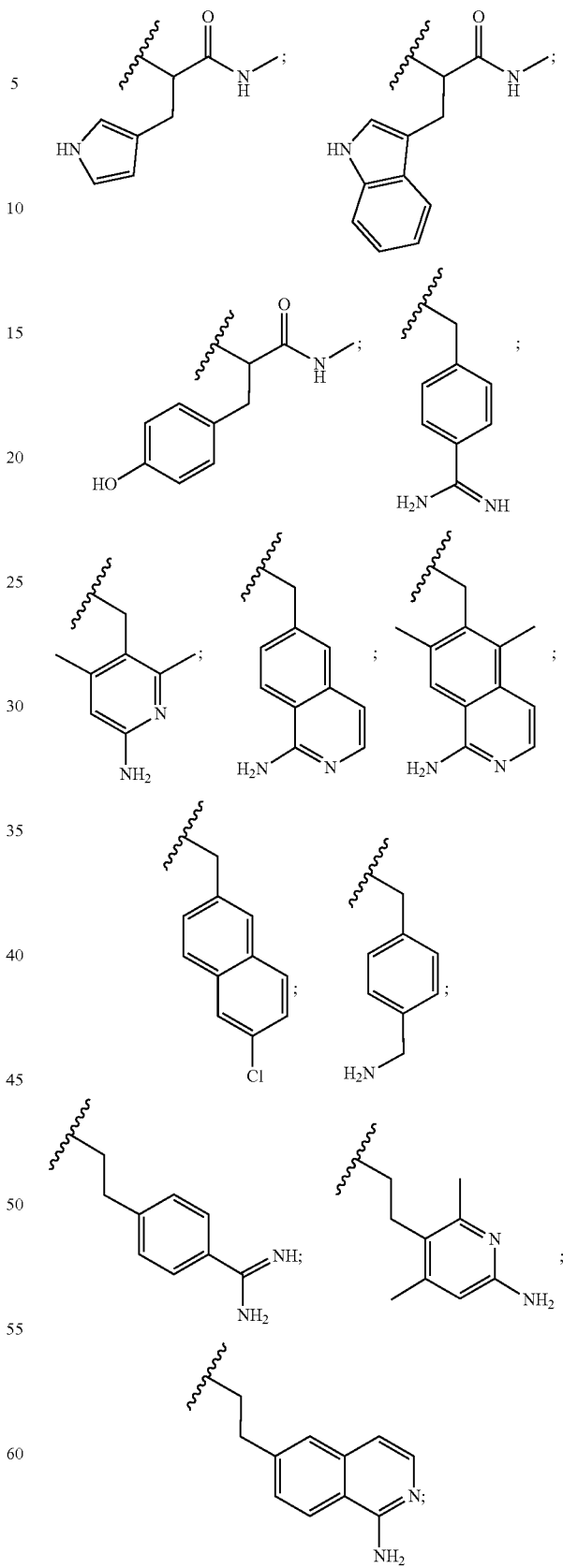

In certain embodiments, R³ is of the formula:
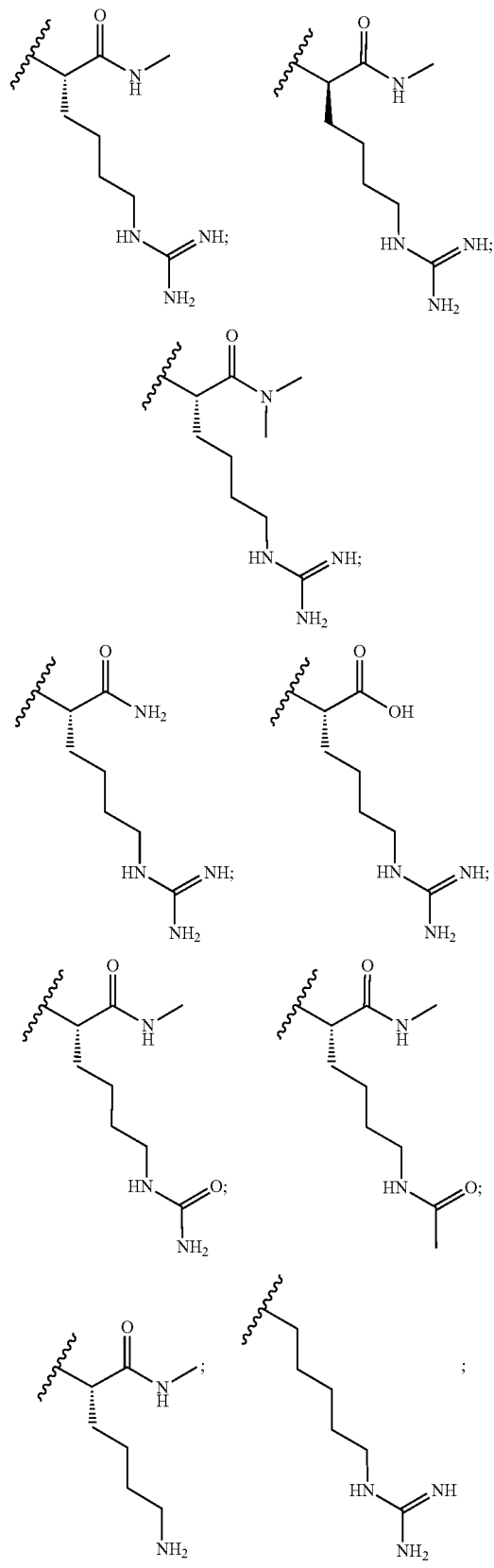
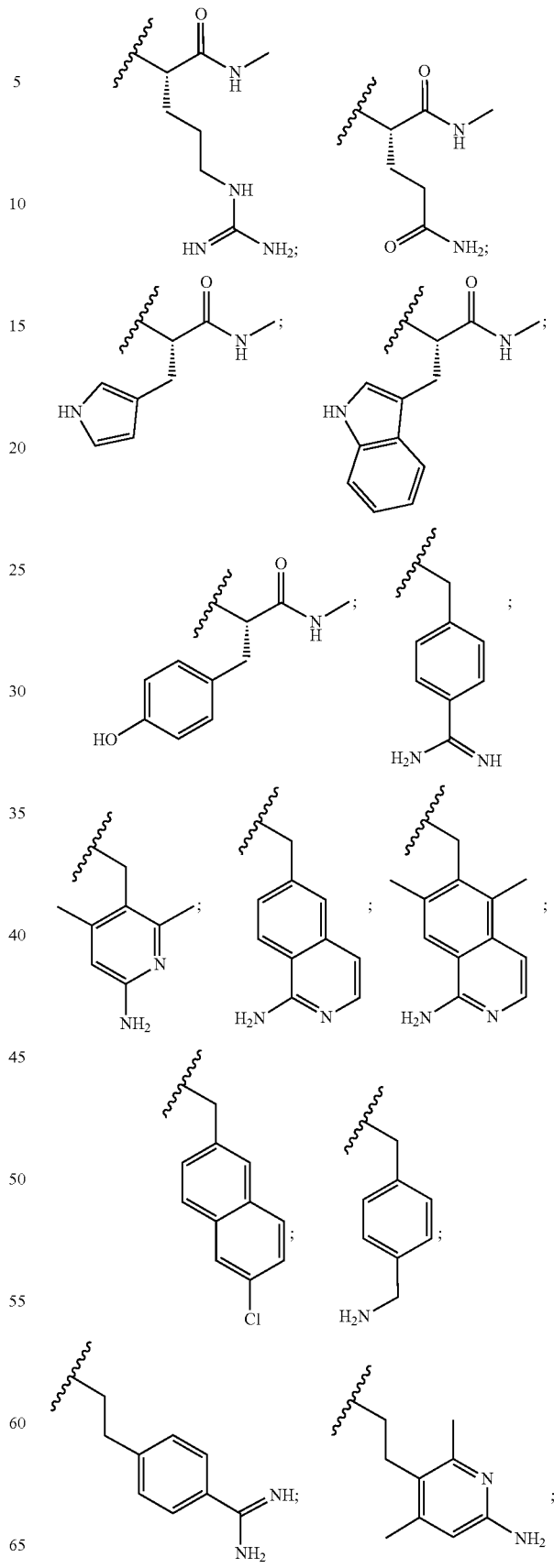

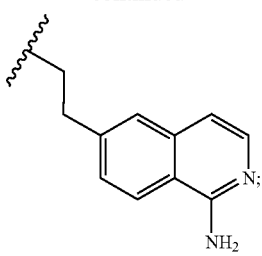
In certain embodiments, R³ is of the formula:
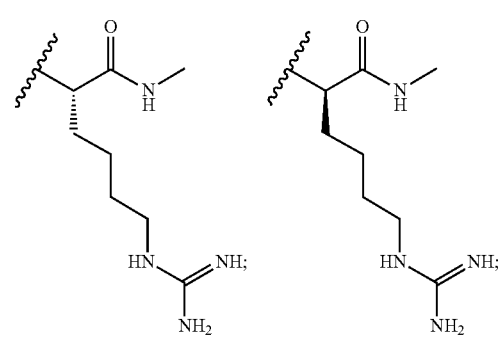
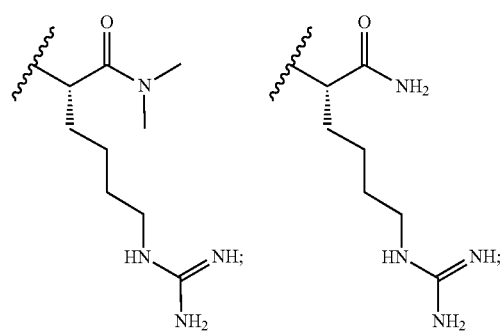
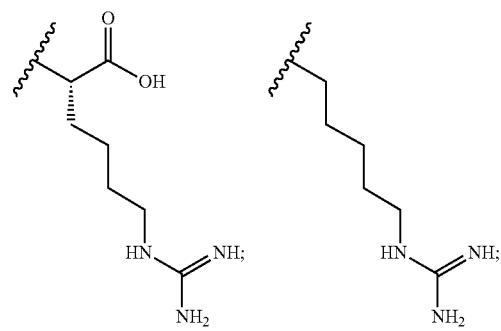
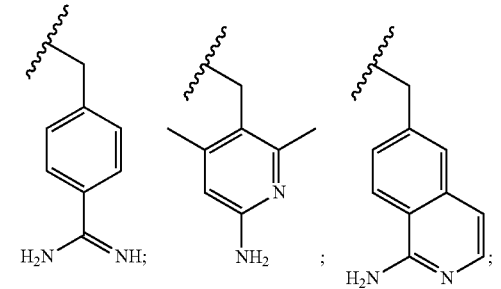
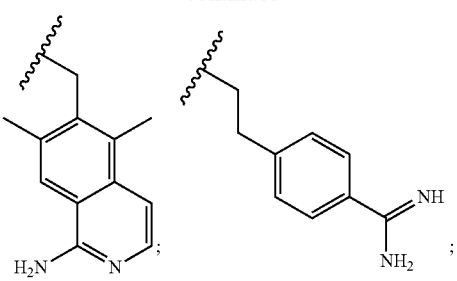
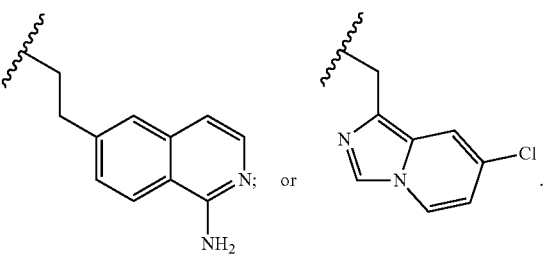
In certain embodiments, R³ is of the formula:
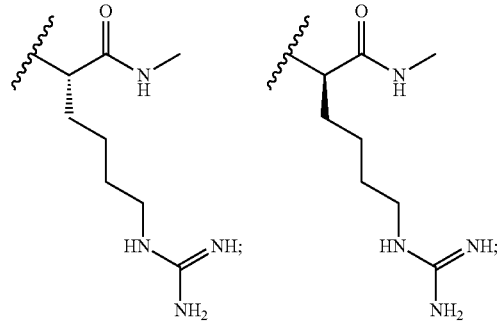
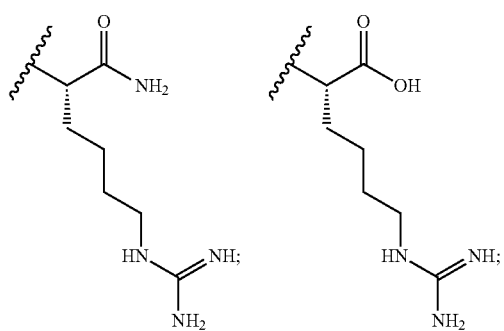
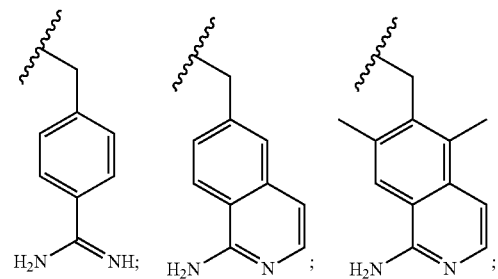

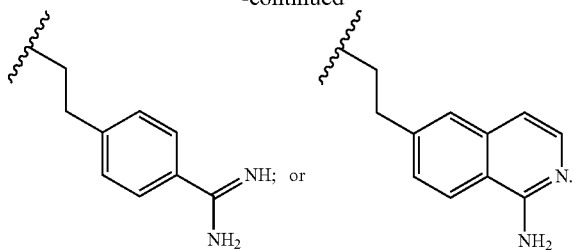

In certain embodiments, R is of the formula:

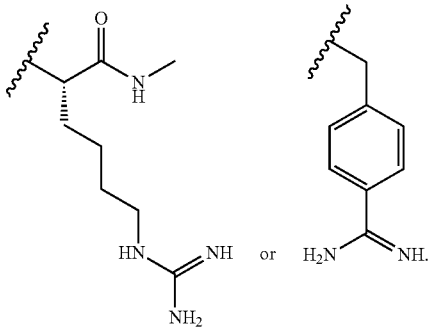 [SMILES: *[C@@H](CCCCNC(=N)N)C(=O)NC ; *Cc1ccc(C(=N)N)cc1]

In certain embodiments, R³ is of the formula:

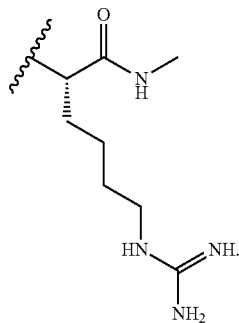 [SMILES: *[C@@H](CCCCNC(=N)N)C(=O)NC]

Group $R^A$

In certain embodiments, $R^A$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, or an oxygen protecting group when attached to an oxygen atom, or two $R^A$ groups are joined to form a substituted or unsubstituted heterocyclic ring. In certain embodiments, $R^A$ is, independently, hydrogen, substituted or unsubstituted acyl, substituted or unsubstituted alkyl, a nitrogen protecting group when attached to a nitrogen atom, or an oxygen protecting group when attached to an oxygen atom. In certain embodiments, $R^A$ is, independently, hydrogen, substituted or unsubstituted alkyl, or a nitrogen protecting group. In certain embodiments, $R^A$ is, independently, hydrogen, substituted or unsubstituted $C_{1-6}$ alkyl, or a nitrogen protecting group. In certain embodiments, $R^A$ is, independently, hydrogen or substituted or unsubstituted $C_{1-6}$ alkyl. In certain embodiments, $R^A$ is, independently, hydrogen or unsubstituted $C_{1-6}$ alkyl. In certain embodiments, $R^A$ is, independently, hydrogen or unsubstituted $C_{1-4}$ alkyl. In certain embodiments, $R^A$ is, independently, hydrogen or unsubstituted $C_{1-2}$ alkyl. In certain embodiments, $R^A$ is hydrogen. In certain embodiments, $R^A$ is unsubstituted $C_{1-2}$ alkyl.

Embodiments of Formula I

In certain embodiments, the compound of Formula I is a compound of Formula I-a:

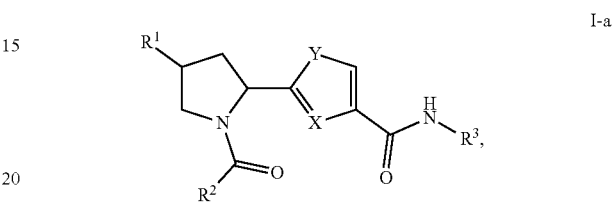

or a pharmaceutically acceptable salt, co-crystal, tautomer, stereoisomer, solvate, hydrate, polymorph, isotopically enriched derivative, or prodrug thereof;
wherein;
X is N or $CR^y$;
Y is O, S, or $NR^x$; and
$R^x$ and $R^y$ are, independently, hydrogen or substituted or unsubstituted alkyl.

In certain embodiments of Formula I-a, X is N; and Y is O, S, or $NR^x$.

In certain embodiments of Formula I-a, Y is O or S.

In certain embodiments of Formula I-a, X is N; and Y is O or S.

In certain embodiments of Formula I-a, Y is S.

In certain embodiments of Formula I-a, X is N; and Y is S.

In certain embodiments of Formula I-a, each occurrence of $R^A$ is, independently, hydrogen, substituted or unsubstituted acyl, substituted or unsubstituted alkyl, a nitrogen protecting group when attached to a nitrogen atom, or an oxygen protecting group when attached to an oxygen atom. In certain embodiments of Formula I-a, each occurrence of $R^A$ is, independently, hydrogen, substituted or unsubstituted alkyl, or a nitrogen protecting group.

In certain embodiments of Formula I-a, $R^1$ is —NH₂.

In certain embodiments of Formula I-a, $R^2$ is substituted or unsubstituted aryl, substituted or unsubstituted heteroaryl, substituted or unsubstituted alkyl, —$OR^A$, or —$N(R^A)_2$.

In certain embodiments of Formula I-a, $R^2$ is substituted or unsubstituted aryl, or substituted or unsubstituted heteroaryl.

In certain embodiments of Formula I-a, $R^2$ is substituted or unsubstituted heteroaryl.

In certain embodiments of Formula I-a, $R^2$ is substituted or unsubstituted fused bicyclic heteroaryl.

In certain embodiments of Formula I-a, $R^3$ is substituted or unsubstituted alkyl, substituted or unsubstituted heteroalkyl, substituted or unsubstituted acyl, substituted or unsubstituted aralkyl, or substituted or unsubstituted heteroaralkyl, wherein any carbon of $R^3$, valence permitting, is optionally replaced with —O—, —$NR^A$—, —C(O)—, —C(=$NR^A$)—, —S—, —S(O)—, or —$S(O)_2$—.

In certain embodiments of Formula I-a, $R^3$ is substituted or unsubstituted alkyl, substituted or unsubstituted heteroalkyl, substituted or unsubstituted aralkyl, or substituted or unsubstituted heteroaralkyl, wherein any carbon of $R^3$, valence permitting, is optionally replaced with —O—, —$NR^4$—, —C(O)—, or —C(=$NR^4$)—.

In certain embodiments of Formula I-a, $R^3$ is substituted or unsubstituted alkyl, or substituted or unsubstituted heteroalkyl, wherein any carbon of $R^3$, valence permitting, is optionally replaced with —O—, —$NR^4$—, —C(O)—, or —C(=$NR^4$)—.

In certain embodiments, the compound of Formula I-a is a compound of Formula I-a-1:

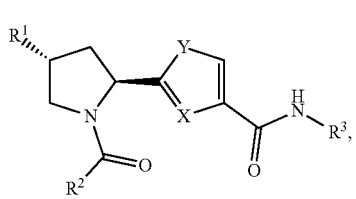

I-a-1 or a pharmaceutically acceptable salt, co-crystal, tautomer, stereoisomer, solvate, hydrate, polymorph, isotopically enriched derivative, or prodrug thereof.

In certain embodiments, the compound of Formula I is a compound of Formula I-b:

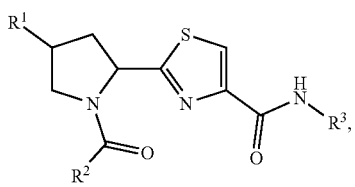

I-b or a pharmaceutically acceptable salt, co-crystal, tautomer, stereoisomer, solvate, hydrate, polymorph, isotopically enriched derivative, or prodrug thereof.

In certain embodiments of Formula I-b, each occurrence of $R^4$ is, independently, hydrogen, substituted or unsubstituted acyl, substituted or unsubstituted alkyl, a nitrogen protecting group when attached to a nitrogen atom, or an oxygen protecting group when attached to an oxygen atom. In certain embodiments of Formula I-b, each occurrence of $R^4$ is, independently, hydrogen, substituted or unsubstituted alkyl, or a nitrogen protecting group.

In certain embodiments of Formula I-b, $R^1$ is —$NH_2$.

In certain embodiments of Formula I-b, $R^2$ is substituted or unsubstituted aryl, substituted or unsubstituted heteroaryl, substituted or unsubstituted alkyl, —$OR^4$, or —$N(R^4)_2$.

In certain embodiments of Formula I-b, $R^2$ is substituted or unsubstituted aryl, or substituted or unsubstituted heteroaryl.

In certain embodiments of Formula I-b, $R^2$ is substituted or unsubstituted heteroaryl.

In certain embodiments of Formula I-b, $R^2$ is substituted or unsubstituted fused bicyclic heteroaryl.

In certain embodiments of Formula I-b, $R^3$ is substituted or unsubstituted alkyl, substituted or unsubstituted heteroalkyl, substituted or unsubstituted acyl, substituted or unsubstituted aralkyl, or substituted or unsubstituted heteroaralkyl, wherein any carbon of $R^3$, valence permitting, is optionally replaced with —O—, —$NR^4$—, —C(O)—, —C(=$NR^4$)—, —S—, —S(O)—, or —$S(O)_2$—.

In certain embodiments of Formula I-b, $R^3$ is substituted or unsubstituted alkyl, substituted or unsubstituted heteroalkyl, substituted or unsubstituted aralkyl, or substituted or unsubstituted heteroaralkyl, wherein any carbon of $R^3$, valence permitting, is optionally replaced with —O—, —$NR^4$—, —C(O)—, or —C(=$NR^4$)—.

In certain embodiments of Formula I-b, $R^3$ is substituted or unsubstituted alkyl, or substituted or unsubstituted heteroalkyl, wherein any carbon of $R^3$, valence permitting, is optionally replaced with —O—, —$NR^4$—, —C(O)—, or —C(=$NR^4$)—.

In certain embodiments, the compound of Formula I-b is a compound of Formula I-b-1:

I-b-1 or a pharmaceutically acceptable salt, co-crystal, tautomer, stereoisomer, solvate, hydrate, polymorph, isotopically enriched derivative, or prodrug thereof.

In certain embodiments, the compound of Formula I is a compound of Formula I-c:

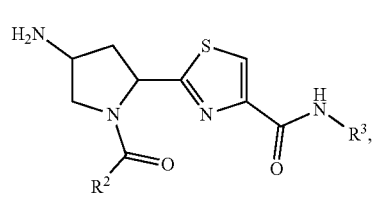

I-c or a pharmaceutically acceptable salt, co-crystal, tautomer, stereoisomer, solvate, hydrate, polymorph, isotopically enriched derivative, or prodrug thereof.

In certain embodiments of Formula I-c, $R^2$ is substituted or unsubstituted aryl, substituted or unsubstituted heteroaryl, substituted or unsubstituted alkyl, —$OR^4$, or —$N(R^4)_2$.

In certain embodiments of Formula I-c, $R^2$ is substituted or unsubstituted aryl, or substituted or unsubstituted heteroaryl.

In certain embodiments of Formula I-c, $R^2$ is substituted or unsubstituted heteroaryl.

In certain embodiments of Formula I-c, $R^2$ is substituted or unsubstituted fused bicyclic heteroaryl.

In certain embodiments of Formula I-c, $R^3$ is substituted or unsubstituted alkyl, substituted or unsubstituted heteroalkyl, substituted or unsubstituted acyl, substituted or unsubstituted aralkyl, or substituted or unsubstituted heteroaralkyl, wherein any carbon of $R^3$, valence permitting, is optionally replaced with —O—, —$NR^4$—, —C(O)—, —C(=$NR^4$)—, —S—, —S(O)—, or —$S(O)_2$—.

In certain embodiments of Formula I-c, $R^3$ is substituted or unsubstituted alkyl, substituted or unsubstituted heteroalkyl, substituted or unsubstituted aralkyl, or substituted or unsubstituted heteroaralkyl, wherein any carbon of $R^3$, valence permitting, is optionally replaced with —O—, —$NR^4$—, —C(O)—, or —C(=$NR^4$)—.

In certain embodiments of Formula I-c, $R^3$ is substituted or unsubstituted alkyl, or substituted or unsubstituted heteroalkyl, wherein any carbon of $R^3$, valence permitting, is optionally replaced with —O—, —$NR^4$—, —C(O)—, or —C(=$NR^4$)—.

In certain embodiments of Formula I-c, $R^2$ is substituted or unsubstituted aryl, or substituted or unsubstituted heteroaryl; and $R^3$ is substituted or unsubstituted alkyl, substituted or unsubstituted heteroalkyl, substituted or unsubstituted aralkyl, or substituted or unsubstituted heteroaralkyl, wherein any carbon of $R^3$, valence permitting, is optionally replaced with —O—, —$NR^4$—, —C(O)—, or —C(=$NR^4$)—.

In certain embodiments of Formula I-c, $R^2$ is substituted or unsubstituted fused bicyclic heteroaryl; and $R^3$ is substituted or unsubstituted alkyl, substituted or unsubstituted heteroalkyl, substituted or unsubstituted aralkyl, or substituted or unsubstituted heteroaralkyl, wherein any carbon of $R^3$, valence permitting, is optionally replaced with —O—, —$NR^4$—, —C(O)—, or —C(=$NR^4$)—.

In certain embodiments, the compound of Formula I-c is a compound of Formula I-c-1:

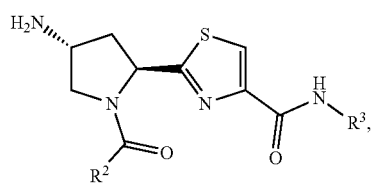

I-c-1 or a pharmaceutically acceptable salt, co-crystal, tautomer, stereoisomer, solvate, hydrate, polymorph, isotopically enriched derivative, or prodrug thereof.

In certain embodiments, the compound of Formula I is a compound of Formula I-d:

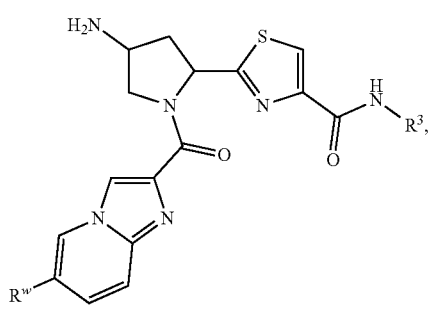

I-d or a pharmaceutically acceptable salt, co-crystal, tautomer, stereoisomer, solvate, hydrate, polymorph, isotopically enriched derivative, or prodrug thereof;
wherein:
  $R^w$ is hydrogen, halogen, alkoxy, alkoxyalkyl, haloalkoxy, or haloalkyl.

In certain embodiments of Formula I-d, $R^w$ is halogen, alkoxy, haloalkoxy, or haloalkyl.

In certain embodiments of Formula I-d, $R^w$ is halogen, haloalkoxy, or haloalkyl.

In certain embodiments of Formula I-d, $R^w$ is halogen or haloalkyl.

In certain embodiments of Formula I-d, $R^w$ is halogen.

In certain embodiments of Formula I-d, $R^3$ is substituted or unsubstituted alkyl, substituted or unsubstituted heteroalkyl, substituted or unsubstituted acyl, substituted or unsubstituted aralkyl, or substituted or unsubstituted heteroaralkyl, wherein any carbon of $R^3$, valence permitting, is optionally replaced with —O—, —$NR^4$—, —C(O)—, —C(=$NR^4$)—, —S—, —S(O)—, or —S(O)$_2$—.

In certain embodiments of Formula I-d, $R^3$ is substituted or unsubstituted alkyl, substituted or unsubstituted heteroalkyl, substituted or unsubstituted aralkyl, or substituted or unsubstituted heteroaralkyl, wherein any carbon of $R^3$, valence permitting, is optionally replaced with —O—, —$NR^4$—, —C(O)—, or —C(=$NR^4$)—.

In certain embodiments of Formula I-d, $R^3$ is substituted or unsubstituted aralkyl, or substituted or unsubstituted heteroaralkyl, wherein any carbon of $R^3$, valence permitting, is optionally replaced with —O—, —$NR^4$—, —C(O)—, or —C(=$NR^4$)—.

In certain embodiments of Formula I-d, $R^3$ is substituted or unsubstituted alkyl, or substituted or unsubstituted heteroalkyl, wherein any carbon of $R^3$, valence permitting, is optionally replaced with —O—, —$NR^4$—, —C(O)—, or —C(=$NR^4$)—.

In certain embodiments, the compound of Formula I-d is a compound of Formula I-d-1:

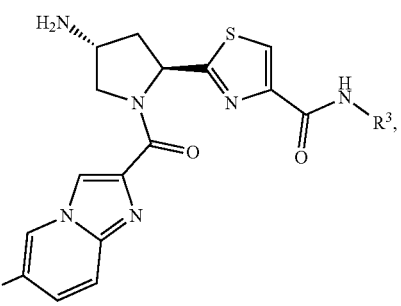

I-d-1 or a pharmaceutically acceptable salt, co-crystal, tautomer, stereoisomer, solvate, hydrate, polymorph, isotopically enriched derivative, or prodrug thereof.

In certain embodiments, the compound of Formula I is a compound of Formula I-e:

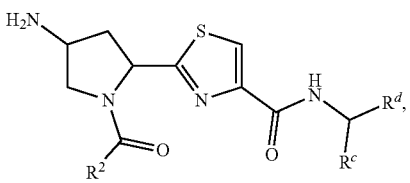

I-e or a pharmaceutically acceptable salt, co-crystal, tautomer, stereoisomer, solvate, hydrate, polymorph, isotopically enriched derivative, or prodrug thereof;
wherein:
  $R^c$ is hydrogen, substituted or unsubstituted alkyl, substituted or unsubstituted aryl, substituted or unsubstituted heteroaryl, substituted or unsubstituted aralkyl, or substituted or unsubstituted heteroaralkyl, wherein any carbon of $R^c$, valence permitting, is optionally replaced with —$NR^4$—, —C(O)—, or —C(=$NR^4$)—;

$R^d$ is hydrogen, —C(O)N($R^A$)$_2$, or —C(O)O$R^A$; and each occurrence of $R^A$ is, independently, hydrogen or substituted or unsubstituted alkyl.

In certain embodiments of Formula I-e, $R^2$ is substituted or unsubstituted aryl, substituted or unsubstituted heteroaryl, substituted or unsubstituted alkyl, —O$R^A$, or —N($R^A$)$_2$.

In certain embodiments of Formula I-e, $R^2$ is substituted or unsubstituted aryl, or substituted or unsubstituted heteroaryl.

In certain embodiments of Formula I-e, $R^2$ is substituted or unsubstituted heteroaryl.

In certain embodiments of Formula I-e, $R^2$ is substituted or unsubstituted fused bicyclic heteroaryl.

In certain embodiments, the compound of Formula I-e is a compound of Formula I-e-1:

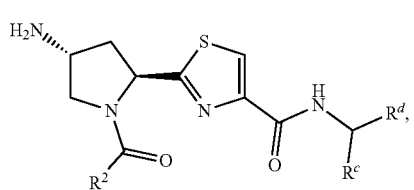

I-e-1 or a pharmaceutically acceptable salt, co-crystal, tautomer, stereoisomer, solvate, hydrate, polymorph, isotopically enriched derivative, or prodrug thereof.

In certain embodiments, the compound of Formula I is a compound of Formula I-f:

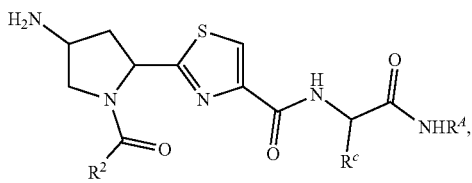

I-f or a pharmaceutically acceptable salt, co-crystal, tautomer, stereoisomer, solvate, hydrate, polymorph, isotopically enriched derivative, or prodrug thereof;
wherein:
$R^c$ is substituted or unsubstituted alkyl, substituted or unsubstituted aryl, substituted or unsubstituted heteroaryl, substituted or unsubstituted aralkyl, or substituted or unsubstituted heteroaralkyl, wherein any carbon of $R^c$, valence permitting, is optionally replaced with —N$R^A$—, —C(O)—, or —C(=N$R^A$)—; and each occurrence of $R^A$ is, independently, hydrogen or substituted or unsubstituted alkyl.

In certain embodiments of Formula I-f, $R^2$ is substituted or unsubstituted aryl, substituted or unsubstituted heteroaryl, substituted or unsubstituted alkyl, —O$R^A$, or —N($R^A$)$_2$.

In certain embodiments of Formula I-f, $R^2$ is substituted or unsubstituted aryl, or substituted or unsubstituted heteroaryl.

In certain embodiments of Formula I-f, $R^2$ is substituted or unsubstituted heteroaryl.

In certain embodiments of Formula I-f, $R^2$ is substituted or unsubstituted fused bicyclic heteroaryl.

In certain embodiments, the compound of Formula I-f is a compound of Formula I-f-1:

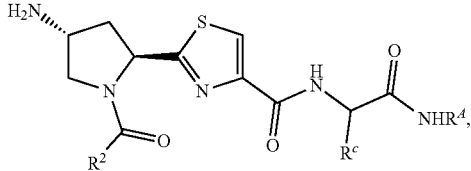

I-f-1 or a pharmaceutically acceptable salt, co-crystal, tautomer, stereoisomer, solvate, hydrate, polymorph, isotopically enriched derivative, or prodrug thereof.

In certain embodiments, the compound of Formula I-f is a compound of Formula I-f-2:

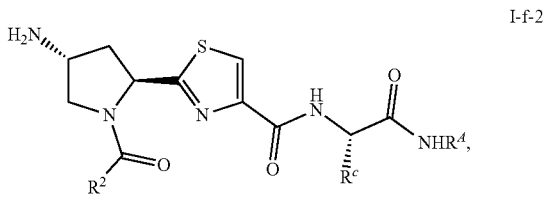

I-f-2 or a pharmaceutically acceptable salt, co-crystal, tautomer, stereoisomer, solvate, hydrate, polymorph, isotopically enriched derivative, or prodrug thereof.

In certain embodiments, the compound of Formula I is a compound 1 of Formula I-g:

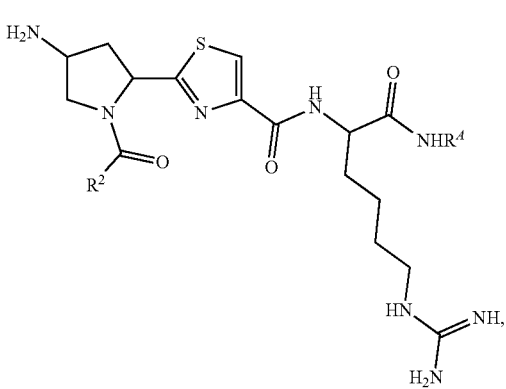

I-g or a pharmaceutically acceptable salt, co-crystal, tautomer, stereoisomer, solvate, hydrate, polymorph, isotopically enriched derivative, or prodrug thereof;

In certain embodiments of Formula I-g, $R^A$ is hydrogen or substituted or unsubstituted alkyl. In certain embodiments of Formula I-g, $R^A$ is hydrogen. In certain embodiments of Formula I-g, $R^A$ is unsubstituted alkyl.

In certain embodiments of Formula I-g, $R^2$ is substituted or unsubstituted aryl, substituted or unsubstituted heteroaryl, substituted or unsubstituted alkyl, —O$R^A$, or —N($R^A$)$_2$.

In certain embodiments of Formula I-g, $R^2$ is substituted or unsubstituted aryl, or substituted or unsubstituted heteroaryl.

In certain embodiments of Formula I-g, $R^2$ is substituted or unsubstituted heteroaryl.

In certain embodiments of Formula I-g, $R^2$ is substituted or unsubstituted fused bicyclic heteroaryl.

In certain embodiments, the compound of Formula I-g is a compound of Formula I-g-1:

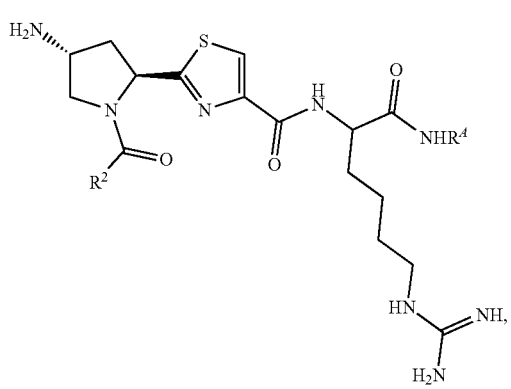

I-g-1 or a pharmaceutically acceptable salt, co-crystal, tautomer, stereoisomer, solvate, hydrate, polymorph, isotopically enriched derivative, or prodrug thereof.

In certain embodiments, the compound of Formula I-g is a compound of Formula I-g-2:

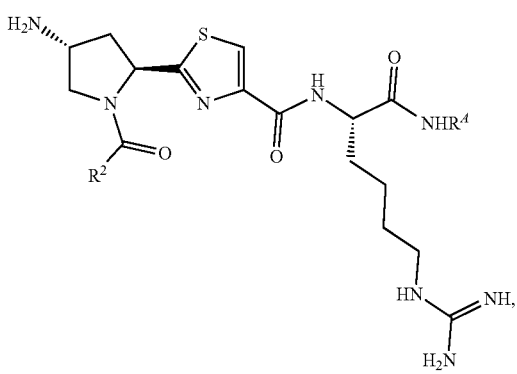

I-g-2 or a pharmaceutically acceptable salt, co-crystal, tautomer, stereoisomer, solvate, hydrate, polymorph, isotopically enriched derivative, or prodrug thereof.

In certain embodiments the compound of Formula I is a compound of Formula I-h:

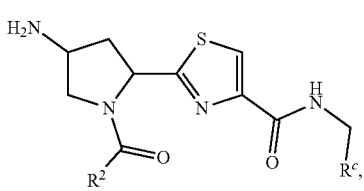

I-h or a pharmaceutically acceptable salt, co-crystal, tautomer, stereoisomer, solvate, hydrate, polymorph, isotopically enriched derivative, or prodrug thereof;
wherein:
  $R^c$ is substituted or unsubstituted alkyl, substituted or unsubstituted aryl, substituted or unsubstituted heteroaryl, substituted or unsubstituted aralkyl, or substituted or unsubstituted heteroaralkyl, wherein any carbon of $R^c$, valence permitting, is optionally replaced with —$NR^A$—, —C(O)—, or —C(=$NR^A$)—; and
  each occurrence of $R^A$ is, independently, hydrogen or substituted or unsubstituted alkyl.

In certain embodiments of Formula I-h, $R^2$ is substituted or unsubstituted aryl, substituted or unsubstituted heteroaryl, substituted or unsubstituted alkyl, —$OR^A$, or —$N(R^A)_2$.

In certain embodiments of Formula I-h, $R^2$ is substituted or unsubstituted aryl, or substituted or unsubstituted heteroaryl.

In certain embodiments of Formula I-h, $R^2$ is substituted or unsubstituted heteroaryl.

In certain embodiments of Formula I-h, $R^2$ is substituted or unsubstituted fused bicyclic heteroaryl.

In certain embodiments, the compound of Formula I-h is a compound of Formula I-h-1:

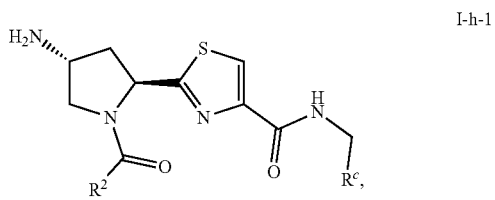

I-h-1 or a pharmaceutically acceptable salt, co-crystal, tautomer, stereoisomer, solvate, hydrate, polymorph, isotopically enriched derivative, or prodrug thereof In certain embodiments, the compound of Formula I is a compound of Formula I-i:

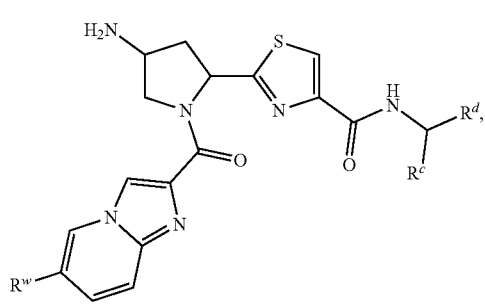

I-i or a pharmaceutically acceptable salt, co-crystal, tautomer, stereoisomer, solvate, hydrate, polymorph, isotopically enriched derivative, or prodrug thereof;
wherein:
  $R^w$ is hydrogen, halogen, alkoxy, alkoxyalkyl, haloalkoxy, or haloalkyl;
  $R^c$ is hydrogen, substituted or unsubstituted alkyl, substituted or unsubstituted aryl, substituted or unsubstituted heteroaryl, substituted or unsubstituted aralkyl, or substituted or unsubstituted heteroaralkyl, wherein any carbon of $R^c$, valence permitting, is optionally replaced with —$NR^A$—, —C(O)—, or —C(=$NR^A$)—;
  $R^d$ is hydrogen, —C(O)N($R^A$)$_2$, or —C(O)O$R^A$; and
  each occurrence of $R^A$ is, independently, hydrogen or substituted or unsubstituted alkyl.

In certain embodiments of Formula I-i, $R^w$ is halogen, alkoxy, haloalkoxy, or haloalkyl. In certain embodiments of Formula I-i, $R^w$ is halogen, haloalkoxy, or haloalkyl. In certain embodiments of Formula I-i, $R^w$ is halogen or haloalkyl. In certain embodiments of Formula I-i, $R^w$ is halogen. In certain embodiments of Formula I-i, $R^w$ is fluoro, chloro, bromo, or iodo. In certain embodiments of Formula I-i, $R^w$ is chloro, bromo, or iodo. In certain embodiments of Formula I-i, $R^w$ is chloro. In certain embodiments of Formula I-i, $R^w$ is bromo.

In certain embodiments of Formula I-i, $R^w$ is iodo.

In certain embodiments of Formula I-i, $R^3$ is substituted or unsubstituted alkyl, substituted or unsubstituted heteroalkyl, substituted or unsubstituted acyl, substituted or unsubstituted aralkyl, or substituted or unsubstituted heteroaralkyl, wherein any carbon of $R^3$, valence permitting, is optionally replaced with —O—, —NR$^A$—, —C(O)—, —C(=NR$^A$)—, —S—, —S(O)—, or —S(O)$_2$—.

In certain embodiments of Formula I-i, $R^3$ is substituted or unsubstituted alkyl, substituted or unsubstituted heteroalkyl, substituted or unsubstituted aralkyl, or substituted or unsubstituted heteroaralkyl, wherein any carbon of $R^3$, valence permitting, is optionally replaced with —O—, —NR$^A$—, —C(O)—, or —C(=NR$^A$)—.

In certain embodiments of Formula I-i, $R^3$ is substituted or unsubstituted aralkyl, or substituted or unsubstituted heteroaralkyl, wherein any carbon of $R^3$, valence permitting, is optionally replaced with —O—, —NR$^A$—, —C(O)—, or —C(=NR$^A$)—.

In certain embodiments of Formula I-i, $R^3$ is substituted or unsubstituted alkyl, or substituted or unsubstituted heteroalkyl, wherein any carbon of $R^3$, valence permitting, is optionally replaced with —O—, —NR$^A$—, —C(O)—, or —C(=NR$^A$)—.

In certain embodiments, the compound of Formula I-i is a compound of Formula I-i-1:

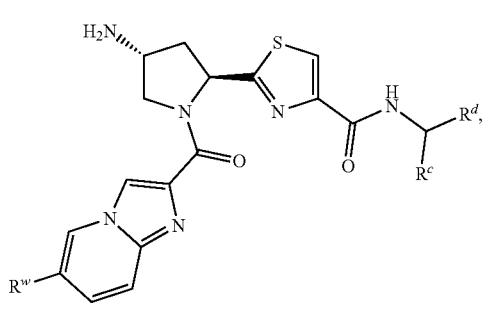

I-i-1 or a pharmaceutically acceptable salt, co-crystal, tautomer, stereoisomer, solvate, hydrate, polymorph, isotopically enriched derivative, or prodrug thereof.

In certain embodiments, the compound of Formula I is a compound of Formula I-j:

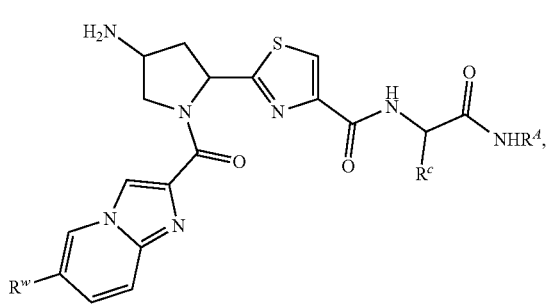

I-j or a pharmaceutically acceptable salt, co-crystal, tautomer, stereoisomer, solvate, hydrate, polymorph, isotopically enriched derivative, or prodrug thereof;

wherein:
- $R^w$ is hydrogen, halogen, alkoxy, alkoxyalkyl, haloalkoxy, or haloalkyl;
- $R^c$ is substituted or unsubstituted alkyl, substituted or unsubstituted aryl, substituted or unsubstituted heteroaryl, substituted or unsubstituted aralkyl, or substituted or unsubstituted heteroaralkyl, wherein any carbon of $R^c$, valence permitting, is optionally replaced with —NR$^A$—, —C(O)—, or —C(=NR$^A$)—; and
- each occurrence of $R^A$ is, independently, hydrogen or substituted or unsubstituted alkyl.

In certain embodiments of Formula I-j, $R^w$ is halogen, alkoxy, haloalkoxy, or haloalkyl. In certain embodiments of Formula I-j, $R^w$ is halogen, haloalkoxy, or haloalkyl. In certain embodiments of Formula I-j, $R^w$ is halogen or haloalkyl. In certain embodiments of Formula I-j, $R^w$ is halogen. In certain embodiments of Formula I-j, $R^w$ is fluoro, chloro, bromo, or iodo. In certain embodiments of Formula I-j, $R^w$ is chloro, bromo, or iodo. In certain embodiments of Formula I-j, $R^w$ is chloro. In certain embodiments of Formula I-j, $R^w$ is bromo. In certain embodiments of Formula I-j, $R^w$ is iodo.

In certain embodiments of Formula I-j, $R^A$ is hydrogen. In certain embodiments of Formula I-j, $R^A$ is unsubstituted alkyl.

In certain embodiments, the compound of Formula I-j is a compound of Formula I-j-1:

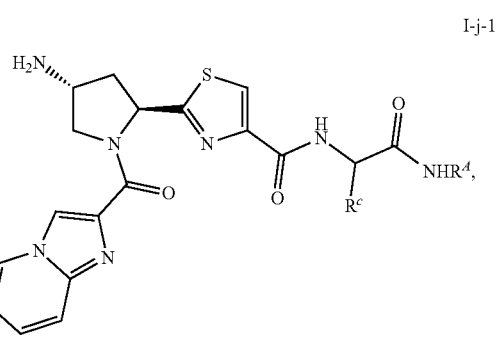

I-j-1 or a pharmaceutically acceptable salt, co-crystal, tautomer, stereoisomer, solvate, hydrate, polymorph, isotopically enriched derivative, or prodrug thereof.

In certain embodiments, the compound of Formula I-j is a compound of Formula I-j-2:

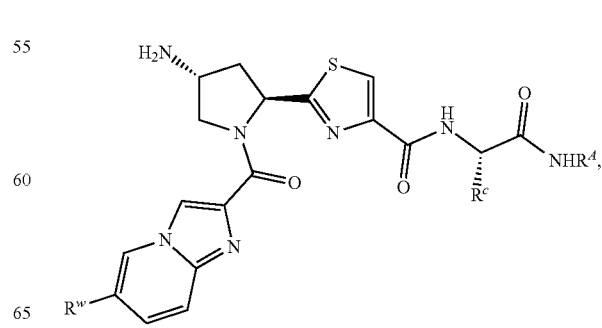

I-j-2, or a pharmaceutically acceptable salt, co-crystal, tautomer, stereoisomer, solvate, hydrate, polymorph, isotopically enriched derivative, or prodrug thereof.

In certain embodiments, the compound of Formula I is a compound of Formula I-k:

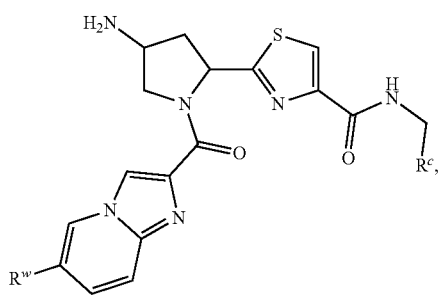

I-k or a pharmaceutically acceptable salt, co-crystal, tautomer, stereoisomer, solvate, hydrate, polymorph, isotopically enriched derivative, or prodrug thereof;
wherein:
- $R^w$ is hydrogen, halogen, alkoxy, alkoxyalkyl, haloalkoxy, or haloalkyl;
- $R^c$ is substituted or unsubstituted alkyl, substituted or unsubstituted aryl, substituted or unsubstituted heteroaryl, substituted or unsubstituted aralkyl, or substituted or unsubstituted heteroaralkyl, wherein any carbon of $R^c$, valence permitting, is optionally replaced with $-NR^A-$, $-C(O)-$, or $-C(=NR^A)-$; and
- each occurrence of $R^A$ is, independently, hydrogen or substituted or unsubstituted alkyl.

In certain embodiments of Formula I-k, $R^w$ is halogen, alkoxy, haloalkoxy, or haloalkyl. In certain embodiments of Formula I-k, $R^w$ is halogen, haloalkoxy, or haloalkyl. In certain embodiments of Formula I-k, $R^w$ is halogen or haloalkyl. In certain embodiments of Formula I-k, $R^w$ is halogen. In certain embodiments of Formula I-k, $R^w$ is fluoro, chloro, bromo, or iodo. In certain embodiments of Formula I-k, $R^w$ is chloro, bromo, or iodo. In certain embodiments of Formula I-k, $R^w$ is chloro. In certain embodiments of Formula I-k, $R^w$ is bromo. In certain embodiments of Formula I-k, $R^w$ is iodo.

In certain embodiments of Formula I-k, $R^A$ is hydrogen. In certain embodiments of Formula I-k, $R^A$ is unsubstituted alkyl.

In certain embodiments, the compound of Formula I-k is a compound of Formula I-k-1:

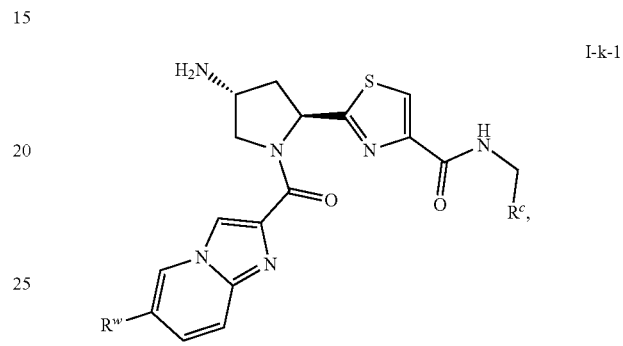

I-k-1 or a pharmaceutically acceptable salt, co-crystal, tautomer, stereoisomer, solvate, hydrate, polymorph, isotopically enriched derivative, or prodrug thereof.

In certain embodiments, the compound of Formula I is one of the following compounds of Table 1, or a pharmaceutically acceptable salt, co-crystal, tautomer, stereoisomer, solvate, hydrate, polymorph, isotopically enriched derivative, or prodrug thereof:

TABLE 1

Exemplary pKal Inhibitory Compounds

| 1 | | 2-((2R,4R)-4-amino-1-(6-chloroimidazo[1,2-a]pyridine-2-carbonyl)pyrrolidin-2-yl)-N-((S)-6-guanidino-1-(methylamino)-1-oxohexan-2-yl)thiazole-4-carboxamide |
|---|---|---|

TABLE 1-continued

Exemplary pKal Inhibitory Compounds

| | | |
|---|---|---|
| 2 | | 2-((2R,4R)-4-amino-1-(6-chloroimidazo[1,2-a]pyridine-2-carbonyl)pyrrolidin-2-yl)-N-((R)-6-guanidino-1-(methylamino)-1-oxohexan-2-yl)thiazole-4-carboxamide |
| 5 | | 2-((2R,4R)-4-acetamido-1-(6-chloroimidazo[1,2-a]pyridine-2-carbonyl)pyrrolidin-2-yl)-N-((S)-6-guanidino-1-(methylamino)-1-oxohexan-2-yl)thiazole-4-carboxamide |
| 6 | | 2-((2R,4S)-4-amino-1-(6-chloroimidazo[1,2-a]pyridine-2-carbonyl)pyrrolidin-2-yl)-N-((S)-6-guanidino-1-(methylamino)-1-oxohexan-2-yl)thiazole-4-carboxamide |
| 11 | | 2-((2S,4R)-4-amino-1-(6-chloroimidazo[1,2-a]pyridine-2-carbonyl)pyrrolidin-2-yl)-N-((S)-6-guanidino-1-(methylamino)-1-oxohexan-2-yl)thiazole-4-carboxamide |

TABLE 1-continued

Exemplary pKal Inhibitory Compounds

| 12 | 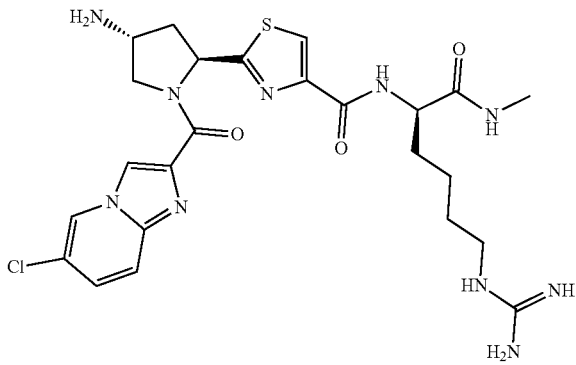 [SMILES: CNC(=O)[C@@H](CCCCNC(=N)N)NC(=O)c1csc([C@@H]2C[C@@H](N)CN2C(=O)c2cn3cc(Cl)ccc3n2)n1] | 2-((2S,4R)-4-amino-1-(6-chloroimidazo[1,2-a]pyridine-2-carbonyl)pyrrolidin-2-yl)-N-((R)-6-guanidino-1-(methylamino)-1-oxohexan-2-yl)thiazole-4-carboxamide |
| --- | --- | --- |
| 13 | 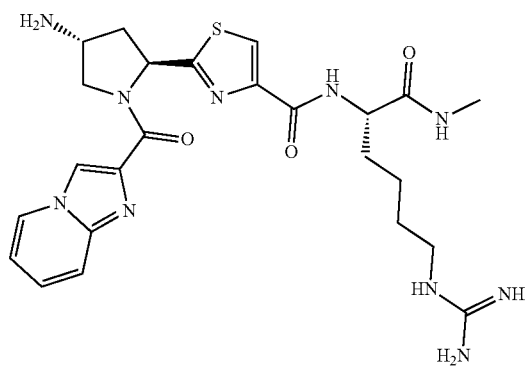 [SMILES: CNC(=O)[C@H](CCCCNC(=N)N)NC(=O)c1csc([C@@H]2C[C@@H](N)CN2C(=O)c2cn3ccccc3n2)n1] | 2-((2S,4R)-4-amino-1-(imidazo[1,2-a]pyridine-2-carbonyl)pyrrolidin-2-yl)-N-((S)-6-guanidino-1-(methylamino)-1-oxohexan-2-yl)thiazole-4-carboxamide |
| 14 | 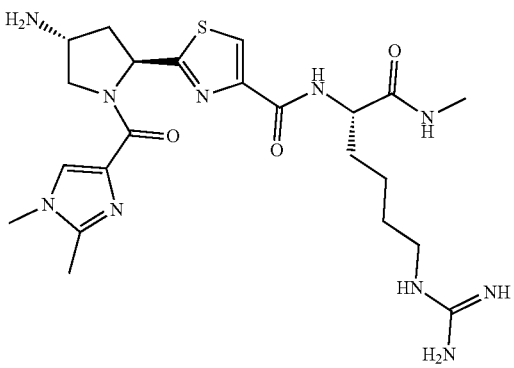 [SMILES: CNC(=O)[C@H](CCCCNC(=N)N)NC(=O)c1csc([C@@H]2C[C@@H](N)CN2C(=O)c2cn(C)c(C)n2)n1] | 2-((2S,4R)-4-amino-1-(1,2-dimethyl-1H-imidazole-4-carbonyl)pyrrolidin-2-yl)-N-((S)-6-guanidino-1-(methylamino)-1-oxohexan-2-yl)thiazole-4-carboxamide |
| 15 | 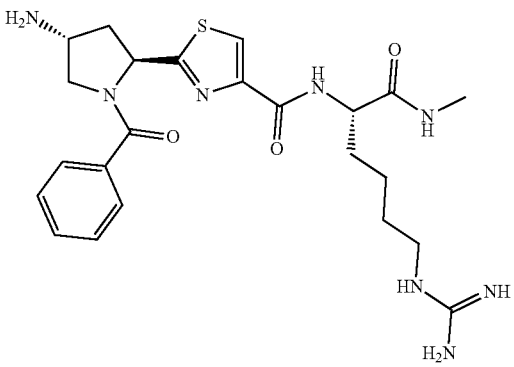 [SMILES: CNC(=O)[C@H](CCCCNC(=N)N)NC(=O)c1csc([C@@H]2C[C@@H](N)CN2C(=O)c2ccccc2)n1] | 2-((2S,4R)-4-amino-1-benzoylpyrrolidin-2-yl)-N-((S)-6-guanidino-1-(methylamino)-1-oxohexan-2-yl)thiazole-4-carboxamide |

TABLE 1-continued

Exemplary pKal Inhibitory Compounds

| 16 | 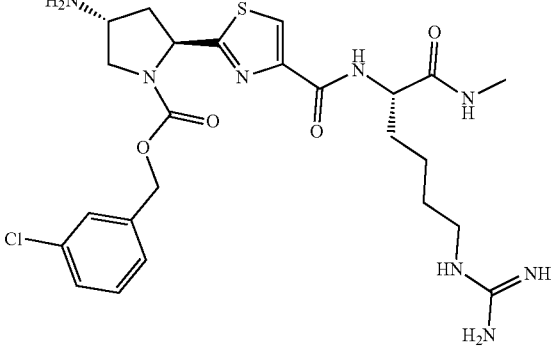 | 3-chlorobenzyl (2S,4R)-4-amino-2-(4-(((S)-6-guanidino-1-(methylamino)-1-oxohexan-2-yl)carbamoyl)thiazol-2-yl)pyrrolidine-1-carboxylate |
| --- | --- | --- |
| 17 | 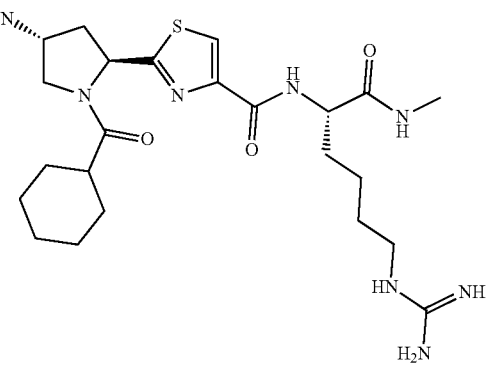 | 2-((2S,4R)-4-amino-1-(cyclohexanecarbonyl)pyrrolidin-2-yl)-N-((S)-6-guanidino-1-(methylamino)-1-oxohexan-2-yl)thiazole-4-carboxamide |
| 18 | 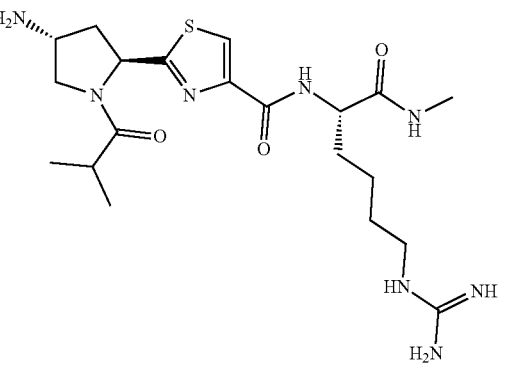 | 2-((2S,4R)-4-amino-1-isobutyrylpyrrolidin-2-yl)-N-((S)-6-guanidino-1-(methylamino)-1-oxohexan-2-yl)thiazole-4-carboxamide |
| 19 | 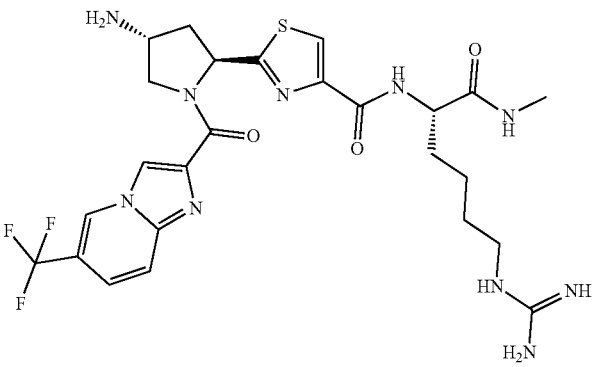 [SMILES: CNC(=O)[C@H](CCCCNC(=N)N)NC(=O)c1csc([C@@H]2C[C@@H](N)CN2C(=O)c2cn3cc(C(F)(F)F)ccc3n2)n1] | 2-((2S,4R)-4-amino-1-(6-(trifluoromethyl)imidazo[1,2-a]pyridine-2-carbonyl)pyrrolidin-2-yl)-N-((S)-6-guanidino-1-(methylamino)-1-oxohexan-2-yl)thiazole-4-carboxamide |

TABLE 1-continued

Exemplary pKal Inhibitory Compounds

| 20 | 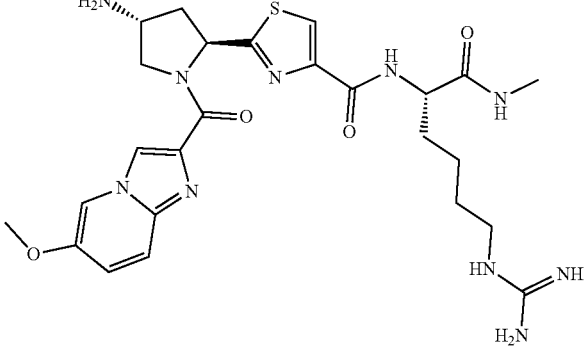 | 2-((2S,4R)-4-amino-1-(6-methoxyimidazo[1,2-a]pyridine-2-carbonyl)pyrrolidin-2-yl)-N-((S)-6-guanidino-1-(methylamino)-1-oxohexan-2-yl)thiazole-4-carboxamide |
| --- | --- | --- |
| 21 | 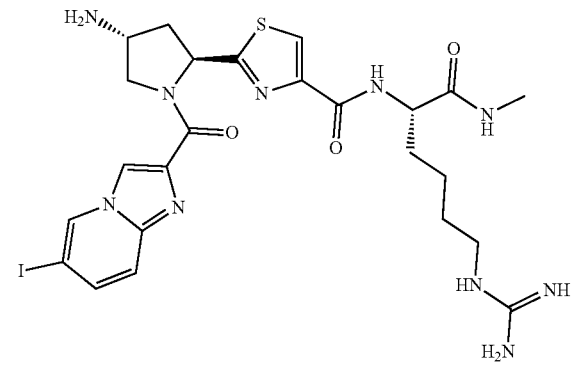 [SMILES: CNC(=O)[C@H](CCCCNC(=N)N)NC(=O)c1csc([C@@H]2C[C@@H](N)CN2C(=O)c2cn3cc(I)ccc3n2)n1] | 2-((2S,4R)-4-amino-1-(6-iodoimidazo[1,2-a]pyridine-2-carbonyl)pyrrolidin-2-yl)-N-((S)-6-guanidino-1-(methylamino)-1-oxohexan-2-yl)thiazole-4-carboxamide |
| 22 | 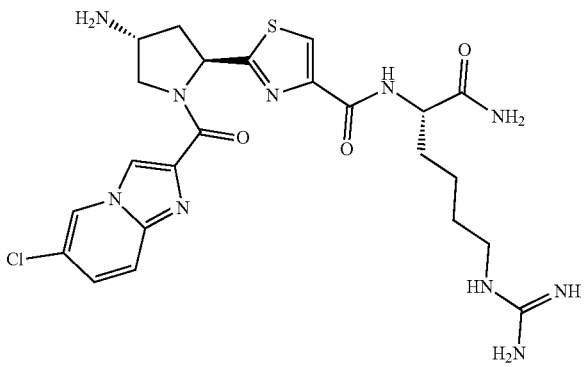 [SMILES: N=C(N)NCCCC[C@H](NC(=O)c1csc([C@@H]2C[C@@H](N)CN2C(=O)c2cn3cc(Cl)ccc3n2)n1)C(N)=O] | 2-((2S,4R)-4-amino-1-(6-chloroimidazo[1,2-a]pyridine-2-carbonyl)pyrrolidin-2-yl)-N-((S)-1-amino-6-guanidino-1-oxohexan-2-yl)thiazole-4-carboxamide |
| 23 | 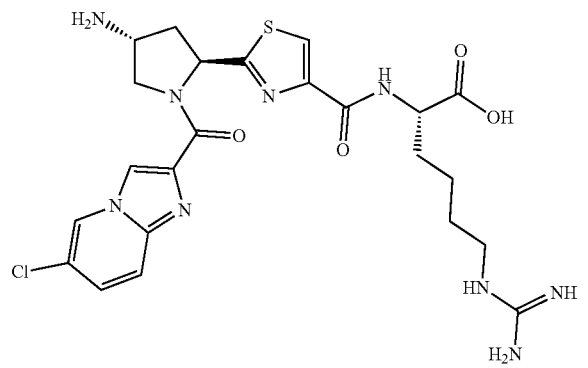 [SMILES: N=C(N)NCCCC[C@H](NC(=O)c1csc([C@@H]2C[C@@H](N)CN2C(=O)c2cn3cc(Cl)ccc3n2)n1)C(=O)O] | $N^2$-(2-((2S,4R)-4-amino-1-(6-chloroimidazo[1,2-a]pyridine-2-carbonyl)pyrrolidin-2-yl)thiazole-4-carbonyl)-N6-carbamimidoyl-L-lysine |

TABLE 1-continued

Exemplary pKal Inhibitory Compounds

| | | |
|---|---|---|
| 24 | 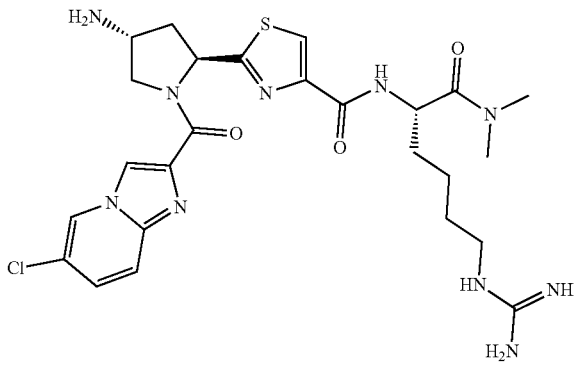 [SMILES: CN(C)C(=O)[C@H](CCCCNC(=N)N)NC(=O)c1csc([C@@H]2C[C@@H](N)CN2C(=O)c2cn3cc(Cl)ccc3n2)n1] | 2-((2S,4R)-4-amino-1-(6-chloroimidazo[1,2-a]pyridine-2-carbonyl)pyrrolidin-2-yl)-N-((S)-1-(dimethylamino)-6-guanidino-1-oxohexan-2-yl)thiazole-4-carboxamide |
| 25 | 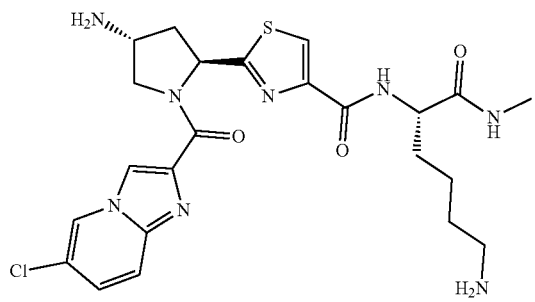 [SMILES: CNC(=O)[C@H](CCCCN)NC(=O)c1csc([C@@H]2C[C@@H](N)CN2C(=O)c2cn3cc(Cl)ccc3n2)n1] | 2-((2S,4R)-4-amino-1-(6-chloroimidazo[1,2-a]pyridine-2-carbonyl)pyrrolidin-2-yl)-N-((S)-6-amino-1-(methylamino)-1-oxohexan-2-yl)thiazole-4-carboxamide |
| 26 | 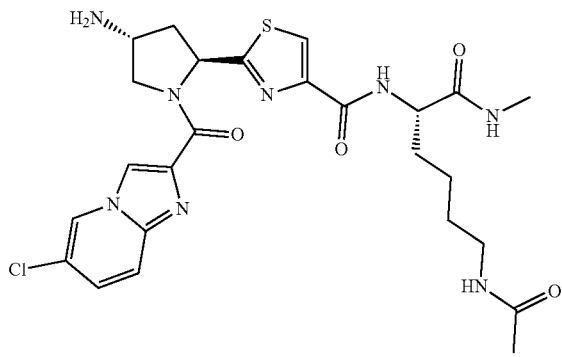 [SMILES: CNC(=O)[C@H](CCCCNC(C)=O)NC(=O)c1csc([C@@H]2C[C@@H](N)CN2C(=O)c2cn3cc(Cl)ccc3n2)n1] | N-((S)-6-acetamido-1-(methylamino)-1-oxohexan-2-yl)-2-((2S,4R)-4-amino-1-(6-chloroimidazo[1,2-a]pyridine-2-carbonyl)pyrrolidin-2-yl)thiazole-4-carboxamide |
| 27 | 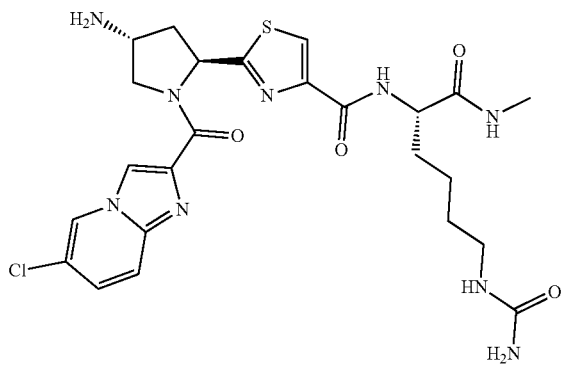 [SMILES: CNC(=O)[C@H](CCCCNC(N)=O)NC(=O)c1csc([C@@H]2C[C@@H](N)CN2C(=O)c2cn3cc(Cl)ccc3n2)n1] | 2-((2S,4R)-4-amino-1-(6-chloroimidazo[1,2-a]pyridine-2-carbonyl)pyrrolidin-2-yl)-N-((S)-1-(methylamino)-1-oxo-6-ureidohexan-2-yl)thiazole-4-carboxamide |

TABLE 1-continued

Exemplary pKal Inhibitory Compounds

| 28 | | 2-((2S,4R)-4-amino-1-(6-chloroimidazo[1,2-a]pyridine-2-carbonyl)pyrrolidin-2-yl)-N-((S)-5-guanidino-1-(methylamino)-1-oxopentan-2-yl)thiazole-4-carboxamide |
|---|---|---|
| 29 | | (S)-2-(2-((2S,4R)-4-amino-1-(6-chloroimidazo[1,2-a]pyridine-2-carbonyl)pyrrolidin-2-yl)thiazole-4-carboxamido)-N1-methylpentanediamide |
| 30 | | N-((S)-3-(1H-imidazol-4-yl)-1-(methylamino)-1-oxopropan-2-yl)-2-((2S,4R)-4-amino-1-(6-chloroimidazo[1,2-a]pyridine-2-carbonyl)pyrrolidin-2-yl)thiazole-4-carboxamide |
| 31 | | N-((S)-3-(1H-indol-3-yl)-1-(methylamino)-1-oxopropan-2-yl)-2-((2S,4R)-4-amino-1-(6-chloroimidazo[1,2-a]pyridine-2-carbonyl)pyrrolidin-2-yl)thiazole-4-carboxamide |
| 32 | | 2-((2S,4R)-4-amino-1-(6-chloroimidazo[1,2-a]pyridine-2-carbonyl)pyrrolidin-2-yl)-N-((S)-3-(4-hydroxyphenyl)-1-(methylamino)-1-oxopropan-2-yl)thiazole-4-carboxamide |

TABLE 1-continued

Exemplary pKal Inhibitory Compounds

| | | |
|---|---|---|
| 35 | | 2-((2S,4R)-4-acetamido-1-(6-chloroimidazo[1,2-a]pyridine-2-carbonyl)pyrrolidin-2-yl)-N-((S)-6-guanidino-1-(methylamino)-1-oxohexan-2-yl)thiazole-4-carboxamide |
| 36 | | 2-((2S,4S)-4-amino-1-(6-chloroimidazo[1,2-a]pyridine-2-carbonyl)pyrrolidin-2-yl)-N-((S)-6-guanidino-1-(methylamino)-1-oxohexan-2-yl)thiazole-4-carboxamide |
| 40 | | 2-((2S,4R)-1-(2-naphthoyl)-4-aminopyrrolidin-2-yl)-N-((S)-6-guanidino-1-(methylamino)-1-oxohexan-2-yl)thiazole-4-carboxamide |
| 41 | | 2-((2S,4R)-4-amino-1-(3-chloroquinoline-6-carbonyl)pyrrolidin-2-yl)-N-((S)-6-guanidino-1-(methylamino)-1-oxohexan-2-yl)thiazole-4-carboxamide |

TABLE 1-continued

Exemplary pKal Inhibitory Compounds

| 42 | 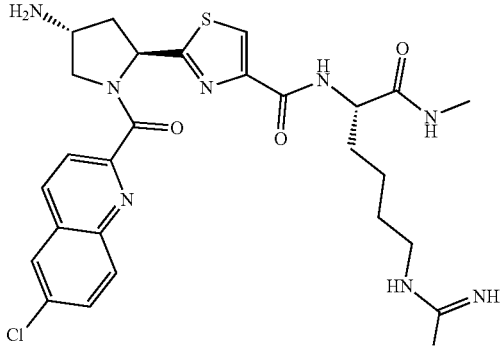 | 2-((2S,4R)-4-amino-1-(6-chloroquinoline-2-carbonyl)pyrrolidin-2-yl)-N-((S)-6-guanidino-1-(methylamino)-1-oxohexan-2-yl)thiazole-4-carboxamide |
| --- | --- | --- |
| 43 | 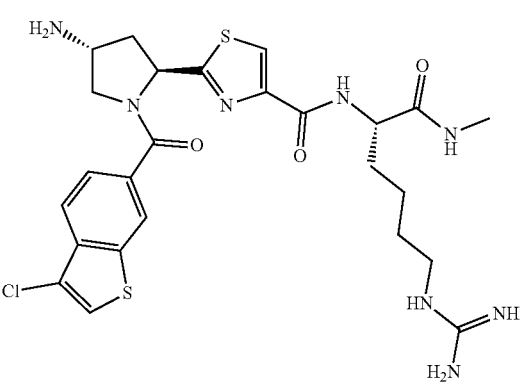 [SMILES: CNC(=O)[C@H](CCCCNC(=N)N)NC(=O)c1csc([C@@H]2C[C@@H](N)CN2C(=O)c2ccc3c(Cl)csc3c2)n1] | 2-((2S,4R)-4-amino-1-(3-chlorobenzo[b]thiophene-6-carbonyl)pyrrolidin-2-yl)-N-((S)-6-guanidino-1-(methylamino)-1-oxohexan-2-yl)thiazole-4-carboxamide |
| 44 | 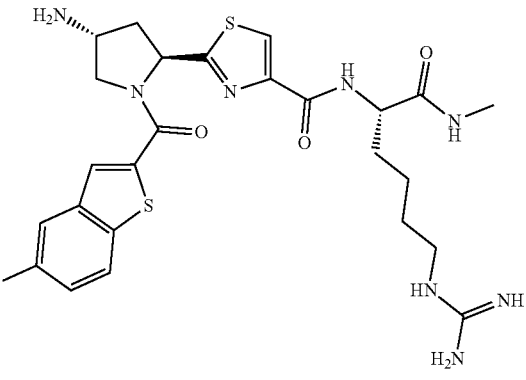 | 2-((2S,4R)-4-amino-1-(5-chlorobenzo[b]thiophene-2-carbonyl)pyrrolidin-2-yl)-N-((S)-6-guanidino-1-(methylamino)-1-oxohexan-2-yl)thiazole-4-carboxamide |
| 45 | 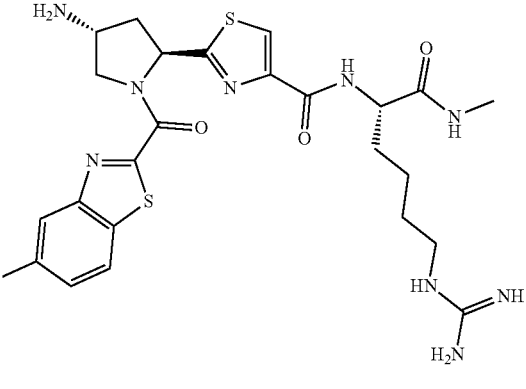 | 2-((2S,4R)-4-amino-1-(5-chlorobenzo[d]thiazole-2-carbonyl)pyrrolidin-2-yl)-N-((S)-6-guanidino-1-(methylamino)-1-oxohexan-2-yl)thiazole-4-carboxamide |

TABLE 1-continued

Exemplary pKal Inhibitory Compounds

| | | |
|---|---|---|
| 46 | 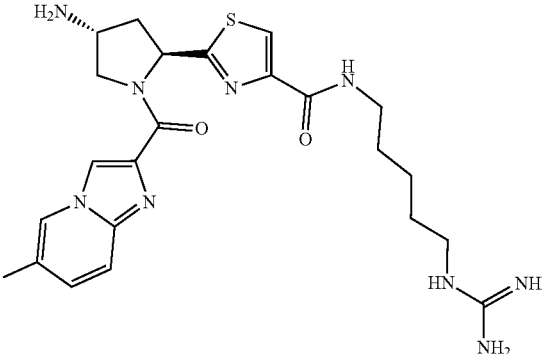 | 2-((2S,4R)-4-amino-1-(6-chloroimidazo[1,2-a]pyridine-2-carbonyl)pyrrolidin-2-yl)-N-(5-guanidinopentyl)thiazole-4-carboxamide |
| 47 | 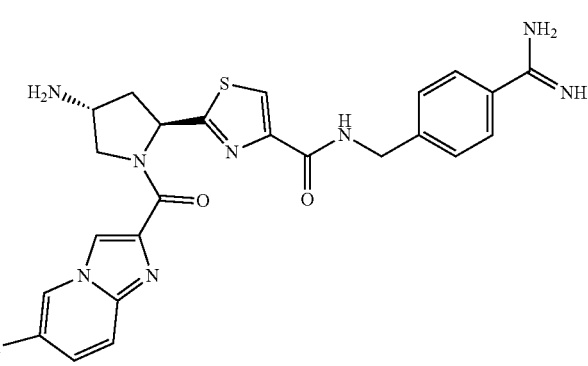 | 2-((2S,4R)-4-amino-1-(6-chloroimidazo[1,2-a]pyridine-2-carbonyl)pyrrolidin-2-yl)-N-(4-carbamimidoylbenzyl)thiazole-4-carboxamide |
| 48 | 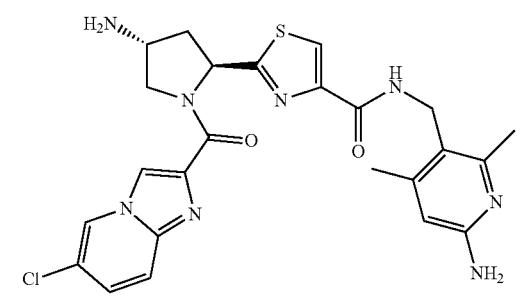 [SMILES: Cc1cc(N)nc(C)c1CNC(=O)c1csc([C@@H]2C[C@@H](N)CN2C(=O)c2cn3cc(Cl)ccc3n2)n1] | 2-((2S,4R)-4-amino-1-(6-chloroimidazo[1,2-a]pyridine-2-carbonyl)pyrrolidin-2-yl)-N-((6-amino-2,4-dimethylpyridin-3-yl)methyl)thiazole-4-carboxamide |
| 49 | 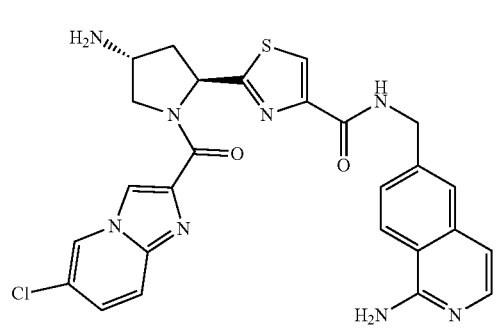 [SMILES: Nc1nccc2cc(CNC(=O)c3csc([C@@H]4C[C@@H](N)CN4C(=O)c4cn5cc(Cl)ccc5n4)n3)ccc12] | 2-((2S,4R)-4-amino-1-(6-chloroimidazo[1,2-a]pyridine-2-carbonyl)pyrrolidin-2-yl)-N-((1-aminoisoquinolin-6-yl)methyl)thiazole-4-carboxamide |

TABLE 1-continued

Exemplary pKal Inhibitory Compounds

| 50 | 2-((2S,4R)-4-amino-1-(6-chloroimidazo[1,2-a]pyridine-2-carbonyl)pyrrolidin-2-yl)-N-(4-(aminomethyl)benzyl)thiazole-4-carboxamide |
| 51 | 2-((2S,4R)-4-amino-1-(6-chloroimidazo[1,2-a]pyridine-2-carbonyl)pyrrolidin-2-yl)-N-(4-carbamimidoylphenethyl)thiazole-4-carboxamide |
| 52 | 2-((2S,4R)-4-amino-1-(6-chloroimidazo[1,2-a]pyridine-2-carbonyl)pyrrolidin-2-yl)-N-(2-(6-amino-2,4-dimethylpyridin-3-yl)ethyl)thiazole-4-carboxamide |
| 53 | 2-((2S,4R)-4-amino-1-(6-chloroimidazo[1,2-a]pyridine-2-carbonyl)pyrrolidin-2-yl)-N-(2-(1-aminoisoquinolin-6-yl)ethyl)thiazole-4-carboxamide |
| 54 | 2-((2S,4R)-4-amino-1-(6-chloroimidazo[1,2-a]pyridine-2-carbonyl)pyrrolidin-2-yl)-N-(4-(aminomethyl)phenethyl)thiazole-4-carboxamide |

TABLE 1-continued

Exemplary pKal Inhibitory Compounds

| 55 | 2-((2S,4R)-4-amino-1-(6-chloroimidazo[1,2-a]pyridine-2-carbonyl)pyrrolidin-2-yl)-N-((7-chloroimidazo[1,5-a]pyridin-1-yl)methyl)thiazole-4-carboxamide |
| 56 | 2-((2S,4R)-4-amino-1-(6-chloroimidazo[1,2-a]pyridine-2-carbonyl)pyrrolidin-2-yl)-N-((6-chloronaphthalen-2-yl)methyl)thiazole-4-carboxamide |
| 57 | 2-((2S,4R)-4-amino-1-(5-chlorobenzo[b]thiophene-2-carbonyl)pyrrolidin-2-yl)-N-((R)-6-guanidino-1-(methylamino)-1-oxohexan-2-yl)thiazole-4-carboxamide |
| 58 | 2-((2S,4R)-4-amino-1-(6-chloroimidazo[1,2-a]pyridine-2-carbonyl)pyrrolidin-2-yl)-N-((5-chloro-1H-indazol-3-yl)methyl)thiazole-4-carboxamide |
| 59 | 2-((2S,4R)-4-amino-1-(6-chloroimidazo[1,2-a]pyridine-2-carbonyl)pyrrolidin-2-yl)-N-((6-chloro-1H-indazol-3-yl)methyl)thiazole-4-carboxamide |

TABLE 1-continued

Exemplary pKal Inhibitory Compounds

60 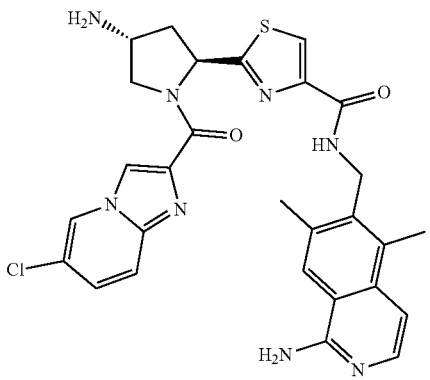 [SMILES: Cc1cc2c(N)nccc2c(C)c1CNC(=O)c1csc([C@@H]2C[C@@H](N)CN2C(=O)c2cn3cc(Cl)ccc3n2)n1] 2-((2S,4R)-4-amino-1-(6-chloroimidazo[1,2-a]pyridine-2-carbonyl)pyrrolidin-2-yl)-N-((1-amino-5,7-dimethylisoquinolin-6-yl)methyl)thiazole-4-carboxamide 61 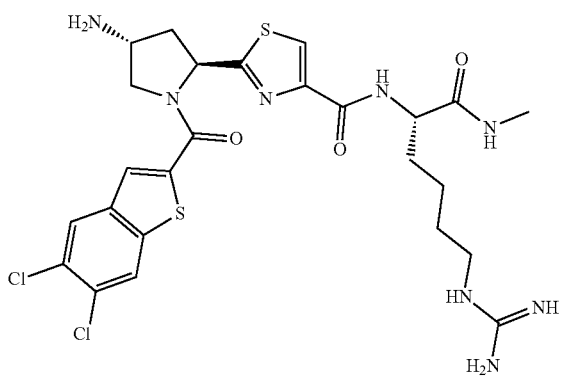 [SMILES: CNC(=O)[C@H](CCCCNC(=N)N)NC(=O)c1csc([C@@H]2C[C@@H](N)CN2C(=O)c2cc3cc(Cl)c(Cl)cc3s2)n1] 2-((2S,4R)-4-amino-1-(5,6-dichlorobenzo[b]thiophene-2-carbonyl)pyrrolidin-2-yl)-N-((S)-6-guanidino-1-(methylamino)-1-oxohexan-2-yl)thiazole-4-carboxamide 62 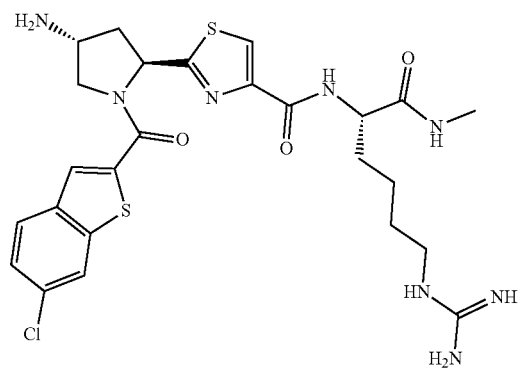 [SMILES: CNC(=O)[C@H](CCCCNC(=N)N)NC(=O)c1csc([C@@H]2C[C@@H](N)CN2C(=O)c2cc3ccc(Cl)cc3s2)n1] 2-((2S,4R)-4-amino-1-(6-chlorobenzo[b]thiophene-2-carbonyl)pyrrolidin-2-yl)-N-((S)-6-guanidino-1-(methylamino)-1-oxohexan-2-yl)thiazole-4-carboxamide 63 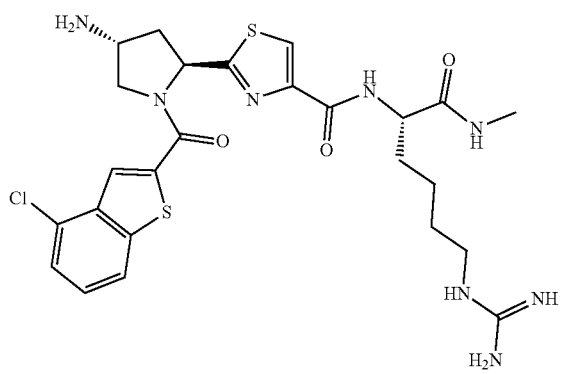 [SMILES: CNC(=O)[C@H](CCCCNC(=N)N)NC(=O)c1csc([C@@H]2C[C@@H](N)CN2C(=O)c2cc3c(Cl)cccc3s2)n1] 2-((2S,4R)-4-amino-1-(4-chlorobenzo[b]thiophene-2-carbonyl)pyrrolidin-2-yl)-N-((S)-6-guanidino-1-(methylamino)-1-oxohexan-2-yl)thiazole-4-carboxamide TABLE 1-continued Exemplary pKal Inhibitory Compounds

| | | |
|---|---|---|
| 64 | 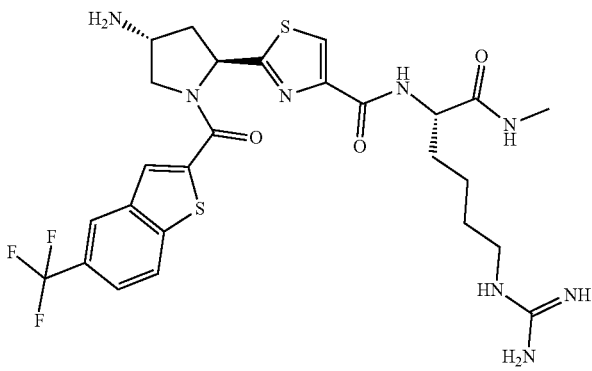 [SMILES: CNC(=O)[C@H](CCCCNC(=N)N)NC(=O)c1csc([C@@H]2C[C@@H](N)CN2C(=O)c2cc3cc(C(F)(F)F)ccc3s2)n1] | 2-((2S,4R)-4-amino-1-(5-(trifluoromethyl)benzo[b]thiophene-2-carbonyl)pyrrolidin-2-yl)-N-((S)-6-guanidino-1-(methylamino)-1-oxohexan-2-yl)thiazole-4-carboxamide |
| 65 | 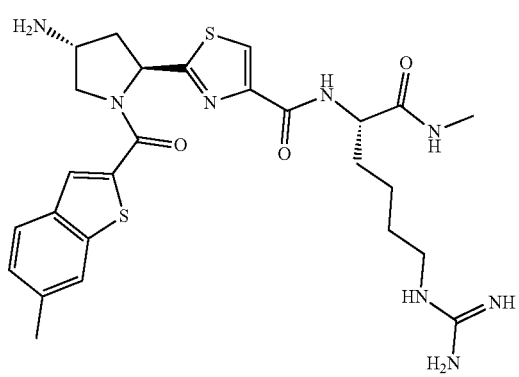 [SMILES: CNC(=O)[C@H](CCCCNC(=N)N)NC(=O)c1csc([C@@H]2C[C@@H](N)CN2C(=O)c2cc3ccc(C)cc3s2)n1] | 2-((2S,4R)-4-amino-1-(6-methylbenzo[b]thiophene-2-carbonyl)pyrrolidin-2-yl)-N-((S)-6-guanidino-1-(methylamino)-1-oxohexan-2-yl)thiazole-4-carboxamide |
| 66 | 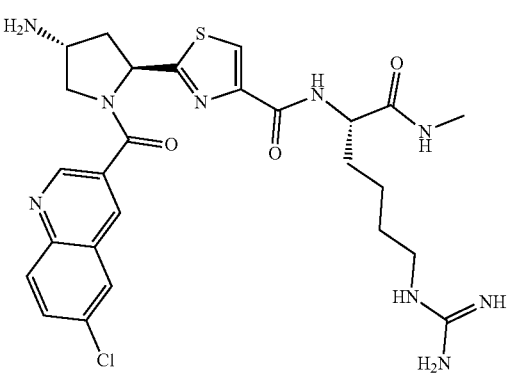 [SMILES: CNC(=O)[C@H](CCCCNC(=N)N)NC(=O)c1csc([C@@H]2C[C@@H](N)CN2C(=O)c2cnc3ccc(Cl)cc3c2)n1] | 2-((2S,4R)-4-amino-1-(6-chloroquinoline-3-carbonyl)pyrrolidin-2-yl)-N-((S)-6-guanidino-1-(methylamino)-1-oxohexan-2-yl)thiazole-4-carboxamide |
| 67 | 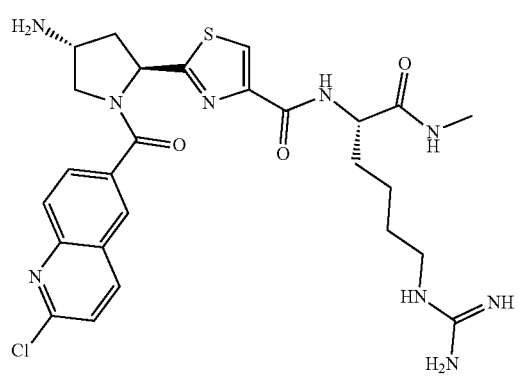 [SMILES: CNC(=O)[C@H](CCCCNC(=N)N)NC(=O)c1csc([C@@H]2C[C@@H](N)CN2C(=O)c2ccc3nc(Cl)ccc3c2)n1] | 2-((2S,4R)-4-amino-1-(2-chloroquinoline-6-carbonyl)pyrrolidin-2-yl)-N-((S)-6-guanidino-1-(methylamino)-1-oxohexan-2-yl)thiazole-4-carboxamide |

In certain embodiments, the compound of Formula I inhibits pKal with an $EC_{50}$ of less than 100,000 nM, less than 50,000 nM, less than 20,000 nM, less than 10,000 nM, less than 5,000 nM, less than 2,500 nM, less than 1,000 nM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 5 nM, less than 4 nM, less than 3 nM, less than 2 nM, or less than 1 nM.

Pharmaceutical Compositions, Kits, and Administration

The present disclosure also provides pharmaceutical compositions comprising a compound of Formula I, or a pharmaceutically acceptable salt, co-crystal, tautomer, stereoisomer, solvate, hydrate, polymorph, isotopically enriched derivative, or prodrug thereof, and optionally a pharmaceutically acceptable excipient. In certain embodiments, the pharmaceutical composition described herein comprises a compound of Formula I, or a pharmaceutically acceptable salt thereof, and a pharmaceutically acceptable excipient.

In certain embodiments, the compound of Formula I is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating a pKal-mediated disease in a subject in need thereof. In certain embodiments, the effective amount is an amount effective for preventing or reducing the risk for a pKal-mediated disease in a subject in need thereof. In certain embodiments, the effective amount is an amount effective for alleviating one or more symptoms of edema (e.g., HAE or DME) or for reducing the risk of edema attack in a subject in need of the treatment. In certain embodiments, the effective amount is an amount effective for preventing occurrence of edema, such as HAE or DME. In certain embodiments, the effective amount is an amount effective for inhibiting the activity of pKal in a subject or cell.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In certain embodiments, the effective amount is an amount effective for inhibiting the activity of pKal by at least about 10%, at least about 20%, at least about 30%, at least about 40%, at least about 50%, at least about 60%, at least about 70%, at least about 80%, at least about 90%, at least about 95%, at least about 98%, or at least about 99%. In certain embodiments, the effective amount is an amount effective for inhibiting the activity of pKal by a range between a percentage described in this paragraph and another percentage described in this paragraph, inclusive.

The present disclosure provides pharmaceutical compositions comprising a compound that interacts with pKal for use in treating a pKal-mediated disease or disorder in a subject in need thereof.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, and/or in reducing the risk to develop a disease in a subject in need thereof), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent exhibit a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a pKal-mediated disease such as edema. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

In certain embodiments, the compound or pharmaceutical composition is a solid. In certain embodiments, the compound or pharmaceutical composition is a powder. In certain embodiments, the compound or pharmaceutical composition can be dissolved in a liquid to make a solution. In certain embodiments, the compound or pharmaceutical composition is dissolved in water to make an aqueous solution. In certain embodiments, the pharmaceutical composition is a liquid for parental injection. In certain embodiments, the pharmaceutical composition is a liquid for oral administration (e.g., ingestion). In certain embodiments, the pharmaceutical composition is a liquid (e.g., aqueous solution) for intravenous injection. In certain embodiments, the pharmaceutical composition is a liquid (e.g., aqueous solution) for subcutaneous injection.

After formulation with an appropriate pharmaceutically acceptable excipient in a desired dosage, the pharmaceutical compositions of the present disclosure can be administered to humans and other animals orally, parenterally, intracisternally, intraperitoneally, topically, bucally, or the like, depending on the disease or condition being treated.

In certain embodiments, a pharmaceutical composition comprising a compound of Formula I is administered, orally or parenterally, at dosage levels of each pharmaceutical composition sufficient to deliver from about 0.001 mg/kg to about 200 mg/kg in one or more dose administrations for one or several days (depending on the mode of administration). In certain embodiments, the effective amount per dose varies from about 0.001 mg/kg to about 200 mg/kg, about 0.001 mg/kg to about 100 mg/kg, about 0.01 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, of subject body weight per day, one or more times a day, to obtain the desired therapeutic and/or prophylactic effect. In certain embodiments, the compounds described herein may be at dosage levels sufficient to deliver from about 0.001 mg/kg to about 200 mg/kg, from about 0.001 mg/kg to about 100 mg/kg, from about 0.01 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). In certain embodiments, the composition described herein is administered at a dose that is below the dose at which the agent causes non-specific effects.

In certain embodiments, the pharmaceutical composition is administered at a dose of about 0.001 mg to about 1000 mg per unit dose. In certain embodiments, the pharmaceutical composition is administered at a dose of about 0.01 mg to about 200 mg per unit dose. In certain embodiments, the pharmaceutical composition is administered at a dose of about 0.01 mg to about 100 mg per unit dose. In certain embodiments, pharmaceutical composition is administered at a dose of about 0.01 mg to about 50 mg per unit dose. In certain embodiments, the pharmaceutical composition is administered at a dose of about 0.01 mg to about 10 mg per unit dose. In certain embodiments, the pharmaceutical composition is administered at a dose of about 0.1 mg to about 10 mg per unit dose.

Pharmaceutical compositions described herein can be prepared by any method known in the art of pharmacology. In general, such preparatory methods include the steps of bringing the composition comprising a compound of Formula I into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80)), polyoxyethylene esters (e.g. polyoxyethylene monostearate (Myrj® 45), polyoxyethylene hydrogenated castor oil, polyethoxylated castor oil, polyoxymethylene stearate, and Solutol), sucrose fatty acid esters, polyethylene glycol fatty acid esters (e.g. Cremophor™) polyoxyethylene ethers, (e.g. polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazelnut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include, but are not limited to, pharmaceutically acceptable emulsions, microemulsions, solutions, suspensions, syrups, and elixirs. In addition to the active agents, the liquid dosage forms may contain inert diluents commonly used in the art such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, oral compositions can also include adjuvants such as wetting agents, emulsifying and suspending agents, sweetening, flavoring, and perfuming agents. In certain embodiments for parenteral administration, agents of the invention are mixed with solubilizing agents such CREMOPHOR EL® (polyethoxylated castor oil), alcohols, oils, modified oils, glycols, polysorbates, cyclodextrins, polymers, and combinations thereof.

Injectable preparations, for example, sterile injectable aqueous or oleaginous suspensions, may be formulated according to the known art using suitable dispersing or wetting agents and suspending agents. Sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active agents can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Formulations suitable for topical administration include liquid or semi-liquid preparations such as liniments, lotions, gels, applicants, oil-in-water or water-in-oil emulsions such as creams, ointments, or pastes; or solutions or suspensions such as drops. Formulations for topical administration to the skin surface can be prepared by dispersing the drug with a dermatologically acceptable carrier such as a lotion, cream, ointment, or soap. Useful carriers are capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used. Ophthalmic formulation, ear drops, and eye drops are also contemplated as being within the scope of this invention. Additionally, the present disclosure contemplates the use of transdermal patches, which have the added advantage of providing controlled delivery of an agent to the body. Such dosage forms can be made by dissolving or dispensing the agent in the proper medium. Absorption enhancers can also be used to increase the flux of the agent across the skin. The rate can be controlled by either providing a rate controlling membrane or by dispersing the agent in a polymer matrix or gel.

Additionally, the carrier for a topical formulation can be in the form of a hydroalcoholic system (e.g., liquids and gels), an anhydrous oil or silicone based system, or an emulsion system, including, but not limited to, oil-in-water, water-in-oil, water-in-oil-in-water, and oil-in-water-in-silicone emulsions. The emulsions can cover a broad range of consistencies including thin lotions (which can also be suitable for spray or aerosol delivery), creamy lotions, light creams, heavy creams, and the like. The emulsions can also include microemulsion systems. Other suitable topical carriers include anhydrous solids and semisolids (such as gels and sticks); and aqueous based mousse systems.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a pKal-mediated disease in a subject in need thereof. In certain embodiments, the kits are useful for preventing a pKal-related disease in a subject in need thereof. In certain embodiments, the kits are useful for reducing the risk of developing a pKal-related disease in a subject in need thereof. In certain embodiments, the kits are useful for inhibiting the activity of pKal in a subject or cell.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits and instructions provide for treating a pKal-mediated disease in a subject in need thereof. In certain embodiments, the kits and instructions provide for preventing a pKal-mediated disease in a subject in need thereof. In certain embodiments, the kits and instructions provide for reducing the risk of developing a pKal-mediated disease in a subject in need thereof. In certain embodiments, the kits and instructions provide for inhibiting the activity of pKal in a subject or cell. A kit described herein may include one or more additional pharmaceutical agents described herein as a separate composition.

Methods of Treatment

The present disclosure provides the use of any of the pKal inhibitory compounds described herein for inhibiting the activity of pKal, which would be beneficial to treatment of pKal-mediated diseases and conditions. Exemplary pKal-mediated disorders include edema, which refers to swelling in the whole body of a subject or a part thereof due to inflammation or injury when small blood vessels become leaky and releases fluid into nearby tissues. In some examples, the edema is HAE. In other examples, the edema occurs in eyes, e.g., diabetic macular edema (DME).

In some embodiments, the pKal-mediated disease described herein is an ocular disorder, for example, those associated with vascular leakage caused by abnormal pKal activities. Examples include, but are not limited to, DME, wet age-related macular degeneration (wAMD), and dry age-related macular degeneration (dAMD), and diabetic retinopathy. In other embodiments, the pKal-mediated disease is an ischemia reperfusion injury or systemic inflammatory responses, which may be associated with a surgical procedure.

Any of the pKal inhibitory compounds described herein may also be used for reducing blood loss in a subject, e.g., a human patient subject to a surgical procedure. The pKal inhibitory compound may be co-used with an anti-thrombolytic agent or an anti-fibrinolytic agent. In some instances, the pKal inhibitory compound can be used for preserving an organ in vitro.

The present disclosure provides methods of inhibiting the activity of pKal. In certain embodiments, the application provides a method of inhibiting the activity of pKal in vitro via contacting any of the pKal inhibitory compounds described herein with pKal molecules in a sample, such as a biological sample. In certain embodiments, the application provides a method of inhibiting the activity of pKal in vivo via delivering an effective amount of any of the pKal inhibitory compounds described herein to a subject in need of the treatment through a suitable route.

In certain embodiments, the methods comprise administering to a subject in need thereof (e.g., a subject such as a human patient with edema) any of the pKal inhibitory compounds described herein or a pharmaceutically acceptable salt thereof. In certain embodiments, the methods comprise administering a compound of Formula I, or a pharmaceutically acceptable salt, co-crystal, tautomer, stereoisomer, solvate, hydrate, polymorph, isotopically enriched derivative, or prodrug, or composition thereof, to a subject in need thereof. In some embodiments, the method comprises administering a pharmaceutical composition comprising a compound of Formula I, or a pharmaceutically acceptable salt, co-crystal, tautomer, stereoisomer, solvate, hydrate, polymorph, isotopically enriched derivative, or prodrug, or composition thereof, to a subject in need thereof.

In certain embodiments, the subject to be treated by any of the methods described herein is a human patient having, suspected of having, or at risk for edema, for example, HAE or diabetic macular edema (DME). A subject having an edema can be identified by routine medical examination, e.g., laboratory tests. A subject suspected of having an edema might show one or more symptoms of the disease/disorder. A subject at risk for edema can be a subject having one or more of the risk factors associated with the disease, for example, deficiency in $C_1$—INH as for HAE.

In certain embodiments, provided herein are methods of alleviating one or more symptoms of HAE in a human patient who is suffering from an HAE attack. Such a patient can be identified by routine medical procedures. An effective amount of one or more of the pKal inhibitory compounds can be given to the human patient via a suitable route, for example, those described herein. The pKal inhibitory compounds described herein may be used alone, or may be used in combination with other anti-HAE agents, for example, a $C_1$ esterase inhibitor (e.g., Cinryze® or Berinert®), a pKal inhibitor (e.g., ecallantide or lanadelumab) or a bradykinin B2 receptor antagonist (e.g., Firazyr®).

In other embodiments, provided herein are methods or reducing the risk of HAE attack in a human HAE patient who is in quiescent stage. Such a patient can be identified based on various factors, including history of HAE attack. An effective amount of one or more of the pKal inhibitory compounds can be given to the human patient via a suitable route, for example, those described herein. The pKal inhibitory compounds described herein may be used alone, or may be used in combination with other anti-HAE agents, for example, a $C_1$ esterase inhibitor (e.g., Cinryze® or Berinert®), a pKal inhibitor (e.g., ecallantide or lanadelumab) or a bradykinin B2 receptor antagonist (e.g., Firazyr®).

In yet other embodiments, provided herein are prophylactic treatment of HAE in human patients having risk to HAE attacks with one or more of the pKal inhibitory compounds described herein. Patients suitable for such prophylactic treatment may be human subjects having history of HAE attacks (e.g., human subjects experiencing more than 2 attacks per month). Alternatively, patients suitable for the prophylactic treatment may be human subjects having no HAE attack history but bearing one or more risk factors for HAE (e.g., family history, genetic defects in $C_1$—INH gene, etc.) Such prophylactic treatment may involve the pKal inhibitory compounds described herein as the sole active agent, or involve additional anti-HAE agents, such as those described herein.

In certain embodiments, provided herein are methods for preventing or reducing edema in an eye of a subject (e.g., a human patient). In some examples, the human patient is a diabetic having, suspected of having, or at risk for diabetic macular edema (DME). DME is the proliferative form of diabetic retinopathy characterized by swelling of the retinal layers, neovascularization, vascular leak, and retinal thickening in diabetes mellitus due to leaking of fluid from blood vessels within the macula. To practice this method, an effective amount of more or more of the pKal inhibitory compounds described herein, or pharmaceutically acceptable salts thereof, may be delivered into the eye of the subject where treatment is needed. For example, the compound may be delivered by intraocular injection, or intravitreal injection. A subject may be treated with the pKal inhibitor compound as described herein, either as the sole active agent, or in combination with another treatment for DME. Non-limiting examples of treatment for DME include laser photocoagulation, steroids, VEGF pathway targeting agents (e.g., Lucentis® (ranibizumab) or Eylea® (aflibercept)), and/or anti-PDGF agents.

In certain embodiments, the methods disclosed herein comprise administering to the subject an effective amount of a compound of Formula I, or a pharmaceutically acceptable salt, co-crystal, tautomer, stereoisomer, solvate, hydrate, polymorph, isotopically enriched derivative, or prodrug, or composition thereof. In some embodiments, the effective amount is a therapeutically effective amount. In some embodiments, the effective amount is a prophylactically effective amount.

In certain embodiments, the subject being treated is an animal. The animal may be of either sex and may be at any stage of development. In certain embodiments, the subject is a mammal. In certain embodiments, the subject being treated is a human. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal.

Certain methods described herein may comprise administering one or more additional pharmaceutical agent(s) in combination with the compounds described herein. The additional pharmaceutical agent(s) may be administered at the same time as the compound of Formula I, or at different times than the compound of Formula I. For example, the compound of Formula I and any additional pharmaceutical agent(s) may be on the same dosing schedule or different dosing schedules. All or some doses of the compound of Formula I may be administered before all or some doses of an additional pharmaceutical agent, after all or some does an additional pharmaceutical agent, within a dosing schedule of an additional pharmaceutical agent, or a combination thereof. The timing of administration of the compound of Formula I and additional pharmaceutical agents may be different for different additional pharmaceutical agents.

In certain embodiments, the additional pharmaceutical agent comprises an agent useful in the treatment of an edema, such as HAE or DME. Examples of such agents are provided herein.

EXAMPLES

In order that the invention described herein may be more fully understood, the following examples are set forth. The examples described in this application are offered to illustrate the compounds, pharmaceutical compositions, and methods provided herein and are not to be construed in any way as limiting their scope.

Example 1: Exemplary Synthetic Schemes and Procedures for Synthesizing Exemplary Compounds of Formula I All reactions were conducted under an atmosphere of dry nitrogen unless specified otherwise. TLC plates were visualised with ultraviolet light. Flash chromatography refers to column chromatography over silica gel (40-60 μm) using glass columns. Alternatively, automated chromatography was performed using Biotage SP1 or Biotage Isolera systems with ultraviolet detection at 220 or 254 nm and employing Biotage normal phase or reverse phase silica cartridges. Further details can be found under the relevant experimental procedure.

The following system was used for LCMS: Agilent 6120 (Binary Gradient Module pump), XBridge analytical column C18, 5 μm, 4.6×50 mm, 25° C., 5 μL injection volume, 2 mL/min, with a gradient of acetonitrile in aqueous 0.1% Ammonium acetate according to the following timings:

| Time (min) | Acetonitrile (%) | 0.1% aqueous Ammonium acetate (%) |
|---|---|---|
| 0.00 | 5 | 95 |
| 3.00 | 95 | 5 |
| 4.00 | 95 | 5 |

The following systems were used for HPLC (no mass spectrometry): Waters 2767 (Binary Gradient Module pump), XBridge prep C18 column, 5 μm, 19×150 mm, 15 mL/min, 25° C.; gradient 30-80% acetonitrile in aqueous 0.1% ammonium bicarbobate over 9.5 min; or gradient 30-80% acetonitrile in aqueous 0.1% ammonium hydroxide over 9.5 min; or gradient 30-80% acetonitrile in aqueous 0.1% 2,2,2-trifluoroacetic acid over 9.5 min.

NMR spectra were measured with a Varian Mercury spectrometer operating at 400 MHz ($^1$H), 376 MHz ($^{19}$F) or 75 MHz ($^{13}$C). Solvents used for samples are specified in the experimental procedures for each compound.

2-((2R,4R)-4-amino-1-(6-chloroimidazo[1,2-a]pyridine-2-carbonyl)pyrrolidin-2-yl)-N—((S)-6-guanidino-1-(methylamino)-1-oxohexan-2-yl)thiazole-4-carboxamide (1)

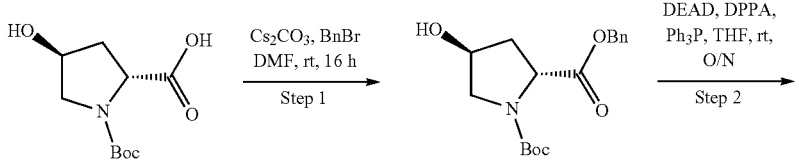

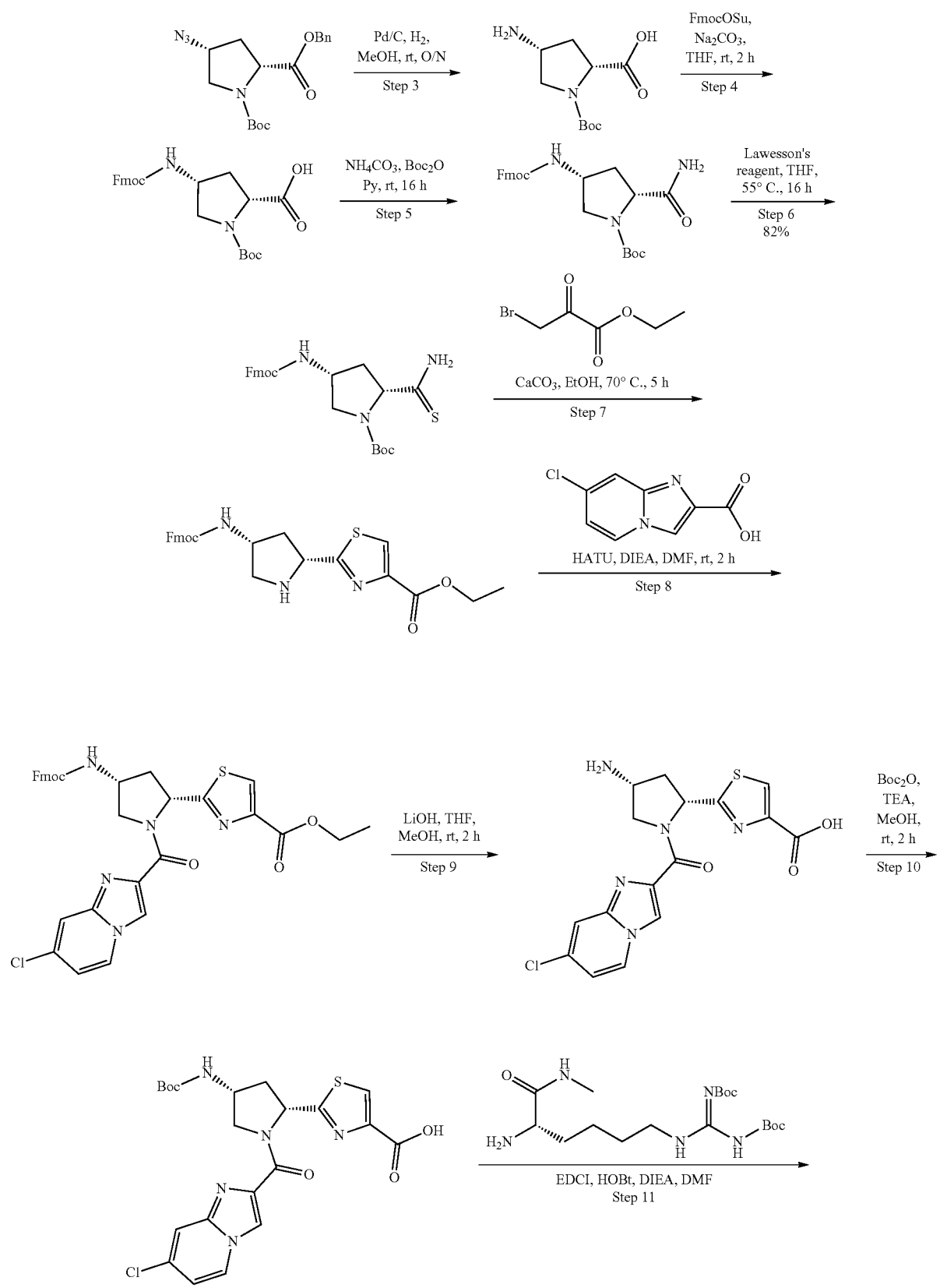

-continued

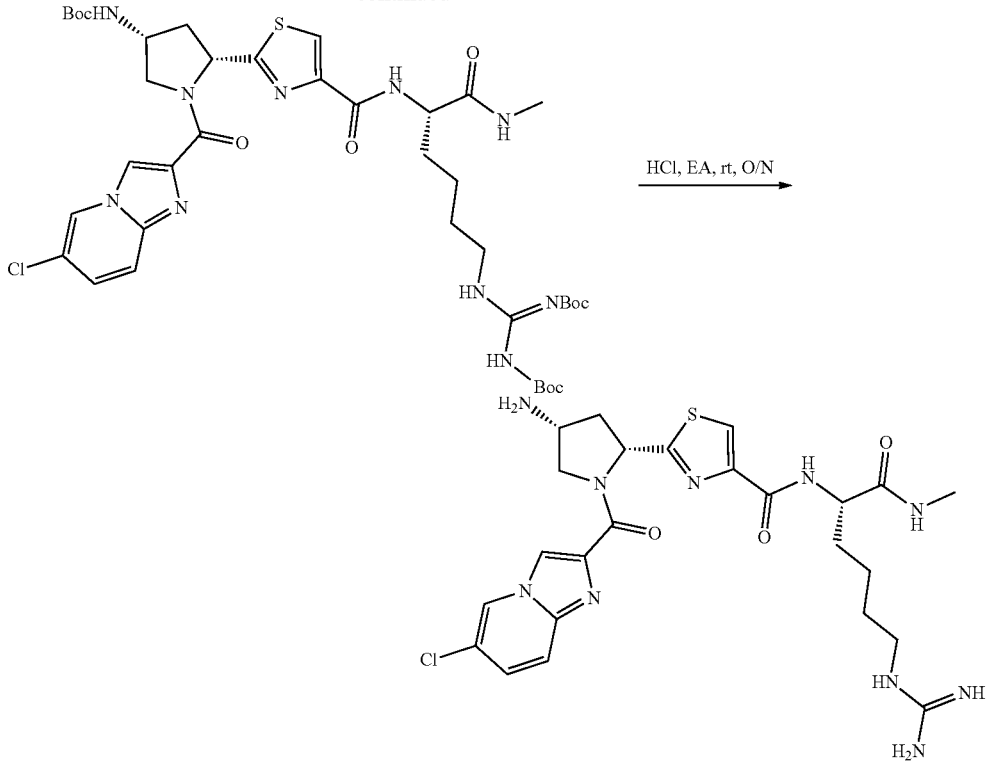

1

Step 1: Synthesis of (2R,4S)-2-benzyl 1-tert-butyl 4-hydroxypyrrolidine-1,2-dicarboxylate (2R,4S)-1-(tert-butoxycarbonyl)-4-hydroxypyrrolidine-2-carboxylic acid (3.0 g, 13.0 mmol) in methanol (50 mL) was cooled to 0° C. Aqueous cesium carbonate (2.12 g in 32 mL water) was added. The solution was concentrated and sufficient N,N-dimethylformamide was added to azeotrope the water, leaving a white solid which was dissolved in N,N-dimethylformamide (60 mL). Benzyl bromide (1.5 mL, 13.0 mmol) was added at 0° C. and the mixture was stirred vigorously at room temperature for 20 h. The reaction mixture was concentrated in vacuo, the resulting residue was dissolved in ethyl acetate (40 mL), washed with water (2×40 mL) and brine (2×40 mL). The organic layer was dried over Sodium sulfate, filtered, and concentrated in vacuo to produce a residue, which was purified by silica gel flash chromatography (petroleum ether:ethyl acetate=50:50) affording (2R,4S)-2-benzyl 1-tert-butyl 4-hydroxypyrrolidine-1,2-dicarboxylate (4.18 g) as a colorless oil. $^1$H NMR (400 Hz, CDCl$_3$) δ 7.35-7.34 (m, 5H), 5.23-5.07 (m, 2H), 4.51-4.41 (m, 2H), 3.65-3.46 (m, 2H), 2.33-2.23 (m, 1H), 2.09-2.03 (m, 1H), 1.45-1.35 (s, 9H).

Step 2: Synthesis of (2R,4R)-2-benzyl 1-tert-butyl 4-azidopyrrolidine-1,2-dicarboxylate A solution of diethyl azodicarboxylate (6.78 g of a 40% solution in toluene, 39.0 mmol) and diphenylphosphoryl azide (10.2 g, 39.0 mmol) in tetrahydrofuran (15 mL) was added dropwise over 30 min to a solution of (2R,4S)-2-benzyl 1-tert-butyl 4-hydroxypyrrolidine-1, 2-dicarboxylate (4.18 g, 13 mmol) and triphenylphosphine (10.2 g, 39.0 mmol) in tetrahydrofuran (50 mL) at 0° C. The resulting mixture was stirred for 24 h at room temperature. After addition of ethanol (20 mL), the solvent was concentrated to dryness in vacuo. The resulting residue was purified by silica gel flash chromatography (petroleum ether:ethyl acetate=80:20 to 70:30) to afford (2R,4R)-2-benzyl 1-tert-butyl 4-azidopyrrolidine-1,2-dicarboxylate as a yellowish oil. MS(ESI) m/z 291.1 [M+H–56]+.

Step 3: Synthesis of (2R,4R)-4-amino-1-(tert-butoxycarbonyl)pyrrolidine-2-carboxylic acid To a solution of (2R,4R)-2-benzyl 1-tert-butyl 4-azidopyrrolidine-1, 2-dicarboxylate (4.49 g, 12.9 mmol) in methanol (30 mL) was added Palladium on carbon (10%, 449 mg). The reaction vessel was evacuated by aspirator and thoroughly purged with hydrogen (three times), and the resulting heterogeneous mixture was stirred under a hydrogen balloon for 24 h at room temperature. The mixture was filtered through a pad of Celite and the pad was washed with methanol. The filtrate was concentrated in vacuo to give (2R,4R)-4-amino-1-(tert-butoxycarbonyl)pyrrolidine-2-carboxylic acid (3 g) which was used in the next step without purification. MS (ESI) m/z 175.1 [M+H–56]$^+$.

Step 4: Synthesis of (2R,4R)-4-((((9H-fluoren-9-yl)methoxy)carbonyl)amino)-1-(tert-butoxycarbonyl)pyrrolidine-2-carboxylic acid To a solution of (2R,4R)-4-amino-1-(tert-butoxycarbonyl)pyrrolidine-2-carboxylic acid (3 g, crude, 12.9 mmol) in Tetrahydrofuran (30 mL), 10% aqueous sodium bicarbonate solution (40 mL) was added. The solution was precooled to 0° C., N-(9-Fluorenylmethoxycarbonyloxy)succinimide (4.37 g, 13 mmol) dissolved in tetrahydrofuran (20 mL) was then added. The reaction mixture was stirred for 2 h at room temperature and concentrated in vacuo to leave a residue which was dissolved in ethyl acetate (100 mL) and treated with saturated aqueous ammonium chloride solution. The mixture was extracted with ethyl acetate (3×100 mL) and the organic layers were collected, dried over anhydrous sodium sulfate, filtered, and concentrated to afford a crude residue, which was purified by silica gel flash chromatography (ethyl acetate:methanol=70:30) to afford (2R,4R)-4-((((9H-fluoren-9-yl)methoxy)carbonyl)amino)-1-(tert-butoxycarbonyl) pyrrolidine-2-carboxylic acid (4 g) as a white solid. $^1$H NMR (400 Hz, CDCl$_3$) δ 7.73-7.71 (m, 2H), 7.58-7.48 (m, 2H), 7.37-7.33 (m, 2H), 7.29-7.26 (m, 2H), 4.29-4.16 (m, 5H), 3.69-3.44 (m, 2H), 2.45 (s, 1H), 2.31-2.14 (m, 2H), 1.43 (s, 9H).

Step 5: Synthesis of (2R,4R)-tert-butyl 4-((((9H-fluoren-9-yl)methoxy)carbonyl)amino)-2-carbamoylpyrrolidine-1-carboxylate To a solution of (2R,4R)-4-((((9H-fluoren-9-yl)methoxy) carbonyl)amino)-1-(tert-butoxycarbonyl)pyrrolidine-2-carboxylic acid (4 g, 8.83 mmol) in dioxane (30 mL) at 25° C. was added pyridine (1.06 g, 13.24 mmol), di-tert-butyl dicarbonate (2.86 g, 13.24 mmol), followed by ammonium bicarbonate (1.06 g, 13.24 mmol). After addition, the resulting mixture was stirred for 16 h at 25° C. Upon removal of the solvent, the residue was diluted with ethyl acetate (150 mL), washed with water (200 mL×3), 1 N hydrochloride acid (200 mL) and brine (200 mL). The organic layer was dried with over anhydrous sodium sulfate, filtered and concentrated to afford a crude residue which was purified by silica gel flash chromatography (ethyl acetate) to afford (2R,4R)-tert-butyl 4-((((9H-fluoren-9-yl)methoxy)carbonyl)amino)-2-carbamoylpyrrolidine-1-carboxylate (2.7 g) as a white solid. MS (ESI) m/z: 452.1[M+H]$^+$.

Step 6: Synthesis of (2R,4R)-tert-butyl 4-((((9H-fluoren-9-yl)methoxy)carbonyl)amino)-2-carbamothioylpyrrolidine-1-carboxylate To a solution of (2R,4R)-tert-butyl 4-((((9H-fluoren-9-yl) methoxy)carbonyl)amino)-2-carbamoylpyrrolidine-1-carboxylate (2.7 g, 6 mmol) in tetrahydrofuran (50 mL) at 25° C. was added Lawesson's reagent (1.21 g, 3 mmol). The resulting mixture was stirred for 16 h at 55° C. Upon removal of the solvent, the residue was diluted with water, extracted with ethyl acetate (40 mL×3). The combined organic layers were dried with over anhydrous sodium sulfate and concentrated. The crude product was purified by silica column chromatography (petroleum ether:ethyl acetate=1:1) to afford (2R,4R)-tert-butyl 4-((((9H-fluoren-9-yl)methoxy)carbonyl)amino)-2-carbamothioylpyrrolidine-1-carboxylate (2.3 g) as white solid. MS(ESI) m/z: 468.2 [M+H]$^+$.

Step 7: Synthesis of ethyl 2-((2R,4R)-4-((((9H-fluoren-9-yl)methoxy)carbonyl)amino) pyrrolidin-2-yl)thiazole-4-carboxylate To a solution of (2R, 4R)-tert-butyl 4-((((9H-fluoren-9-yl)methoxy)carbonyl)amino)-2-carbamothioylpyrrolidine-1-carboxylate (2.3 g, 4.9 mmol) in ethanol (60 mL) at 25° C. was added ethyl 3-bromo-2-oxopropanoate (1.15 g, 5.9 mmol) and calcium carbonate (1.47 g, 14.7 mmol). The resulting mixture was stirred at 70° C. for 5 h. After the reaction was completion, the mixture was concentrated and the residue was diluted with water, extracted with ethyl acetate (40 mL×4). The combined organic layers were dried with over anhydrous sodium sulfate and concentrated. The crude product were purified by silica column chromatography (petroleum ether:ethyl acetate=1:1) to afford ethyl 2-((2R,4R)-4-((((9H-fluoren-9-yl)methoxy)carbonyl) amino) pyrrolidin-2-yl)thiazole-4-carboxylate (1.6 g) as yellow oil. MS(ESI) m/z: 464.2 [M+H]$^+$.

Step 8: Synthesis of ethyl 2-((2R,4R)-4-((((9H-fluoren-9-yl)methoxy)carbonyl)amino)-1-(7-chloroimidazo[1,2-a]pyridine-2-carbonyl)pyrrolidin-2-yl) thiazole-4-carboxylate To a solution of 7-Chloro-imidazo[1,2-a]pyridine-2-carboxylic acid (0.71 g, 3.6 mmol) in N,N-dimethylformamide (25 mL) at 25° C. was added ethyldiisopropylamine (DIEA, 1.19 g, 9 mmol), 1-[bis(dimethylamino)methylene]-1H-1,2,3-triazolo[4,5-b]pyridinium 3-oxid hexafluorophosphate (HATU, 1.72 g, 4.5 mmol). After addition of ethyl 2-((2R, 4R)-4-((((9H-fluoren-9-yl)methoxy)carbonyl)amino)pyrrolidin-2-yl)thiazole-4-carboxylate (1.4 g, 3.0 mmol), the resulting mixture was stirred for 2 h at room temperature. After the reaction was completion, the solvent was removed and residue was diluted with water, extracted with ethyl acetate (40 mL×3), washed with 1 N lithium chloride (30 mL×3), the organic layer was dried with over anhydrous sodium sulfate and concentrated. The residues were purified by silica column chromatography (petroleum ether:ethyl acetate=1:1) to afford ethyl 2-((2R,4R)-4-((((9H-fluoren-9-yl)methoxy)carbonyl)amino)-1-(7-chloroimidazo[1,2-a] pyridine-2-carbonyl)pyrrolidin-2-yl)thiazole-4-carboxylate (800 mg) as white solid. MS(ESI) m/z: 642.2[M+H]$^+$.

Step 9: Synthesis of 2-((2R,4R)-4-amino-1-(7-chloroimidazo[1,2-a]pyridine-2-carbonyl) pyrrolidin-2-yl)thiazole-4-carboxylic acid To a solution of ethyl 2-((2R,4R)-4-((((9H-fluoren-9-yl) methoxy)carbonyl)amino)-1-(7-chloroimidazo[1,2-a]pyridine-2-carbonyl)pyrrolidin-2-yl)thiazole-4-carboxylate (800 mg, 1.25 mmol) in methanol (20 mL), tetrahydrofuran (30 mL) and water (30 mL) at room temperature was added lithium hydroxide (102 mg, 2.5 mmol). After addition, the resulting mixture was stirred for 16 h at room temperature. The mixture was removed organic solvent to afford 2-((2R, 4R)-4-amino-1-(7-chloroimidazo [1,2-a]pyridine-2-carbonyl)pyrrolidin-2-yl)thiazole-4-carboxylic acid as a solution in water. MS(ESI) m/z 392.2 [M+H]$^+$.

Step 10: Synthesis of 2-((2R,4R)-4-((tert-butoxycarbonyl)amino)-1-(7-chloroimidazo [1,2-a]pyridine-2-carbonyl)pyrrolidin-2-yl)thiazole-4-carboxylic acid To a solution of 2-((2R,4R)-4-amino-1-(7-chloroimidazo [1,2-a]pyridine-2-carbonyl)pyrrolidin-2-yl)thiazole-4-carboxylic acid (crude, 1.25 mmol) in water (about 20 mL) and methanol (30 mL) was added triethylamine (252 mg, 2.5 mmol). After addition di-tert-butyl dicarbonate (Boc$_2$O, 269 mg, 1.25 mmol), the resulting mixture was stirred for 16 h at room temperature. The mixture was concentrated and purified by reversed phase-LC (acetonitrile in water: 10% to 95%) to afford 2-((2R,4R)-4-((tert-butoxycarbonyl)amino)-

1-(7-chloroimidazo[1,2-a]pyridine-2-carbonyl)pyrrolidin-2-yl)thiazole-4-carboxylic acid (300 mg) as a white solid. MS(ESI) m/z 492.2 [M+H]+.

Step 11: Synthesis of 2-((2R,4R)-(4-tert-butoxycarbonyl)amino-1-(6-chloroimidazo[1,2-a]pyridine-2-carbonyl)pyrrolidin-2-yl)-N—((S)-6-(2,3-bis(tert-butoxycarbonyl))guanidino-1-(methylamino)-1-oxohexan-2-yl)thiazole-4-carboxamide To a solution of 2-((2R,4R)-4-((tert-butoxycarbonyl)amino)-1-(7-chloroimidazo[1,2-a]pyridine-2-carbonyl)pyrrolidin-2-yl)thiazole-4-carboxylic acid (150 mg, 0.3 mmol) in N,N-dimethylformamide (10 mL) at room temperature was added (S)-2-amino-6-(2,3-bis(tert-butoxycarbonyl))guanidino-N-methylhexanamide (122 mg, 0.3 mmol), ethyldiisopropylamine (DIEA, 200 mg, 1.5 mmol), 1-(3-dimethylaminopropyl)-3-ethylcarbodiimide hydrochloride (EDCI, 117 mg, 0.61 mmol) and 1-hydroxybenzotriazole (HOBt, 41 mg, 0.3 mmol). The resulting mixture was stirred for 16 h at room temperature. The solvent was removed and residue was diluted with water, extracted with ethyl acetate (30 mL×3), the combined organic layer was dried with over anhydrous sodium sulfate, filtered and concentrated. The resulting residues were purified by Prep-TLC (methanol:dichloromethane=1:15) to give 2-((2R,4R)-(4-tert-butoxycarbonyl)amino-1-(6-chloroimidazo[1,2-a]pyridine-2-carbonyl)pyrrolidin-2-yl)-N—((S)-6-(2,3-bis(tert-butoxycarbonyl))guanidino-1-(methylamino)-1-oxohexan-2-yl)thiazole-4-carboxamide (160 mg) as white solid. MS(ESI) m/z 875.2 [M+H]+.

Step 12: Synthesis of 2-((2R,4R)-4-amino-1-(6-chloroimidazo[1,2-a]pyridine-2-carbonyl) pyrrolidin-2-yl)-N—((S)-6-guanidino-1-(methylamino)-1-oxohexan-2-yl)thiazole-4-carboxamide (1)

To a solution of 2-((2R,4R)-(4-tert-butoxycarbonyl)amino-1-(6-chloroimidazo[1,2-a]pyridine-2-carbonyl)pyrrolidin-2-yl)-N—((S)-6-(2,3-bis(tert-butoxycarbonyl))guanidino-1-(methylamino)-1-oxohexan-2-yl)thiazole-4-carboxamide (160 mg, 0.25 mmol) in dichloromethane (5 mL) at room temperature was added hydrochloric acid/Ethyl acetate (3 N, 10 mL). The resulting mixture was stirred for 6 h at 25° C. The mixture was concentrated and the resulting residues were purified by reversed phase-HPLC (ACN/0.1% TFA in H2O) to afford 2-((2R,4R)-4-amino-1-(6-chloroimidazo[1,2-a]pyridine-2-carbonyl)pyrrolidin-2-yl)-N—((S)-6-guanidino-1-(methylamino)-1-oxohexan-2-yl)thiazole-4-carboxamide (50 mg) as a white solid. MS(ESI) m/z 575.0 [M+H]+. 1H NMR (400 MHz, DMSO) δ 9.03 (s, 1H), 8.80 (br, 2H), 8.76 (br, 1H), 8.59 (s, 1H), 8.31 (d, J=8.4 Hz, 1H), 8.27 (s, 1H), 8.23-8.14 (m, 1H), 7.85-7.80 (m, 1H), 7.79 (d, J=9.6 Hz, 1H), 7.73 (d, J=9.6 Hz, 1H), 7.03 (br, 4H), 5.67 (t, J=7.2 Hz, 1H), 4.62-4.57 (m, 1H), 4.47-4.30 (m, 1H), 4.27-4.22 (m, 1H), 4.07-4.00 (m, 1H), 3.12-3.08 (m, 2H), 2.89-2.85 (m, 1H), 2.70-2.65 (m, 1H), 2.61 (d, J=4.8 Hz, 3H), 1.80-1.73 (m, 2H), 1.50-1.44 (m, 2H), 1.36-1.23 (m, 2H).

2-((2R,4R)-4-Amino-1-(6-chloroimidazo[1,2-a]pyridine-2-carbonyl) pyrrolidin-2-yl)-N—((R)-6-guanidino-1-(methylamino)-1-oxohexan-2-yl)thiazole-4-carboxamide (2)

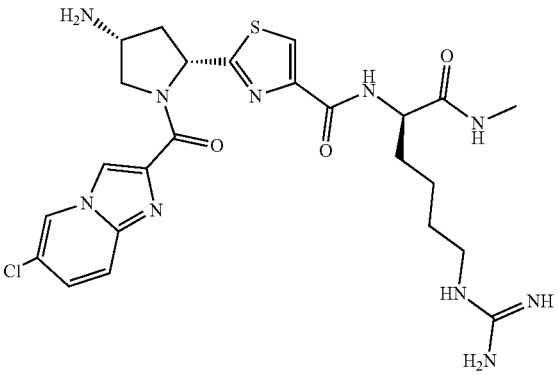 [SMILES: CNC(=O)[C@@H](CCCCNC(=N)N)NC(=O)c1csc([C@H]2C[C@@H](N)CN2C(=O)c2cn3cc(Cl)ccc3n2)n1]

Compound 2 was synthesized according to the method for synthesis of Compound 1, but using (R)-2-amino-6-(2,3-bis(tert-butoxycarbonyl))guanidino-N-methylhexanamide in step 11. MS(ESI) m/z 575.0 [M+H]+. 1H NMR (400 MHz, DMSO) δ 9.01 (s, 1H), 8.81 (br, 3H), 8.56 (s, 1H), 8.37 (d, J=8.4 Hz, 1H), 8.26 (s, 1H), 8.18-8.16 (m, 1H), 7.88-7.80 (m, 1H), 7.79 (d, J=9.6 Hz, 1H), 7.57 (d, J=9.6 Hz, 1H), 7.53-6.8 (m, 4H), 5.68 (t, J=7.2 Hz, 1H), 4.79-4.74 (m, 1H), 4.47-4.34 (m, 1H), 4.26-4.21 (m, 1H), 4.08-4.00 (m, 1H), 3.14-3.09 (m, 2H), 2.89-2.80 (m, 1H), 2.70-2.63 (m, 1H), 2.59 (d, J=4.4 Hz, 3H), 1.85-1.74 (m, 2H), 1.53-1.43 (m, 2H), 1.41-1.22 (m, 2H).

2-((R)-1-(6-Chloroimidazo[1,2-a]pyridine-2-carbonyl)pyrrolidin-2-yl)-N—((S)-6-guanidino-1-(methylamino)-1-oxohexan-2-yl)thiazole-4-carboxamide (3)

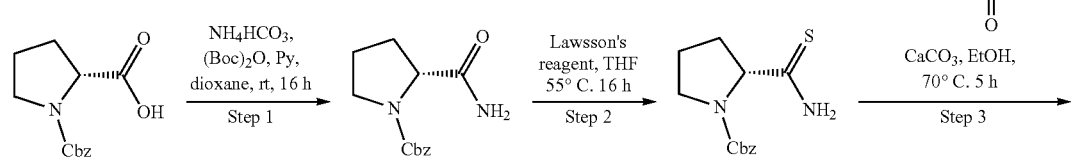

US 11,905,285 B2

115                                                                                               116

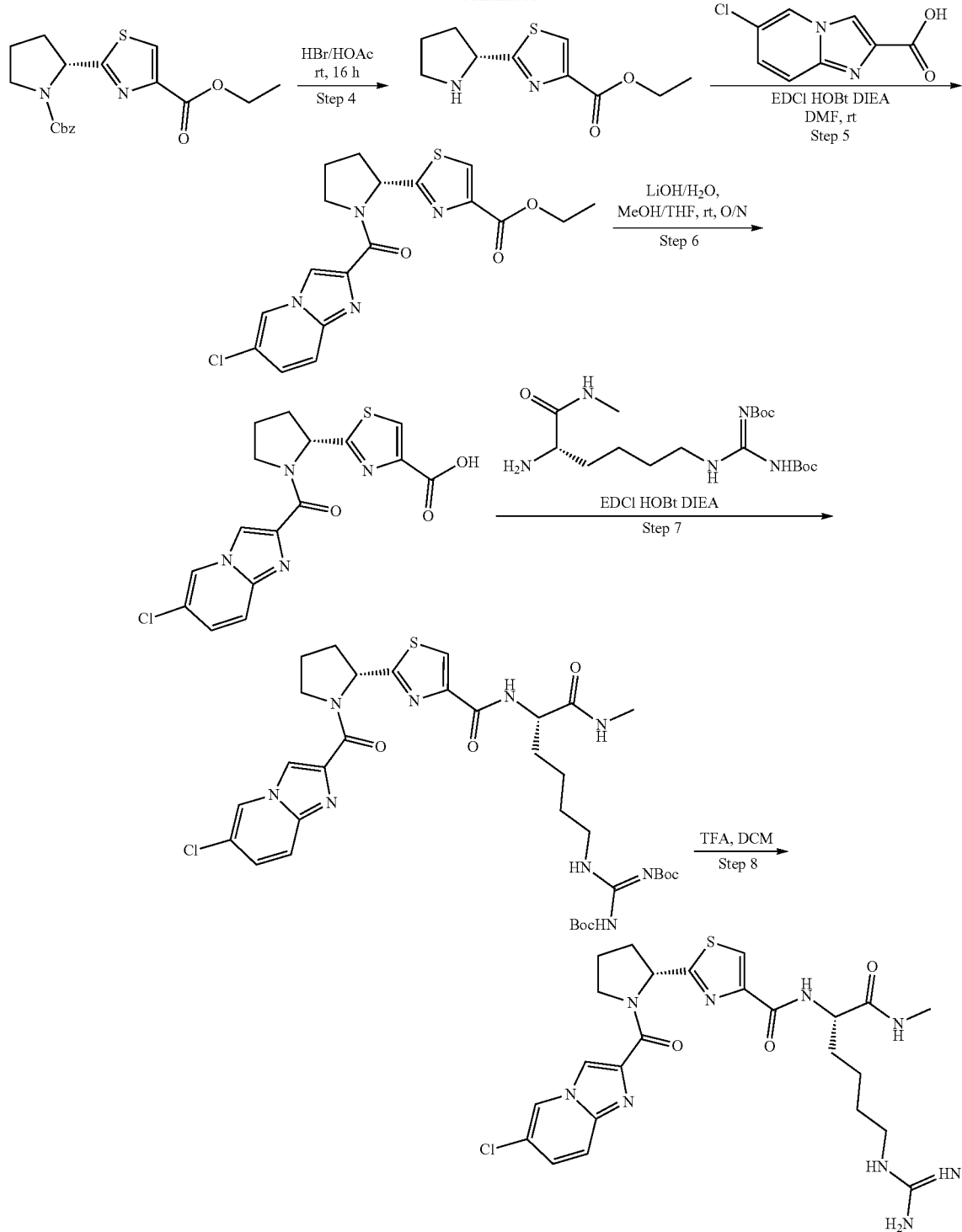

Step 1: Synthesis of (R)-benzyl 2-carbamoylpyrrolidine-1-carboxylate

To a solution of (R)-1-((benzyloxy)carbonyl)pyrrolidine-2-carboxylic acid (15 g, 60.2 mmol) in dioxane (200 mL) was added pyridine (6.19 g, 78.26 mmol), di-tert-butyl dicarbonate (16.9 g, 78.26 mmol), followed by ammonium bicarbonate (6.19 g, 78.26 mmol). The resulting mixture was stirred for 16 h at room temperature. Upon removal of the solvent, the residue was diluted with 150 mL ethyl acetate, washed with water (200 mL×3), 1 N hydrochloride acid (200 mL) and brine (200 mL). The organic layer was dried with over anhydrous sodium sulfate and concentrated to afford (R)-benzyl 2-carbamoylpyrrolidine-1-carboxylate (16.15 g) as yellow oil. MS(ESI) m/z 249.1[M+H]+.

Step 2: Synthesis of (R)-benzyl 2-carbamothioylpyrrolidine-1-carboxylate

To a solution of (R)-benzyl 2-carbamoylpyrrolidine-1-carboxylate (5.4 g, 21.8 mmol) in tetrahydrofuran (120 mL) was added Lawesson's reagent (4.84 g, 11.98 mmol). The resulting mixture was stirred for 16 h at 55° C. Upon removal of the solvent, the residue was diluted with 200 mL water, extracted with ethyl acetate (40 mL×4). The combined organic layers were dried with over anhydrous sodium sulfate, filtered and concentrated. The crude product was purified by silica column chromatography (petroleum ether:ethyl acetate=1:1) to afford (R)-benzyl 2-carbamothioylpyrrolidine-1-carboxylate (4.97) as yellow oil. MS(ESI) m/z 265.1[M+H]+.

Step 3: Synthesis of (R)-ethyl 2-(1-((benzyloxy)carbonyl)pyrrolidin-2-yl)thiazole-4-carboxylate To a solution of (R)-benzyl 2-carbamothioylpyrrolidine-1-carboxylate (4.67 g, 17.69 mmol) in ethanol (60 mL) was added ethyl 3-bromo-2-oxopropanoate (5.18 g, 26.54 mmol) and calcium carbonate (5.30 g, 53.07 mmol). The resulting mixture was stirred for 5 h at 70° C. The mixture was concentrated and the residue was diluted with 100 mL water, extracted with ethyl acetate (40 mL×4). The combined organic layers were dried with over anhydrous sodium sulfate and concentrated. The crude product were purified by silica column chromatography (petroleum ether:ethyl acetate=1:1) to give (R)-ethyl 2-(1-((benzyloxy)carbonyl)pyrrolidin-2-yl)thiazole-4-carboxylate (4.9 g) as a yellow oil. MS(ESI) m/z 361.1 [M+H]+.

Step 4: Synthesis of (R)-ethyl 2-(pyrrolidin-2-yl)thiazole-4-carboxylate (R)-ethyl 2-(1-((benzyloxy)carbonyl)pyrrolidin-2-yl)thiazole-4-carboxylate (1.0 g, 2.78 mmol) was added to the solution of hydrobromic acid in acetic acid (30%, 60 mL). The resulting mixture was stirred for 16 h at room temperature. Upon removal of the solvent, (R)-ethyl 2-(pyrrolidin-2-yl)thiazole-4-carboxylate hydrobromide (853.5 mg) was used for the next step without further purification. MS(ESI) m/z 227.1 [M+H]+.

Step 5: Synthesis of (R)-ethyl 2-(1-(6-chloroimidazo[1,2-a]pyridine-2-carbonyl)pyrrolidin-2-yl) thiazole-4-carboxylate To a solution of 6-chloroimidazo[1,2-a]pyridine-2-carboxylic acid (454.1 mg, 2.31 mmol) in N,N-dimethylformamide (25 mL) at room temperature was added (R)-ethyl 2-(pyrrolidin-2-yl)thiazole-4-carboxylate hydrobromide (853.5 mg, 2.78 mmol), ethyldiisopropylamine (DIEA, 1.49 g, 11.55 mmol), 1-(3-Dimethylaminopropyl)-3-ethylcarbodiimide hydrochloride (EDCI, 662.8 mg, 3.47 mmol) and 1-Hydroxybenzotriazole (HOBt, 626.6 mg, 4.62 mmol). The resulting mixture was stirred for 16 h at room temperature. The solvent was removed and residue was diluted with 30 mL water, extracted with Chloroform:isopropanol (v:v=3:1, 30 mL×4), washed with 1 N hydrochloric acid (30 mL) and saturated sodium bicarbonate aqueous (30 mL). The organic layer was dried with over anhydrous sodium sulfate, filtered and concentrated. The residue was purified by silica column chromatography (petroleum ether:ethyl acetate=1:1) to afford (R)-ethyl 2-(1-(6-chloroimidazo[1,2-a]pyridine-2-carbonyl) pyrrolidin-2-yl)thiazole-4-carboxylate (321 mg) as white solid. MS(ESI) m/z 405.1 [M+H]+.

Step 6: Synthesis of (R)-2-(1-(6-chloroimidazo[1,2-a]pyridine-2-carbonyl)pyrrolidin-2-yl) thiazole-4-carboxylic acid To a solution of (R)-ethyl 2-(1-(6-chloroimidazo[1,2-a]pyridine-2-carbonyl)pyrrolidin-2-yl)thiazole-4-carboxylate (321.0 mg, 0.80 mmol) in Methanol (20 mL), Tetrahydrofuran (30 mL) and water (30 mL) was added lithium hydroxide (166.8 mg, 3.98 mmol). The resulting mixture was stirred for 16 h at room temperature. The mixture was concentrated and the residue was diluted with 20 mL water, extracted with Ethyl acetate (20 mL×2). The water layer was adjusted pH to 2-3 with 1 N hydrochloride and concentrated. The residue was diluted with Methanol:Dichloromethane (v:v=1:10, 20 mL), the organic layer was dried with over anhydrous sodium sulfate, filtered and concentrated to afford (R)-2-(1-(6-chloroimidazo[1,2-a]pyridine-2-carbonyl)pyrrolidin-2-yl)thiazole-4-carboxylic acid (487 mg) as white solid. MS(ESI) m/z 377.1 [M+H]+.

Step 7: Synthesis of 2-((R)-1-(6-chloroimidazo[1,2-a]pyridine-2-carbonyl)pyrrolidin-2-yl)-N—((S)-6-(2,3-bis(tert-butoxycarbonyl))guanidino-1-(methylamino)-1-oxohexan-2-yl)thiazole-4-carboxamide To a solution of (R)-2-(1-(6-chloroimidazo[1,2-a]pyridine-2-carbonyl)pyrrolidin-2-yl)thiazole-4-carboxylic acid (200 mg, 0.53 mmol) in N,N-dimethylformamide (10 mL) was added (S)-2-amino-6-(2,3-bis(tert-butoxycarbonyl))guanidino-N-methylhexanamide (187.7 mg, 0.47 mmol), ethyldiisopropylamine (DIEA, 343.1 g, 2.66 mmol), 1-(3-dimethylaminopropyl)-3-ethylcarbodiimide hydrochloride (EDCI, 252.7 mg, 1.32 mmol) and 1-hydroxybenzotriazole (HOBt, 193.8 mg, 1.43 mmol). The resulting mixture was stirred for 16 h at room temperature. The solvent was removed and residue was diluted with 50 mL water, extracted with ethyl acetate (30 mL×3), the combined organic layer was dried with over anhydrous sodium sulfate, filtered and concentrated. The residues were purified by Prep-TLC (methanol:dichloromethane=1:10) to give 2-((R)-1-(6-chloroimidazo[1,2-a]pyridine-2-carbonyl)pyrrolidin-2-yl)-N—((S)-6-(2,3-bis(tert-butoxycarbonyl))guanidino-1-(methylamino)-1-oxohexan-2-yl)thiazole-4-carboxamide (220 mg) as yellow solid. MS(ESI) m/z 760.3 [M+H]+.

Step 8: Synthesis of 2-((R)-1-(6-chloroimidazo[1,2-a]pyridine-2-carbonyl)pyrrolidin-2-yl)-N—((S)-6-guanidino-1-(methylamino)-1-oxohexan-2-yl)thiazole-4-carboxamide (3)

To a solution of 2-((R)-1-(6-chloroimidazo[1,2-a]pyridine-2-carbonyl)pyrrolidin-2-yl)-N—((S)-6-(2,3-bis(tert-butoxycarbonyl))guanidino-1-(methylamino)-1-oxohexan-2-yl)thiazole-4-carboxamide (220 mg, 0.29 mmol) in dichloromethane (5 mL) was added 2,2,2-trifluoroacetic acid (1 mL). The resulting mixture was stirred for 6 h at room temperature. The mixture was concentrated and the residues were purified by RP-HPLC (ACN/0.1% NH₃ in H₂O) to afford 2-((R)-1-(6-chloroimidazo[1,2-a]pyridine-2-carbonyl)pyrrolidin-2-yl)-N—((S)-6-guanidino-1-(methylamino)-1-oxohexan-2-yl)thiazole-4-carboxamide (71.2 mg) as white solid. MS (ESI) m/z 560.0 [M+H]+. ¹H NMR (400

MHz, DMSO, mixture of rotamers) δ 8.87 (s, 0.7H), 8.83 (s, 0.3H), 8.40 (s, 0.7H), 8.36 (s, 0.3H), 8.17 (s, 1.4H), 8.09 (s, 0.6H), 7.74-7.69 (m, 1H), 7.55-7.50 (m, 0.7H), 7.43-7.39 (m, 1H), 7.33-7.29 (m, 0.3H), 6.77-6.74 (m, 0.3H), 5.59-5.55 (m, 0.7H), 4.44-4.35 (m, 2H), 4.18-4.11 (m, 1H), 3.78-3.72 (m, 1H), 3.05 (s, 2H), 2.62 (s, 3H), 2.46-2.32 (m, 2H), 2.17-1.97 (m, 3H), 1.80-1.63 (m, 3H), 1.51-1.42 (m, 2H), 1.35-1.23 (m, 3H).

Compound 4 was synthesized according to the method for synthesis of Compound 3, but using (R)-2-amino-6-(2,3-bis(tert-butoxycarbonyl))guanidino-N-methylhexanamide in step 7. MS(ESI) m/z 560.0 [M+H]$^+$. $^1$H NMR (400 MHz, DMSO, mixture of rotamers) δ 8.87 (s, 0.7H), 8.83 (s, 0.3H), 8.40 (s, 0.7H), 8.38 (s, 0.3H), 8.17 (s, 1.4H), 8.09 (s, 0.6H), 7.74-7.71 (m, 1H), 7.55-7.50 (m, 0.7H), 7.43-7.39 (m, 1H), 7.35-7.32 (m, 0.3H), 6.77-6.75 (m, 0.3H), 5.59-5.55 (m, 0.7H), 4.47-4.37 (m, 2H), 4.19-4.11 (m, 1H), 3.77-3.74 (m, 1H), 3.03 (s, 2H), 2.61 (s, 3H), 2.44-2.33 (m, 2H), 2.16-1.96 (m, 3H), 1.82-1.64 (m, 3H), 1.47-1.45 (m, 2H), 1.33-1.23 (m, 3H).

2-((R)-1-(6-Chloroimidazo[1,2-a]pyridine-2-carbonyl)pyrrolidin-2-yl)-N—((R)-6-guanidino-1-(methylamino)-1-oxohexan-2-yl)thiazole-4-carboxamide (4)

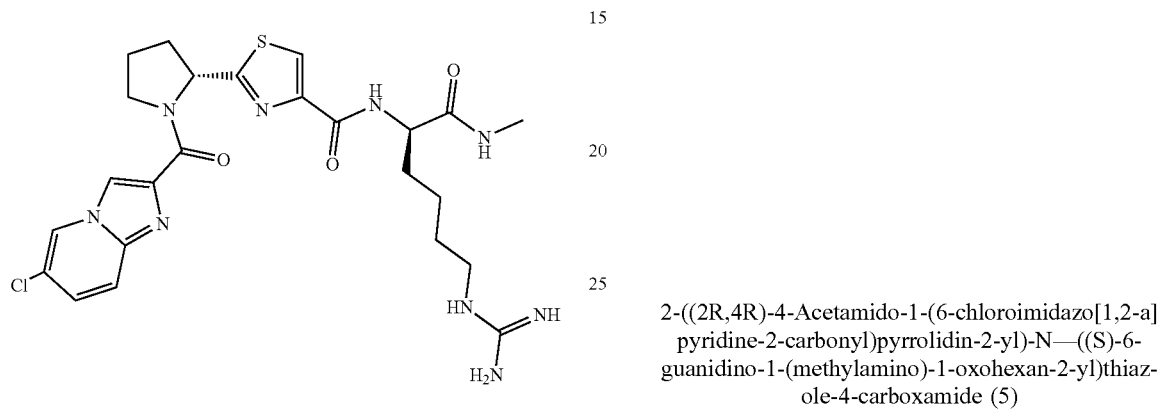

2-((2R,4R)-4-Acetamido-1-(6-chloroimidazo[1,2-a]pyridine-2-carbonyl)pyrrolidin-2-yl)-N—((S)-6-guanidino-1-(methylamino)-1-oxohexan-2-yl)thiazole-4-carboxamide (5)

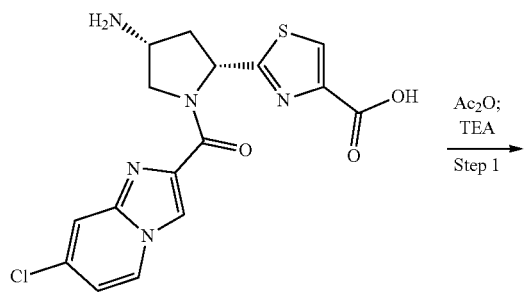

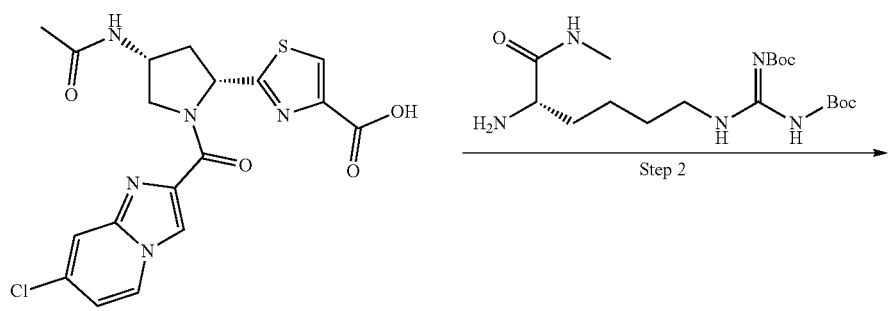

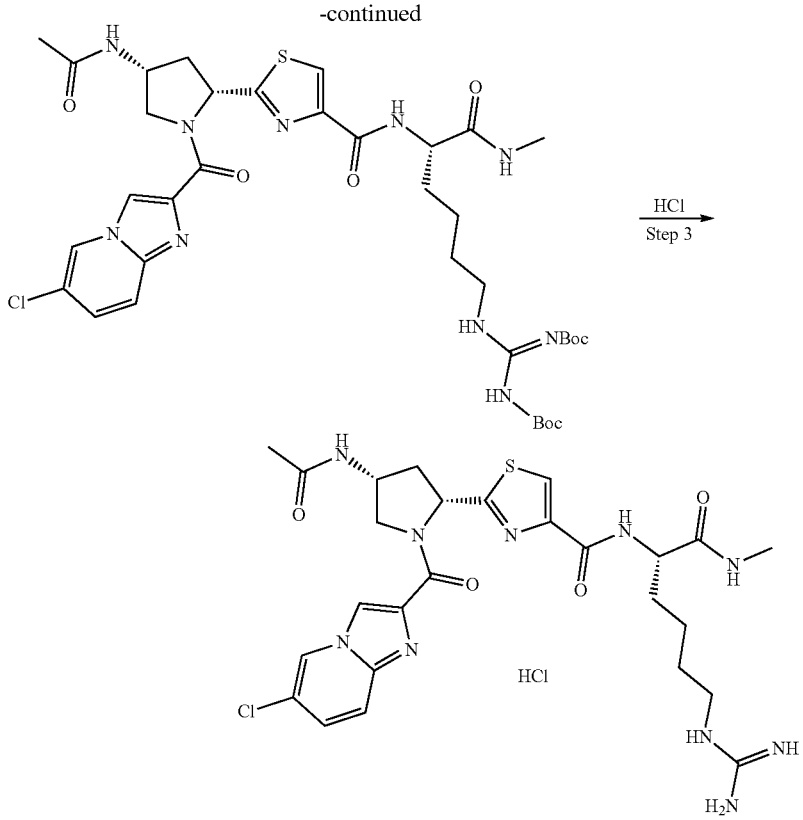

Step 1: Synthesis of 2-((2R,4R)-4-acetamido-1-(7-chloroimidazo[1,2-a]pyridine-2-carbonyl) pyrrolidin-2-yl)thiazole-4-carboxylic acid To a solution of 2-((2R,4R)-4-amino-1-(7-chloroimidazo[1,2-a]pyridine-2-carbonyl) pyrrolidin-2-yl)thiazole-4-carboxylic acid (180 mg) in water (about 20 mL) and methanol (30 mL) was added triethylamine (137 mg, 1.35 mmol). After addition of acetic anhydride (46 mg, 0.45 mmol), the resulting mixture was stirred for 2 h at room temperature. The mixture was concentrated and purified by Reversed phase-LC (Acetonitrile in water: 10% to 95%) to afford 2-((2R,4R)-4-acetamido-1-(7-chloroimidazo[1,2-a]pyridine-2-carbonyl)pyrrolidin-2-yl)thiazole-4-carboxylic acid (110 mg) as a white solid. MS(ESI) m/z 434.1 [M+H]$^+$.

Step 2: Synthesis of 2-((2R,4R)-4-acetamido-1-(6-chloroimidazo[1,2-a]pyridine-2-carbonyl) pyrrolidin-2-yl)-N—((S)-6-(2,3-bis(tert-butoxycarbonyl)) guanidino-1-(methylamino)-1-oxohexan-2-yl) thiazole-4-carboxamide To a solution of 2-((2R,4R)-4-acetamido-1-(7-chloroimidazo[1,2-a]pyridine-2-carbonyl) pyrrolidin-2-yl)thiazole-4-carboxylic acid (110 mg, 0.253 mmol) in N,N-dimethylformamide (10 mL) was added (S)-2-amino-6-(2,3-bis(tert-butoxycarbonyl))guanidino-N-methylhexanamide (102 mg, 0.253 mmol), ethyldiisopropylamine (DIEA, 166 mg, 1.26 mmol), 1-(3-Dimethylaminopropyl)-3-ethylcarbodiimide hydrochloride (EDCI, 97 mg, 0.507 mmol) and 1-Hydroxybenzotriazole (HOBt, 35 mg, 0.253 mmol). The resulting mixture was stirred for 16 h at room temperature. The solvent was removed and residue was diluted with 50 mL water, extracted with Ethyl acetate (30 mL×3), the combined organic layer was dried with over anhydrous sodium sulfate, filtered and concentrated. The residues were purified by Prep-TLC (Methanol:Dichloromethane=1:15) to give 2-((2R,4R)-4-acetamido-1-(6-chloroimidazo[1,2-a]pyridine-2-carbonyl)pyrrolidin-2-yl)-N—((S)-6-(2,3-bis(tert-butoxycarbonyl))guanidino-1-(methylamino)-1-oxohexan-2-yl)thiazole-4-carboxamide (140 mg) as white solid. MS(ESI) m/z 817.3 [M+H]$^+$ Step 3: Synthesis of 2-((2R,4R)-4-acetamido-1-(6-chloroimidazo[1,2-a]pyridine-2-carbonyl) pyrrolidin-2-yl)-N—((S)-6-guanidino-1-(methylamino)-1-oxohexan-2-yl)thiazole-4-carboxamide To a solution of 2-((2R,4R)-4-acetamido-1-(6-chloroimidazo[1,2-a]pyridine-2-carbonyl)pyrrolidin-2-yl)-N—((S)-6-(2,3-bis(tert-butoxycarbonyl))guanidino-1-(methylamino)-1-oxohexan-2-yl)thiazole-4-carboxamide (140 mg, 0.17 mmol) in Dichloromethane (5 mL) was added hydrochloric acid/Ethyl acetate (10 mL, 3 N). The resulting mixture was stirred for 6 h at room temperature. After the reaction was completion, the mixture was concentrated and the residues were purified by RP-HPLC (ACN/0.1% TFA in H$_2$O) to afford 2-((2R,4R)-4-acetamido-1-(6-chloroimidazo[1,2-a]pyridine-2-carbonyl)pyrrolidin-2-yl)-N—((S)-6-guanidino-1-(methylamino)-1-oxohexan-2-yl)thiazole-4-carboxamide hydrochloride salt (40 mg) as white solid. MS(ESI) m/z 617.0 [M+H]$^+$. $^1$H NMR (400 MHz, DMSO) δ 9.08 (s, 1H), 8.75 (s, 1H), 8.50 (d, J=6.4 Hz, 1H), 8.27 (s, 1H), 8.14 (d, J=8.4 Hz, 1H), 7.89-7.78 (m, 3H), 5.61 (t, J=8.0 Hz, 1H), 4.53-4.36 (m, 3H), 3.90-3.78 (m, 1H), 3.10-3.05 (m, 2H), 2.77-2.65 (m, 1H), 2.61 (d, J=4.4 Hz, 3H), 2.36-2.26 (m, 1H), 1.83 (s, 3H), 1.80-1.67 (m, 2H), 1.51-1.44 (m, 2H), 1.36-1.23 (m, 2H).

2-((2R,4S)-4-Amino-1-(6-chloroimidazo[1,2-a]pyridine-2-carbonyl)pyrrolidin-2-yl)-N—((S)-6-guanidino-1-(methylamino)-1-oxohexan-2-yl)thiazole-4-carboxamide (6)

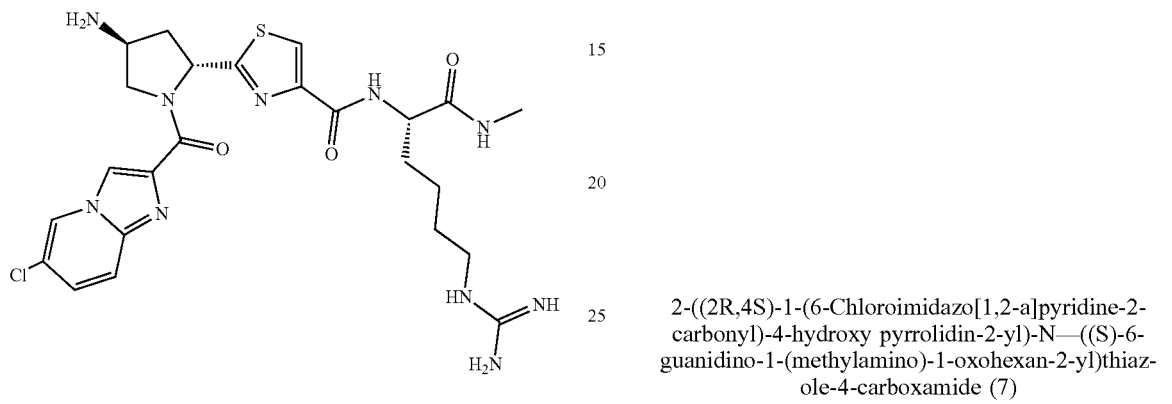

Compound 6 was synthesized according to the method for synthesis of Compound 1, starting with (2R,4R)-1-(tert-butoxycarbonyl)-4-hydroxypyrrolidine-2-carboxylic acid in step 1. MS(ESI) m/z 575.0[M+H]$^+$. 1H NMR (400 MHz, DMSO) δ 9.01 (s, 1H), 8.72 (br, 3H), 8.59 (s, 1H), 8.24-8.23 (m, 2H), 8.16-8.11 (m, 1H), 7.84-7.77 (m, 2H), 7.64-7.57 (m, 1H), 7.55-6.86 (m, 5H), 5.79 (t, J=6.8 Hz, 1H), 4.55-4.41 (m, 3H), 4.10-4.00 (m, 1H), 3.09-3.08 (m, 2H), 2.77-2.65 (m, 2H), 2.62 (2s, 3H), 1.80-1.69 (m, 2H), 1.49-1.46 (m, 2H), 1.36-1.23 (m, 2H).

2-((2R,4S)-1-(6-Chloroimidazo[1,2-a]pyridine-2-carbonyl)-4-hydroxy pyrrolidin-2-yl)-N—((S)-6-guanidino-1-(methylamino)-1-oxohexan-2-yl)thiazole-4-carboxamide (7)

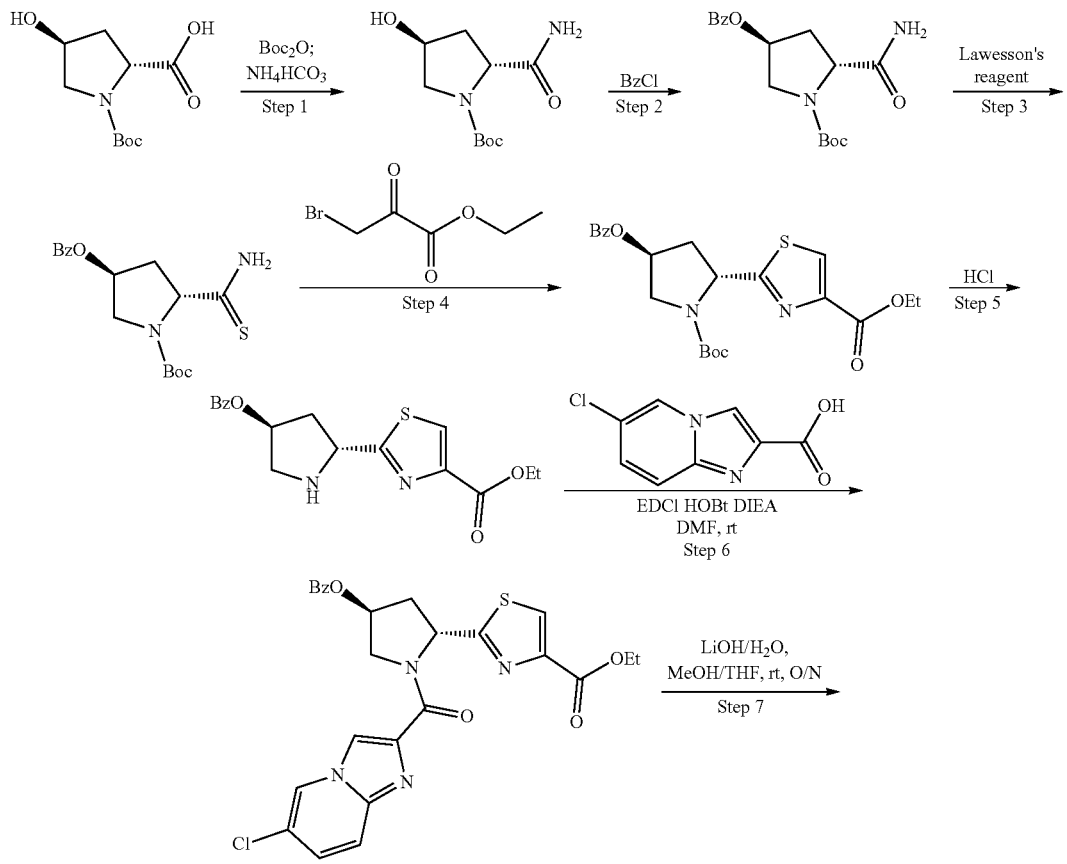

-continued

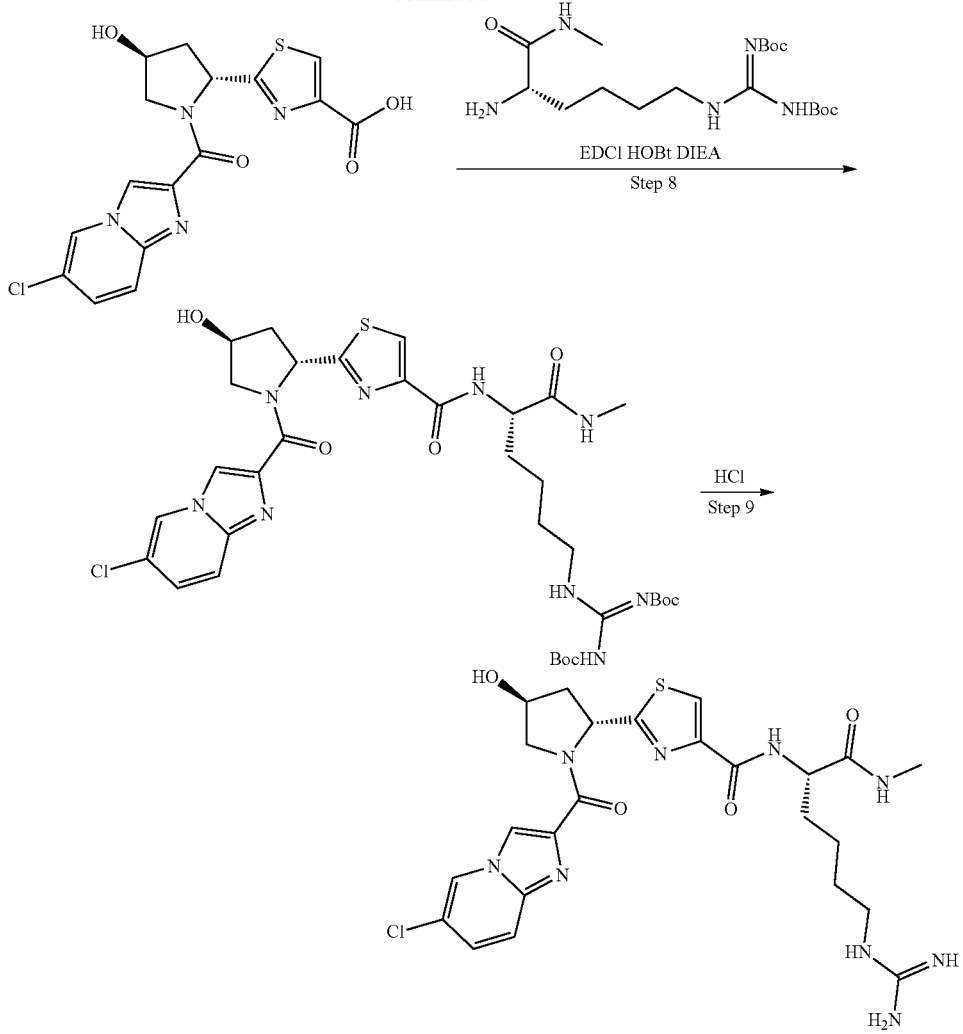

Step 1: Synthesis of (2R,4S)-tert-butyl 2-carbamoyl-4-hydroxypyrrolidine-1-carboxylate To a solution of (2R,4S)-1-(tert-butoxycarbonyl)-4-hydroxypyrrolidine-2-carboxylic acid (6.0 g, 26 mmol) in dioxane (60 mL) was added pyridine (3.0 mL, 37 mmol), di-tert-butyl dicarbonate (7.3 g, 34 mmol), followed by Ammonium bicarbonate (2.7 g, 34 mmol). The resulting mixture was stirred for 16 h at room temperature. Upon removal of the solvent, the residue was diluted with 200 mL Ethyl acetate, washed with water (30 mL×3), 1 N hydrochloric acid (30 mL) and brine (30 mL). The organic layer was dried with over anhydrous sodium sulfate and concentrated to afford a crude residue, which was purified by silica gel flash chromatography (ethyl acetate:methanol=8:1) to afford (2R,4S)-tert-butyl 2-carbamoyl-4-hydroxyl pyrrolidine-1-carboxylate (5.8 g) as a white solid. MS(ESI) m/z 231.1 [M+H]$^+$.

Step 2: Synthesis of (2R,4S)-tert-butyl 4-(benzoyloxy)-2-carbamoylpyrrolidine-1-carboxylate To a solution of (2R,4S)-tert-butyl 2-carbamoyl-4-hydroxypyrrolidine-1-carboxylate (5.8 g, 25 mmol) in dichloromethane (120 mL) was added benzoyl chloride (4.3 g, 31 mmol) and 4-dimethylaminopyridine (3.7 g, 31 mmol) at 0° C. The mixture was stirred for 2 h at 0° C. The solvent was removed and residue was diluted with water (100 mL), extracted with dichloroform (120 mL×3), washed with saturated sodium bicarbonate aqueous (100 mL), the organic layer was dried with over sodium sulfate and concentrated. The residues were purified by silica column chromatography (ethyl acetate) to afford (2R,4S)-tert-butyl 4-(benzoyloxy)-2-carbamoylpyrrolidine-1-carboxylate (7.1 g) as colorless oil. MS(ESI) m/z 335.2 [M+H]$^+$.

Step 3: Synthesis of (2R,4S)-tert-butyl 4-(benzoyloxy)-2-carbamothioylpyrrolidine-1-carboxylate To a solution of (2R,4S)-tert-butyl 4-(benzoyloxy)-2-carbamoylpyrrolidine-1-carboxylate (7.2 g, 22 mmol) in Tetrahydrofuran (120 mL) at 25° C. was added Lawesson's reagent (4.8 g, 12 mmol). The resulting mixture was stirred for 16 h at 55° C. Upon removal of the solvent, the residue was diluted with 50 mL water, extracted with Ethyl acetate (50 mL×4). The combined organic layers were dried with over anhydrous sodium sulfate and concentrated. The crude product was purified by silica column chromatography (petroleum ether:ethyl acetate=2:1) to afford (2R,4S)-tert-butyl 4-(benzoyloxy)-2-carbamothioylpyrrolidine-1-carboxylate (4.9 g) as green solid. MS(ESI) m/z 351.1[M+H]$^+$.

Step 4: Synthesis of ethyl 2-((2R,4S)-4-(benzoyloxy)-1-(tert-butoxycarbonyl)pyrrolidin-2-yl) thiazole-4-carboxylate To a solution of (2R,4S)-tert-butyl 4-(benzoyloxy)-2-carbamothioyl pyrrolidine-1-carboxylate (4.9 g, 14 mmol) in ethanol (110 mL) was added ethyl 3-bromo-2-oxopropanoate (4.1 g, 21 mmol) and Calcium carbonate (4.0 g, 40 mmol). The resulting mixture was stirred for 4 h at 70° C. The solid was filtered off and the filtrate was concentrated to give the crude product which were purified by silica column chromatography (petroleum ether:ethyl acetate=5:1) to give ethyl 2-((2R,4S)-4-(benzoyloxy)-1-(tert-butoxycarbonyl)pyrrolidin-2-yl)thiazole-4-carboxylate (4.2 g) as yellow oil. MS(ESI) m/z 447.2 [M+H]$^+$.

Step 5: Synthesis of ethyl 2-((2R,4S)-4-(benzoyloxy)pyrrolidin-2-yl)thiazole-4-carboxylate The solution of ethyl 2-((2R,4S)-4-(benzoyloxy)-1-(tert-butoxycarbonyl)pyrrolidin-2-yl) thiazole-4-carboxylate (2.7 g, 6.1 mmol) in hydrochloric acid/ethyl acetate (3M, 20 mL) was stirred for 1 h at room temperature. After removing the solvent, the residue was neutralized with sodium hydroxide (aq.) to pH-8, and then extracted with ethyl acetate (40 mL×4). The combined organic layers were dried over anhydrous sodium sulfate and concentrated to give ethyl 2-((2R, 4S)-4-(benzoyloxy)pyrrolidin-2-yl)thiazole-4-carboxylate (2.0 g crude) as yellow oil, which was used to the next step without further purification. MS(ESI) m/z 347.1 [M+H]$^+$.

Step 6: Synthesis of ethyl 2-((2R,4S)-4-(benzoyloxy)-1-(6-chloroimidazo[1,2-a]pyridine-2-carbonyl)pyrrolidin-2-yl)thiazole-4-carboxylate To a solution of 6-chloroimidazo[1,2-a]pyridine-2-carboxylic acid (1.4 g, 6.9 mmol) in N,N-dimethylformamide (35 mL) was added 1-[Bis(dimethylamino)methylene]-1H-1,2,3-triazolo[4,5-b]pyridinium 3-oxid hexafluorophosphate (HATU, 3.3 g, 8.7 mmol) and ethyldiisopropylamine (3.7 g, 29 mmol). The mixture stirred at room temperature for 20 mins. Then ethyl 2-((2R,4S)-4-(benzoyloxy)pyrrolidin-2-yl)thiazole-4-carboxylate (2.0 g, 5.8 mmol) was added. The mixture was stirred for 16 h at room temperature. The solvent was removed and the residue was diluted with 30 mL water, extracted with ethyl acetate (40 mL×3), washed with 1 N lithium chloride (30 mL×3). The organic layer was dried over anhydrous sodium sulfate and concentrated. The residues were purified by silica column chromatography (petroleum ether:ethyl acetate=1:1) to afford ethyl 2-((2R,4S)-4-(benzoyloxy)-1-(6-chloroimidazo[1,2-a]pyridine-2-carbonyl)pyrrolidin-2-yl)thiazole-4-carboxylate (2.1 g) as yellow solid. MS(ESI) m/z 525.1[M+H]$^+$. $^1$H NMR (400 MHz, DMSO, mixture of rotamers) δ 8.85 (d, J=1.2 Hz, 1H), 8.46 (s, 1H), 8.41 (s, 1H), 7.96 (s, 1H), 7.94 (s, 1H), 7.74-7.61 (m, 2H), 7.59-7.49 (m, 2H), 7.41 (dd, J=9.6, 2.0 Hz, 1H), 5.80 (t, J=8.0 Hz, 1H), 5.66 (s, 1H), 4.73 (d, J=13.2 Hz, 1H), 4.47 (dd, J=13.2, 4.0 Hz, 1H), 4.34-4.27 (m, 2H), 2.81-2.76 (m, 1H), 2.68-2.61 (m, 1H), 1.31 (t, J=7.2 Hz, 3H).

Step 7: Synthesis of 2-((2R,4S)-1-(6-chloroimidazo[1,2-a]pyridine-2-carbonyl)-4-hydroxy pyrrolidin-2-yl)thiazole-4-carboxylic acid To a solution of ethyl 2-((2R,4S)-4-(benzoyloxy)-1-(6-chloroimidazo[1,2-a]pyridine-2-carbonyl)pyrrolidin-2-yl) thiazole-4-carboxylate (600 mg, 1.1 mmol) in methanol (30 mL) and tetrahydrofuran (30 mL) was added lithium hydroxide (2M, 2.0 mL, 4.0 mmol). The resulting mixture was stirred for 16 h at room temperature. The mixture was quenched with hydrochloric acid (2 N) and adjusted pH to 6. After removed the solvent and the crude product was purified by RP-LC (Acetonitrile in water: 10% to 95%) to afford 2-((2R,4S)-1-(6-chloroimidazo[1,2-a]pyridine-2-carbonyl)-4-hydroxypyrrolidin-2-yl)thiazole-4-carboxylic acid (329 mg) as white solid. MS(ESI) m/z 393.0 [M+H]$^+$.

Step 8: Synthesis of 2-((2R,4S)-1-(6-chloroimidazo[1,2-a]pyridine-2-carbonyl)-4-hydroxy pyrrolidin-2-yl)-N—((S)-6-(2,3-bis(tert-butoxycarbonyl))guanidino-1-(methylamino)-1-oxohexan-2-yl)thiazole-4-carboxamide To a solution of 2-((2R,4S)-1-(6-chloroimidazo[1,2-a] pyridine-2-carbonyl)-4-hydroxypyrrolidin-2-yl)thiazole-4-carboxylic acid (119 mg, 0.3 mmol) in N,N-dimethylformamide (3 mL) was added 1-[bis(dimethylamino) methylene]-1H-1,2,3-triazolo[4,5-b]pyridinium 3-oxid hexafluorophosphate (HATU, 171 mg, 0.5 mmol) and ethyldiisopropylamine (193 mg, 1.5 mmol). The mixture stirred at room temperature for 20 mins. Then (S)-2-amino-6-(2,3-bis(tert-butoxycarbonyl))guanidino-N-methylhexanamide (122 mg, 0.3 mmol) was added. The mixture was stirred for 2 h. The solvent was removed and the residue was diluted with 10 mL water, extracted with ethyl acetate (20 mL×3), washed with 1 N lithium chloride (10 mL×3). The organic layer was dried over anhydrous sodium sulfate and concentrated. The residues were purified by silica column chromatography (dichloromethane:methanol=12:1) to afford 2-((2R,4S)-1-(6-chloroimidazo[1,2-a]pyridine-2-carbonyl)-4-hydroxypyrrolidin-2-yl)-N—((S)-6-(2,3-bis(tert-butoxycarbonyl))guanidino-1-(methylamino)-1-oxohexan-2-yl)thiazole-4-carboxamide (179 mg) as colorless oil. MS(ESI) m/z 776.3 [M+H]$^+$.

Step 9: Synthesis of 2-((2R,4S)-1-(6-chloroimidazo[1,2-a]pyridine-2-carbonyl)-4-hydroxy pyrrolidin-2-yl)-N—((S)-6-guanidino-1-(methylamino)-1-oxohexan-2-yl)thiazole-4-carboxamide 2-((2R,4S)-1-(6-chloroimidazo[1,2-a]pyridine-2-carbonyl)-4-hydroxypyrrolidin-2-yl)-N—((S)-6-(2,3-bis(tert-butoxycarbonyl))guanidino-1-(methylamino)-1-oxohexan-2-yl)thiazole-4-carboxamide (141 mg, 0.2 mmol) in hydrochloric acid/Ethyl acetate (3N, 5 mL) was stirred for 1 h at room temperature. The solvent was removed and the crude product was purified by RP-HPLC (ACN/0.1% NH$_3$ in H$_2$O) to afford 2-((2R,4S)-1-(6-chloroimidazo[1,2-a]pyridine-2-carbonyl)-4-hydroxypyrrolidin-2-yl)-N—((S)-6-guanidino-1-(methylamino)-1-oxohexan-2-yl)thiazole-4-carboxamide (45 mg) as white solid. MS(ESI) m/z 576.0 [M+H]$^+$. $^1$H NMR (400 MHz, DMSO) δ 8.86 (s, 0.84H), 8.81 (s, 0.16H), 8.41 (s, 0.84H), 8.34 (s, 0.16H), 8.18 (s, 0.84H), 8.05 (s, 0.16H), 7.72 (d, J=9.6 Hz, 0.84H), 7.55 (d, J=9.6 Hz, 0.16H), 7.41 (dd, J=1.6, 10.0 Hz, 0.84H), 7.32 (dd, J=1.6, 10.0 Hz, 0.16H), 6.77-6.75 (m, 0.16H), 5.59 (t, J=8.0 Hz, 0.84H), 4.46-4.41 (m, 2.0H), 4.29-4.18 (m, 2.0H), 3.01 (t, J=6.4 Hz, 2.0H), 2.66 (s, 3.0H), 2.40-2.38 (m, 1.0H), 2.31-2.28 (m, 1H), 1.77-1.67 (m, 2H), 1.48-1.44 (m, 2H), 1.30-1.26 (m, 2H).

2-((2R,4S)-1-(6-Chloroimidazo[1,2-a]pyridine-2-carbonyl)-4-hydroxypyrrolidin-2-yl)-N—((R)-6-guanidino-1-(methylamino)-1-oxohexan-2-yl)thiazole-4-carboxamide (8)

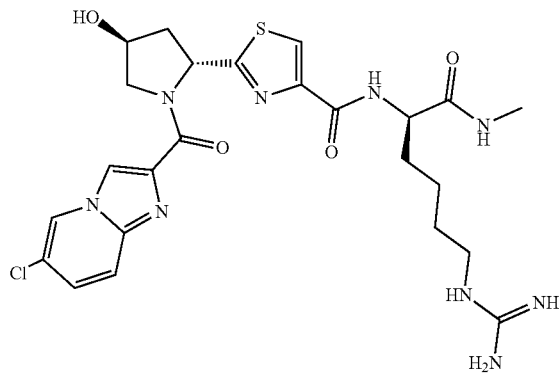 [SMILES: CNC(=O)[C@@H](CCCCNC(=N)N)NC(=O)c1csc([C@H]2C[C@H](O)CN2C(=O)c2cn3cc(Cl)ccc3n2)n1]

Compound 8 was synthesized in a manner analogous to the method used for the synthesis of Compound 7, but using (R)-2-amino-6-(2,3-bis(tert-butoxycarbonyl))guanidino-N-methylhexanamide in step 8. MS(ESI) m/z 576.0 [M+H]$^+$. $^1$H NMR (400 MHz, DMSO) δ 8.91 (d, J=1.2 Hz, 0.84H), 8.85 (s, 0.14H), 8.46 (s, 0.86H), 8.38 (s, 0.14H), 8.23 (s, 0.86H), 8.10 (s, 0.14H), 7.77 (d, J=9.6 Hz, 0.86H), 7.59 (d, J=9.6 Hz, 0.14H), 7.46 (dd, J=2.0, 9.6 Hz, 0.86H), 7.39 (dd, J=1.6, 9.6 Hz, 0.14H), 6.81-6.77 (m, 0.14H), 5.64 (t, J=8.0 Hz, 0.86H), 4.50-4.47 (m, 2H), 4.34-4.24 (m, 2H), 3.08 (t, J=6.8 Hz, 2H), 2.66 (s, 3H), 2.45-2.42 (m, 1H), 2.34-2.31 (m, 1H), 1.82-1.74 (m, 2H), 1.54-1.49 (m, 2H), 1.38-1.33 (m, 2H).

2-((2R,4R)-1-(6-Chloroimidazo[1,2-a]pyridine-2-carbonyl)-4-hydroxy pyrrolidin-2-yl)-N—((S)-6-guanidino-1-(methylamino)-1-oxohexan-2-yl)thiazole-4-carboxamide (9)

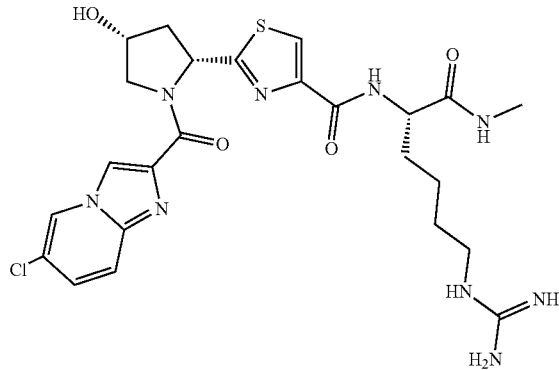 [SMILES: CNC(=O)[C@H](CCCCNC(=N)N)NC(=O)c1csc([C@H]2C[C@@H](O)CN2C(=O)c2cn3cc(Cl)ccc3n2)n1]

Compound 9 was synthesized in a manner analogous to the method used for the synthesis of Compound 7 from (2R,4R)-1-(tert-butoxycarbonyl)-4-hydroxypyrrolidine-2-carboxylic acid. MS(ESI) m/z 576.0 [M+H]$^+$. $^1$H NMR (400 MHz, DMSO) δ 8.80 (s, 1H), 8.41 (s, 1H), 8.15 (s, 2H), 7.72 (d, J=12.0 Hz, 1H), 7.50-7.44 (m, 1H), 5.63-5.60 (m, 1H), 4.51-4.49 (m, 2H), 4.46-4.40 (m, 2H), 3.64 (br, 3H), 3.06 (t, J=7.6 Hz, 2H), 2.66-2.65 (m, 3H), 2.26-2.20 (m, 1H), 1.84-1.66 (m, 2H), 1.56-1.46 (m, 2H), 1.48-1.44 (m, 2H), 1.34-1.26 (m, 4H).

2-((2R,4R)-1-(6-Chloroimidazo[1,2-a]pyridine-2-carbonyl)-4-hydroxy pyrrolidin-2-yl)-N—((R)-6-guanidino-1-(methylamino)-1-oxohexan-2-yl)thiazole-4-carboxamide (10)

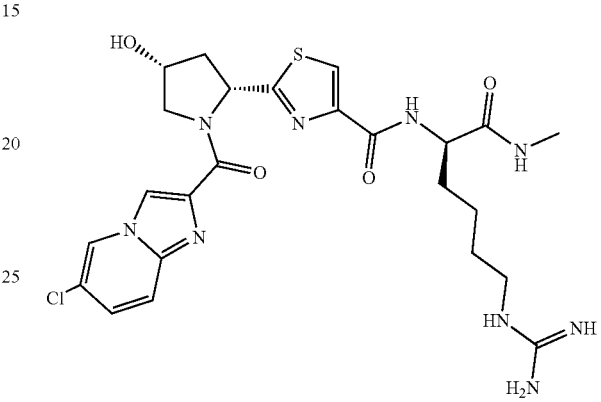

Compound 10 was synthesized in a manner analogous to the method used for the synthesis of Compound 9 using (R)-2-amino-6-(2,3-bis(tert-butoxycarbonyl))guanidino-N-methylhexanamide in Step 8. MS(ESI) m/z 576.0 [M+H]$^+$. $^1$H NMR (400 MHz, DMSO+D2O) δ 8.82 (s, 1H), 8.42 (s, 1H), 8.14 (s, 2H), 7.73 (d, J=9.6 Hz, 1H), 7.49-7.43 (m, 1H), 5.62-5.58 (m, 1H), 4.48-4.40 (m, 3H), 4.39-4.31 (m, 1H), 4.29-4.21 (m, 1H), 3.64 (br, 3H), 3.06 (t, J=6.4 Hz, 2H), 2.64 (s, 3H), 2.24-2.20 (m, 2H), 1.82-1.67 (m, 2H), 1.50-1.39 (m, 2H), 1.33-1.22 (m, 4H).

2-((2S,4R)-4-amino-1-(6-chloroimidazo[1,2-a]pyridine-2-carbonyl)pyrrolidin-2-yl)-N—((S)-6-guanidino-1-(methylamino)-1-oxohexan-2-yl)thiazole-4-carboxamide (11)

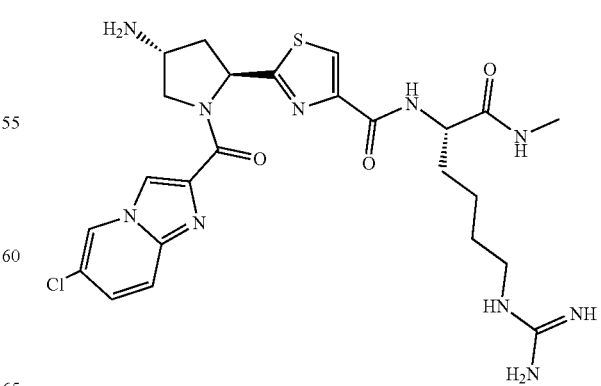

Step 1: Synthesis of (2S,4R)-4-((((9H-fluoren-9-yl)methoxy)carbonyl)amino)-1-(tert-butoxycarbonyl)pyrrolidine-2-carboxylic acid

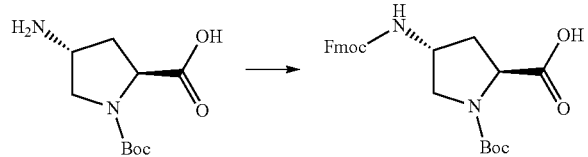

To a solution of (2S,4R)-4-amino-1-(tert-butoxycarbonyl) pyrrolidine-2-carboxylic acid (30 g, 0.13 mol) in tetrahydrofuran (600 mL), aqueous sodium bicarbonate solution (Na₂CO₃, 40 g, 0.377 mol in 240 mL H₂O) was added. The mixture was cooled to 0° C., and a solution of N-(9-Fluorenylmethoxycarbonyloxy)succinimide (12.3 g, 36.45 mmol) dissolved in tetrahydrofuran (20 mL) was then added. The reaction mixture was stirred for 2 h at room temperature and concentrated in vacuo to remove tetrahydrofuran. The aqueous layer was adjusted pH to 6 by hydrochloric acid (1N) and extracted with ethyl acetate and the organic layers were collected, dried over anhydrous sodium sulfate, filtered, and concentrated to afford a crude residue (2S,4R)-4-((((9H-fluoren-9-yl)methoxy)carbonyl)amino)-1-(tert-butoxycarbonyl)pyrrolidine-2-carboxylic acid (59 g) which was used to the next step without further purification as a white solid. MS(ESI) m/z 353.1 [M-Boc]⁺

Step 2: Synthesis of (2S,4R)-tert-butyl 4-((((9H-fluoren-9-yl)methoxy)carbonyl)amino)-2-carbamoylpyrrolidine-1-carboxylate

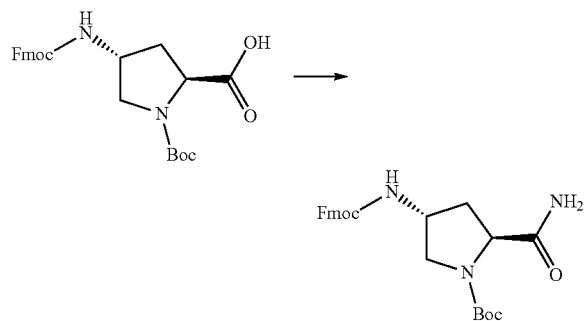

To a mixture of (2S,4R)-4-((((9H-fluoren-9-yl)methoxy)carbonyl)amino)-1-(tert-butoxycarbonyl)pyrrolidine-2-carboxylic acid (59 g crude, 0.13 mol, 1 eq), pyridine (56.6 mL, 0.52 mol, 4 eq), and di-tert-butyl dicarbonate (59.3 mL, 0.26 mol, 2 eq) in dioxane (600 mL), was added ammonium bicarbonate (21 g, 0.26 mol, 2 eq). The mixture was stirred at room temperature for 16 h. TLC showed that the starting material was disappeared. The mixture was concentrated and purified by column chromatography (petroleum ether:ethyl acetate=2:1 to ethyl acetate) to give (2S,4R)-tert-butyl-4-((((9H-fluoren-9-yl)methoxy)carbonyl)amino)-2-carbamoyl pyrrolidine-1-carboxylate (58 g) as white solid. MS (ESI) m/z 452.2[M+H]⁺; 352.2 [M+H-Boc]⁺

Step 3: Synthesis of (2S,4R)-tert-butyl 4-((((9H-fluoren-9-yl)methoxy)carbonyl)amino)-2-carbamothioylpyrrolidine-1-carboxylate

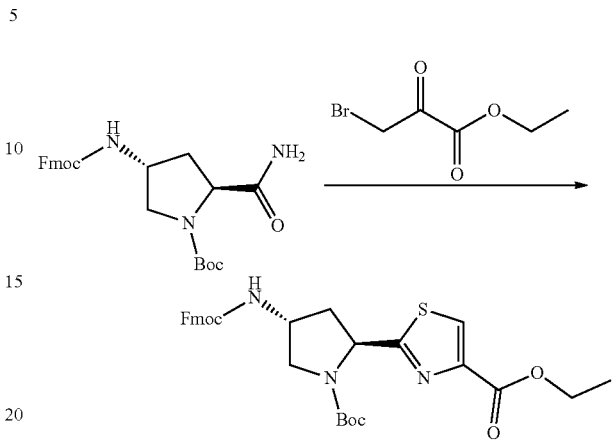

To a solution of (2S,4R)-tert-butyl 4-((((9H-fluoren-9-yl)methoxy)carbonyl)amino)-2-carbamoylpyrrolidine-1-carboxylate (59 g, 0.13 mol, 1 eq) in tetrahydrofuran (500 mL) was added Lawesson's reagent (28.4 g, 71.5 mmol, 0.55 eq). The resulting mixture was stirred at 55° C. for 12 h. TLC showed that the reaction was completed. The mixture was concentrated and purified by column chromatography (petroleum ether:ethyl acetate=4:1 to 1:1) to give (2S,4R)-tert-butyl 4-((((9H-fluoren-9-yl)methoxy) carbonyl)amino)-2-carbamothioylpyrrolidine-1-carboxylate (49.8 g) as white solid. MS(ESI) m/z 468.2 [M+H]⁺.

Step 4: Synthesis of ethyl 2-((2S,4R)-4-((((9H-fluoren-9-yl)methoxy)carbonyl)amino)-1-(tert-butoxycarbonyl)pyrrolidin-2-yl)thiazole-4-carboxylate

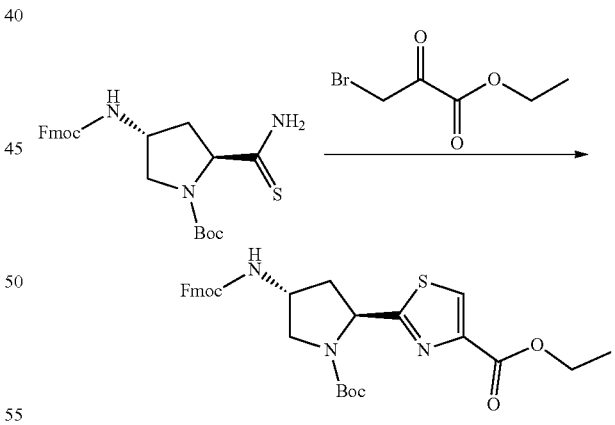

To a solution of (2S,4R)-tert-butyl 4-((((9H-fluoren-9-yl)methoxy) carbonyl)amino)-2-carbamothioylpyrrolidine-1-carboxylate (49.8 g, 106.6 mmol, 1 eq) in ethanol (60 mL) was added ethyl 3-bromo-2-oxopropanoate (20 mL, 31 g, 160 mmol, 1.5 eq) and calcium carbonate (32 g, 320 mmol, 3 eq). The resulting mixture was stirred at 70° C. for 5 h. TLC showed that the starting material was completed disappeared. The mixture was filtered and filtrate was concentrated. The residue was diluted with dichloromethane, washed with water, dried over anhydrous sodium sulfate and filtered to afford a solution of 5 and de-Boc product 6, which was added triethylamine (44.4 mL, 32.3 g, 320 mmol, 3 eq) and Di-tert-butyl dicarbonate (36.4 mL, 34.58 g, 160 mmol, 1.5 eq). The mixture was stirred at room temperature for 2 hrs and concentrated. The residue was purified by column chromatography (petroleum ether:ethyl acetate=10:1 to 2:1) to afford ethyl 2-((2S,4R)-4-((((9H-fluoren-9-yl) methoxy) carbonyl)amino)-1-(tert-butoxycarbonyl)pyrrolidin-2-yl) thiazole-4-carboxylate (26 g) as brown solid. MS (ESI) m/z 564.2 [M+H]⁺. ¹H NMR (400 MHz, CDCl3) δ 8.09 (s, 1H), 7.74-7.76 (m, 2H), 7.57-7.56 (m, 2H), 7.42-7.39 (m, 2H), 7.33-7.26 (m, 2H), 5.35-5.24 (m, 1H), 4.89 (s, 1H), 4.43-4.39 (m, 4H), 4.33-4.30 (m, 1H), 4.21-4.18 (m, 1H), 3.93-3.85 (m, 1H), 3.47-3.26 (m, 1H), 2.69-2.24 (m, 2H), 1.46-1.32 (m, 12H).

Step 5: Synthesis of ethyl 2-((2S,4R)-4-((((9H-fluoren-9-yl)methoxy)carbonyl)amino) pyrrolidin-2-yl) thiazole-4-carboxylate

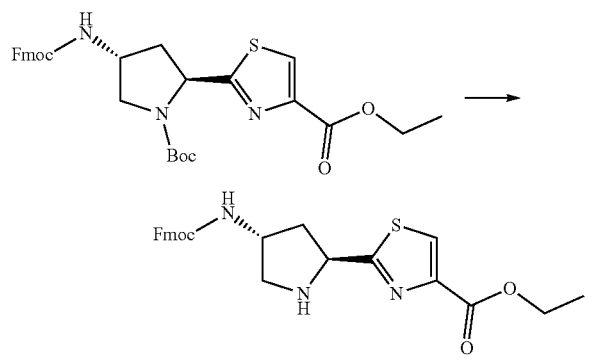

The solution of ethyl 2-((2S,4R)-4-((((9H-fluoren-9-yl) methoxy)carbonyl)amino)-1-(tert-butoxycarbonyl)pyrrolidin-2-yl)thiazole-4-carboxylate (26 g, 46.2 mmol) in hydrochloric acid/ethyl acetate (3N, 500 mL) was stirred at room temperature for 4 h. The mixture was concentrated and diluted with water, adjust pH to 8 with sat. sodium bicarbonate solution and extracted with ethyl acetate. The combined organic layers were dried over anhydrous sodium sulfate, filtered, and concentrated to afford ethyl 2-((2S,4R)-4-((((9H-fluoren-9-yl)methoxy)carbonyl)amino)pyrrolidin-2-yl)thiazole-4-carboxylate (22 g) as brown solid. MS (ESI) m/z 464.2 [M+H]⁺.

Step 6: Synthesis of ethyl 2-((2S,4R)-4-((((9H-fluoren-9-yl)methoxy)carbonyl)amino)-1-(6-chloroimidazo[1,2-a]pyridine-2-carbonyl)pyrrolidin-2-yl)thiazole-4-carboxylate

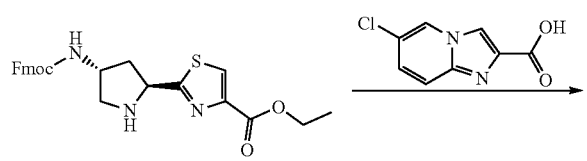

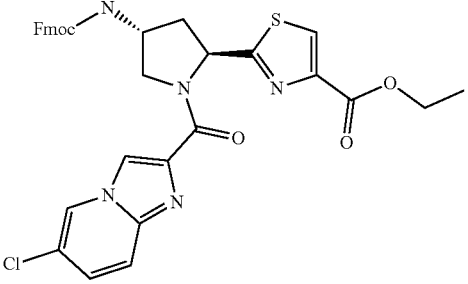

To a solution of 7-chloro-imidazo[1,2-a]pyridine-2-carboxylic acid (1.65 g, 8.41 mmol) in N,N-dimethylformamide (20 mL) was added 1-[bis(dimethylamino)methylene]-1H-1,2,3-triazolo[4,5-b]pyridinium 3-oxid hexafluorophosphate (HATU, 3.7 mg, 9.71 mmol), ethyldiisopropylamine (4.2 g, 32.4 mmol). The resulting mixture was stirred at room temperature for 30 min. Ethyl 2-((2S,4R)-4-((((9H-fluoren-9-yl)methoxy) carbonyl)amino)pyrrolidin-2-yl)thiazole-4-carboxylate (3.0 g, 6.47 mmol) was added. The mixture was stirred at room temperature for 2 h. The mixture was diluted with ethyl acetate, washed with water. The organic layer was concentrated and purified by column chromatography (petroleum ether:ethyl acetate=10:1 to 1:1) to give ethyl 2-((2S,4R)-4-((((9H-fluoren-9-yl)methoxy)carbonyl)amino)-1-(6-chloroimidazo[1,2-a]pyridine-2-carbonyl)pyrrolidin-2-yl)thiazole-4-carboxylate (3.0 g) as a yellow solid. MS(ESI) m/z 642.2 [M+H]⁺.

Step 7: Synthesis of 2-((2S,4R)-4-amino-1-(6-chloroimidazo[1,2-a]pyridine-2-carbonyl) pyrrolidin-2-yl)thiazole-4-carboxylic acid

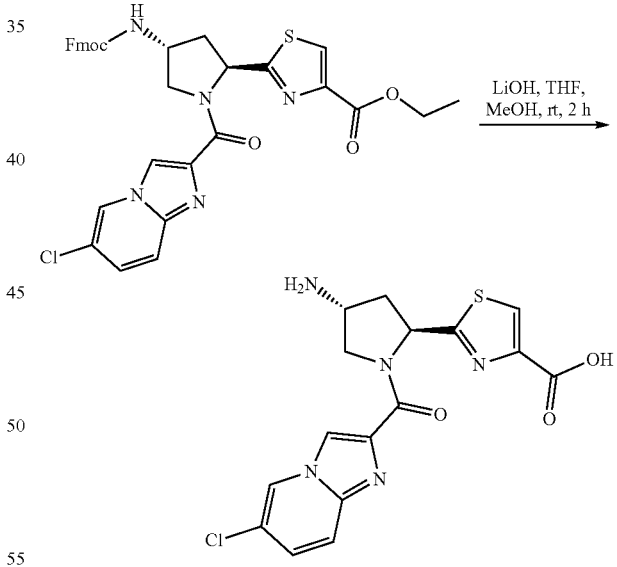

To a solution of ethyl 2-((2S,4R)-4-((((9H-fluoren-9-yl) methoxy)carbonyl) amino)-1-(6-chloroimidazo[1,2-a]pyridine-2-carbonyl)pyrrolidin-2-yl)thiazole-4-carboxylate (2.0 g, 3.11 mmol) in methanol (10 mL) and tetrahydrofuran (10 mL) was added aqueous lithium hydroxide (2N, 4 mL, 8.0 mmol). The resulting mixture was stirred at room temperature for 12 h. The mixture was concentrated to give 2-((2S, 4R)-4-amino-1-(6-chloroimidazo[1,2-a]pyridine-2-carbonyl)pyrrolidin-2-yl)thiazole-4-carboxylic acid as a solution in water which was used directly to the next step without further purification. MS (ESI) m/z 392.1 [M+H]⁺.

Step 8: Synthesis of 2-((2S,4R)-4-((tert-butoxycarbonyl)amino)-1-(6-chloroimidazo[1,2-a]pyridine-2-carbonyl)pyrrolidin-2-yl)thiazole-4-carboxylic acid

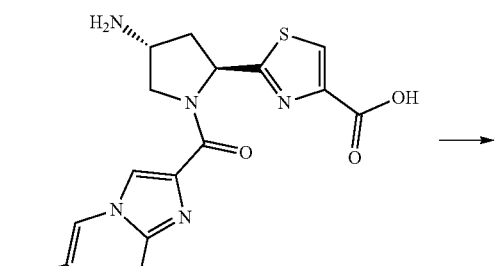

To a solution of 2-((2S,4R)-4-amino-1-(6-chloroimidazo[1,2-a]pyridine-2-carbonyl)pyrrolidin-2-yl)thiazole-4-carboxylic acid (3.11 mmol) in water (10 mL), methanol (10 mL) and tetrahydrofuran (10 mL) was added triethylamine (1.80 g, 18.5 mmol) and di-tert-butyl dicarbonate (1.6 g, 7.4 mmol). The resulting mixture was stirred at room temperature for 3 h. The mixture was concentrated and the residue was purified by RP-LC (Acetonitrile in water: 10% to 95%) to give 2-((2S,4R)-4-((tert-butoxycarbonyl)amino)-1-(6-chloroimidazo[1,2-a]pyridine-2-carbonyl)pyrrolidin-2-yl) thiazole-4-carboxylic acid (700 mg) as a white solid. MS (ESI) m/z 492.1 [M+H]$^+$.

Step 9: 2-((2S,4R)-4-(tert-butoxycarbonyl)amino-1-(6-chloroimidazo[1,2-a]pyridine-2-carbonyl) pyrrolidin-2-yl)-N—((S)-6-(2,3-bis(tert-butoxycarbonyl)) guanidino-1-(methylamino)-1-oxohexan-2-yl) thiazole-4-carboxamide

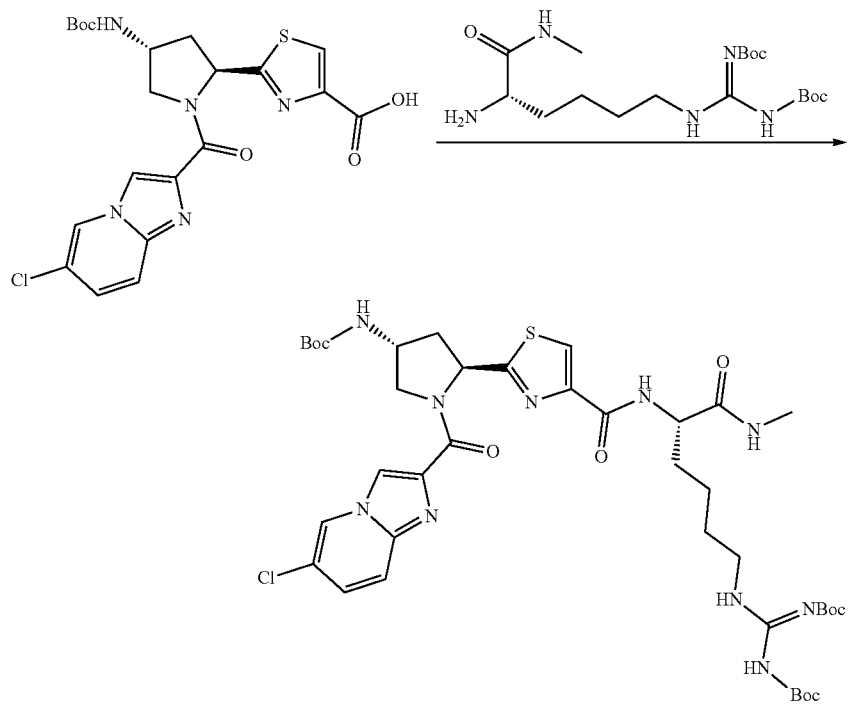

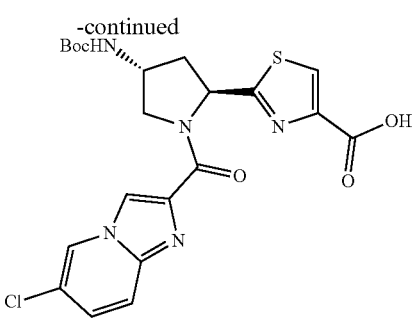

To a solution of 2-((2S,4R)-4-((tert-butoxycarbonyl)amino)-1-(6-chloroimidazo[1,2-a]pyridine-2-carbonyl)pyrrolidin-2-yl)thiazole-4-carboxylic acid (90 mg, 0.2 mmol) in N,N-dimethylformamide (3 mL) was added Ethyldiisopropylamine (DIEA, 200 mg, 1.5 mmol), 1-(3-Dimethylaminopropyl)-3-ethylcarbodiimide hydrochloride (EDCI, 117 mg, 0.61 mmol), 1-Hydroxybenzotriazole (HOBt, 41 mg, 0.3 mmol) and (S)-2-amino-6-(2,3-bis(tert-butoxycarbonyl))guanidino-N-methylhexanamide (853.5 mg, 2.78 mmol). The resulting mixture was stirred at room temperature overnight. The solvent was removed and residue was diluted with 50 mL water, extracted with ethyl acetate (30 mL×3). The combined organic layers were dried over anhydrous sodium sulfate and concentrated. The residues were purified by RP-HPLC (ACN/0.1% NH$_3$ in H$_2$O) to afford 2-((2S,4R)-4-(tert-butoxycarbonyl)amino-1-(6-chloroimidazo[1,2-a]pyridine-2-carbonyl) pyrrolidin-2-yl)-N—((S)-

6-(2,3-bis(tert-butoxycarbonyl))guanidino-1-(methylamino)-1-oxohexan-2-yl)thiazole-4-carboxamide (80 mg) as white solid. MS (ESI) m/z 875.4 [M+H]⁺.

Step 10: Synthesis of 2-((2S,4R)-4-amino-1-(6-chloroimidazo[1,2-a]pyridine-2-carbonyl) pyrrolidin-2-yl)-N—((S)-6-guanidino-1-(methylamino)-1-oxohexan-2-yl)thiazole-4-carboxamide (11)

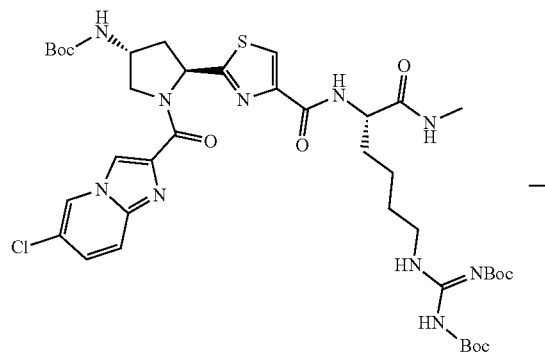

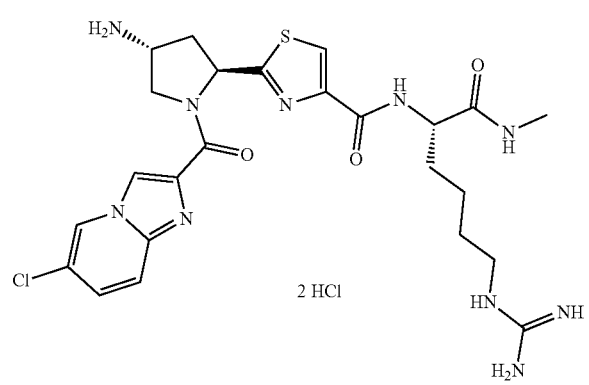

The solution of 2-((2S,4R)-4-(tert-butoxycarbonyl)amino-1-(6-chloroimidazo[1,2-a]pyridine-2-carbonyl) pyrrolidin-2-yl)-N—((S)-6-(2,3-bis(tert-butoxycarbonyl))guanidino-1-(methylamino)-1-oxohexan-2-yl)thiazole-4-carboxamide (80 mg, 0.09 mmol) in hydrochloric acid/Ethyl acetate (3N, 10 mL) was stirred for 2 h at room temperature. The solvent was evaporated and the residue was lyophilized to afford 2-((2S,4R)-4-amino-1-(6-chloroimidazo [1,2-a] pyridine-2-carbonyl)pyrrolidin-2-yl)-N—((S)-6-guanidino-1-(methylamino)-1-oxohexan-2-yl)thiazole-4-carboxamide (40 mg) as yellow solid. MS (ESI) m/z 575.0 [M+H]⁺. ¹H NMR (400 MHz, DMSO) δ 8.97 (d, J=1.2 Hz, 0.75H), 8.91 (s, 0.25H), 8.57 (s, 0.75H), 8.48 (s, 0.25H), 8.24 (s, 0.75H), 8.16 (s, 0.25H), 7.76 (d, J=10.0 Hz, 0.75H), 7.62 (d, J=10.0 Hz, 0.25H), 7.55 (dd, J=1.6; 9.6 Hz, 0.75H), 7.45 (dd, J=1.6; 9.6 Hz, 0.25H), 6.90 (d, J=8.4 Hz, 0.25H), 5.79 (t, J=6.8 Hz, 0.75H), 4.57-3.99 (m, 4.0H), 3.09 (t, J=7.2 Hz, 2.0H), 2.78-2.64 (m, 2.0H), 2.61 (s, 3H), 1.78-1.67 (m, 2H), 1.52-1.43 (m, 2H), 1.35-1.23 (m, 2H).

2-((2S,4R)-4-Amino-1-(6-chloroimidazo[1,2-a]pyridine-2-carbonyl)pyrrolidin-2-yl)-N—((R)-6-guanidino-1-(methylamino)-1-oxohexan-2-yl)thiazole-4-carboxamide (12)

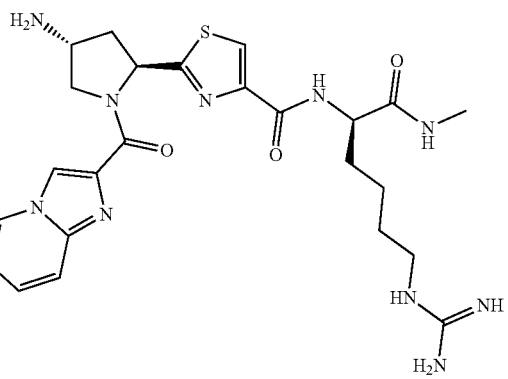

Compound 12 synthesized in a manner analogous to the method used for the synthesis of Compound 11 using (S)-2-amino-6-(2,3-bis(tert-butoxycarbonyl))guanidino-N-methylhexanamide as starting material in Step 9. MS (ESI) m/z 575.0 [M+H]⁺. ¹H NMR (400 MHz, DMSO, mixture of rotamers) δ 9.03 (s, 1H), 8.79-8.76 (br, 3H), 8.63 (s, 1H), 8.25-8.22 (m, 2H), 8.17-8.13 (m, 1H), 7.88-7.78 (m, 2H), 7.66-7.58 (m, 1H), 7.49-7.00 (br, 3H), 5.80 (t, J=7.2 Hz, 1H), 4.57-4.53 (m, 1H), 4.49-4.43 (m, 2H), 4.11-4.00 (m, 1H), 3.10-3.16 (m, 2H), 2.67-2.66 (m, 2H), 2.62 (s, 3H), 1.79-1.72 (m, 2H), 1.49-1.46 (m, 2H), 1.34-1.28 (m, 2H).

2-((2S,4R)-4-Amino-1-(imidazo[1,2-a]pyridine-2-carbonyl)pyrrolidin-2-yl)-N—((S)-6-guanidino-1-(methylamino)-1-oxohexan-2-yl)thiazole-4-carboxamide (13)

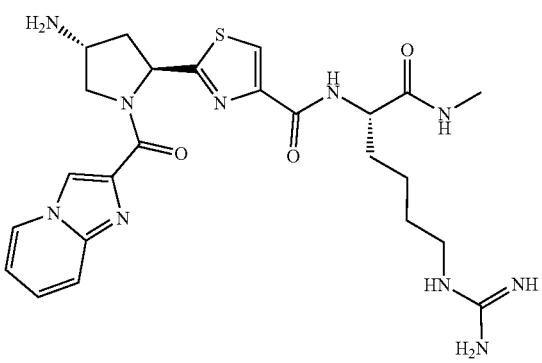 [SMILES: CNC(=O)[C@H](CCCCNC(=N)N)NC(=O)c1csc([C@@H]2C[C@@H](N)CN2C(=O)c2cn3ccccc3n2)n1]

Step 1: Synthesis of ethyl 2-((2S,4R)-4-((((9H-fluoren-9-yl)methoxy)carbonyl)amino)-1-(imidazo[1,2-a]pyridine-2-carbonyl)pyrrolidin-2-yl)thiazole-4-carboxylate

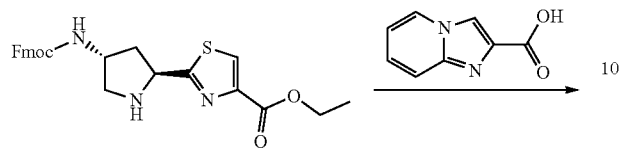

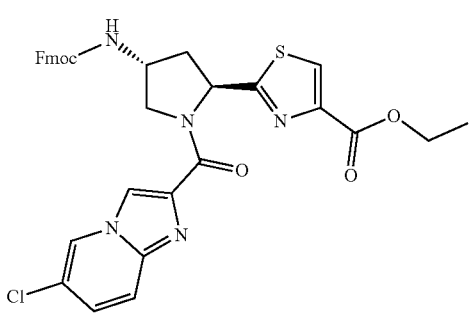

To a solution of imidazo[1,2-a]pyridine-2-carboxylic acid (262 mg, 1.62 mmol) in N,N-dimethylformamide (5 mL) was added 1-[bis(dimethylamino)methylene]-1H-1,2,3-triazolo[4,5-b]pyridinium 3-oxid hexafluorophosphate (HATU, 616 mg, 1.62 mmol), ethyldiisopropylamine (697 mg, 5.40 mmol). The resulting mixture was stirred at room temperature for 30 min. Ethyl 2-((2S,4R)-4-((((9H-fluoren-9-yl) methoxy)carbonyl)amino)pyrrolidin-2-yl)thiazole-4-carboxylate (500 mg, 1.08 mmol) was added. The mixture was stirred at room temperature for 12 h. The mixture was concentrated, dissolved in ethyl acetate, washed with 1 N lithium chloride. The organic layer was concentrated to give ethyl 2-((2S,4R)-4-((((9H-fluoren-9-yl)methoxy)carbonyl)amino)-1-(imidazo[1,2-a]pyridine-2-carbonyl)pyrrolidin-2-yl)thiazole-4-carboxylate as a brown solid. MS(ESI) m/z 608.2 [M+H]$^+$.

Step 2: Synthesis of 2-((2S,4R)-4-amino-1-(imidazo[1,2-a]pyridine-2-carbonyl)pyrrolidin-2-yl) thiazole-4-carboxylic acid

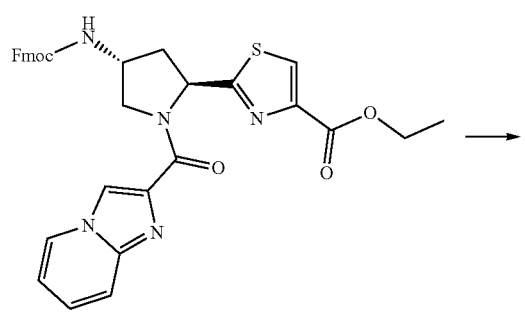

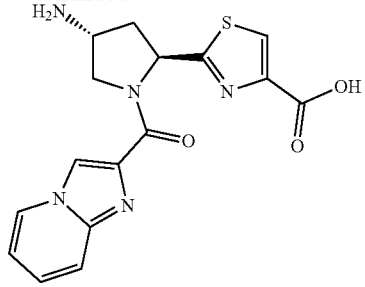

To a solution of ethyl 2-((2S,4R)-4-((((9H-fluoren-9-yl)methoxy)carbonyl)amino)-1-(imidazo[1,2-a]pyridine-2-carbonyl)pyrrolidin-2-yl)thiazole-4-carboxylate (655 mg, 1.08 mmol) in methanol (4 mL) and tetrahydrofuran (4 mL) was added lithium hydroxide (2N, 2.16 mL, 4.32 mmol). The resulting mixture was stirred at room temperature for 12 h. The mixture was concentrated to give 2-((2S,4R)-4-amino-1-(imidazo[1,2-a]pyridine-2-carbonyl)pyrrolidin-2-yl)thiazole-4-carboxylic acid (385 mg crude), which was used directly to next step. MS (ESI) m/z 358.0 [M+H]$^+$ Step 3: Synthesis of 2-((2S,4R)-4-((tert-butoxycarbonyl)amino)-1-(imidazo[1,2-a]pyridine-2-carbonyl)pyrrolidin-2-yl)thiazole-4-carboxylic acid

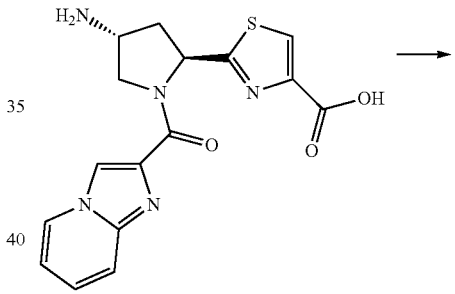

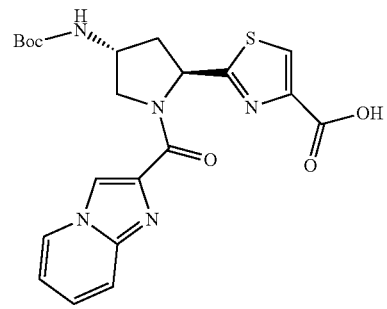

To a solution of 2-((2S,4R)-4-amino-1-(imidazo[1,2-a]pyridine-2-carbonyl)pyrrolidin-2-yl)thiazole-4-carboxylic acid (385 mg, 1.08 mmol) in methanol (4 mL) and tetrahydrofuran (4 mL) was added triethylamine (0.3 mL, 2.16 mmol) and di-tert-butyl dicarbonate (Boc$_2$O, 0.5 mL, 2.16 mmol). The mixture was stirred at room temperature for 2 h. The mixture was concentrated, dissolved in water, added hexanes, extracted with water. The aqueous layer was adjusted to pH 4 with 1N hydrochloric acid, and extracted with ethyl acetate. The combined organic layers were concentrated, purified by RP-LC (Acetonitrile in water: 10% to 95%) to give 2-((2S,4R)-4-((tert-butoxycarbonyl)amino)-1-

(imidazo[1,2-a]pyridine-2-carbonyl)pyrrolidin-2-yl)thiazole-4-carboxylic acid (280 mg) as a white solid. MS(ESI) m/z 458.1 [M+H]+.

Step 4: Synthesis of 2-((2S,4R)-4-(tert-butoxycarbonyl)amino-1-(imidazo[1,2-a]pyridine-2-carbonyl)pyrrolidin-2-yl)-N—((S)-6-(2,3-bis(tert-butoxycarbonyl))guanidino-1-(methylamino)-1-oxohexan-2-yl)thiazole-4-carboxamide Step 5: Synthesis of 2-((2S,4R)-4-amino-1-(imidazo[1,2-a]pyridine-2-carbonyl)pyrrolidin-2-yl)-N—((S)-6-guanidino-1-(methylamino)-1-oxohexan-2-yl)thiazole-4-carboxamide (13)

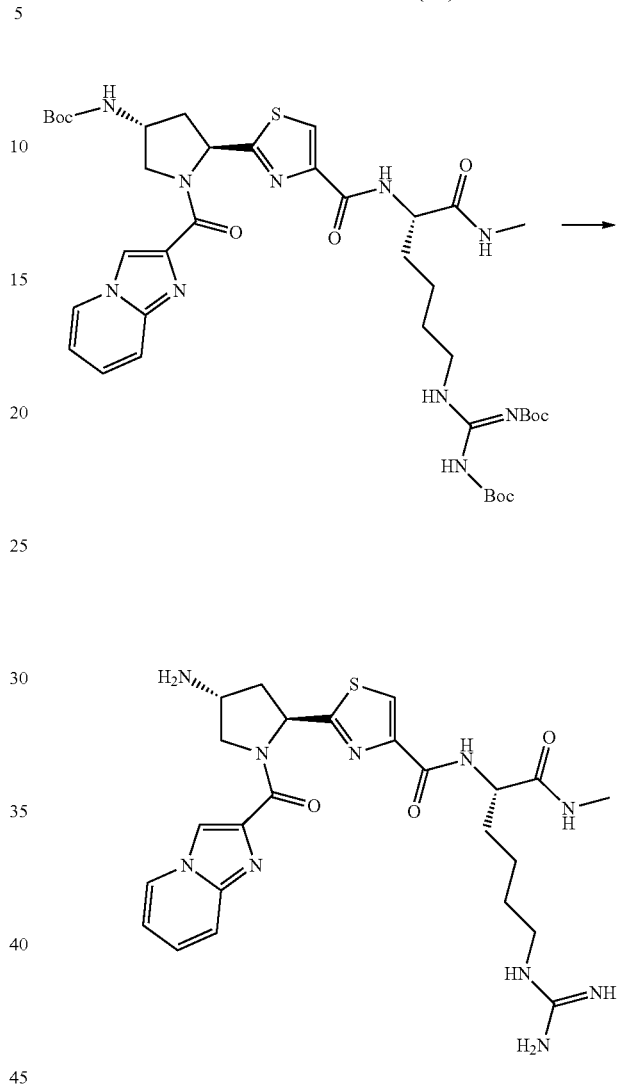

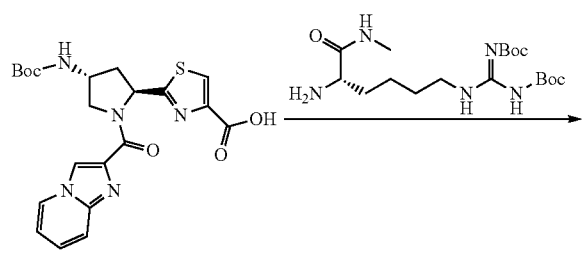

To a solution of 2-((2S,4R)-4-((tert-butoxycarbonyl)amino)-1-(imidazo[1,2-a]pyridine-2-carbonyl)pyrrolidin-2-yl)thiazole-4-carboxylic acid (140 mg, 0.306 mmol) in N,N-dimethyl-formamide (3 mL) was added ethyldiisopropylamine (DIEA, 151 mg, 1.53 mmol), 1-(3-dimethylaminopropyl)-3-ethylcarbodiimide hydrochloride (EDCI, 147 mg, 0.765 mmol) and 1-hydroxybenzotriazole (HOBt, 50 mg, 0.368 mmol). After stirring at room temperature for 0.5 h, (S)-2-amino-6-(2,3-bis(tert-butoxycarbonyl))guanidino-N-methylhexanamide (148 mg, 0.368 mmol) was added and the mixture was stirred at room temperature for 12 h. The mixture was concentrated, dissolved in ethyl acetate, washed with 1N lithium chloride. The organic layer was concentrated and purified by RP-HPLC (ACN/0.1% $NH_3$ in $H_2O$) to give 2-((2S,4R)-4-(tert-butoxycarbonyl)amino-1-(imidazo[1,2-a]pyridine-2-carbonyl)pyrrolidin-2-yl)-N—((S)-6-(2,3-bis(tert-butoxycarbonyl))guanidino-1-(methylamino)-1-oxohexan-2-yl)thiazole-4-carboxamide (110 mg) as a white solid. MS (ESI) m/z 841.4 [M+H]+.

A solution of 2-((2S,4R)-4-(tert-butoxycarbonyl)amino-1-(imidazo[1,2-a]pyridine-2-carbonyl)pyrrolidin-2-yl)-N—((S)-6-(2,3-bis(tert-butoxycarbonyl))guanidino-1-(methylamino)-1-oxohexan-2-yl)thiazole-4-carboxamide (110 mg, 0.131 mmol) in hydrochloric acid/ethyl acetate (3N, 20 mL) was stirred at room temperature for 24 h. The solvent was evaporated and the residue was lyophilized to afford 2-((2S,4R)-4-amino-1-(imidazo[1,2-a]pyridine-2-carbonyl)pyrrolidin-2-yl)-N—((S)-6-guanidino-1-(methylamino)-1-oxohexan-2-yl)thiazole-4-carboxamide 2-((2S,4R)-4-amino-1-(6-chloroimidazo[1,2-a]pyridine-2-carbonyl)pyrrolidin-2-yl)-N—((R)-6-guanidino-1-(methylamino)-1-oxohexan-2-yl)thiazole-4-carboxamide salt (60 mg) as a pink solid. MS (ESI) m/z 541.0 [M+H]+. $^1$H NMR (400 MHz, DMSO, mixture of rotamers) δ 8.89-8.74 (m, 5H), 8.29-8.10 (m, 3H), 7.87-7.63 (m, 3H), 7.56-6.94 (br, 4H), 5.82 (t, J=7.6 Hz, 1H), 4.65-4.36 (m, 4H), 4.15-4.02 (m, 2H), 3.11-3.06 (m, 2H), 2.74-2.63 (m, 2H), 2.60 (d, J=4.4 Hz, 3H), 1.78-1.67 (m, 2H), 1.52-1.43 (m, 2H), 1.35-1.23 (m, 2H).

2-((2S,4R)-4-Amino-1-(1,2-dimethyl-1H-imidazole-4-carbonyl)pyrrolidin-2-yl)-N—((S)-6-guanidino-1-(methylamino)-1-oxohexan-2-yl)thiazole-4-carboxamide (14)

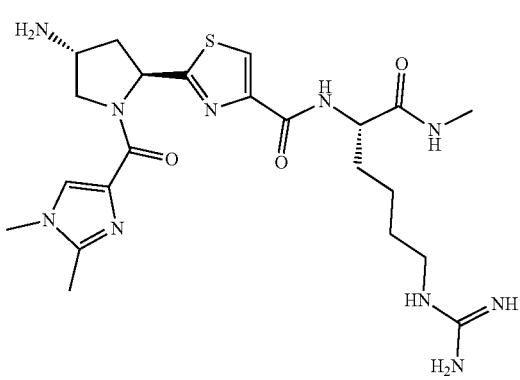 [SMILES: CNC(=O)[C@H](CCCCNC(=N)N)NC(=O)c1csc([C@@H]2C[C@@H](N)CN2C(=O)c2cn(C)c(C)n2)n1]

Step 1: Synthesis of ethyl 2-((2S,4R)-4-((((9H-fluoren-9-yl)methoxy)carbonyl)amino)-1-(1,2-dimethyl-1H-imidazole-4-carbonyl)pyrrolidin-2-yl)thiazole-4-carboxylate

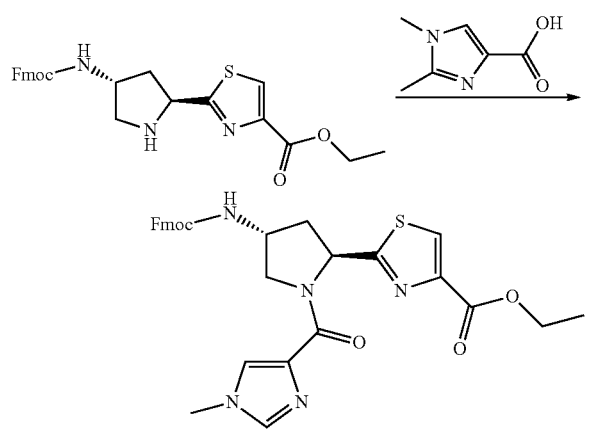

To a solution of 1,2-dimethyl-1H-imidazole-4-carboxylic acid (200 mg, 1.4 mmol) in N,N-dimethyl-formamide (5 mL) at 25° C. was added 1-[Bis(dimethylamino)methylene]-1H-1,2,3-triazolo[4,5-b]pyridinium 3-oxid hexafluorophosphate (HATU, 814 mg, 2.1 mmol) and ethyldiisopropylamine (553 mg, 4.3 mmol). The mixture stirred at room temperature for 20 mins, and then ethyl 2-((2S,4R)-4-((((9H-fluoren-9-yl)methoxy)carbonyl)amino)pyrrolidin-2-yl)thiazole-4-carboxylate (500 g, 1.1 mmol) was added. The mixture was stirred for 2 h and concentrated. The residue was diluted with 20 mL water, extracted with ethyl acetate (30 mL×3), washed with 1 N lithium chloride (20 mL×3). The organic layer was dried with over anhydrous sodium sulphate and concentrated to afford ethyl 2-((2S,4R)-4-((((9H-fluoren-9-yl)methoxy)carbonyl)amino)-1-(1,2-dimethyl-1H-imidazole-4-carbonyl)pyrrolidin-2-yl)thiazole-4-carboxylate (837 mg) as brown oil which was used without further purification. MS (ESI) m/z 586.1 [M+H]$^+$.

Step 2: Synthesis of 2-((2S,4R)-4-amino-1-(1,2-dimethyl-1H-imidazole-4-carbonyl)pyrrolidin-2-yl)thiazole-4-carboxylic acid

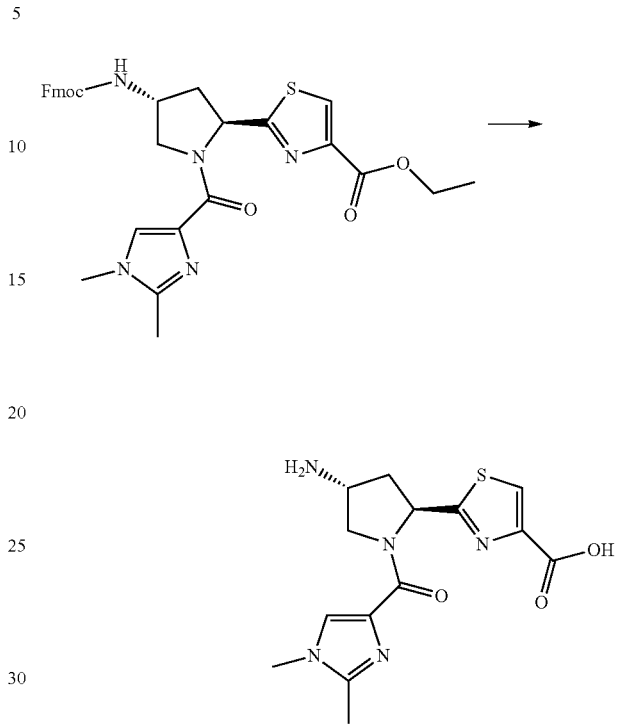

To a solution of ethyl 2-((2S,4R)-4-((((9H-fluoren-9-yl)methoxy)carbonyl)amino)-1-(1,2-dimethyl-1H-imidazole-4-carbonyl)pyrrolidin-2-yl)thiazole-4-carboxylate (900 mg, 0.6 mmol) in methanol (5 mL), tetrahydrofuran (5 mL) and water (1 mL) at 25° C. was added lithium hydroxide (1.3 mL, 2.6 mmol). After addition, the resulting mixture was stirred for 16 h at room temperature. The mixture was concentrated to afford 2-((2S,4R)-4-amino-1-(1,2-dimethyl-1H-imidazole-4-carbonyl)pyrrolidin-2-yl)thiazole-4-carboxylic acid as a solution in water which was used without further purification. MS (ESI) m/z 336.2 [M+H]$^+$.

Step 3: Synthesis of 2-((2S,4R)-4-((tert-butoxycarbonyl)amino)-1-(1,2-dimethyl-1H-imidazole-4-carbonyl)pyrrolidin-2-yl)thiazole-4-carboxylic acid

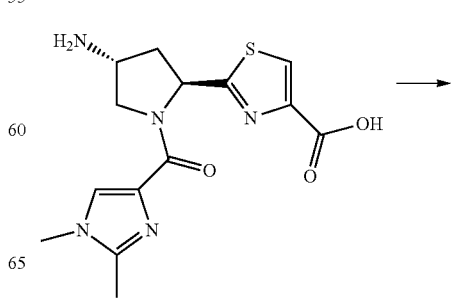

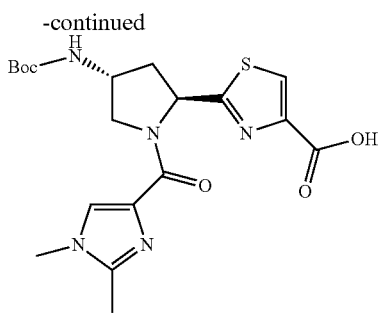

To a solution of 2-((2S,4R)-4-amino-1-(1,2-dimethyl-1H-imidazole-4-carbonyl) pyrrolidin-2-yl)thiazole-4-carboxylic acid (0.6 mmol) in water (2 mL) and methanol (8 mL) at 25° C., was added 4-dimethylaminopyridine (117 mg, 1.0 mmol) and di-tert-butyl dicarbonate (Boc₂O, 207 mg, 1.0 mmol). The resulting mixture was stirred for 4 h at room temperature and concentrated, diluted with water (40 mL) and the mixture was extracted with petroleum ether (40 mL×3). The aqueous layer was adjusted pH-6 with Hydrochloride (2N) and concentrated. The residue was purified by RP-LC (acetonitrile in water: 10% to 95%) to give 2-((2S,4R)-4-((tert-butoxycarbonyl)amino)-1-(1,2-dimethyl-1H-imidazole-4-carbonyl)pyrrolidin-2-yl)thiazole-4-carboxylic acid (140 mg) as white solid. MS (ESI) m/z 436.2 [M+H]⁺.

Step 4: Synthesis of 2-((2S,4R)-4-(tert-butoxycarbonyl)amino-1-(1,2-dimethyl-1H-imidazole-4-carbonyl)pyrrolidin-2-yl)-N—((S)-6-(2,3-bis(tert-butoxycarbonyl))guanidino-1-(methylamino)-1-oxohexan-2-yl)thiazole-4-carboxamide

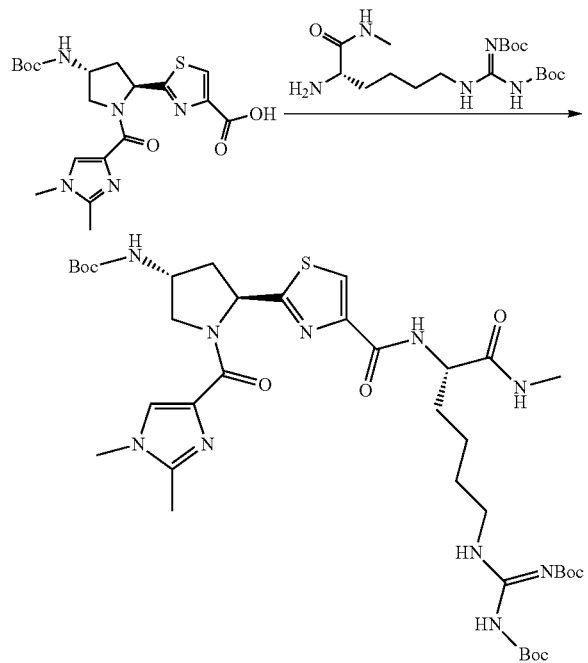

To a solution of 2-((2S,4R)-4-((tert-butoxycarbonyl)amino)-1-(1,2-dimethyl-1H-imidazole-4-carbonyl)pyrrolidin-2-yl)thiazole-4-carboxylic acid (8, 100 mg, 0.2 mmol) in N,N-dimethyl-formamide (3 mL) at 25° C. was added 1-[Bis(dimethylamino)methylene]-1H-1,2,3-triazolo[4,5-b]pyridinium 3-oxid hexafluorophosphate (HATU, 131 mg, 0.4 mmol) and ethyldiisopropylamine (89 mg, 0.7 mmol). The mixture stirred at room temperature for 20 min. Then (S)-2-amino-6-(2,3-bis(tert-butoxycarbonyl))guanidino-N-methylhexanamide (100 mg, 0.3 mmol) was added, and the mixture was stirred for 2 h at 25° C. The solvent was removed and the residue was purified by RP-HPLC (ACN/0.1% NH₃ in H₂O) to afford 2-((2S,4R)-4-(tert-butoxycarbonyl)amino-1-(1,2-dimethyl-1H-imidazole-4-carbonyl)pyrrolidin-2-yl)-N—((S)-6-(2,3-bis(tert-butoxycarbonyl))guanidino-1-(methylamino)-1-oxohexan-2-yl)thiazole-4-carboxamide (130 mg) as white solid. ¹H NMR (400 MHz, DMSO, mixture of rotamers) δ 11.49 (s, 1H), 8.29-8.26 (m, 1H), 8.13 (s, 1H), 8.09-8.02 (m, 2H), 7.65-7.62 (m, 1H), 7.33-7.23 (m, 1H), 5.58 (t, J=6.8 Hz, 1H), 4.44-3.92 (m, 4H), 3.59-3.53 (m, 3H), 3.28-3.23 (m, 2H), 2.60 (d, J=8.4 Hz, 3H), 2.32-2.16 (m, 5H), 1.78-1.65 (m, 2H), 1.52-1.24 (m, 31H).

Step 5: Synthesis of 2-((2S,4R)-4-amino-1-(1,2-dimethyl-1H-imidazole-4-carbonyl)pyrrolidin-2-yl)-N—((S)-6-guanidino-1-(methylamino)-1-oxohexan-2-yl)thiazole-4-carboxamide (14)

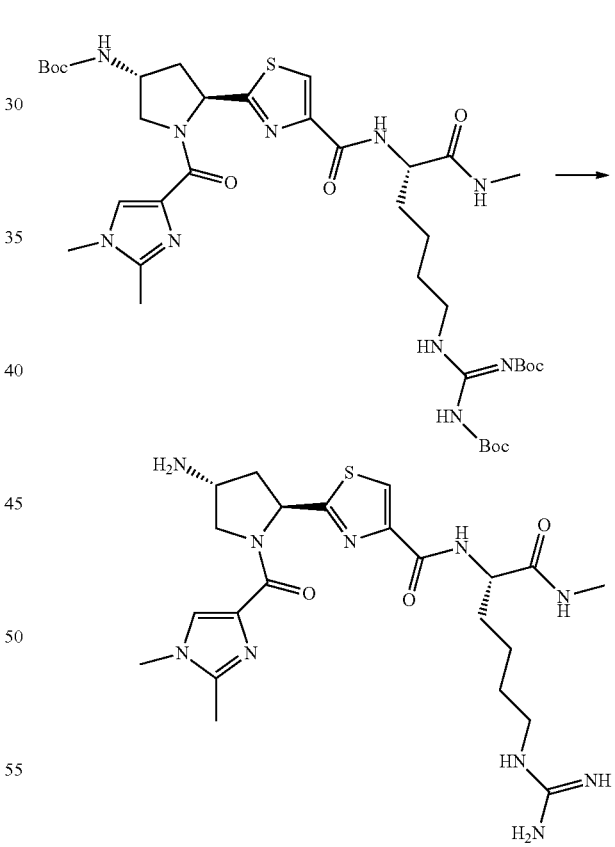

A solution of 2-((2S,4R)-4-(tert-butoxycarbonyl)amino-1-(1,2-dimethyl-1H-imidazole-4-carbonyl)pyrrolidin-2-yl)-N—((S)-6-(2,3-bis(tert-butoxycarbonyl))guanidino-1-(methylamino)-1-oxohexan-2-yl)thiazole-4-carboxamide (130 mg, 0.16 mmol) in hydrochloric acid/Ethyl acetate (3N, 10 mL) was stirred for 4 h at 25° C. T The solvent was evaporated and the residue was lyophilized to afford 2-((2S,4R)-4-amino-1-(1,2-dimethyl-1H-imidazole-4-carbonyl)

pyrrolidin-2-yl)-N—((S)-6-guanidino-1-(methylamino)-1-oxohexan-2-yl)thiazole-4-carboxamide hydrochloride salt (65 mg) as yellow solid. MS (ESI) m/z 519.1 [M+H]⁺. ¹H NMR (400 MHz, DMSO, mixture of rotamers) δ 8.85 (s, 3H), 8.40 (s, 1H), 8.26-8.22 (m, 2H), 8.13 (d, J=8.4 Hz, 1H), 7.84 (s, 1H), 7.49-7.05 (br, 2H), 5.77 (t, J=7.2 Hz, 1H), 4.46-4.11 (m, 4H), 3.99-3.91 (br, 3H), 3.79 (s, 3H), 3.12-3.07 (m, 2H), 2.77-2.60 (m, 8H), 1.80-1.72 (m, 2H), 1.49-1.46 (m, 2H), 1.33-1.29 (m, 2H).

2-((2S,4R)-4-Amino-1-benzoylpyrrolidin-2-yl)-N—((S)-6-guanidino-1-(methylamino)-1-oxohexan-2-yl)thiazole-4-carboxamide (15)

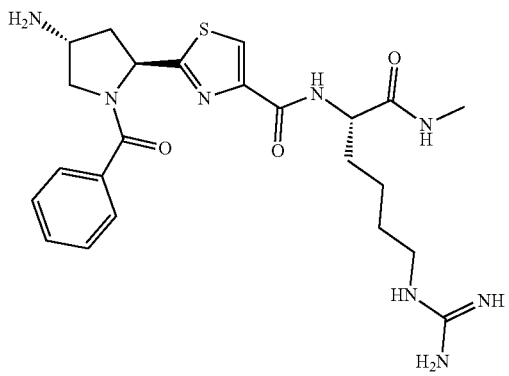 [SMILES: CNC(=O)[C@H](CCCCNC(=N)N)NC(=O)c1csc([C@@H]2C[C@@H](N)CN2C(=O)c2ccccc2)n1]

Compound 15 was synthesized in a manner analogous to the method used for the synthesis of Compound 14, using benzoic acid in Step 1. MS (ESI) m/z 501.0. [M+H]⁺ ¹H NMR (400 MHz, DMSO, mixture of rotamers) δ 8.71-8.45 (m, 3H), 8.25-8.11 (m, 3H), 7.85-7.29 (m, 10H), 5.76-6.65 (m, 1H), 4.48-4.39 (m, 1H), 4.15-4.11 (m, 1H), 3.95-3.94 (m, 1H), 3.71-3.63 (m, 2H), 3.08 (q, J=6.4 Hz, 2H), 2.75-2.69 (m, 1H), 2.62 (s, 3H), 1.77-1.66 (m, 2H), 1.50-1.41 (m, 2H), 1.37-1.24 (m, 2H).

(2S,4R)-3-Chlorobenzyl 4-amino-2-(4-(((S)-6-guanidino-1-(methylamino)-1-oxohexan-2-yl)carbamoyl)thiazol-2-yl)pyrrolidine-1-carboxylate (16)

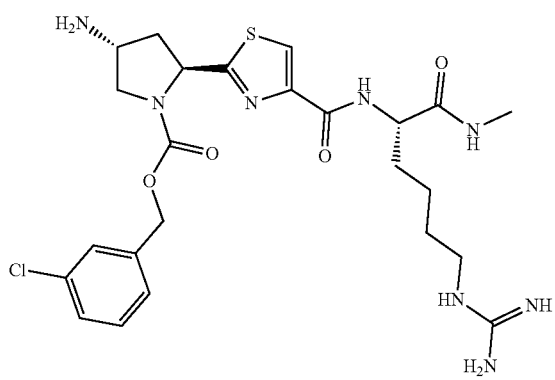 [SMILES: CNC(=O)[C@H](CCCCNC(=N)N)NC(=O)c1csc([C@@H]2C[C@@H](N)CN2C(=O)OCc2cccc(Cl)c2)n1]

Compound 16 was synthesized in a manner analogous to the method used for the synthesis of Compound 14, beginning at step 2, using ethyl 2-((2S,4R)-4-((((9H-fluoren-9-yl)methoxy)carbonyl)amino)-1-(((3-chlorobenzyl)oxy)carbonyl)pyrrolidin-2-yl)thiazole-4-carboxylate. MS (ESI) m/z 565.0 [M+H]⁺. ¹H NMR (400 MHz, DMSO, mixture of rotamers) δ 8.73 (s, 3H), 8.25-8.06 (m, 3H), 7.81-7.79 (m, 1H), 7.49-6.97 (br, 9H), 5.53-5.42 (m, 1H), 5.13-4.97 (m, 2H), 4.44-4.42 (m, 1H), 3.93-3.79 (m, 3H), 3.08 (s, 2H), 2.68-2.37 (m, 5H), 1.76-1.71 (m, 2H), 1.49-1.46 (m, 2H), 1.36-1.21 (m, 2H).

Synthesis of ethyl 2-((2S,4R)-4-((((9H-fluoren-9-yl)methoxy)carbonyl)amino)-1-(((3-chlorobenzyl)oxy)carbonyl)pyrrolidin-2-yl)thiazole-4-carboxylate

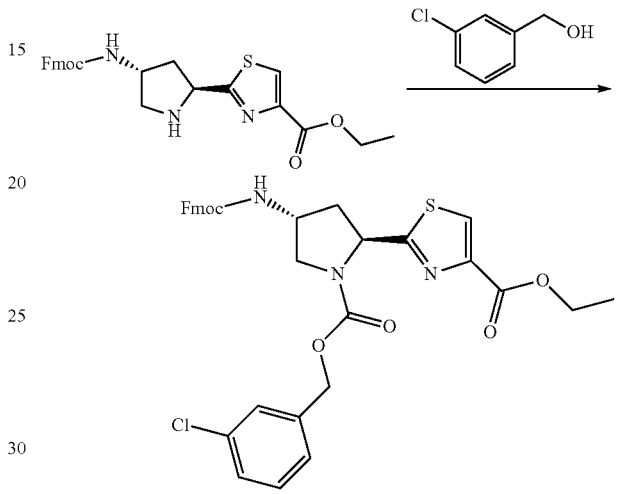

To a solution of (3-chloro-phenyl)-methanol (149 mg, 1.04 mmol) in dichloromethane (4 mL) was added 1,1'-carbonyldiimidazole (CDI, 169 mg, 1.04 mmol). The resulting mixture was stirred at room temperature for 3 h. Then ethyl 2-((2S,4R)-4-((((9H-fluoren-9-yl)methoxy)carbonyl)amino)pyrrolidin-2-yl)thiazole-4-carboxylate (400 mg, 0.864 mmol) was added. The mixture was stirred at room temperature for 24 h. The mixture was concentrated and purified by silica column chromatography (petroleum ether: ethyl acetate=4:1) to give ethyl 2-((2S,4R)-4-((((9H-fluoren-9-yl)methoxy)carbonyl)amino)-1-(((3-chlorobenzyl)oxy)carbonyl)pyrrolidin-2-yl)thiazole-4-carboxylate (356 mg) as white solid. MS (ESI) m/z 632.1 [M+H]⁺.

2-((2S,4R)-4-Amino-1-(cyclohexanecarbonyl)pyrrolidin-2-yl)-N—((S)-6-guanidino-1-(methylamino)-1-oxohexan-2-yl)thiazole-4-carboxamide (17)

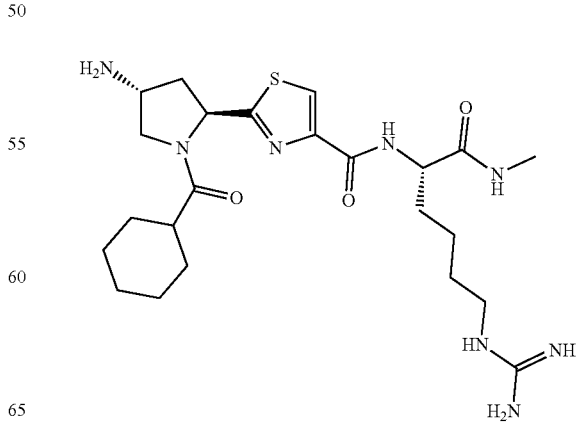

Compound 17 was synthesized in a manner analogous to the method used for the synthesis of Compound 14, using cyclohexanecarboxylic acid in Step 1. MS (ESI) m/z 507.3 [M+H]⁺. ¹H NMR (400 MHz, DMSO, mixture of rotamers) δ 8.85-8.07 (m, 8H), 7.82-6.97 (m, 4H), 5.82-5.47 (m, 1H), 4.44 (q, J=5.6 Hz, 1H), 4.04-3.76 (m, 3H), 3.11-3.08 (m, 2H), 2.61 (d, J=4.4 Hz, 3H), 2.57-2.34 (m, 3H), 1.78-1.63 (m, 6H), 1.49-1.45 (m, 2H), 1.40-1.16 (m, 8H).

2-((2S,4R)-4-Amino-1-isobutyrylpyrrolidin-2-yl)-N—((S)-6-guanidino-1-(methylamino)-1-oxohexan-2-yl)thiazole-4-carboxamide (18)

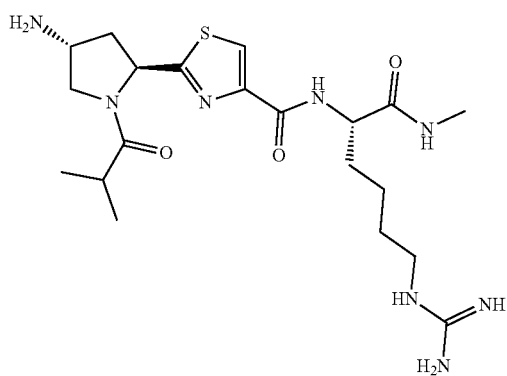 [SMILES: CNC(=O)[C@H](CCCCNC(=N)N)NC(=O)c1csc([C@@H]2C[C@@H](N)CN2C(=O)C(C)C)n1]

Compound 18 was synthesized in a manner analogous to the method used for the synthesis of Compound 14, using isobutyric acid in Step 1. MS (ESI) m/z 467.1 [M+H]⁺. ¹H NMR (400 MHz, DMSO, mixture of rotamers) δ 8.63 (br, 3H), 8.21 (s, 1H), 8.11-8.05 (m, 1H), 7.75-7.69 (m, 1H), 7.50-7.20 (br, 2H), 5.51-5.48 (m, 1H), 4.47-4.42 (m, 1H), 4.02-3.72 (m, 7H), 3.10-3.05 (m, 2H), 2.76-2.71 (m, 1H), 2.61 (d, J=4.4 Hz, 3H), 2.57-2.53 (m, 2H), 1.82-1.62 (m, 2H), 1.50-1.45 (m, 2H), 1.33-1.23 (m, 2H).

2-((2S,4R)-4-Amino-1-(6-(trifluoromethyl)imidazo[1,2-a]pyridine-2-carbonyl)pyrrolidin-2-yl)-N—((S)-6-guanidino-1-(methylamino)-1-oxohexan-2-yl)thiazole-4-carboxamide (19)

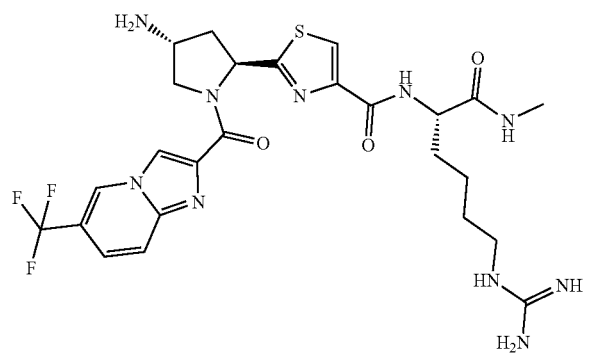 [SMILES: CNC(=O)[C@H](CCCCNC(=N)N)NC(=O)c1csc([C@@H]2C[C@@H](N)CN2C(=O)c2cn3cc(C(F)(F)F)ccc3n2)n1]

Compound 19 was synthesized in a manner analogous to the method used for the synthesis of Compound 14, using 6-trifluoromethyl-imidazo[1,2-a]pyridine-2-carboxylic acid in Step 1. MS (ESI) m/z 609.0 [M+H]⁺. ¹H NMR (400 MHz, DMSO, mixture of rotamers) δ 9.35-9.30 (m, 1H), 8.71-8.59 (m, 4H), 8.23-8.07 (m, 3H), 7.90-7.74 (m, 2H), 7.66-7.56 (m, 2H), 7.55-6.78 (m, 4H), 5.80 (t, J=6.8 Hz, 1H), 4.60-4.40 (m, 3H), 4.17-4.15 (m, 1H), 3.17-3.07 (m, 2H), 2.76-2.60 (m, 5H), 1.78-1.70 (m, 2H), 1.50-1.45 (m, 2H), 1.36-1.30 (m, 2H).

2-((2S,4R)-4-Amino-1-(6-methoxyimidazo[1,2-a]pyridine-2-carbonyl)pyrrolidin-2-yl)-N—((S)-6-guanidino-1-(methylamino)-1-oxohexan-2-yl)thiazole-4-carboxamide (20)

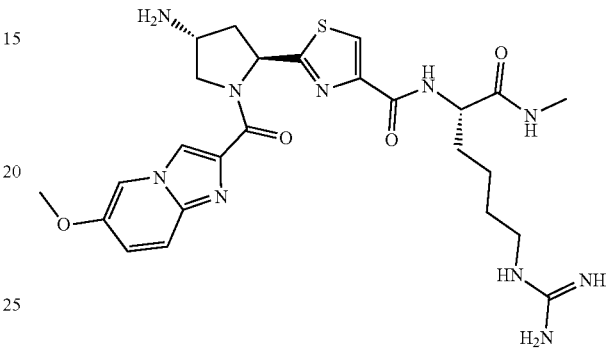

Compound 20 was synthesized in a manner analogous to the method used for the synthesis of Compound 14, using 6-methoxyimidazo[1,2-a]pyridine-2-carboxylic acid in Step 1. MS (ESI) m/z 571.0 [M+H]⁺. ¹H NMR (400 MHz, DMSO, mixture of rotamers) δ 8.80 (br, 4H), 8.60-8.52 (m, 1H), 8.26-8.10 (m, 3H), 7.90-7.74 (m, 2H), 7.65-7.56 (m, 1H), 7.42 (br, 3H), 5.82 (t, J=6.4 Hz, 1H), 4.53-4.35 (m, 4H), 4.17 (s, 2H), 3.88 (s, 3H), 3.14-3.06 (m, 2H), 2.80-2.65 (m, 2H), 2.61-2.59 (m, 3H), 1.82-1.68 (m, 2H), 1.52-1.42 (m, 2H), 1.38-1.26 (m, 2H).

2-((2S,4R)-4-Amino-1-(6-iodoimidazo[1,2-a]pyridine-2-carbonyl) pyrrolidin-2-yl)-N—((S)-6-guanidino-1-(methylamino)-1-oxohexan-2-yl)thiazole-4-carboxamide (21)

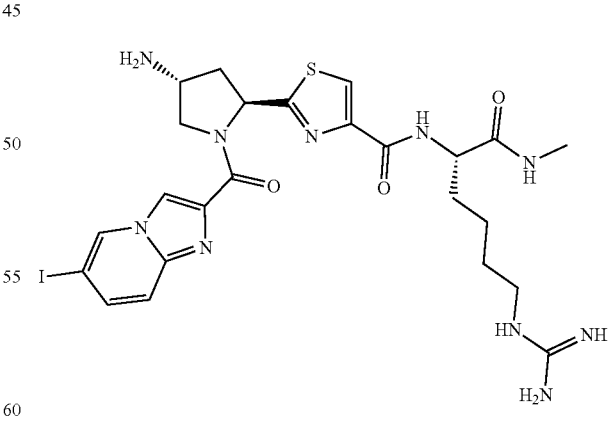

Compound 21 was synthesized in a manner analogous to the method used for the synthesis of 14, using 6-iodoimidazo[1,2-a]pyridine-2-carboxylic acid in Step 1. MS(ESI) m/z 666.9. [M+H]⁺. ¹H NMR (400 MHz, DMSO, mixture of rotamers) δ 9.14 (s, 1H), 8.78 (br, 3H), 8.61 (s, 1H), 8.24 (s, 2H), 8.20-8.09 (m, 1H), 7.90-7.74 (m, 2H), 7.70-7.56 (m, 1H), 7.52-6.72 (m, 3H), 5.80 (t, J=6.0 Hz, 1H), 4.60-4.50 (m, 2H), 4.48-4.40 (m, 4H), 4.03 (s, 1H), 3.15-3.05 (m, 2H), 2.80-2.62 (m, 2H), 2.60 (s, 3H), 1.85-1.65 (m, 2H), 1.52-1.40 (m, 2H), 1.38-1.26 (m, 2H).

Synthesis of 2-((2S,4R)-4-amino-1-(6-chloroimidazo[1,2-a]pyridine-2-carbonyl) pyrrolidin-2-yl)-N—((S)-1-amino-6-guanidino-1-oxohexan-2-yl)thiazole-4-carboxamide (22)

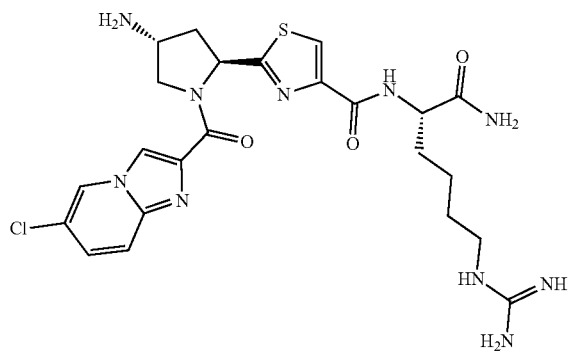 [SMILES: N=C(N)NCCCC[C@H](NC(=O)c1csc([C@@H]2C[C@@H](N)CN2C(=O)c2cn3cc(Cl)ccc3n2)n1)C(N)=O]

Compound 22 was synthesized in a manner analogous to the method used for the synthesis of 14, using (S)-2-amino-6-(2,3-bis(tert-butoxycarbonyl)guanidino)-hexanamide in Step 9. MS (ESI) m/z 561.0 [M+H]⁺. ¹H NMR (400 MHz, DMSO, mixture of rotamers) δ 9.06 (s, 1H), 8.80-8.76 (m, 3H), 8.66 (s, 1H), 8.25 (s, 1H), 8.17-8.12 (m, 1H), 7.86-7.80 (m, 2H), 7.37 (br, 1H), 7.66-7.62 (m, 1H), 7.54-6.80 (br, 6H), 5.80 (t, J=7.2 Hz, 1H), 4.55-4.42 (m, 3H), 4.12-4.11 (m, 1H), 3.13-3.08 (m, 2H), 2.74-2.62 (m, 2H), 1.83-1.73 (m, 2H), 1.50-1.47 (m, 2H), 1.34-1.23 (m, 2H).

(S)-2-(2-((2S,4R)-4-Amino-1-(6-chloroimidazo[1,2-a]pyridine-2-carbonyl)pyrrolidin-2-yl)thiazole-4-carboxamido)-6-guanidinohexanoic acid (23)

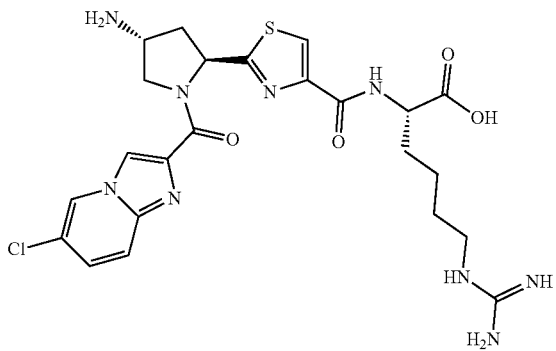 [SMILES: N=C(N)NCCCC[C@H](NC(=O)c1csc([C@@H]2C[C@@H](N)CN2C(=O)c2cn3cc(Cl)ccc3n2)n1)C(=O)O]

Step 1: Synthesis of (S)-methyl 2-(2-((2S,4R)-4-(tert-butoxycarbonyl)amino-1-(6-chloroimidazo[1,2-a]pyridine-2-carbonyl)pyrrolidin-2-yl)thiazole-4-carboxamido)-6-(2,3-bis(tert-butoxycarbonyl)guanidine-hexanoate

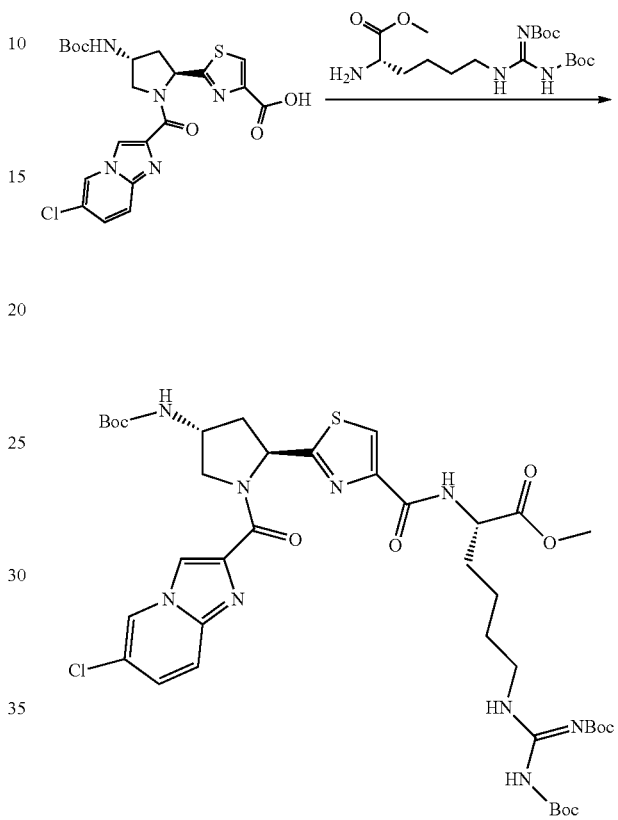

To a solution of 2-((2R,4R)-4-((tert-butoxycarbonyl)amino)-1-(7-chloroimidazo[1,2-a]pyridine-2-carbonyl)pyrrolidin-2-yl)thiazole-4-carboxylic acid (150 mg, 0.305 mmol) in N,N-dimethylformamide (10 mL) at 25° C. was added (S)-methyl 2-amino-6-(2,3-bis(tert-butoxycarbonyl)guanidino)hexanoate ((S)-2, 122 mg, 0.305 mmol), ethyldiisopropylamine (DIEA, 179 mg, 0.915 mmol), 1-(3-Dimethylaminopropyl)-3-ethylcarbodiimide hydrochloride (EDCI, 146 mg, 0.762 mmol) and 1-Hydroxybenzotriazole (HOBt, 42 mg, 0.305 mmol). The resulting mixture was stirred overnight. The solvent was removed and the residue was diluted with 50 mL water, extracted with ethyl acetate (30 mL×3). The combined organic layers were dried over anhydrous sodium sulphate and concentrated. The residues were purified by Prep-TLC (methanol:dichloro-methane=1:15) to give (S)-methyl 2-(2-((2S,4R)-4-(tert-butoxycarbonyl)amino-1-(6-chloroimidazo[1,2-a]pyridine-2-carbonyl)pyrrolidin-2-yl)thiazole-4-carboxamido)-6-(2,3-bis(tert-butoxycarbonyl)guanidinohexanoate (70 mg) as white solid. MS (ESI) m/z 876.4 [M+H]⁺.

Step 2: Synthesis of (S)-2-(2-((2S,4R)-4-amino-1-(6-chloroimidazo[1,2-a]pyridine-2-carbonyl) pyrrolidin-2-yl)thiazole-4-carboxamido)-6-guanidinohexanoic acid (23)

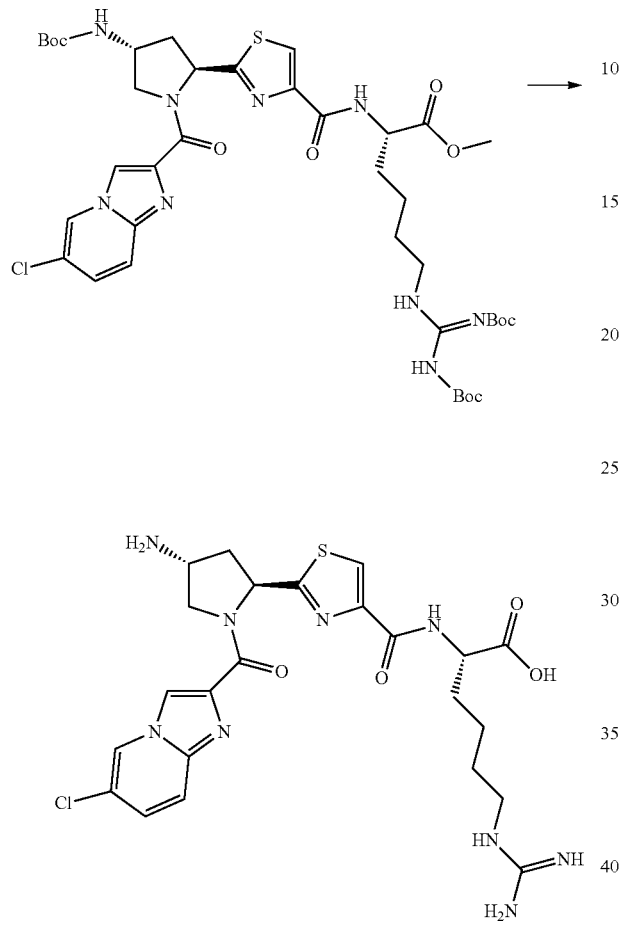

To a solution of (S)-methyl 2-(2-((2S,4R)-4-(tert-butoxycarbonyl)amino-1-(6-chloroimidazo[1,2-a]pyridine-2-carbonyl)pyrrolidin-2-yl)thiazole-4-carboxamido)-6-(2,3-bis(tert-butoxycarbonyl)guanidinohexanoate (70 mg, 0.080 mmol) in 5 mL of methanol and 5 mL of tetrahydrofuran, was added lithium hydroxide (13 mg, 0.024 mmol) in 5 mL of water. After 1 h, LCMS show the reaction was completed and the mixture was concentrated. The residue was dissolved in dichloromethane (5 mL) and hydrochloric acid/Ethyl acetate (3N, 10 mL) was added. The resulting mixture was stirred for 6 h and concentrated. The residues were purified by RP-HPLC (ACN/0.1% TFA in H$_2$O) to afford (S)-2-(2-((2S,4R)-4-amino-1-(6-chloroimidazo[1,2-a]pyridine-2-carbonyl)pyrrolidin-2-yl)thiazole-4-carboxamido)-6-guanidinohexanoic acid hydrochloride salt (30 mg) as white solid. MS (ESI) m/z 561.9 [M+H]$^+$. $^1$H NMR (400 MHz, DMSO, mixture of rotamers) δ 9.01 (s, 1H), 8.64 (s, 1H), 8.52-8.45 (m, 1H), 8.22 (br, 2H), 8.09-8.07 (m, 1H), 7.83-7.81 (m, 2H), 7.65-7.62 (m, 1H), 7.55-6.80 (m, 5H), 5.72 (t, J=6.4 Hz, 1H), 4.80-4.44 (m, 3H), 4.03-4.01 (m, 1H), 3.10-3.08 (m, 2H), 2.61 (s, 3H), 2.45-2.41 (m, 2H), 1.82 (s, 3H), 1.81-1.72 (m, 2H), 1.49-1.46 (m, 2H), 1.33-1.30 (m, 2H).

2-((2S,4R)-4-Amino-1-(6-chloroimidazo[1,2-a]pyridine-2-carbonyl)pyrrolidin-2-yl)-N—((S)-1-(dimethylamino)-6-guanidino-1-oxohexan-2-yl)thiazole-4-carboxamide (24)

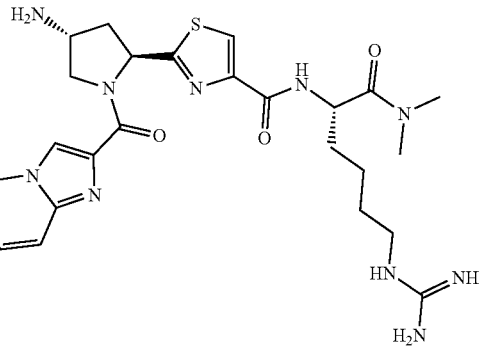

Compound 24 was synthesized in a manner analogous to the method used for the synthesis of Compound 11, using (S)-2-amino-6-(2,3-bis(tert-butoxycarbonyl)guanidino)-N,N-dimethylhexanamide in Step 9. MS (ESI) m/z 589.0 [M+H]$^+$. 1H NMR (400 MHz, DMSO, mixture of rotamers) δ 9.04 (s, 1H), 8.80-8.76 (m, 3H), 8.63 (s, 1H), 8.24 (s, 1H), 8.18-8.17 (m, 1H), 7.93-7.86 (m, 1H), 7.80 (d, J=9.6 Hz, 1H), 7.63-7.53 (m, 1H), 7.54-6.80 (br, 4H), 5.79 (t, J=7.2 Hz, 1H), 4.93-4.88 (m, 1H), 4.56-4.36 (m, 2H), 4.10-4.08 (m, 1H), 3.12-3.04 (m, 2H), 3.08 (s, 3H), 2.86 (s, 3H), 2.73-2.59 (m, 2H), 1.77-1.67 (m, 2H), 1.51-1.44 (m, 2H), 1.37-1.30 (m, 2H).

2-((2S,4R)-4-Amino-1-(6-chloroimidazo[1,2-a]pyridine-2-carbonyl)pyrrolidin-2-yl)-N—((S)-6-amino-1-(methylamino)-1-oxohexan-2-yl)thiazole-4-carboxamide (25)

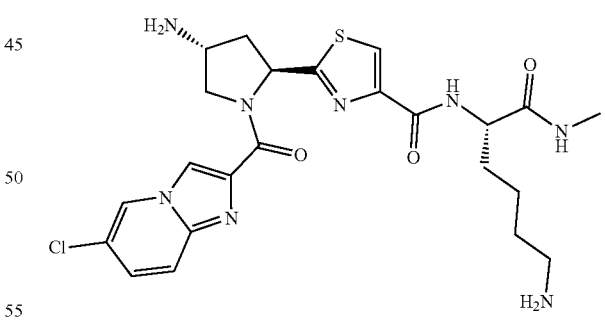

Compound 25 was synthesized by the same reaction sequence as Compound 11, using tert-butyl (S)-(5-amino-6-(methylamino)-6-oxohexyl)carbamate in Step 9. MS (ESI) m/z 533.0 [M+H]$^+$. $^1$H NMR (400 MHz, DMSO, mixture of rotamers) δ 9.04 (s, 1H), 8.80 (br, 3H), 8.63 (s, 1H), 8.24-8.20 (m, 2H), 8.16-8.08 (m, 3H), 7.81-7.79 (m, 1H), 7.62-7.60 (m, 1H), 5.80 (t, J=6.0 Hz, 1H), 4.56-4.53 (m, 1H), 4.45-4.42 (m, 2H), 4.13-4.02 (m, 1H), 2.74-2.60 (m, 7H), 1.81-1.72 (m, 2H), 1.59-1.58 (m, 2H), 1.36-1.32 (m, 2H).

N—((S)-6-Acetamido-1-(methylamino)-1-oxohexan-2-yl)-2-((2S,4R)-4-amino-1-(6-chloroimidazo[1,2-a]pyridine-2-carbonyl)pyrrolidin-2-yl)thiazole-4-carboxamide (26)

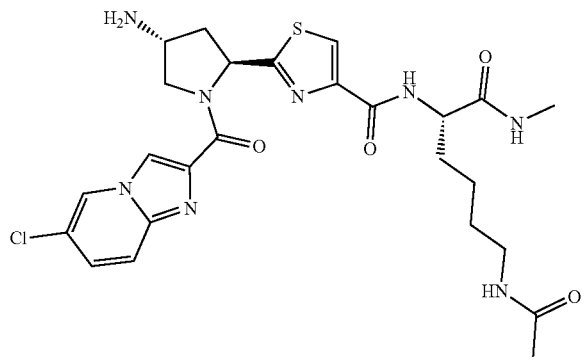 [SMILES: CNC(=O)[C@H](CCCCNC(C)=O)NC(=O)c1csc([C@@H]2C[C@@H](N)CN2C(=O)c2cn3cc(Cl)ccc3n2)n1]

Compound 26 was synthesized in a manner analogous to the method used for the synthesis of Compound 11, using (S)-6-acetamido-2-amino-N-methylhexanamide in Step 9. MS (ESI) m/z 575.0 [M+H]$^+$. $^1$H NMR (400 MHz, DMSO, mixture of rotamers) δ 8.97 (d, J=0.8 Hz, 1H), 8.74-8.67 (m, 3H), 8.55 (d, J=9.6 Hz, 1H), 8.24 (d, J=10.4 Hz, 1H), 8.16-8.08 (m, 2H), 7.93 (br, 1H), 7.77 (d, J=9.6 Hz, 1H), 7.56-7.53 (m, 1H), 5.80-5.65 (m, 1H), 4.69-4.00 (m, 4H), 3.00-2.97 (m, 2H), 2.86-2.59 (m, 5H), 1.78-1.70 (m, 5H), 1.41-1.23 (m, 4H).

Step 1: Synthesis of (S)-benzyl (6-amino-1-(methylamino)-1-oxohexan-2-yl)carbamate

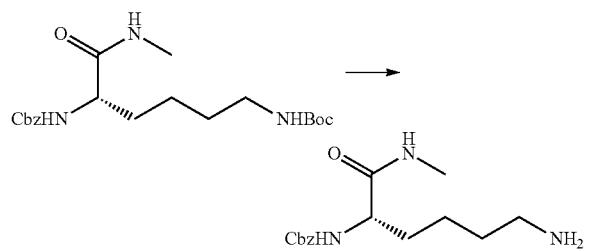

To a solution of (S)-benzyl tert-butyl (6-(methylamino)-6-oxohexane-1,5-diyl dicarbamate (1.0 g, 2.5 mmol) in ethyl acetate (5 mL) at 25° C. was added hydrochloric acid/Ethyl acetate (3N, 20 mL). After addition, the resulting mixture was stirred for 2 h at 25° C. The mixture was concentrated to give (S)-benzyl (6-amino-1-(methylamino)-1-oxohexan-2-yl)carbamate (800 mg, crude) as white solid which was used without further purification. MS (ESI) m/z 294.2 [M+H]$^+$.

Step 2: Synthesis of (S)-benzyl (6-acetamido-1-(methylamino)-1-oxohexan-2-yl)carbamate

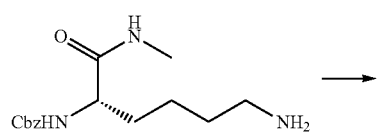

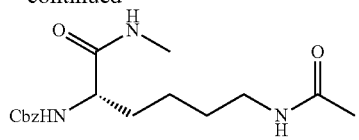

A solution of (S)-benzyl (6-amino-1-(methylamino)-1-oxohexan-2-yl)carbamate (400 mg, 1.21 mmol) and triethylamine (1.38 g, 13.7 mmol) in dichloromethane (20 mL) stirred at 25° C. for 10 minutes and cooled to 0° C. Acetyl chloride (129 mg, 1.64 mmol) was added. The mixture was stirred at 0° C. for 1 h. Water (25 mL) and dichloromethane (25 mL) was added, the organic phase was dried and concentrated to give (S)-benzyl (6-acetamido-1-(methylamino)-1-oxohexan-2-yl)carbamate (265 mg) as white solid which was used to the next step without further purification. MS (ESI) m/z 336.2 [M+H]$^+$.

Step 3: Synthesis of (S)-6-acetamido-2-amino-N-methylhexanamide

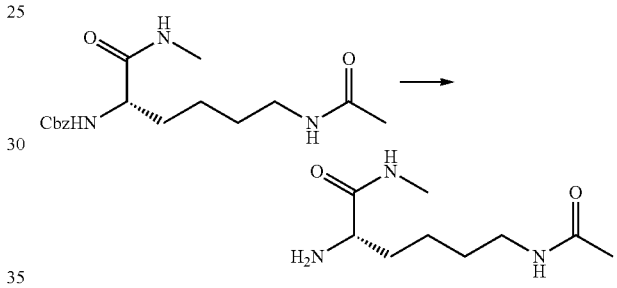

A solution of (S)-benzyl (6-acetamido-1-(methylamino)-1-oxohexan-2-yl)carbamate (50 mg, 0.15 mmol) in hydrogen bromide (3 N in aceticacid, 1 mL) was stirred for 2 h and concentrated to give (S)-6-acetamido-2-amino-N-methylhexanamide (30 mg crude) as yellow oil which was used without further purification. MS (ESI) m/z 202.2 [M+H]$^+$.

2-((2S,4R)-4-Amino-1-(6-chloroimidazo[1,2-a]pyridine-2-carbonyl)pyrrolidin-2-yl)-N—((S)-1-(methylamino)-1-oxo-6-ureidohexan-2-yl)thiazole-4-carboxamide (27)

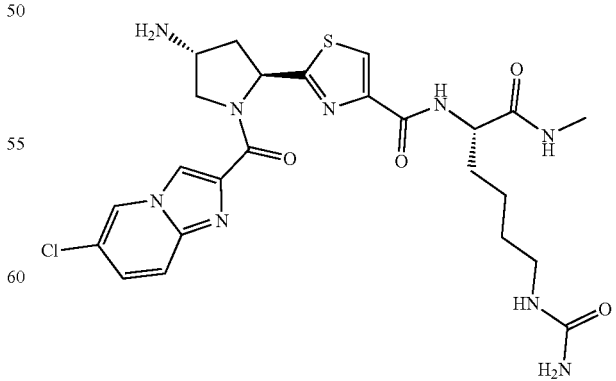

Compound 27 was synthesized in a manner analogous to the method used for the synthesis of Compound 11, using (S)-2-amino-N-methyl-6-ureidohexanamide in Step 9. MS (ESI) m/z 576.0 [M+H]+. ¹H NMR (400 MHz, DMSO, mixture of rotamers) δ 8.98 (s, 1H), 8.65 (s, 3H), 8.56 (s, 1H), 8.23 (s, 1H), 8.16-8.08 (m, 2H), 7.77 (d, J=10.0 Hz, 1H), 7.55 (dd, J=9.6, 2.0 Hz, 1H), 5.79 (t, J=7.2 Hz, 1H), 5.30-5.29 (br, 4H), 4.55-4.00 (m, 4H), 2.99 (t, J=6.4 Hz, 2H), 2.68-2.60 (m, 5H), 1.77-1.69 (m, 2H), 1.42-1.24 (m, 4H).

Step 1: Synthesis of (S)-benzyl (1-(methylamino)-1-oxo-6-ureidohexan-2-yl)carbamate

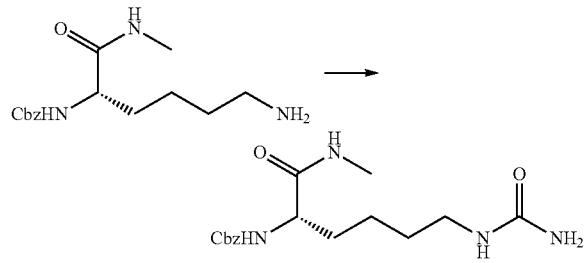

To the mixture of (S)-benzyl (6-amino-1-(methylamino)-1-oxohexan-2-yl)carbamate (157 mg, 0.54 mmol) in hydrochloride (0.5 mL) and water (1 mL) was added potassium cyanate (437 mg, 5.4 mmol in 0.5 mL of H₂O). The mixture stirred at 90° C. for 4 hours and diluted with Water (10 mL). The aqueous layer was neutralized with aq, NaOH (2N) to pH-8. The solid was precipitated and filtered to give (S)-benzyl (1-(methylamino)-1-oxo-6-ureidohexan-2-yl)carbamate (310 mg) as white solid which was used without further purification. MS (ESI) m/z 337.2 [M+H]+.

Step 2: Synthesis of (S)-2-amino-N-methyl-6-ureidohexanamide

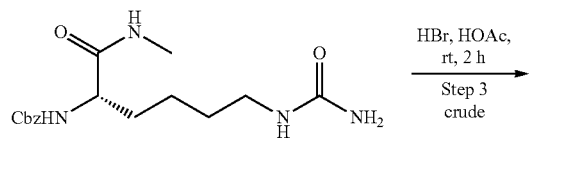

A mixture of (S)-benzyl (1-(methylamino)-1-oxo-6-ureidohexan-2-yl)carbamate (40 mg, 0.12 mmol) in hydrogen bromide (3 N in acetic acid, 1 mL) was stirred for 2 h at 25° C., and concentrated to afford (S)-2-amino-N-methyl-6-ureidohexanamide (59 mg crude) as yellow oil which was used without further purification. MS (ESI) m/z 203.1 [M+H]+.

2-((2S,4R)-4-Amino-1-(6-chloroimidazo[1,2-a]pyridine-2-carbonyl)pyrrolidin-2-yl)-N—((S)-5-guanidino-1-(methylamino)-1-oxopentan-2-yl)thiazole-4-carboxamide (28)

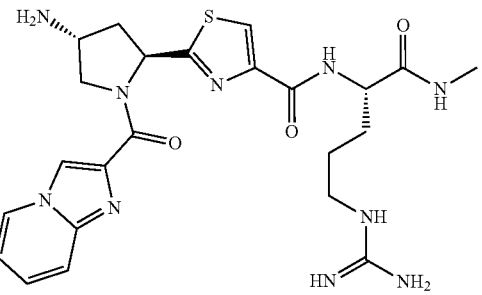

Compound 28 was synthesized in a manner analogous to the method used for the synthesis of Compound 11, using (S)-2-amino-6-(2,3-bis(tert-butoxycarbonyl))guanidino-N-methylpentanamide in Step 9. MS (ESI) m/z 561.0 [M+H]+. ¹H NMR (400 MHz, DMSO, mixture of rotamers) δ 8.93 (s, 1H), 8.60-8.58 (br, 3H), 8.49 (s, 1H), 8.23 (s, 1H), 8.21-8.13 (m, 1H), 7.86-7.72 (m, 2H), 7.58-6.8 (m, 4H), 5.78 (t, J=8.4 Hz, 1H), 4.59-4.43 (m, 3H), 4.10-4.00 (m, 1H), 3.14-3.09 (m, 2H), 2.67-2.55 (m, 5H), 1.82-1.70 (m, 2H), 1.47-1.44 (m, 2H).

Step 1: Synthesis of (S)-2-benzyl carbamate-6-(2,3-bis(tert-butoxycarbonyl))guanidino-pentanamide

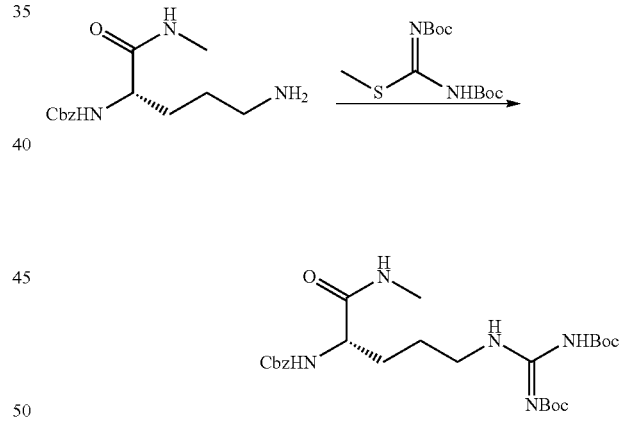

To a solution of (S)-benzyl (5-amino-1-(methylamino)-1-oxopentan-2-yl)carbamate (crude, 2.1 mmol) and 1,3-bis(tert-butoxycarbonyl)-2-methyl-2-thiopseudourea (0.915 g, 3.15 mmol) in dichloromethane (10 mL) at 25° C. was added Ethyldiisopropylamine (DIEA, 1.34 g, 10.5 mmol). After addition, the resulting mixture was stirred at 25° C. overnight. The mixture was concentrated and the residues were purified by silica column chromatography (Petroleum ether:ethyl acetate=1:1) to afford (S)-2-benzyl carbamate-6-(2,3-bis(tert-butoxycarbonyl))guanidino-pentanamide (560 mg) as colorless oil. MS (ESI) m/z 522.1 [M+H]+.

Step 2: Synthesis of (S)-2-amino-6-(2,3-bis(tert-butoxycarbonyl))guanidino-N-methylpentanamide

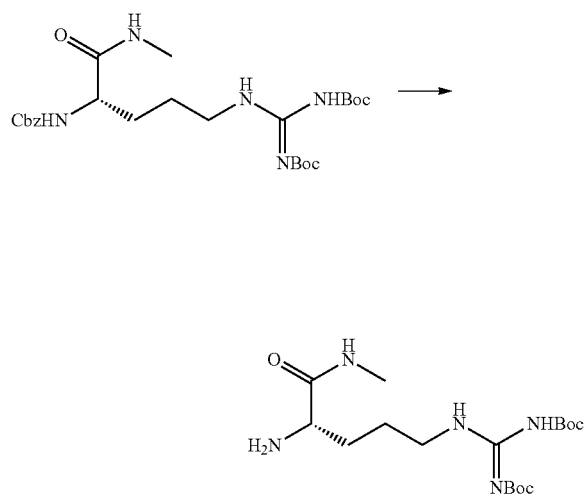

To a solution of (S)-2-benzyl carbamate-6-(2,3-bis(tert-butoxycarbonyl))guanidino-pentanamide (560 mg, 1.07 mmol) in methanol (20 mL) at 25° C., was added Pd/C (56 mg, 10%). The resulting mixture was stirred at room temperature under hydrogen atmosphere overnight. After filtered through a pad of Celite, the filtrate was concentrated to afford (S)-2-amino-6-(2,3-bis(tert-butoxycarbonyl))guanidino-N-methylpentanamide (300 mg) as a colorless oil. MS (ESI) m/z 380.4 [M+H]$^+$.

(S)-2-(2-((2S,4R)-4-Amino-1-(6-chloroimidazo[1,2-a]pyridine-2-carbonyl)pyrrolidin-2-yl)thiazole-4-carboxamido)-$N_1$-methylpentanediamide (29)

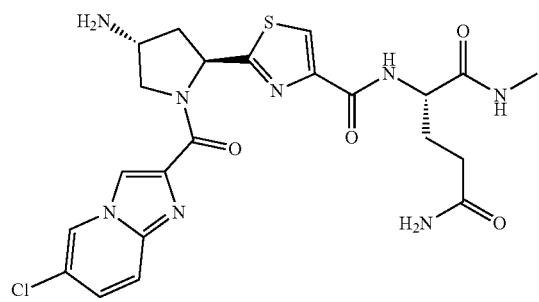 [SMILES: CNC(=O)[C@H](CCC(N)=O)NC(=O)c1csc([C@@H]2C[C@@H](N)CN2C(=O)c2cn3cc(Cl)ccc3n2)n1]

Compound 29 was synthesized in a manner analogous to the method used for the synthesis of Compound 11, using (S)-2-amino-$N_1$-methylpentanediamide in Step 9. MS (ESI) m/z 532.9 [M+H]$^+$. $^1$H NMR (400 MHz, DMSO, mixture of rotamers) δ 8.92-8.88 (m, 1H), 8.56-8.35 (m, 5H), 8.20-8.06 (m, 2H), 7.74-7.62 (m, 1H), 7.48-7.39 (m, 2H), 6.97-6.86 (m, 1H), 5.77 (t, J=5.2 Hz, 1H), 4.57-4.53 (m, 1H), 4.49-4.44 (m, 1H), 4.39-4.30 (m, 1H), 4.25-4.23 (m, 1H), 2.60-2.58 (m, 5H), 2.14-2.10 (m, 2H), 2.02-1.88 (m, 2H).

N—((S)-3-(1H-Imidazol-4-yl)-1-(methylamino)-1-oxopropan-2-yl)-2-((2S,4R)-4-amino-1-(6-chloro-imidazo[1,2-a]pyridine-2-carbonyl)pyrrolidin-2-yl)thiazole-4-carboxamide (30)

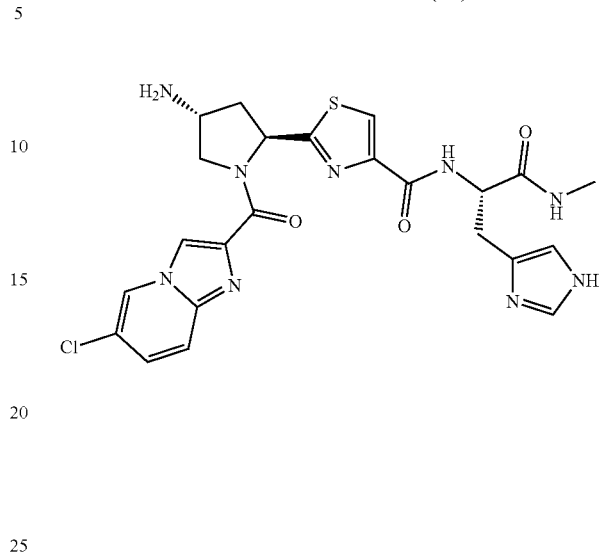

Compound 30 was synthesized in a manner analogous to the method used for the synthesis of Compound 11, using (S)-2-amino-N-methyl-3-(1-trityl-1H-imidazol-4-yl)propanamide in Step 9. MS (ESI) m/z 541.9 [M+H]$^+$. $^1$H NMR (400 MHz, DMSO, mixture of rotamers) δ 14.66 (br, 1H), 14.44 (br, 1H), 9.03-8.94 (m, 2H), 8.80-8.74 (m, 3H), 8.56-8.40 (m, 2H), 8.29-8.13 (m, 2H), 7.76 (d, J=9.6 Hz, 1H), 7.59-7.39 (m, 2H), 5.78 (t, J=6.4 Hz, 1H), 4.78-4.76 (m, 1H), 4.60-4.55 (m, 1H), 4.49-4.42 (m, 1H), 4.15-4.08 (m, 1H), 3.30-3.23 (m, 2H), 2.64-2.62 (m, 2H), 2.61 (s, 3H).

N—((S)-3-(1H-Indol-3-yl)-1-(methylamino)-1-oxopropan-2-yl)-2-((2S,4R)-4-amino-1-(6-chloroimidazo[1,2-a]pyridine-2-carbonyl)pyrrolidin-2-yl)thiazole-4-carboxamide (31)

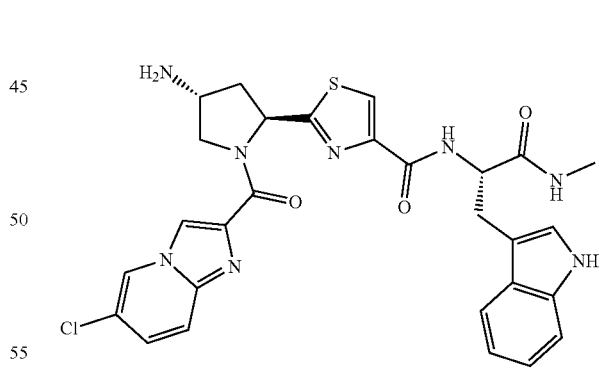

Compound 31 was synthesized in a manner analogous to the method used for the synthesis of Compound 11, using (S)-2-amino-3-(1H-indol-3-yl)-N-methylpropanamide in Step 9. MS (ESI) m/z 591.2 [M+H]$^+$. $^1$H NMR (400 MHz, DMSO, mixture of rotamers) δ 10.83 (s, 1H), 8.86 (s, 1H), 8.39 (s, 1H), 8.11-7.94 (m, 3H), 7.71 (d, J=4.0 Hz, 1H), 7.57 (d, J=4.0 Hz, 1H), 7.42-7.31 (m, 2H), 7.14-6.96 (m, 3H), 5.63-5.57 (m, 1H), 4.68-4.64 (m, 1H), 4.40-4.35 (m, 1H), 3.98-3.70 (m, 2H), 3.57-3.43 (m, 4H), 3.20-3.18 (m, 2H), 2.58 (d, J=4.0 Hz, 3H), 2.31-2.11 (m, 2H).

161

(S)-2-amino-3-(1H-indol-3-yl)-N-methylpropanamide

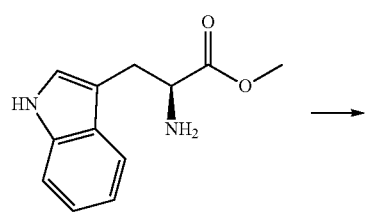

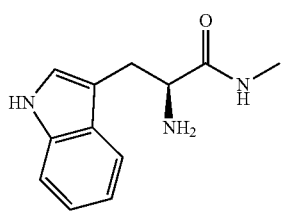

A solution of (S)-methyl 2-amino-3-(1H-indol-3-yl)propanoate (254 mg, 1.0 mmol) and methylamine (5 mL, 10 mmol) in ethanol (5 mL) was heated at 40° C. for 48 hours. The mixture was concentrated in vacuo to give (S)-2-amino-3-(1H-indol-3-yl)-N-methylpropanamide (130 mg) as a yellow solid. MS (ESI) m/z 218.1 [M+H]$^+$

N—((S)-3-(1H-Indol-3-yl)-1-(methylamino)-1-oxopropan-2-yl)-2-((2S,4R)-4-amino-1-(6-chloroimidazo[1,2-a]pyridine-2-carbonyl)pyrrolidin-2-yl)thiazole-4-carboxamide (32)

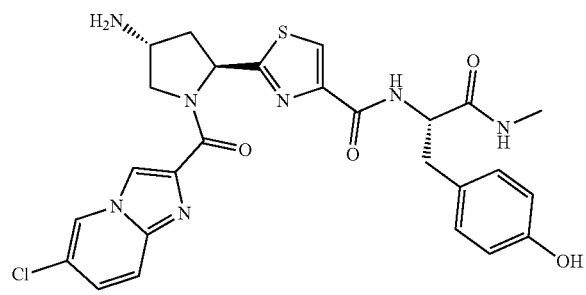 [SMILES: CNC(=O)[C@H](Cc1ccc(O)cc1)NC(=O)c1csc([C@@H]2C[C@@H](N)CN2C(=O)c2cn3cc(Cl)ccc3n2)n1]

Compound 32 was synthesized in a manner analogous to the method used for the synthesis of Compound 11, using (S)-2-amino-3-(4-hydroxyphenyl)-N-methylpropanamide in Step 9. MS (ESI) m/z 568.1 [M+H]$^+$. $^1$H NMR (400 MHz, DMSO, mixture of rotamers) δ 8.88 (s, 1H), 8.40 (s, 1H), 8.11 (s, 1H), 8.05-7.96 (m, 3H), 7.73 (d, J=4.0 Hz, 1H), 7.43-7.40 (m, 1H), 7.00 (d, J=4.2 Hz, 2H), 6.66 (d, J=8.4 Hz, 2H), 5.63-5.60 (m, 1H), 4.58-4.55 (m, 1H), 4.42-4.37 (m, 1H), 3.92-3.88 (m, 1H), 3.72-3.69 (m, 1H), 2.99-2.89 (m, 2H), 2.60-2.51 (m, 3H), 2.27-2.15 (m, 2H).

162

(S)-2-amino-3-(4-hydroxyphenyl)-N-methylpropanamide

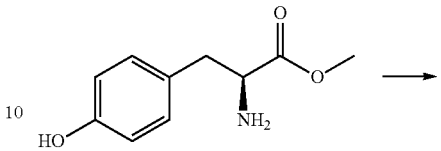

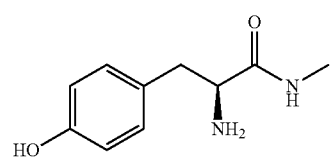

A solution of (S)-methyl 2-amino-3-(4-hydroxyphenyl)propanoate (231 mg, 1.0 mmol) and methylamine (2N, 5 mL, 10 mmol) in ethanol (5 mL) was heated at 40° C. in seal tube for 48 hours. After cooling, the mixture was concentrated in vacuo to give the title compound (S)-2-amino-3-(4-hydroxyphenyl)-N-methylpropanamide (120 mg) as a yellow solid. MS (ESI) m/z 195.1 [M+H]$^+$

2-((S)-1-(6-Chloroimidazo[1,2-a]pyridine-2-carbonyl)pyrrolidin-2-yl)-N—((S)-6-guanidino-1-(methylamino)-1-oxohexan-2-yl)thiazole-4-carboxamide (33)

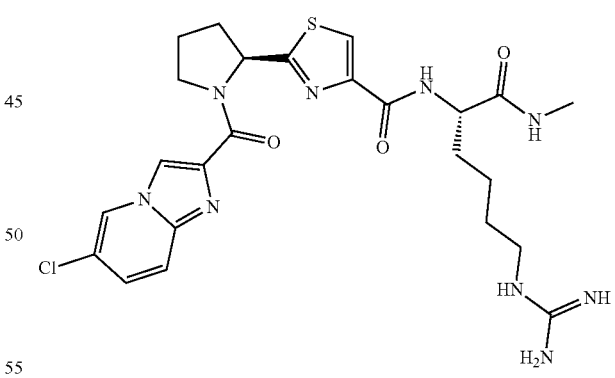

Compound 33 was synthesized in a manner analogous to the method used for the synthesis of Compound 3, using (S)-1-((benzyloxy)carbonyl)pyrrolidine-2-carboxylic acid in Step 1. MS (ESI) m/z 560.0 [M+H]$^+$. $^1$H NMR (400 MHz, DMSO, mixture of rotamers) δ 8.87 (s, 1H), 8.40 (s, 1H), 8.17 (s, 1H), 7.9 (br, 2H), 7.72 (d, J=9.6 Hz, 1H), 7.41 (dd, J=10, 1.6 Hz, 1H), 5.57 (m, J=8.4, 2.8 Hz, 1H), 4.44-4.34 (m, 2H), 4.18-4.11 (m, 1H), 3.78-3.72 (m, 1H), 3.05-3.01 (m, 2H), 2.62 (s, 3H), 2.46-2.32 (m, 2H), 2.17-2.06 (m, 2H), 1.80-1.63 (m, 2H), 1.51-1.42 (m, 2H), 1.36-1.20 (m, 2H).

2-((S)-1-(6-Chloroimidazo[1,2-a]pyridine-2-carbonyl)pyrrolidin-2-yl)-N—((R)-6-guanidino-1-(methylamino)-1-oxohexan-2-yl)thiazole-4-carboxamide (34)

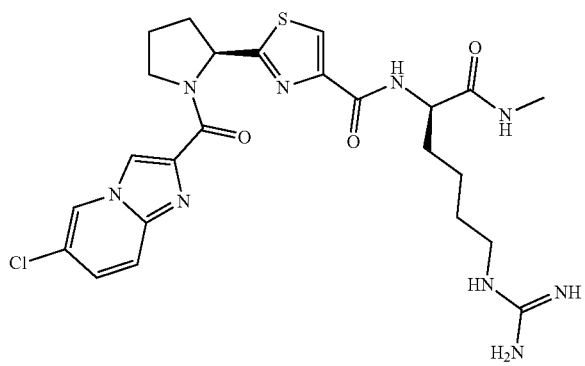 [SMILES: CNC(=O)[C@@H](CCCCNC(=N)N)NC(=O)c1csc([C@@H]2CCCN2C(=O)c2cn3cc(Cl)ccc3n2)n1]

Compound 34 was synthesized in a manner analogous to the method used for the synthesis of Compound 4, using (S)-1-((benzyloxy)carbonyl)pyrrolidine-2-carboxylic acid in Step 1. MS (ESI) m/z 560.0 [M+H]$^+$. $^1$H NMR (400 MHz, DMSO, mixture of rotamers) δ 8.87 (s, 1H), 8.40 (s, 1H), 8.17 (s, 1H), 7.9 (br, 2H), 7.72 (d, J=9.6 Hz, 1H), 7.41 (dd, J=10, 1.6 Hz, 1H), 5.57 (m, J=8.4, 2.8 Hz, 1H), 4.44-4.34 (m, 2H), 4.18-4.11 (m, 1H), 3.78-3.72 (m, 1H), 3.05-3.01 (m, 2H), 2.62 (s, 3H), 2.46-2.32 (m, 2H), 2.17-2.06 (m, 2H), 1.80-1.63 (m, 2H), 1.51-1.42 (m, 2H), 1.36-1.20 (m, 2H).

2-((2S,4R)-4-Acetamido-1-(6-chloroimidazo[1,2-a]pyridine-2-carbonyl)pyrrolidin-2-yl)-N—((S)-6-guanidino-1-(methylamino)-1-oxohexan-2-yl)thiazole-4-carboxamide (35)

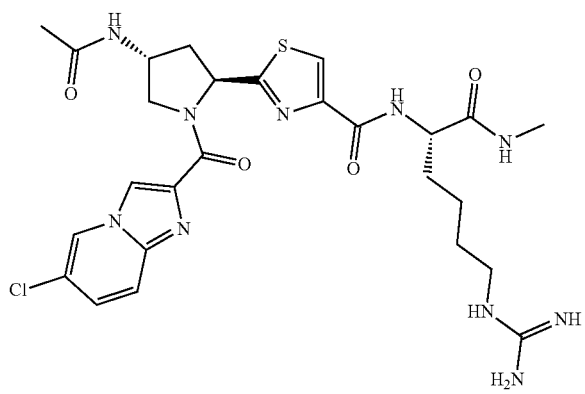 [SMILES: CNC(=O)[C@H](CCCCNC(=N)N)NC(=O)c1csc([C@@H]2C[C@@H](NC(C)=O)CN2C(=O)c2cn3cc(Cl)ccc3n2)n1]

Compound 35 was synthesized in a manner analogous to the method used for the synthesis of Compound 5, using 2-((2S,4R)-4-amino-1-(7-chloroimidazo[1,2-a]pyridine-2-carbonyl) pyrrolidin-2-yl)thiazole-4-carboxylic acid in Step 1. MS (ESI) m/z 617.0 [M+H]$^+$; $^1$H NMR (400 MHz, DMSO, mixture of rotamers) δ 9.01 (s, 1H), 8.64 (s, 1H), 8.52-8.45 (m, 1H), 8.22 (br, 2H), 8.09-8.07 (m, 1H), 7.83-7.81 (m, 2H), 7.65-7.62 (m, 1H), 7.55-6.80 (m, 5H), 5.72 (t, J=6.4 Hz, 1H), 4.80-4.44 (m, 3H), 4.03-4.01 (m, 1H), 3.10-3.08 (m, 2H), 2.61 (s, 3H), 2.45-2.41 (m, 2H), 1.82 (s, 3H), 1.81-1.72 (m, 2H), 1.49-1.46 (m, 2H), 1.33-1.30 (m, 2H).

2-((2S,4S)-4-Amino-1-(6-chloroimidazo[1,2-a]pyridine-2-carbonyl)pyrrolidin-2-yl)-N—((S)-6-guanidino-1-(methylamino)-1-oxohexan-2-yl)thiazole-4-carboxamide (36)

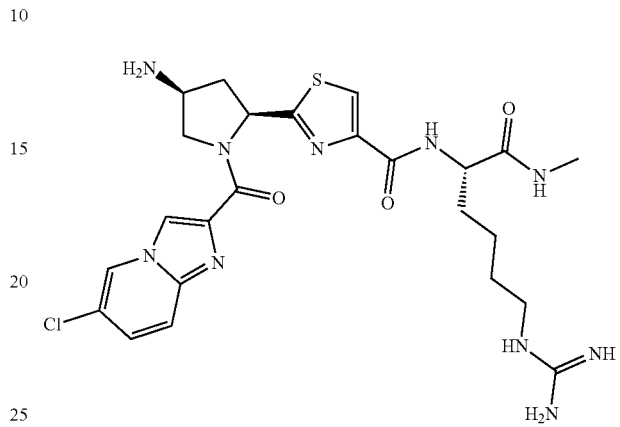

Compound 36 was synthesized in a manner analogous to the method used for the synthesis of Compound 1, but beginning at Step 4 using (2S,4S)-4-amino-1-(tert-butoxycarbonyl)pyrrolidine-2-carboxylic acid. MS (ESI) m/z 575.2 [M+H]$^+$. $^1$H NMR (400 MHz, DMSO, mixture of rotamers) δ 8.99 (s, 1H), 8.81 (br, 3H), 8.54 (s, 1H), 8.35 (d, J=4.0 Hz, 1H), 8.25-8.15 (m, 2H), 7.83-7.76 (m, 2H), 7.53-7.51 (m, 3H), 7.41-6.81 (m, 3H), 5.68-5.65 (m, 1H), 4.70-4.66 (m, 1H), 4.34-4.28 (m, 2H), 4.00 (s, 1H), 3.13-3.10 (m, 2H), 2.82-2.76 (m, 1H), 2.68-2.56 (m, 4H), 1.80-1.78 (m, 2H), 1.48-1.46 (m, 2H), 1.36-1.30 (m, 2H).

2-((2S,4S)-1-(6-Chloroimidazo[1,2-a]pyridine-2-carbonyl)-4-hydroxypyrrolidin-2-yl)-N—((S)-6-guanidino-1-(methylamino)-1-oxohexan-2-yl)thiazole-4-carboxamide (37)

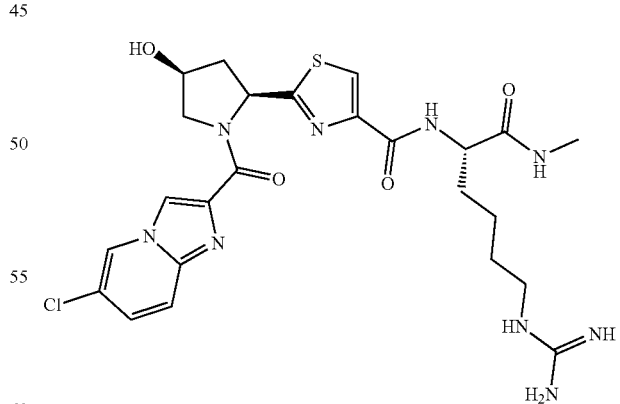

Compound 37 was synthesized in a manner analogous to the method used for the synthesis of Compound 7, using (2S,4S)-1-(tert-butoxycarbonyl)-4-hydroxypyrrolidine-2-carboxylic acid in Step 1. MS (ESI) m/z 576.0 [M+H]$^+$. $^1$H NMR (400 MHz, DMSO, mixture of rotamers) δ 8.86 (d, J=1.2 Hz, 1H), 8.81-8.75 (m, 1H), 8.40 (s, 1H), 8.26-8.18

(m, 1H), 8.11 (s, 1H), 8.05 (d, J=8.0 Hz, 1H), 7.82-7.60 (m, 4H), 7.42-7.39 (dd, J=9.6, 2.0 Hz, 1H), 5.60-5.54 (m, 1H), 4.50-4.24 (m, 4H), 3.54-3.52 (m, 1H), 3.08-2.98 (m, 2H), 2.65-2.60 (m, 3H), 2.18-2.14 (m, 1H), 2.03-1.95 (m, 1H), 1.70-1.64 (m, 2H), 1.52-1.42 (m, 2H), 1.38-1.28 (m, 2H).

2-((2S,4R)-1-(6-Chloroimidazo[1,2-a]pyridine-2-carbonyl)-4-hydroxypyrrolidin-2-yl)-N—((S)-6-guanidino-1-(methylamino)-1-oxohexan-2-yl)thiazole-4-carboxamide (38)

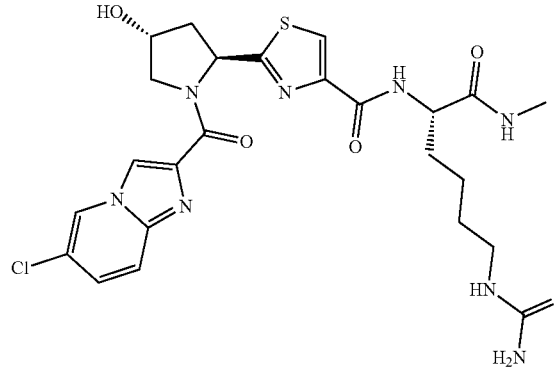

Compound 38 was synthesized in a manner analogous to the method used for the synthesis of Compound 7, using (2S,4R)-1-(tert-butoxycarbonyl)-4-hydroxypyrrolidine-2-carboxylic acid in Step 1. MS (ESI) m/z 576.0 [M+H]+. 1H NMR (400 MHz, DMSO, mixture of rotamers) δ 8.87 (s, 1H), 8.40 (s, 1H), 8.18 (s, 1H), 7.73 (d, J=9.6 Hz, 1H), 7.41 (dd, J=9.6, 2.0 Hz, 1H), 5.59 (t, J=8.0 Hz, 1H), 4.46-4.42 (m, 2H), 4.30-4.19 (m, 2H), 3.77-3.18 (m, 4H), 3.03-3.02 (m, 2H), 2.61 (s, 3H), 2.38-2.36 (m, 1H), 2.28-2.25 (m, 1H), 1.75-1.68 (m, 2H), 1.46-1.45 (m, 2H), 1.32-1.27 (m, 2H).

2-((2S,4R)-1-(6-Chloroimidazo[1,2-a]pyridine-2-carbonyl)-4-hydroxypyrrolidin-2-yl)-N—((R)-6-guanidino-1-(methylamino)-1-oxohexan-2-yl)thiazole-4-carboxamide (39)

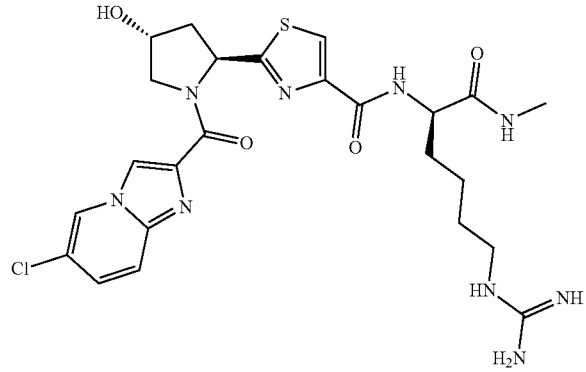 [SMILES: CNC(=O)[C@@H](CCCCNC(=N)N)NC(=O)c1csc([C@@H]2C[C@@H](O)CN2C(=O)c2cn3cc(Cl)ccc3n2)n1]

Compound 39 was synthesized in a manner analogous to the method used for the synthesis of Compound 7, using (2S,4R)-1-(tert-butoxycarbonyl)-4-hydroxypyrrolidine-2-carboxylic acid in Step 1 and (R)-2-amino-6-(2,3-bis(tert-butoxycarbonyl))guanidino-N-methylhexanamide in Step 8.

MS (ESI) m/z 776.3 [M+H]+. 1H NMR (400 MHz, DMSO, mixture of rotamers) δ 11.50 (s, 1H), 8.87 (d, J=1.2 Hz, 1H), 8.40 (s, 1H), 8.31-8.26 (m, 1H), 8.16 (s, 1H), 8.08-8.03 (m, 2H), 7.72 (d, J=9.6 Hz, 1H), 7.41 (dd, J=9.6, 2.4 Hz, 1H), 5.59 (t, J=8.0 Hz, 1H), 5.17 (d, J=3.2 Hz, 1H), 4.45-4.18 (m, 4H), 3.26-3.23 (m, 2H), 2.62 (d, J=4.4 Hz, 3H), 2.42-2.24 (m, 2H), 1.76-1.64 (m, 2H), 1.50-1.38 (m, 2H).

2-((2S,4R)-1-(2-Naphthoyl)-4-aminopyrrolidin-2-yl)-N—((S)-6-guanidino-1-(methylamino)-1-oxohexan-2-yl)thiazole-4-carboxamide (40)

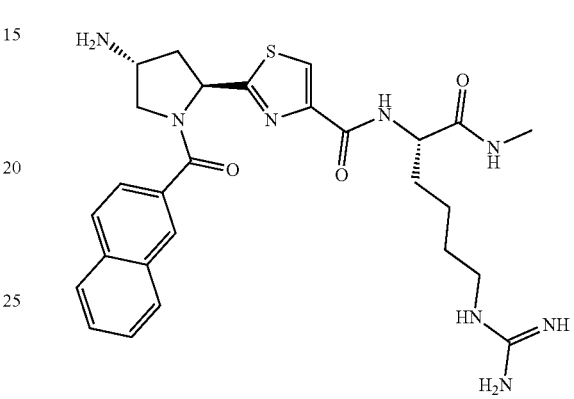

Compound 40 was synthesized in a manner analogous to the method used for the synthesis of Compound 14, using 2-naphthoic acid in Step 1. MS (ESI) m/z 551.2 [M+H]+; 1H NMR (400 MHz, DMSO, mixture of rotamers) δ 8.81 (br, 1H), 8.56 (s, 3H), 8.28-8.00 (m, 7H), 7.75-7.62 (m, 4H), 5.81 (t, J=7.6 Hz, 1H), 4.50-4.45 (m, 1H), 4.26-4.21 (m, 1H), 4.14 (br, 4H), 4.05-3.97 (m, 1H), 3.73 (d, J=12.0 Hz, 1H), 3.12-3.07 (m, 2H), 2.78-2.63 (m, 5H), 1.81-1.71 (m, 2H), 1.48-1.47 (m, 2H), 1.33-1.31 (m, 2H).

2-((2S,4R)-4-Amino-1-(3-chloroquinoline-6-carbonyl)pyrrolidin-2-yl)-N—((S)-6-guanidino-1-(methylamino)-1-oxohexan-2-yl)thiazole-4-carboxamide (41)

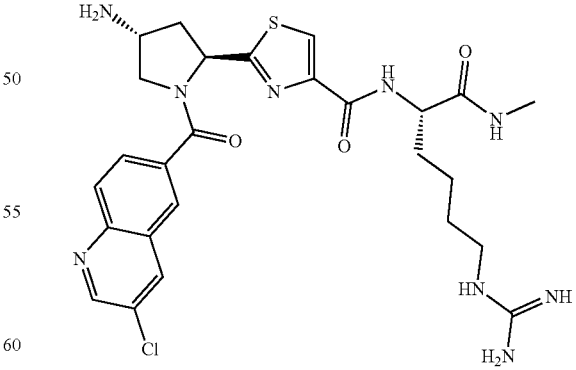

Compound 41 was synthesized in a manner analogous to the method used for the synthesis of Compound 14, using 3-chloroquinoline-6-carboxylic acid in Step 1. MS (ESI) m/z 586.0 [M+H]+; 1H NMR (400 MHz, DMSO, mixture of rotamers) δ 9.04 (br, 2H), 8.95-8.75 (m, 3H), 8.55-8.15 (m, 4H), 8.04-7.90 (m, 2H), 7.68-6.88 (m, 3H), 5.85 (br, 1H), 4.91-4.40 (m, 4H), 4.38-4.18 (m, 1H), 4.15-3.98 (m, 1H), 3.78 (d, J=9.2 Hz, 1H), 3.13 (s, 2H), 2.88-2.68 (m, 2H), 2.65 (s, 3H), 1.88-1.71 (m, 2H), 1.50 (br, 2H), 1.35 (br, 2H).

2-((2S,4R)-4-Amino-1-(6-chloroquinoline-2-carbonyl)pyrrolidin-2-yl)-N—((S)-6-guanidino-1-(methylamino)-1-oxohexan-2-yl)thiazole-4-carboxamide (42)

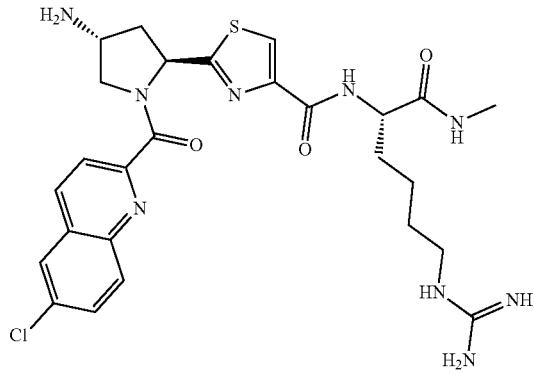 [SMILES: CNC(=O)[C@H](CCCCNC(=N)N)NC(=O)c1csc([C@@H]2C[C@@H](N)CN2C(=O)c2ccc3cc(Cl)ccc3n2)n1]

Compound 42 was synthesized in a manner analogous to the method used for the synthesis of Compound 14, using 6-chloroquinoline-2-carboxylic acid in Step 1. MS (ESI) m/z 568.1 [M+H]$^+$; $^1$H NMR (400 MHz, DMSO, mixture of rotamers) δ 8.78 (s, 2H), 8.62-8.46 (m, 3H), 8.27-8.18 (m, 4H), 8.16-7.91 (m, 2H), 7.90-6.40 (m, 4H), 6.43-5.81 (m, 1H), 4.71-4.68 (m, 2H), 4.49-4.40 (m, 2H), 4.18-4.07 (m, 2H), 3.12-3.08 (m, 2H), 2.75-2.71 (m, 2H), 2.69-2.62 (m, 3H), 1.81-1.67 (m, 2H), 1.48-1.45 (m, 2H), 1.35-1.29 (m, 2H).

2-((2S,4R)-4-Amino-1-(3-chlorobenzo[b]thiophene-6-carbonyl)pyrrolidin-2-yl)-N—((S)-6-guanidino-1-(methylamino)-1-oxohexan-2-yl)thiazole-4-carboxamide (43)

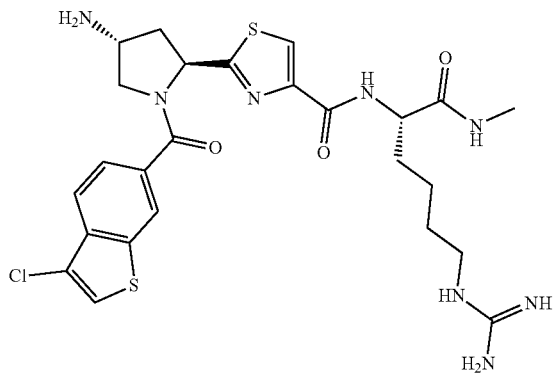 [SMILES: CNC(=O)[C@H](CCCCNC(=N)N)NC(=O)c1csc([C@@H]2C[C@@H](N)CN2C(=O)c2ccc3c(Cl)csc3c2)n1]

Compound 43 was synthesized in a manner analogous to the method used for the synthesis of Compound 14, using 3-chlorobenzo[b]thiophene-6-carboxylic acid in Step 1. MS (ESI) m/z 591.1 [M+H]$^+$; $^1$H NMR (400 MHz, DMSO) δ 8.80-8.79 (br, 1H), 8.56 (br, 3H), 8.41 (s, 1H), 8.28 (s, 1H), 8.20-8.19 (m, 1H), 8.17-8.15 (m, 1H), 8.12 (s, 1H), 7.93-7.91 (m, 1H), 7.75-7.30 (m, 2H), 7.60-6.80 (br, 3H), 5.79 (t, J=7.2 Hz, 1H), 4.21-4.17 (m, 1H), 4.03-3.96 (m, 1H), 3.70-3.67 (m, 1H), 3.11-3.06 (m, 2H), 2.66 (s, 3H), 1.80-1.71 (m, 2H), 1.50-1.46 (m, 2H), 1.34-1.23 (m, 2H).

2-((2S,4R)-4-Amino-1-(5-chlorobenzo[b]thiophene-2-carbonyl)pyrrolidin-2-yl)-N—((S)-6-guanidino-1-(methylamino)-1-oxohexan-2-yl)thiazole-4-carboxamide (44)

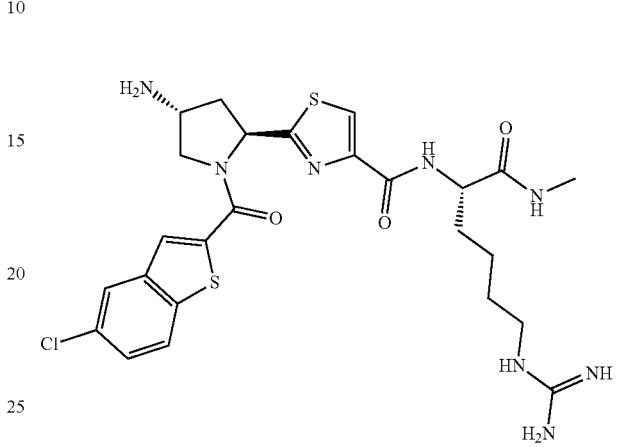

Compound 44 was synthesized in a manner analogous to the method used for the synthesis of Compound 14, using 3-chlorobenzo[b]thiophene-6-carboxylic acid in Step 1. MS (ESI) m/z 591.1 [M+H]$^+$; $^1$H NMR (400 MHz, DMSO) δ 9.41 (br, 1H), 8.74-8.60 (m, 4H), 8.25-8.05 (m, 6H), 7.73 (d, J=4.8 Hz, 1H), 7.54 (d, J=8.4 Hz, 1H), 7.39-6.99 (br, 3H), 5.78 (t, J=7.6 Hz, 1H), 4.46-4.42 (m, 2H), 4.21-4.04 (m, 2H), 3.11-3.07 (m, 2H), 2.77-2.61 (m, 5H), 1.80-1.68 (m, 2H), 1.50-1.46 (m, 2H), 1.32-1.30 (m, 2H).

2-((2S,4R)-4-Amino-1-(5-chlorobenzo[d]thiazole-2-carbonyl)pyrrolidin-2-yl)-N—((S)-6-guanidino-1-(methylamino)-1-oxohexan-2-yl)thiazole-4-carboxamide (45)

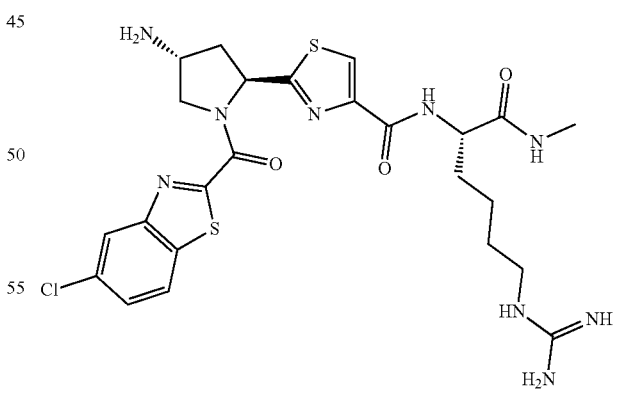

Compound 45 was synthesized in a manner analogous to the method used for the synthesis of Compound 14, using 5-chlorobenzo[d]thiazole-2-carboxylic acid in Step 1. MS(ESI) m/z 592.1 [M+H]$^+$; $^1$H NMR (400 MHz, DMSO, mixture of rotamers) δ 8.62-8.55 (m, 3H), 8.29-8.26 (m, 2H), 8.19-8.11 (m, 2H), 8.01-7.97 (m, 1H), 7.70-7.64 (m, 2H), 7.44-6.99 (m, 5H), 5.82-5.32 (m, 1H), 4.55-4.50 (m, 1H), 4.47-4.42 (m, 1H), 4.18-4.10 (m, 2H), 3.11-3.05 (m, 2H), 2.88-2.84 (m, 1H), 2.72-2.67 (m, 1H), 2.62-2.60 (m, 3H), 2.03-1.96 (m, 2H), 1.79-1.69 (m, 2H), 1.49-1.45 (m, 2H).

2-((2S,4R)-4-Amino-1-(6-chloroimidazo[1,2-a]pyridine-2-carbonyl) pyrrolidin-2-yl)-N-(5-guanidinopentyl)thiazole-4-carboxamide (46)

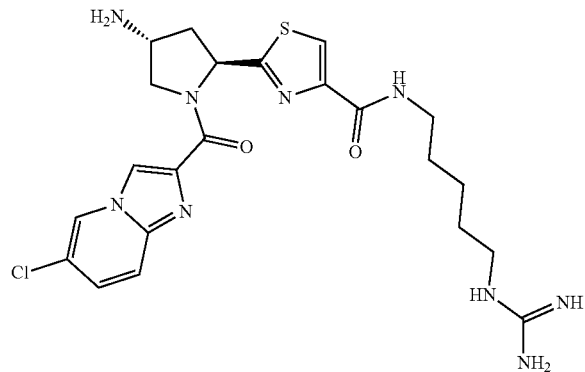 [SMILES: N=C(N)NCCCCCNC(=O)c1csc([C@@H]2C[C@@H](N)CN2C(=O)c2cn3cc(Cl)ccc3n2)n1]

Compound 46 was synthesized in a manner analogous to the method used for the synthesis of Compound 11, using 5-(2,3-bis(tert-butoxycarbonyl))guanidine-pentylamine in Step 9. MS (ESI) m/z 518.1 [M+H]$^+$. $^1$H NMR (400 MHz, DMSO, mixture of rotamers) δ 9.00 (s, 1H), 8.74 (br, 3H), 8.44 (s, 1H), 8.15 (s, 1H), 7.85 (br, 1H), 7.78-7.75 (m, 1H), 7.64-7.44 (m, 2H), 7.40-6.80 (m, 2H), 5.77 (t, J=6.4 Hz, 1H), 4.57-4.52 (m, 1H), 4.45-4.38 (m, 3H), 4.16 (br, 1H), 3.31-3.23 (m, 2H), 3.15-3.05 (m, 2H), 2.78-2.64 (m, 2H), 1.60-1.47 (m, 4H), 1.41-1.25 (m, 2H).

2-((2S,4R)-4-Amino-1-(6-chloroimidazo[1,2-a]pyridine-2-carbonyl)pyrrolidin-2-yl)-N-(4-carbamimidoylbenzyl)thiazole-4-carboxamide (47)

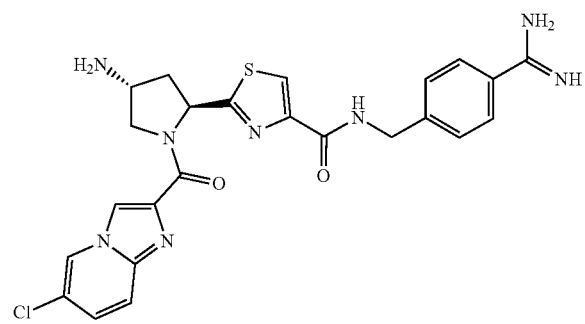 [SMILES: N=C(N)c1ccc(CNC(=O)c2csc([C@@H]3C[C@@H](N)CN3C(=O)c3cn4cc(Cl)ccc4n3)n2)cc1]

Compound 47 was synthesized in a manner analogous to the method used for the synthesis of Compound 11, using 4-(aminomethyl)benzimidamide dihydrochloride in Step 9. MS (ESI) m/z 523.1 [M+H]$^+$. $^1$H NMR (400 MHz, DMSO, mixture of rotamers) δ 9.41 (s, 2H), 9.18 (s, 3H), 8.97 (s, 1H), 8.69 (s, 3H), 8.54 (s, 1H), 8.21 (s, 1H), 7.82-7.73 (m, 3H), 7.63-7.33 (m, 3H), 5.78 (t, J=6.4 Hz, 1H), 4.58-4.53 (m, 3H), 4.51-4.46 (m, 1H), 4.17-4.16 (m, 1H), 2.68-2.63 (m, 2H).

2-((2S,4R)-4-Amino-1-(6-chloroimidazo[1,2-a]pyridine-2-carbonyl)pyrrolidin-2-yl)-N-((6-amino-2,4-dimethylpyridin-3-yl)methyl)thiazole-4-carboxamide (48)

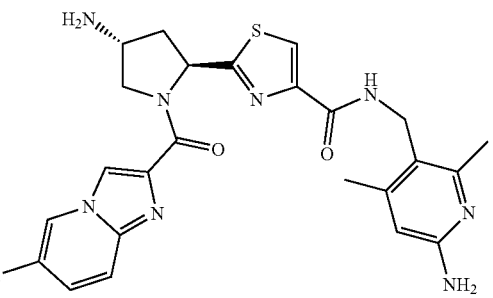

Compound 48 was synthesized in a manner analogous to the method used for the synthesis of Compound 11, using tert-butyl (5-(aminomethyl)-4,6-dimethylpyridin-2-yl)carbamate in Step 9. MS (ESI) m/z 525.0 [M+H]$^+$; $^1$H NMR (400 MHz, DMSO, mixture of rotamers) δ 14.23 (br, 1H), 9.06-8.95 (m, 1H), 8.76 (br, 5H), 8.20 (s, 1H), 7.84-7.42 (m, 4H), 6.66 (s, 1H), 5.76 (t, J=6.4 Hz, 1H), 4.56-4.49 (m, 1H), 4.32 (br, 2H), 4.09 (br, 2H), 2.72-2.58 (m, 2H), 2.56 (s, 3H), 2.38 (s, 3H).

2-((2S,4R)-4-Amino-1-(6-chloroimidazo[1,2-a]pyridine-2-carbonyl)pyrrolidin-2-yl)-N-((1-aminoisoquinolin-6-yl)methyl)thiazole-4-carboxamide (49)

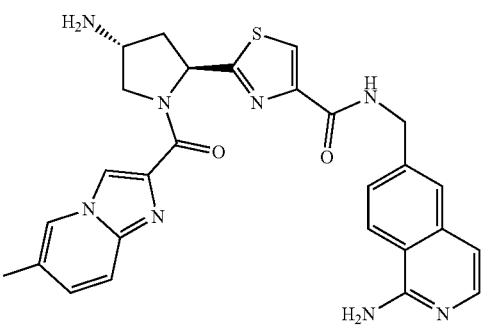

Compound 49 was synthesized in a manner analogous to the method used for the synthesis of Compound 11, using 6-(aminomethyl)isoquinolin-1-amine in Step 9. MS (ESI) m/z 546.9 [M+H]$^+$; $^1$H NMR (400 MHz, DMSO, mixture of rotamers) δ 13.41 (s, 1H), 9.25-9.17 (m, 3H), 8.92 (s, 1H), 8.62 (br, 2H), 8.60 (s, 1H), 8.58 (s, 1H), 8.23 (s, 1H), 7.81 (s, 1H), 7.73-7.59 (m, 3H), 7.47-7.43 (m, 1H), 7.24-7.22 (m, 1H), 5.79 (t, J=7.2 Hz, 1H), 4.67-4.65 (m, 2H), 4.55-4.52 (m, 2H), 4.15-4.10 (m, 2H), 2.68-2.64 (m, 2H).

2-((2S,4R)-4-Amino-1-(6-chloroimidazo[1,2-a]pyridine-2-carbonyl)pyrrolidin-2-yl)-N-(4-(aminomethyl)benzyl)thiazole-4-carboxamide (50)

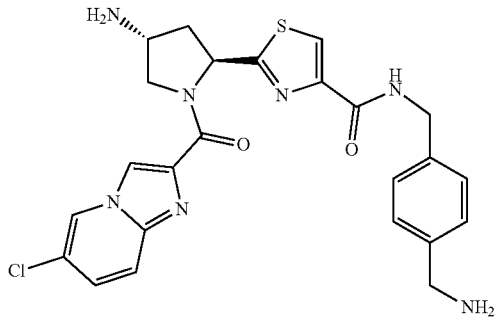 [SMILES: NCc1ccc(CNC(=O)c2csc([C@@H]3C[C@@H](N)CN3C(=O)c3cn4cc(Cl)ccc4n3)n2)cc1]

Compound 50 was synthesized in a manner analogous to the method used for the synthesis of Compound 11, using tert-butyl 4-(aminomethyl)benzylcarbamate in Step 9. MS (ESI) m/z 510.1 [M+H]⁺. ¹H NMR (400 MHz, DMSO, mixture of rotamers) δ 9.06-9.02 (m, 1H), 8.97 (d, J=1.2 Hz, 1H), 8.71 (s, 3H), 8.52-8.45 (m, 4H), 8.19 (s, 1H), 7.74 (d, J=9.2 Hz, 1H), 7.52-7.43 (m, 3H), 7.36-7.34 (m, 2H), 5.77 (t, J=6.8 Hz, 1H), 4.57-4.44 (m, 4H), 4.16-4.12 (m, 1H), 3.99-3.96 (m, 2H), 2.63 (t, J=6.4 Hz, 2H).

2-((2S,4R)-4-Amino-1-(6-chloroimidazo[1,2-a]pyridine-2-carbonyl)pyrrolidin-2-yl)-N-(4-carbamimidoylphenethyl)thiazole-4-carboxamide (51)

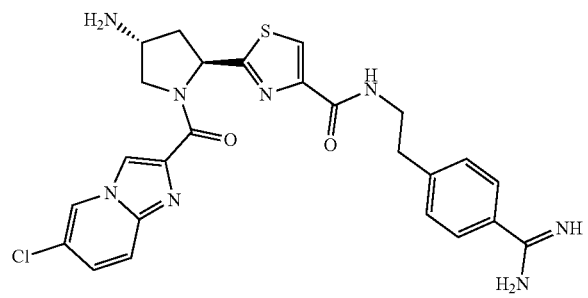 [SMILES: N=C(N)c1ccc(CCNC(=O)c2csc([C@@H]3C[C@@H](N)CN3C(=O)c3cn4cc(Cl)ccc4n3)n2)cc1]

Compound 51 was synthesized in a manner analogous to the method used for the synthesis of Compound 11, using tert-butyl ((4-(2-aminoethyl)phenyl)(imino)methyl)carbamate in Step 9. MS (ESI) m/z 537.2 [M+H]⁺. ¹H NMR (400 MHz, DMSO, mixture of rotamers) δ 9.35-9.20 (m, 4H), 8.90 (s, 1H), 8.60-8.30 (m, 5H), 8.15 (s, 1H), 7.77 (d, J=8.0 Hz, 2H), 7.71 (d, J=10.4 Hz, 1H), 7.53-7.48 (m, 2H), 7.47-7.40 (m, 1H), 5.80-5.70 (m, 1H), 4.61-4.50 (m, 1H), 4.17 (br, 1H), 3.98 (br, 1H), 3.57-3.52 (m, 2H), 3.04-2.95 (m, 2H), 2.70-2.56 (m, 2H).

Step 1: Synthesis of 4-(2-hydroxyethyl)benzimidamide

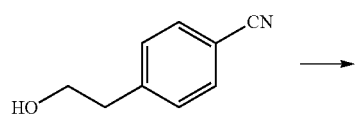

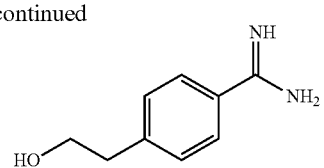

To a mixture was of acetyl chloride (40 mL) and ethanol (80 mL) was added 4-(2-hydroxyethyl)benzonitrile (4 g, 27.2 mmol). The mixture was stirred at room temperature for 16 h and concentrated. The residue is diluted with ammonia (7 N in methanol, 150 mL) and stirred at room temperature for 12 h. The mixture was concentrated to give 4-(2-hydroxyethyl)benzimidamide (4.5 g) as yellow oil, which was used directly to the next step. MS (ESI) m/z 165.1 [M+H]⁺.

Step 2: Synthesis of tert-butyl ((4-(2 hydroxyethyl)phenyl)(imino)methyl) carbamate

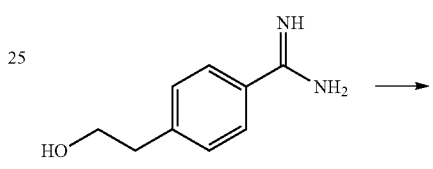

To a solution was of 4-(2-hydroxyethyl)benzimidamide (crude, 27.2 mmol) in tetrahydrofuran (100 mL) and water (20 mL) was added triethylamine (18.8 mL, 136.0 mmol) and di-tert-butyl dicarbonate (12.4 mL, 54.4 mmol). The mixture was stirred at room temperature for 3 h. The mixture was concentrated, dissolved in ethyl acetate, washed with water. The organic layer was concentrated, purified by silica column chromatography (petroleum ether:ethyl acetate=1:1) to give tert-butyl ((4-(2-hydroxyethyl)phenyl)(imino)methyl)carbamate (5 g) as yellow solid. MS (ESI) m/z 265.1 [M+H]⁺.

Step 3: Synthesis of tert-butyl ((4-(2-azidoethyl)phenyl)(imino)methyl)carbamate

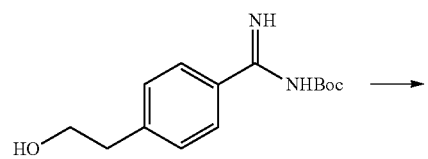

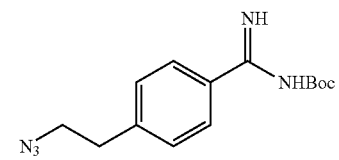

To a solution of tert-butyl ((4-(2-hydroxyethyl)phenyl)(imino)methyl)carbamate (2 g, 7.58 mmol) in tetrahydrofuran (40 mL) was added triphenylphosphine (3.98 g, 15.2 mmol) and diethyl azodicarboxylate (2.4 mL, 15.2 mmol). The mixture was stirred at room temperature for 0.5 h. Diphenylphosphoryl azide was added and the mixture was stirred at room temperature for 12 h. Upon removal of the solvent, the residue was purified by silica column chromatography (petroleum ether:ethyl acetate=4:1) to give tert-butyl ((4-(2-azidoethyl)phenyl)(imino)methyl)carbamate (2.1 g) as yellow oil. MS (ESI) m/z 290.2 [M+H]$^+$.

Step 4: Synthesis of tert-butyl ((4-(2-aminoethyl)phenyl)(imino)methyl) carbamate

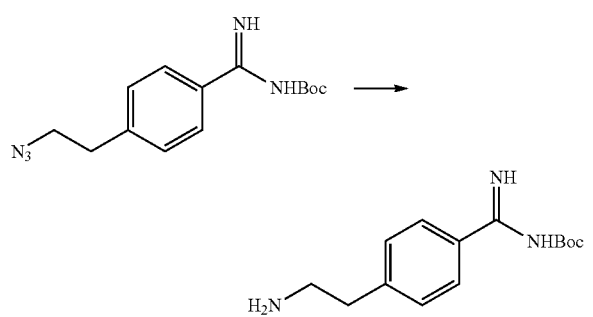

A suspension of tert-butyl ((4-(2-azidoethyl)phenyl)(imino)methyl)carbamate (2.0 g, 6.9 mmol) in ethyl acetate (30 mL) was added 10% Pd/C (250 mg), and the mixture was stirred at 25° C. for 2 h. Filtered and concentrated, the residue was diluted with 20 mL ethyl acetate, extracted with water (10 mL×3). The combined aqueous layers were concentrated to afford tert-butyl ((4-(2-aminoethyl)phenyl)(imino)methyl) carbamate (180 mg) as white solid which was used without further purification. The remained organic layer was concentrate to give crude product (2.0 g) as yellow oil. MS (ESI) m/z 264.2 [M+H]$^+$.

2-((2S,4R)-4-Amino-1-(6-chloroimidazo[1,2-a]pyridine-2-carbonyl)pyrrolidin-2-yl)-N-(2-(6-amino-2,4-dimethylpyridin-3-yl)ethyl)thiazole-4-carboxamide (52)

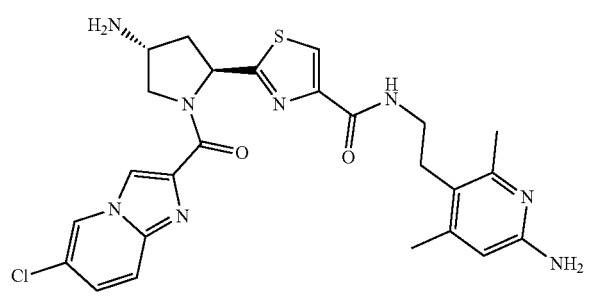 [SMILES: Cc1cc(N)nc(C)c1CCNC(=O)c1csc([C@@H]2C[C@@H](N)CN2C(=O)c2cn3cc(Cl)ccc3n2)n1]

Compound 52 was synthesized in a manner analogous to the method used for the synthesis of Compound 11, using 5-(2-aminoethyl)-4,6-dimethylpyridin-2-amine in Step 9. MS (ESI) m/z 539.1 [M+H]$^+$. $^1$H NMR (400 MHz, DMSO, mixture of rotamers) δ 14.05 (br, 1H), 8.94 (s, 1H), 8.70-8.66 (br, 4H), 8.50 (s, 1H), 8.15 (s, 1H), 7.73 (d, J=9.6 Hz, 1H), 7.59-7.56 (br, 2H), 7.47 (d, J=9.6 Hz, 1H), 6.65 (s, 1H), 5.70 (t, J=6.4 Hz, 1H), 4.52-4.51 (m, 1H), 4.00-3.89 (m, 2H), 3.35-3.31 (m, 2H), 2.73 (t, J=7.6 Hz, 2H), 2.66 (t, J=7.6 Hz, 2H), 2.47 (s, 3H), 2.37 (s, 3H).

Step 1: Synthesis of (E)-4,6-dimethyl-5-(2-nitrovinyl)pyridin-2-amine

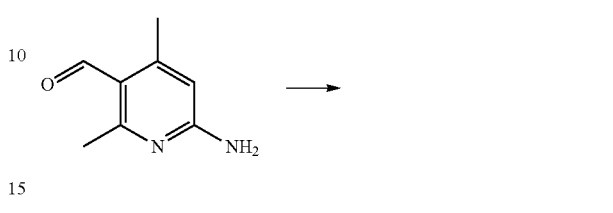

To a solution of 6-amino-2,4-dimethylnicotinaldehyde (1.3 g, 8.6 mmol) in 60 ml of acetic acid/nitromethane, (V/V=1/1), were added acetic ammonia (1.98 g, 25.8 mmol). The mixture was stirred for 24 h at 90° C. After filtered through a pad of Celite, the filtrate was concentrated to dryness in vacuo. The residue was purified by silica gel flash chromatography (petroleum ether:ethyl acetate=40:10) to afford (E)-4,6-dimethyl-5-(2-nitrovinyl)pyridin-2-amine (600 mg) as a red solid. MS (ESI) m/z 194.0 [M+H]$^+$.

Step 2: Synthesis of 5-(2-aminoethyl)-4,6-dimethylpyridin-2-amine

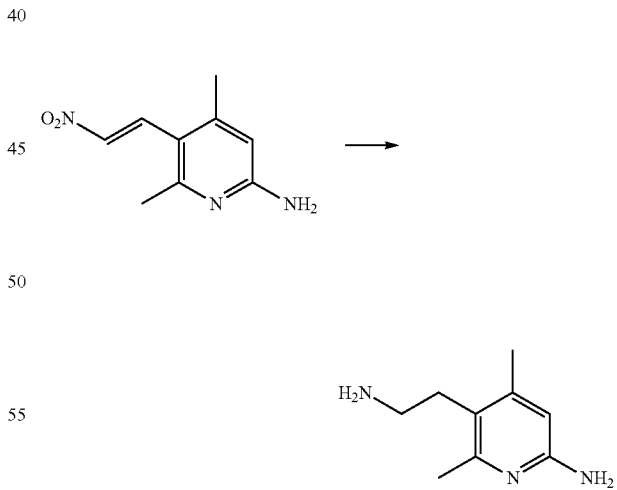

To a solution of (E)-4,6-dimethyl-5-(2-nitrovinyl)pyridin-2-amine (200 mg, 0.96 mmol) in 60 ml of ethanol, were added Pd/C (20 mg, 10%), 1 mL of 1N hydrogen chloride. The mixture was stirred at room temperature for 24 h. After filtered through a pad of celite, the filtrate was concentrated to dryness in vacuo to afford 5-(2-aminoethyl)-4,6-dimethylpyridin-2-amine (200 mg, crude) as a blue solid. MS (ESI) m/z 166.1 [M+H]$^+$.

2-((2S,4R)-4-Amino-1-(6-chloroimidazo[1,2-a]pyridine-2-carbonyl)pyrrolidin-2-yl)-N-(2-(1-aminoisoquinolin-6-yl)ethyl)thiazole-4-carboxamide (53)

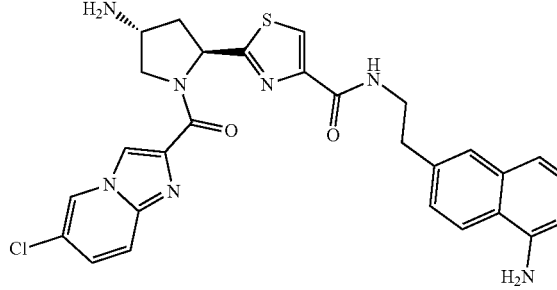

Compound 53 was synthesized in a manner analogous to the method used for the synthesis of Compound 11, using 6-(2-aminoethyl)-N,N-(bis-tert-butoxycarbonyl)-isoquinolin-1-amine in Step 9. MS (ESI) m/z 561.1 [M+H]⁺. ¹H NMR (400 MHz, DMSO, mixture of rotamers) δ 8.87 (s, 1H), 8.43 (t, J=5.6 Hz, 1H), 8.37 (s, 1H), 8.11 (d, J=8.8 Hz, 1H), 8.06 (s, 1H), 7.75-7.70 (m, 2H), 7.52 (s, 1H), 7.42-7.39 (m, 1H), 7.36-7.32 (m, 1H), 6.84 (d, J=6.4 Hz, 1H), 6.68 (br, 2H), 5.61-5.58 (m, 1H), 4.41-4.37 (dd, J=2.4 Hz, 5.2 Hz, 1H), 3.92-3.85 (dd, 7=2.4 Hz, 5.2 Hz, 1H) 3.71 (t, J=0.8 Hz, 1H), 3.52-3.50 (m, 2H), 2.99 (t, J=7.2 Hz, 2H), 2.27-2.22 (m, 1H), 2.16-2.11 (m, 1H).

Step 1: Synthesis of 1-bis(tert-butoxycarbonyl)aminoisoquinoline-6-carbonitrile

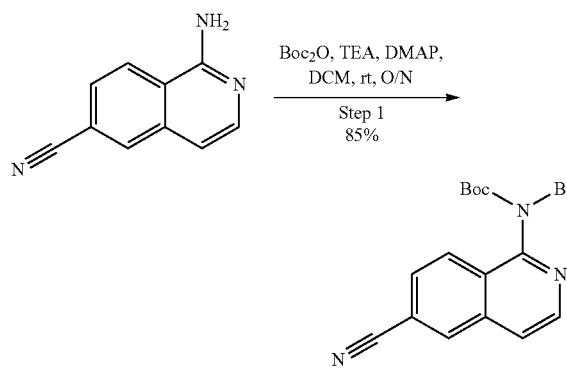

To a precooled (0° C.) solution of 1-aminoisoquinoline-6-carbonitrile (2.0 g, 11.7 mmol) in dichloromethane (300 mL) was added triethylamine (3.56 g, 35 mmol), 4-dimethylaminopyridine (143 mg, 1.16 mmol) and Di-tert-butyl dicarbonate (5.08 g, 23 mmol). The mixture was stirred at ambient overnight and concentrated in vacuo to give a residue which was purified by silica gel flash chromatography (petroleum ether/ethyl acetate=50:10) affording 1-bis (tert-butoxycarbonyl)aminoisoquinoline-6-carbonitrile (4 g) as a white solid. MS (ESI) m/z 370.2 [M+H]⁺. ¹H NMR (400 MHz, CDCl₃) δ 8.58 (d, J=6.0 Hz, 1H), 8.20 (s, 1H), 8.08 (d, J=9.2 Hz, 1H), 7.80-7.78 (m, 1H), 7.73 (d, J=6.0 Hz, 1H), 1.33 (s, 18H).

Step 2: Synthesis of tert-butyl tert-butoxycarbonyl (6-formylisoquinolin-1-yl)bicarbamate

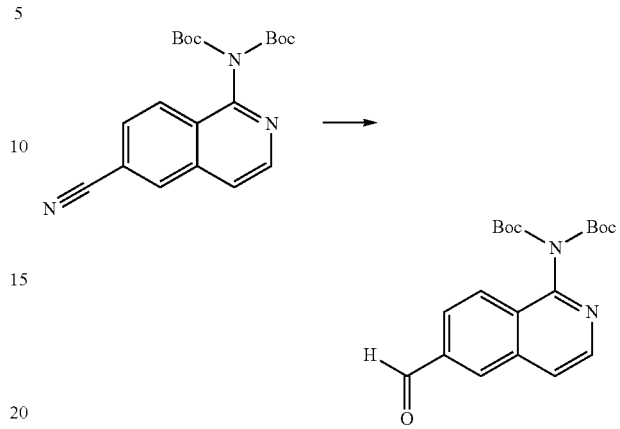

To a solution of 1-bis(tert-butoxycarbonyl)aminoisoquinoline-6-carbonitrile (2 g, 5.4 mmol) in 60 ml of AcOH/pyridine/H₂O(V/V/V=1/2/1), were added sodium hypophosphite (NaH₂PO₂, 3.72 g, 43.5 mmol), Raney-Ni (200 mg, 10%). The mixture was stirred at room temperature overnight. The mixture was filtered, and the filtrate was exacted with ethyl acetate. The combined organic layers were concentrated to give the crude product, which was purified by silica gel flash chromatography (petroleum ether/ethyl acetate 40:10) to afford tert-butyl tert-butoxycarbonyl(6-formylisoquinolin-1-yl)carbamate (760 mg) as a white solid. MS (ESI) m/z 373.2 [M+H]⁺

Step 3: Synthesis of (E)-tert-butyl tert-butoxycarbonyl(6-(2-nitrovinyl)isoquinolin-1-yl)carbamate

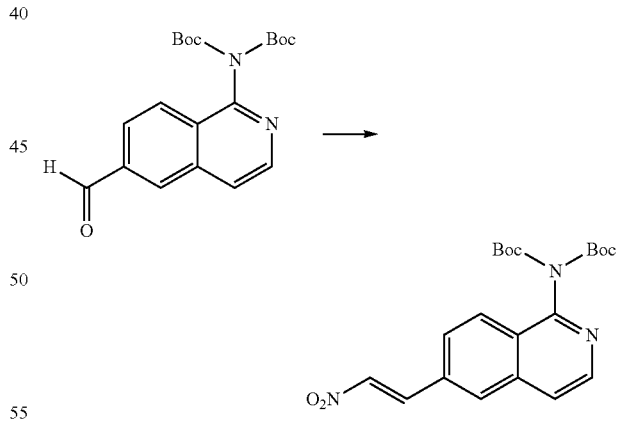

To a solution of tert-butyl tert-butoxycarbonyl(6-formylisoquinolin-1-yl)carbamate (660 mg, 1.77 mmol) in 60 ml of MeCN/Nitromethane (V/V=1/2), were added 4-dimethylaminopyridine (217 mg, 1.77 mmol). The mixture was stirred at room temperature overnight, and then cooled to 0° C., acetic anhydride (270 mg, 2.66 mmol) was added. After stirring for 0.5 h at 0° C., the mixture was concentrated. The residue was purified by silica gel flash chromatography (petroleum ether/ethyl acetate 40:10) to afford (E)-tert-butyl tert-butoxycarbonyl(6-(2-nitrovinyl)isoquinolin-1-yl)carbamate (400 mg) as a white solid. MS (ESI) m/z 416.2

[M+H]+. 1H NMR (400 MHz, CDCl3) δ 8.53 (d, J=5.2 Hz, 1H), 8.16 (d, J=13.6 Hz, 1H), 8.05 (s, 1H), 8.03 (d, J=8.0 Hz, 1H), 7.76-7.71 (m, 3H), 1.34 (m, 18H).

Step 4: Synthesis of tert-butyl tert-butoxycarbonyl (6-(2-aminoethyl)isoquinolin-1-yl)carbamate

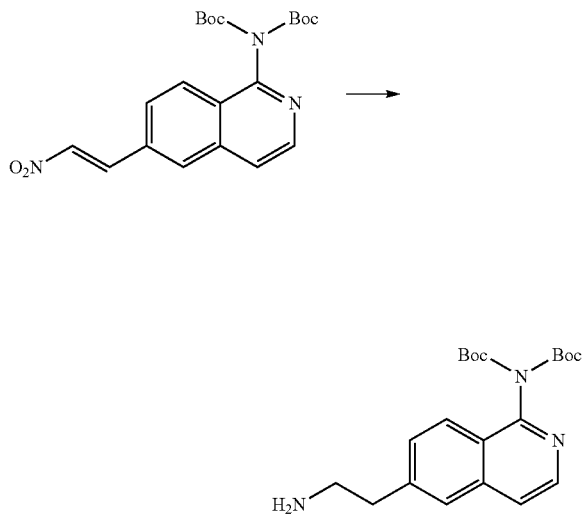

To a solution of (E)-tert-butyl tert-butoxycarbonyl (6-(2-nitrovinyl)isoquinolin-1-yl)carbamate (400 mg, 0.96 mmol) in 60 ml of ethanol, were added Pd/C (66 mg, 10%), 1 mL of 1N HCl. The mixture was stirred at room temperature overnight. After filtered on Celite, the filtrate was concentrated in vacuo to afford tert-butyl tert-butoxycarbonyl (6-(2-aminoethyl)isoquinolin-1-yl)carbamate (51 mg) as a red solid. MS (ESI) m/z 388.1 [M+H]+

2-((2S,4R)-4-Amino-1-(6-chloroimidazo [1,2-a]pyridine-2-carbonyl)pyrrolidin-2-yl)-N-(4-(aminomethyl)phenethyl)thiazole-4-carboxamide (54)

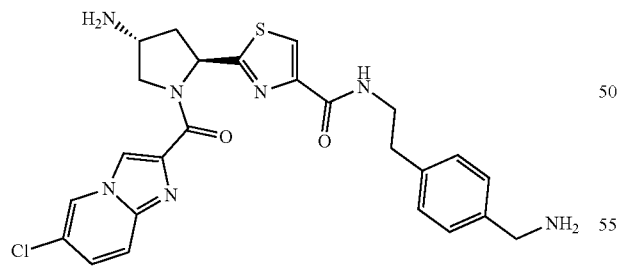

Compound 54 was synthesized in a manner analogous to the method used for the synthesis of Compound 11, using 4-(2-aminoethyl)benzylcarbamate in Step 9. MS (ESI) m/z 523.8 [M+H]+; 1H NMR (400 MHz, DMSO, mixture of rotamers) δ 9.00 (s, 1H), 8.80 (br, 3H), 8.59-8.44 (m, 4H), 8.15 (s, 1H), 7.78-7.50 (m, 1H), 7.48-7.40 (m, 3H), 7.29 (d, J=7.6 Hz, 2H), 5.77 (t, J=6.4 Hz, 1H), 4.58-4.40 (m, 2H), 4.14 (br, 1H), 4.05 (s, 2H), 3.98 (br, 1H), 3.54-3.40 (m, 2H), 2.90-2.84 (m, 2H), 2.74-2.60 (m, 2H).

2-((2S,4R)-4-Amino-1-(6-chloroimidazo[1,2-a]pyridine-2-carbonyl)pyrrolidin-2-yl)-N-((7-chloroimidazo[1,5-a]pyridin-1-yl)methyl)thiazole-4-carboxamide (55)

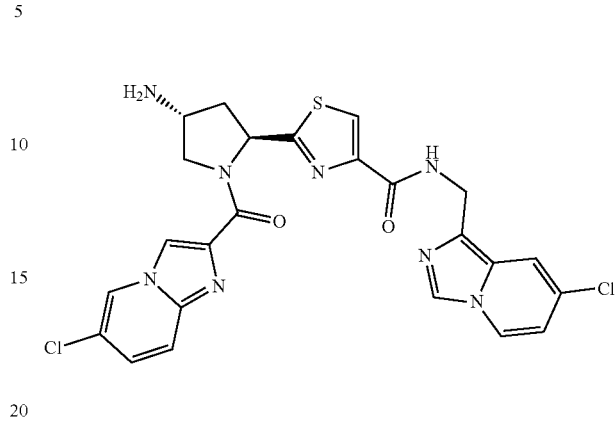

Compound 55 was synthesized in a manner analogous to the method used for the synthesis of Compound 11, using (7-chloroimidazo[1,5-a]pyridin-1-yl)methanamine in Step 9. MS(ESI) m/z 555.2 [M+H]+; 1H NMR (400 MHz, DMSO, mixture of rotamers) δ 9.52-9.50 (m, 1H), 9.22-9.18 (m, 1H), 8.98-8.93 (m, 1H), 8.73 (br, 3H), 8.58-8.45 (m, 2H), 8.24-8.15 (m, 2H), 7.76-7.41 (m, 2H), 7.13-6.87 (m, 1H), 5.77-5.33 (m, 1H), 4.82-4.81 (d, J=4.8 Hz, 2H), 4.58-3.98 (m, 3H), 2.74-2.62 (m, 2H).

2-((2S,4R)-4-Amino-1-(6-chloroimidazo[1,2-a]pyridine-2-carbonyl) pyrrolidin-2-yl)-N-((6-chloronaphthalen-2-yl)methyl)thiazole-4-carboxamide (56)

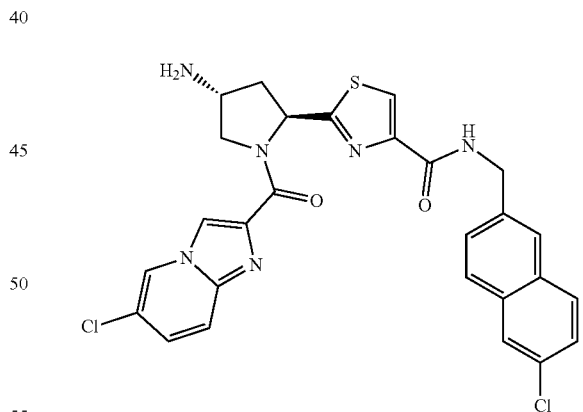

Compound 56 was synthesized in a manner analogous to the method used for the synthesis of Compound 11, using (6-chloronaphthalen-2-yl)methanamine in Step 9. 1H NMR (400 MHz, DMSO, mixture of rotamers) δ 9.08-8.98 (m, 1H), 8.86 (s, 1H), 8.39 (s, 1H), 8.15 (s, 1H), 8.01 (s, 1H), 7.96-7.91 (m, 1H), 7.90-7.85 (m, 1H), 7.83 (s, 1H), 7.71 (d, J=9.6 Hz, 1H), 7.60-7.54 (m, 1H), 7.52-7.45 (m, 1H), 7.43-7.37 (m, 1H), 5.65-5.59 (m, 1H), 4.65-4.59 (m, 2H), 4.45-4.36 (m, 1H), 3.94-3.85 (m, 1H), 3.75-3.66 (m, 1H), 3.60 (br, 1H), 2.34-2.24 (m, 1H), 2.20-2.10 (m, 1H), 2.08-1.90 (m, 1H).

2-((2S,4R)-4-Amino-1-(5-chlorobenzo[b]thiophene-2-carbonyl)pyrrolidin-2-yl)-N—((R)-6-guanidino-1-(methylamino)-1-oxohexan-2-yl)thiazole-4-carboxamide (57)

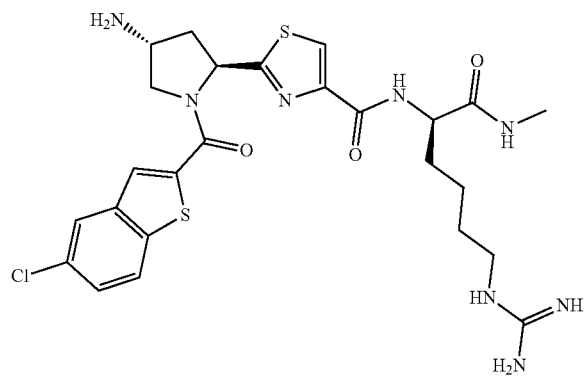 [SMILES: CNC(=O)[C@@H](CCCCNC(=N)N)NC(=O)c1csc([C@@H]2C[C@@H](N)CN2C(=O)c2cc3cc(Cl)ccc3s2)n1]

Compound 57 was synthesized in a manner analogous to the method used for the synthesis of Compound 14, using 3-chlorobenzo[b]thiophene-6-carboxylic acid in Step 1, and (R)-2-amino-6-(2,3-bis(tert-butoxycarbonyl))guanidino-N-methylhexanamide in Step 4. MS (ESI) m/z 591.1 [M+H]+. 1H NMR (400 MHz, DMSO) δ 10.94 (s, 1H), 8.21 (s, 1H), 8.12-8.07 (m, 3H), 7.96-7.92 (m, 2H), 7.52-7.49 (m, 1H), 6.95 (s, 1H), 5.66 (d, J=8.0 Hz, 1H), 5.17 (d, J=11.2 Hz, 1H), 4.94-4.88 (m, 1H), 4.42-4.38 (m, 1H), 4.16 (t, J=8.8 Hz, 1H), 3.60-3.45 (m, 1H), 3.08-2.95 (m, 2H), 2.82-2.78 (m, 1H), 2.60 (d, J=4.4 Hz, 3H), 2.07-1.99 (m, 1H), 1.84-1.76 (m, 1H), 1.71-1.65 (m, 1H), 1.52-1.43 (m, 4H).

2-((2S,4R)-4-Amino-1-(6-chloroimidazo[1,2-a]pyridine-2-carbonyl)pyrrolidin-2-yl)-N-((5-chloro-1H-indazol-3-yl)methyl)thiazole-4-carboxamide (58)

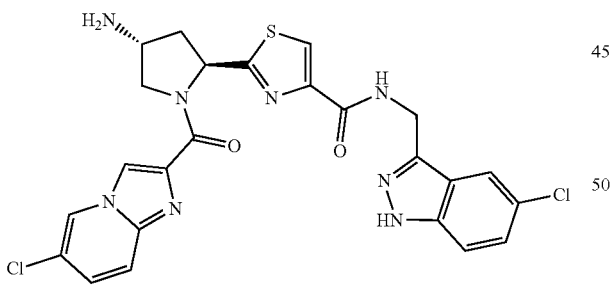

Compound 58 was synthesized in a manner analogous to the method used for the synthesis of Compound 11, using (5-chloro-1H-indazol-3-yl)methanamine hydrochloride in Step 9. MS (ESI) m/z 555.0 [M+H]+. 1H NMR (400 MHz, DMSO, mixture of rotamers) δ 9.01 (t, J=6.0 Hz, 1H), 8.92 (s, 1H), 8.50 (br, 3H), 8.48 (s, 1H), 8.24 (s, 1H), 7.98-7.97 (m, 1H), 7.71 (d, J=10.0 Hz, 1H), 7.58-7.46 (m, 2H), 7.34-7.31 (m, 1H), 5.78-5.75 (m, 1H), 4.78 (d, J=6.4 Hz, 2H), 4.51 (d, J=5.2 Hz, 2H), 3.99-3.97 (m, 1H), 2.68-2.56 (m, 3H).

2-((2S,4R)-4-Amino-1-(6-chloroimidazo[1,2-a]pyridine-2-carbonyl)pyrrolidin-2-yl)-N-((6-chloro-1H-indazol-3-yl)methyl)thiazole-4-carboxamide (59)

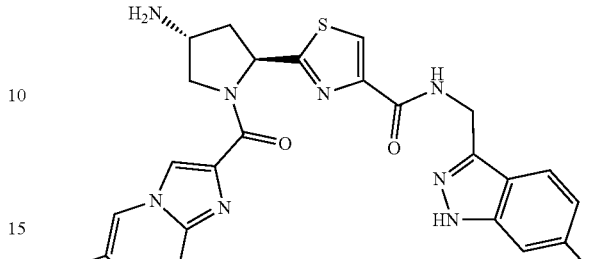

Compound 59 was synthesized in a manner analogous to the method used for the synthesis of Compound 11, using (6-chloro-1H-indazol-3-yl)methanamine hydrochloride in Step 9. MS (ESI) m/z 555.0 [M+H]+. 1H NMR (400 MHz, DMSO, mixture of rotamers) δ 8.97-8.86 (m, 2H), 8.53-8.52 (m, 4H), 8.23 (s, 1H), 7.88 (d, J=8.4 Hz, 1H), 7.71 (d, J=9.6 Hz, 1H), 7.55 (d, J=1.6 Hz, 1H), 7.46-7.44 (m, 1H), 7.07 (dd, J=8.4 Hz, 1.6 Hz, 1H), 5.77-5.74 (m, 1H), 4.79 (d, J=6.4 Hz, 2H), 4.51 (d, J=5.2 Hz, 2H), 4.11-3.96 (m, 2H), 2.75-2.59 (m, 2H).

2-((2S,4R)-4-Amino-1-(6-chloroimidazo[1,2-a]pyridine-2-carbonyl)pyrrolidin-2-yl)-N-((1-amino-5,7-dimethylisoquinolin-6-yl)methyl)thiazole-4-carboxamide (60)

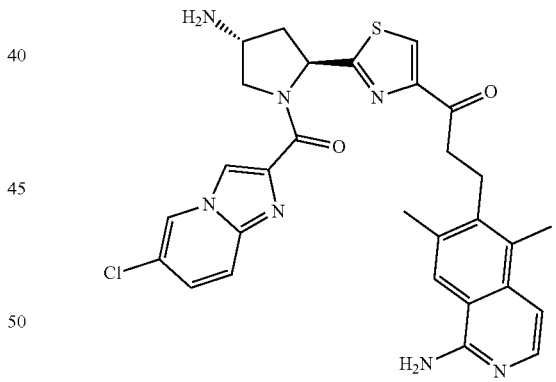

Compound 60 was synthesized in a manner analogous to the method used for the synthesis of Compound 11, using 6-(aminomethyl)-5,7-dimethylisoquinolin-1-amine in Step 9. MS (ESI) m/z 575.1 [M+H]+. 1H NMR (400 MHz, DMSO, mixture of rotamers) δ 8.85 (s, 1H), 8.37 (s, 1H), 8.27-8.20 (m, 1H), 8.13 (s, 1H), 7.90 (s, 1H), 7.80-7.69 (m, 2H), 7.39 (dd, J=9.6, 2.0 Hz, 1H), 6.97 (d, J=6.4 Hz, 1H), 6.60 (br, 2H), 5.55 (dd, J=4.8, 2.8 Hz, 1H), 4.68 (d, J=5.6 Hz, 2H), 4.40-4.34 (m, 1H), 3.88-3.82 (m, 1H), 3.65-3.61 (m, 1H), 2.55 (s, 3H), 2.54 (s, 3H), 2.23-2.15 (m, 1H), 2.12-2.05 (m, 1H).

2-((2S,4R)-4-Amino-1-(5,6-dichlorobenzo[b]thio-phene-2-carbonyl)pyrrolidin-2-yl)-N—((S)-6-guanidino-1-(methylamino)-1-oxohexan-2-yl)thiazole-4-carboxamide (61)

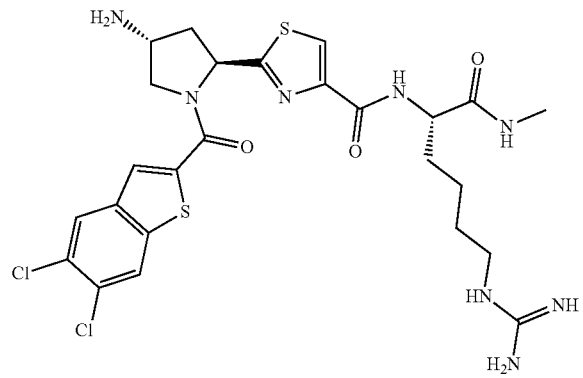 [SMILES: CNC(=O)[C@H](CCCCNC(=N)N)NC(=O)c1csc([C@@H]2C[C@@H](N)CN2C(=O)c2cc3cc(Cl)c(Cl)cc3s2)n1]

2-((2S,4R)-4-Amino-1-(4-chlorobenzo[b]thiophene-2-carbonyl)pyrrolidin-2-yl)-N—((S)-6-guanidino-1-(methylamino)-1-oxohexan-2-yl)thiazole-4-carboxamide (63)

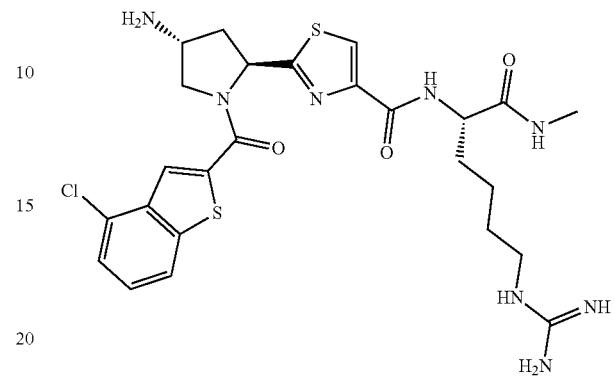

Compound 61 was synthesized in a manner analogous to the method used for the synthesis of Compound 14, using 5,6-dichlorobenzo[b]thiophene-2-carboxylic acid in Step 1. MS (ESI) m/z 625.1 [M+H]$^+$. $^1$H NMR (400 MHz, DMSO, mixture of rotamers) δ 8.88-8.64 (br, 4H), 8.48 (s, 1H), 8.35-8.14 (m, 5H), 7.75-7.31 (m, 1H), 7.56-6.92 (m, 3H), 5.78 (t, J=6.0 Hz, 1H), 4.48-4.42 (m, 2H), 4.21-4.12 (m, 2H), 3.10-3.09 (m, 2H), 2.74-2.66 (m, 2H), 2.62 (d, J=4.0 Hz, 3H), 1.78-1.71 (m, 2H), 1.50-1.49 (m, 2H), 1.36-1.29 (m, 2H).

Compound 63 was synthesized in a manner analogous to the method used for the synthesis of Compound 14, using 4-chlorobenzo[b]thiophene-2-carboxylic acid in Step 1. MS (ESI) m/z 591.1 [M+H]$^+$. $^1$H NMR (400 MHz, DMSO, mixture of rotamers) δ 8.63 (br, 3H), 8.26 (s, 1H), 8.21 (d, J=4.4 Hz, 1H), 8.15 (d, J=8.0 Hz, 1H), 8.07 (d, J=7.6 Hz, 1H), 7.97 (s, 1H), 7.97 (br, 1H), 7.60-7.58 (m, 1H), 7.52 (t, J=8.0 Hz, 1H), 7.46-6.88 (br, 4H), 5.80 (t, J=7.2 Hz, 1H), 4.58-4.54 (m, 1H), 4.46-4.43 (m, 1H), 4.23-4.14 (m, 2H), 3.10-3.09 (m, 2H), 2.74-2.61 (m, 2H), 2.51 (d, J=0.8 Hz, 3H), 1.77-1.71 (m, 2H), 1.52-1.45 (m, 2H), 1.34-1.27 (m, 2H).

2-((2S,4R)-4-Amino-1-(6-chlorobenzo[b]thiophene-2-carbonyl)pyrrolidin-2-yl)-N—((S)-6-guanidino-1-(methylamino)-1-oxohexan-2-yl)thiazole-4-carboxamide (62)

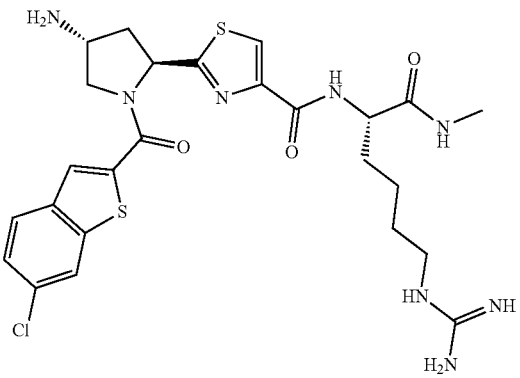 [SMILES: CNC(=O)[C@H](CCCCNC(=N)N)NC(=O)c1csc([C@@H]2C[C@@H](N)CN2C(=O)c2cc3ccc(Cl)cc3s2)n1]

2-((2S,4R)-4-Amino-1-(5-(trifluoromethyl)benzo[b]thiophene-2-carbonyl)pyrrolidin-2-yl)-N—((S)-6-guanidino-1-(methylamino)-1-oxohexan-2-yl)thiazole-4-carboxamide (64)

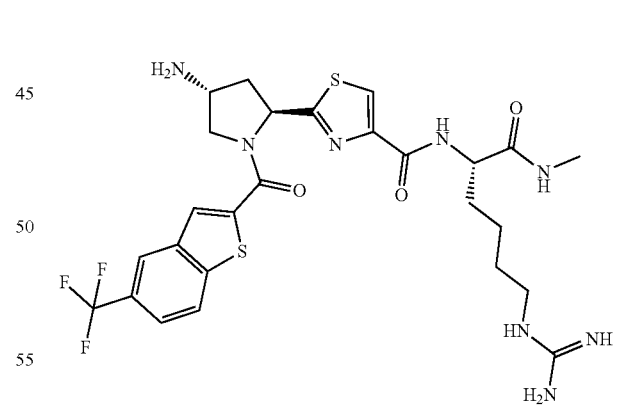

Compound 62 was synthesized in a manner analogous to the method used for the synthesis of Compound 14, using 6-chloro-benzo[b]thiophene-2-carboxylic acid in Step 1. MS (ESI) m/z 591.1 [M+H]$^+$. $^1$H NMR (400 MHz, DMSO, mixture of rotamers) δ 8.51 (br, 3H), 8.25 (s, 2H), 8.19-8.10 (m, 3H), 8.02 (d, J=8.8 Hz, 1H), 7.70-7.63 (m, 1H), 7.53 (d, J=8.4 Hz, 1H), 7.27 (br, 3H), 5.78 (t, J=7.6 Hz, 1H), 4.46-4.43 (m, 2H), 4.4.21-4.11 (m, 2H), 3.11-3.06 (m, 2H), 2.74-2.64 (m, 2H), 2.52 (d, J=4.8 Hz, 3H), 1.80-1.69 (m, 2H), 1.51-1.44 (m, 2H), 1.33-1.23 (m, 2H).

Compound 64 was synthesized in a manner analogous to the method used for the synthesis of Compound 14, using 5-(trifluoromethyl)benzo[b]thiophene-2-carboxylic acid in Step 1. MS (ESI) m/z 625.1 [M+H]$^+$. $^1$H NMR (400 MHz, DMSO, mixture of rotamers) δ 8.55 (br, 3H), 8.44 (s, 1H), 8.33 (d, J=8.8 Hz, 1H), 8.26-8.23 (m, 2H), 8.20-8.19 (m, 1H), 8.13 (d, J=8.4 Hz, 1H), 7.81 (d, J=8.4 Hz, 1H), 7.70-7.69 (m, 1H), 7.35 (br, 3H), 5.79 (t, J=7.6 Hz, 1H), 4.46-4.41 (m, 2H), 4.4.21-4.11 (m, 2H), 3.11-3.06 (m, 2H), 2.74-2.64 (m, 2H), 2.52 (d, J=4.8 Hz, 3H), 1.80-1.69 (m, 2H), 1.51-1.44 (m, 2H), 1.33-1.23 (m, 2H).

2-((2S,4R)-4-Amino-1-(6-methylbenzo[b]thiophene-2-carbonyl)pyrrolidin-2-yl)-N—((S)-6-guanidino-1-(methylamino)-1-oxohexan-2-yl)thiazole-4-carboxamide (65)

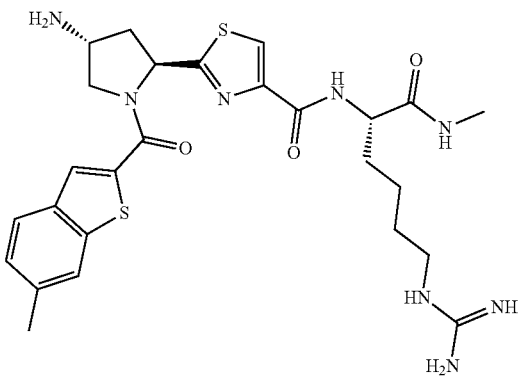 [SMILES: CNC(=O)[C@H](CCCCNC(=N)N)NC(=O)c1csc([C@@H]2C[C@@H](N)CN2C(=O)c2cc3ccc(C)cc3s2)n1]

Compound 65 was synthesized in a manner analogous to the method used for the synthesis of Compound 14, using 6-methylbenzo[b]thiophene-2-carboxylic acid in Step 1. MS (ESI) m/z 571.2 [M+H]+. 1H NMR (400 MHz, DMSO, mixture of rotamers) δ 8.63 (br, 3H), 8.24-8.13 (m, 3H), 8.02 (s, 1H), 7.90-7.74 (m, 3H), 7.57-6.89 (m, 4H), 5.78 (t, J=8.0 Hz, 1H), 4.48-4.42 (m, 2H), 4.21 (d, J=6.0 Hz, 1H), 4.12 (s, 1H), 3.11-3.07 (m, 2H), 2.76-2.59 (m, 5H), 2.45 (s, 3H), 1.81-1.68 (m, 2H), 1.52-1.44 (m, 2H), 1.36-1.28 (m, 2H).

2-((2S,4R)-4-Amino-1-(6-chloroquinoline-3-carbonyl)pyrrolidin-2-yl)-N—((S)-6-guanidino-1-(methylamino)-1-oxohexan-2-yl)thiazole-4-carboxamide (66)

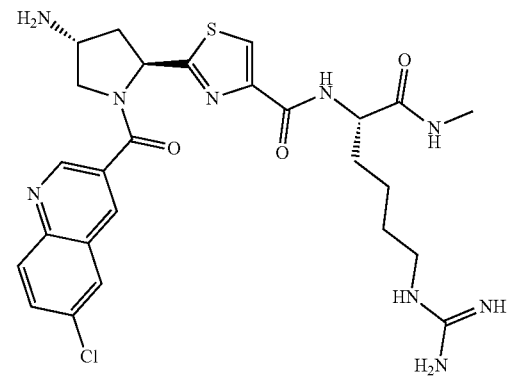 [SMILES: CNC(=O)[C@H](CCCCNC(=N)N)NC(=O)c1csc([C@@H]2C[C@@H](N)CN2C(=O)c2cnc3ccc(Cl)cc3c2)n1]

Compound 66 was synthesized in a manner analogous to the method used for the synthesis of Compound 14, using 6-chloroquinoline-3-carboxylic acid acid in Step 1. MS (ESI) m/z 586.3 [M+H]+. 1H NMR (400 MHz, DMSO-d6, mixture of rotamers) δ 9.11 (s, 1H), 8.98-8.85 (m, 1H), 8.77-8.75 (m, 1H), 8.64-8.58 (m, 2H), 8.37 (s, 1H), 8.31-8.14 (m, 3H), 8.08-7.92 (m, 1H), 7.86-7.73 (m, 1H), 7.43-6.99 (m, 3H), 5.82 (t, J=4.0 Hz, 1H), 4.50-4.44 (m, 4H), 4.28-4.23 (m, 1H), 4.08-4.03 (m, 1H), 3.82-3.79 (m, 1H), 3.12-3.07 (m, 2H), 2.82-2.68 (m, 2H), 2.64-2.61 (d, J=4.4 Hz, 3H), 1.84-1.69 (m, 2H), 1.51-1.45 (m, 2H), 1.36-1.27 (m, 2H).

2-((2S,4R)-4-Amino-1-(2-chloroquinoline-6-carbonyl)pyrrolidin-2-yl)-N—((S)-6-guanidino-1-(methylamino)-1-oxohexan-2-yl)thiazole-4-carboxamide (67)

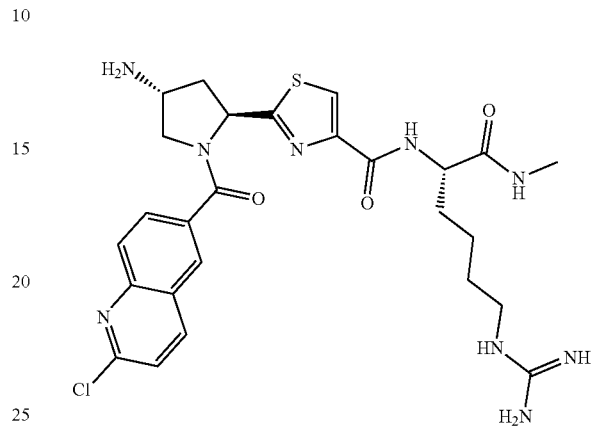

Compound 67 was synthesized in a manner analogous to the method used for the synthesis of Compound 14, using 2-chloroquinoline-6-carboxylic acid in Step 1. MS(ESI) m/z 586.3 [M+H]+. 1H NMR (400 MHz, DMSO, mixture of rotamers) δ 8.83 (br, 1H), 8.79-8.63 (m, 2H), 8.56 (s, 2H), 8.50-8.14 (m, 4H), 8.13-7.89 (m, 2H), 7.83-7.60 (m, 2H), 7.45-6.91 (m, 2H), 5.81 (t, J=8 Hz, 1H), 4.50-4.45 (m, 1H), 4.32-4.19 (m, 1H), 4.01-3.99 (m, 2H), 3.75-3.72 (m, 1H), 3.12-3.06 (m, 2H), 2.79-2.59 (m, 5H), 1.82-1.68 (m, 2H), 1.52-1.45 (m, 2H), 1.36-1.27 (m, 2H).

Example 2: Inhibitory Activity of Exemplary Compounds of Formula I Against Plasma Kallikrein The example compounds were evaluated for inhibition of the human activated kallikrein enzyme in two formats of an assay employing a fluorogenic peptide substrate. In one assay format, the concentrations of reagents were as follows: 20 mM Tris pH 7.5, 1 mM EDTA, 150 mM sodium chloride, 0.1% PEG-400, 0.1% Triton X-100, 500 pM activated kallikrein enzyme, 300 uM Pro-Phe-Arg-7-amido-4-methylcoumarin substrate. Prior to reaction initiation with substrate, enzyme and inhibitors were preincubated for 30 min at room temperature. After initiation with substrate, reactions were incubated for 10 min at room temperature and fluorescence emission at 460 nm from 380 nm excitation measured with a microplate reader. In another assay format, the concentrations of reagents were as follows: 20 mM Tris pH 7.5, 1 mM EDTA, 150 mM sodium chloride, 0.1% PEG-400, 0.1% Triton X-100, 5 pM activated kallikrein enzyme, 300 uM Pro-Phe-Arg-7-amido-4-methylcoumarin substrate. Prior to reaction initiation with substrate, enzyme and inhibitors were preincubated for 30 min at room temperature. After initiation with substrate, reactions were incubated for 18 hr at room temperature and fluorescence emission at 460 nm from 380 nm excitation measured with a microplate reader.

Table 2 provides the results of the assay. For the compounds listed in Table 2, the $EC_{50}$ values are reported according to the following ranges: A≤0.1 µM; B>0.1 µM to ≤1.0 µM; C>1.0 µM to ≤5.0 µM; D>5.0 µM to ≤9.9 µM; E>9.9 µM.

TABLE 2

Inhibitory Activity of Exemplary Compounds of Formula I

| Example | pKal $EC_{50}$ (nM) |
|---|---|
| 1 | C |
| 2 | E |
| 3 | E |
| 4 | E |
| 5 | E |
| 6 | C |
| 7 | E |
| 8 | E |
| 9 | E |
| 10 | E |
| 11 | A |
| 12 | A |
| 13 | B |
| 14 | E |
| 15 | E |
| 16 | C |
| 17 | E |
| 18 | E |
| 19 | A |
| 20 | B |
| 21 | A |
| 22 | A |
| 23 | A |
| 24 | B |
| 25 | E |
| 26 | E |
| 27 | E |
| 28 | D |
| 29 | E |
| 30 | E |
| 31 | E |
| 32 | E |
| 33 | C |
| 34 | E |
| 35 | C |
| 36 | A |
| 37 | C |
| 38 | E |
| 39 | D |
| 40 | C |
| 41 | B |
| 42 | A |
| 43 | D |
| 44 | B |
| 45 | A |
| 46 | B |
| 47 | A |
| 48 | B |
| 49 | A |
| 50 | D |
| 51 | A |
| 52 | E |
| 53 | A |
| 54 | C |
| 55 | B |
| 56 | E |
| 57 | C |
| 58 | D |
| 59 | E |
| 60 | A |
| 61 | B |
| 62 | B |
| 63 | C |
| 64 | B |
| 65 | B |
| 66 | B |
| 67 | C |

Selectivity

Compounds 11, 33, and 53 were evaluated in a selectivity screen of serine proteases. All three compounds were selective inhibitors of pKal as none of the evaluated compounds showed any inhibitory activity of the selected anti-target proteases (Table 2). These results also demonstrate that selectivity for activity against pKal was not dependent upon presence of the amino group corresponding to the $R^1$ position in Formula I.

TABLE 3

Selectivity of Exemplary pKal Inhibitory Compounds

| | | Anti-target panel $IC_{50}$ (µM) | | | |
|---|---|---|---|---|---|
| Compound | pKal $EC_{50}$ (nM) | FXa | Thrombin | Elastase | Trypsin |
| 11 | 32 | >10 | >10 | >10 | >100 |
| 33 | 3240 | >10 | >10 | >10 | >100 |
| 53 | 15 | >10 | >10 | >10 | >100 |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control.

In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula I:

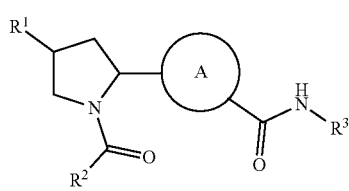

I or a pharmaceutically acceptable salt thereof, wherein:
A is substituted or unsubstituted 5-membered heteroarylene;
$R^1$ is —N($R^A$)$_2$;
$R^2$ is substituted or unsubstituted aryl, substituted or unsubstituted aralkyl, substituted or unsubstituted heteroaryl, substituted or unsubstituted heteroaralkyl, substituted or unsubstituted alkyl, substituted or unsubstituted heteroalkyl, substituted or unsubstituted alkenyl, substituted or unsubstituted alkynyl, —O$R^A$, or —N($R^A$)$_2$;
$R^3$ is substituted or unsubstituted alkyl, substituted or unsubstituted heteroalkyl, substituted or unsubstituted acyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted aralkyl, substituted or unsubstituted heteroaryl, or substituted or unsubstituted heteroaralkyl, wherein any carbon of $R^3$, valence permitting, is optionally replaced with —O—, —N$R^A$—, —C(O)—, —C(=N$R^A$)—, —S—, —S(O)—, or —S(O)$_2$—; and
each occurrence of $R^A$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, or an oxygen protecting group when attached to an oxygen atom, or two $R^A$ groups are joined to form a substituted or unsubstituted heterocyclic ring.

2. The compound of claim 1, or a pharmaceutically acceptable salt thereof, wherein:
$R^1$ is —NH$_2$.

3. The compound of claim 1, or a pharmaceutically acceptable salt thereof, wherein:
$R^2$ is substituted or unsubstituted heteroaryl.

4. The compound of claim 1, or a pharmaceutically acceptable salt thereof, wherein:
$R^2$ is substituted or unsubstituted fused bicyclic heteroaryl.

5. The compound of claim 1, or a pharmaceutically acceptable salt thereof, wherein:
$R^3$ is substituted or unsubstituted alkyl, or substituted or unsubstituted heteroalkyl, wherein any carbon of $R^3$, valence permitting, is optionally replaced with —O—, —N$R^A$—, —C(O)—, or —C(=N$R^A$)—.

6. The compound of claim 1, wherein the compound is of Formula I-a:

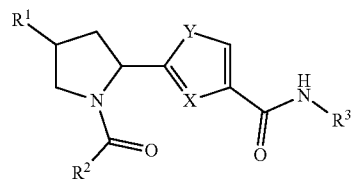

I-a or a pharmaceutically acceptable salt thereof, wherein:
X is N or C$R^y$;
Y is O, S, or N$R^x$; and
$R^x$ and $R^y$ are, independently, hydrogen or substituted or unsubstituted alkyl.

7. The compound of claim 6, or a pharmaceutically acceptable salt thereof, wherein:
X is N; and
Y is O, S, or N$R^x$.

8. The compound of claim 7, or a pharmaceutically acceptable salt thereof, wherein:
Y is O or S.

9. The compound of claim 1, wherein the compound is of Formula I-b:

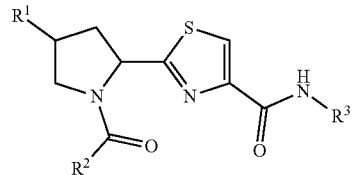

I-b or a pharmaceutically acceptable salt thereof.

10. The compound of claim 1, wherein the compound is of Formula I-c:

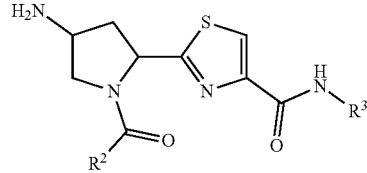

I-c or a pharmaceutically acceptable salt thereof.

11. The compound of claim 10, or a pharmaceutically acceptable salt thereof, wherein:
R² is substituted or unsubstituted bicyclic fused heteroaryl.

12. The compound of claim 1, wherein the compound is of Formula I-d:

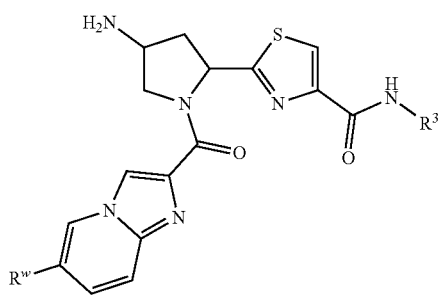

I-d or a pharmaceutically acceptable salt thereof, wherein:
R^w is hydrogen, halogen, alkoxy, alkoxyalkyl, haloalkoxy, or haloalkyl.

13. The compound of claim 12, or a pharmaceutically acceptable salt thereof, wherein:
R³ is substituted or unsubstituted alkyl, or substituted or unsubstituted heteroalkyl, wherein any carbon of R³, valence permitting, is optionally replaced with —O—, —NR⁴—, —C(O)—, or —C(=NR⁴)—.

14. A compound of claim 1, wherein the compound is:
2-((2R,4R)-4-amino-1-(6-chloroimidazo[1,2-a]pyridine-2-carbonyl)pyrrolidin-2-yl)-N—((S)-6-guanidino-1-(methylamino)-1-oxohexan-2-yl)thiazole-4-carboxamide (1);
2-((2R,4R)-4-amino-1-(6-chloroimidazo[1,2-a]pyridine-2-carbonyl)pyrrolidin-2-yl)-N—((R)-6-guanidino-1-(methylamino)-1-oxohexan-2-yl)thiazole-4-carboxamide (2);
2-((2R,4R)-4-acetamido-1-(6-chloroimidazo[1,2-a]pyridine-2-carbonyl)pyrrolidin-2-yl)-N—((S)-6-guanidino-1-(methylamino)-1-oxohexan-2-yl)thiazole-4-carboxamide (5);
2-((2R,4S)-4-amino-1-(6-chloroimidazo[1,2-a]pyridine-2-carbonyl)pyrrolidin-2-yl)-N—((S)-6-guanidino-1-(methylamino)-1-oxohexan-2-yl)thiazole-4-carboxamide (6);
2-((2S,4R)-4-amino-1-(6-chloroimidazo[1,2-a]pyridine-2-carbonyl)pyrrolidin-2-yl)-N—((S)-6-guanidino-1-(methylamino)-1-oxohexan-2-yl)thiazole-4-carboxamide (11);
2-((2S,4R)-4-amino-1-(6-chloroimidazo[1,2-a]pyridine-2-carbonyl)pyrrolidin-2-yl)-N—((R)-6-guanidino-1-(methylamino)-1-oxohexan-2-yl)thiazole-4-carboxamide (12);
2-((2S,4R)-4-amino-1-(imidazo[1,2-a]pyridine-2-carbonyl)pyrrolidin-2-yl)-N—((S)-6-guanidino-1-(methylamino)-1-oxohexan-2-yl)thiazole-4-carboxamide (13);
2-((2S,4R)-4-amino-1-(1,2-dimethyl-1H-imidazole-4-carbonyl)pyrrolidin-2-yl)-N—((S)-6-guanidino-1-(methylamino)-1-oxohexan-2-yl)thiazole-4-carboxamide (14);
2-((2S,4R)-4-amino-1-benzoylpyrrolidin-2-yl)-N—((S)-6-guanidino-1-(methylamino)-1-oxohexan-2-yl)thiazole-4-carboxamide (15);
3-chlorobenzyl (2S,4R)-4-amino-2-(4-(((S)-6-guanidino-1-(methylamino)-1-oxohexan-2-yl)carbamoyl)thiazol-2-yl)pyrrolidine-1-carboxylate (16);
2-((2S,4R)-4-amino-1-isobutyrylpyrrolidin-2-yl)-N—((S)-6-guanidino-1-(methylamino)-1-oxohexan-2-yl)thiazole-4-carboxamide (18);
2-((2S,4R)-4-amino-1-(6-(trifluoromethyl)imidazo[1,2-a]pyridine-2-carbonyl)pyrrolidin-2-yl)-N—((S)-6-guanidino-1-(methylamino)-1-oxohexan-2-yl)thiazole-4-carboxamide (19);
2-((2S,4R)-4-amino-1-(6-methoxyimidazo[1,2-a]pyridine-2-carbonyl)pyrrolidin-2-yl)-N—((S)-6-guanidino-1-(methylamino)-1-oxohexan-2-yl)thiazole-4-carboxamide (20);
2-((2S,4R)-4-amino-1-(6-iodoimidazo[1,2-a]pyridine-2-carbonyl)pyrrolidin-2-yl)-N—((S)-6-guanidino-1-(methylamino)-1-oxohexan-2-yl)thiazole-4-carboxamide (21);
2-((2S,4R)-4-amino-1-(6-chloroimidazo[1,2-a]pyridine-2-carbonyl)pyrrolidin-2-yl)-N—((S)-1-amino-6-guanidino-1-oxohexan-2-yl)thiazole-4-carboxamide (22);
N²-(2(2S,4R)-4-amino-1-(6-chloroimidazo[1,2-a]pyridine-2-carbonyl)pyrrolidin-2-yl)thiazole-4-carbonyl)-N6-carbamimidoyl-L-lysine (23);
2-((2S,4R)-4-amino-1-(6-chloroimidazo[1,2-a]pyridine-2-carbonyl)pyrrolidin-2-yl)-N—((S)-1-(dimethylamino)-6-guanidino-1-oxohexan-2-yl)thiazole-4-carboxamide (24);
2-((2S,4R)-4-amino-1-(6-chloroimidazo[1,2-a]pyridine-2-carbonyl)pyrrolidin-2-yl)-N—((S)-6-amino-1-(methylamino)-1-oxohexan-2-yl)thiazole-4-carboxamide (25);
N—((S)-6-acetamido-1-(methylamino)-1-oxohexan-2-yl)-2-((2S,4R)-4-amino-1-(6-chloroimidazo[1,2-a]pyridine-2-carbonyl)pyrrolidin-2-yl)thiazole-4-carboxamide (26);
2-((2S,4R)-4-amino-1-(6-chloroimidazo[1,2-a]pyridine-2-carbonyl)pyrrolidin-2-yl)-N—((S)-1-(methylamino)-1-oxo-6-ureidohexan-2-yl)thiazole-4-carboxamide (27);
2-((2S,4R)-4-amino-1-(6-chloroimidazo[1,2-a]pyridine-2-carbonyl)pyrrolidin-2-yl)-N—((S)-5-guanidino-1-(methylamino)-1-oxopentan-2-yl)thiazole-4-carboxamide (28);
(S)-2-(2-((2S,4R)-4-amino-1-(6-chloroimidazo[1,2-a]pyridine-2-carbonyl)pyrrolidin-2-yl)thiazole-4-carboxamido)-N1-methylpentanediamide (29);
N—((S)-3-(1H-imidazol-4-yl)-1-(methylamino)-1-oxopropan-2-yl)-2-((2S,4R)-4-amino-1-(6-chloroimidazo[1,2-a]pyridine-2-carbonyl)pyrrolidin-2-yl)thiazole-4-carboxamide (30);
N—((S)-3-(1H-indol-3-yl)-1-(methylamino)-1-oxopropan-2-yl)-2-((2S,4R)-4-amino-1-(6-chloroimidazo[1,2-a]pyridine-2-carbonyl)pyrrolidin-2-yl)thiazole-4-carboxamide (31);
2-((2S,4R)-4-amino-1-(6-chloroimidazo[1,2-a]pyridine-2-carbonyl)pyrrolidin-2-yl)-N—((S)-3-(4-hydroxyphenyl)-1-(methylamino)-1-oxopropan-2-yl)thiazole-4-carboxamide (32);
2-((2S,4R)-4-acetamido-1-(6-chloroimidazo[1,2-a]pyridine-2-carbonyl)pyrrolidin-2-yl)-N—((S)-6-guanidino-1-(methylamino)-1-oxohexan-2-yl)thiazole-4-carboxamide (35);
2-((2S,4S)-4-amino-1-(6-chloroimidazo[1,2-a]pyridine-2-carbonyl)pyrrolidin-2-yl)-N—((S)-6-guanidino-1-(methylamino)-1-oxohexan-2-yl)thiazole-4-carboxamide (36);

2-((2S,4R)-1-(2-naphthoyl)-4-aminopyrrolidin-2-yl)-N—((S)-6-guanidino-1-(methylamino)-1-oxohexan-2-yl)thiazole-4-carboxamide (40);

2-((2S,4R)-4-amino-1-(3-chloroquinoline-6-carbonyl)pyrrolidin-2-yl)-N—((S)-6-guanidino-1-(methylamino)-1-oxohexan-2-yl)thiazole-4-carboxamide (41);

2-((2S,4R)-4-amino-1-(6-chloroquinoline-2-carbonyl)pyrrolidin-2-yl)-N—((S)-6-guanidino-1-(methylamino)-1-oxohexan-2-yl)thiazole-4-carboxamide (42);

2-((2S,4R)-4-amino-1-(3-chlorobenzo[b]thiophene-6-carbonyl)pyrrolidin-2-yl)-N—((S)-6-guanidino-1-(methylamino)-1-oxohexan-2-yl)thiazole-4-carboxamide (43);

2-((2S,4R)-4-amino-1-(5-chlorobenzo[b]thiophene-2-carbonyl)pyrrolidin-2-yl)-N—((S)-6-guanidino-1-(methylamino)-1-oxohexan-2-yl)thiazole-4-carboxamide (44);

2-((2S,4R)-4-amino-1-(5-chlorobenzo[d]thiazole-2-carbonyl)pyrrolidin-2-yl)-N—((S)-6-guanidino-1-(methylamino)-1-oxohexan-2-yl)thiazole-4-carboxamide (45);

2-((2S,4R)-4-amino-1-(6-chloroimidazo[1,2-a]pyridine-2-carbonyl)pyrrolidin-2-yl)-N-(5-guanidinopentyl)thiazole-4-carboxamide (46);

2-((2S,4R)-4-amino-1-(6-chloroimidazo[1,2-a]pyridine-2-carbonyl)pyrrolidin-2-yl)-N-(4-carbamimidoylbenzyl)thiazole-4-carboxamide (47);

2-((2S,4R)-4-amino-1-(6-chloroimidazo[1,2-a]pyridine-2-carbonyl)pyrrolidin-2-yl)-N-((6-amino-2,4-dimethylpyridin-3-yl)methyl)thiazole-4-carboxamide (48);

2-((2S,4R)-4-amino-1-(6-chloroimidazo[1,2-a]pyridine-2-carbonyl)pyrrolidin-2-yl)-N-((1-aminoisoquinolin-6-yl)methyl)thiazole-4-carboxamide (49);

2-((2S,4R)-4-amino-1-(6-chloroimidazo[1,2-a]pyridine-2-carbonyl)pyrrolidin-2-yl)-N-(4-(aminomethyl)benzyl)thiazole-4-carboxamide (50);

2-((2S,4R)-4-amino-1-(6-chloroimidazo[1,2-a]pyridine-2-carbonyl)pyrrolidin-2-yl)-N-(4-carbamimidoylphenethyl)thiazole-4-carboxamide (51);

2-((2S,4R)-4-amino-1-(6-chloroimidazo[1,2-a]pyridine-2-carbonyl)pyrrolidin-2-yl)-N-(2-(6-amino-2,4-dimethylpyridin-3-yl)ethyl)thiazole-4-carboxamide (52);

2-((2S,4R)-4-amino-1-(6-chloroimidazo[1,2-a]pyridine-2-carbonyl)pyrrolidin-2-yl)-N-(2-(1-aminoisoquinolin-6-yl)ethyl)thiazole-4-carboxamide (53);

2-((2S,4R)-4-amino-1-(6-chloroimidazo[1,2-a]pyridine-2-carbonyl)pyrrolidin-2-yl)-N-(4-(aminomethyl)phenethyl)thiazole-4-carboxamide (54);

2-((2S,4R)-4-amino-1-(6-chloroimidazo[1,2-a]pyridine-2-carbonyl)pyrrolidin-2-yl)-N-((7-chloroimidazo[1,5-a]pyridin-1-yl)methyl)thiazole-4-carboxamide (55);

2-((2S,4R)-4-amino-1-(6-chloroimidazo[1,2-a]pyridine-2-carbonyl)pyrrolidin-2-yl)-N-((6-chloronaphthalen-2-yl)methyl)thiazole-4-carboxamide (56);

2-((2S,4R)-4-amino-1-(5-chlorobenzo[b]thiophene-2-carbonyl)pyrrolidin-2-yl)-N—((R)-6-guanidino-1-(methylamino)-1-oxohexan-2-yl)thiazole-4-carboxamide (57);

2-((2S,4R)-4-amino-1-(6-chloroimidazo[1,2-a]pyridine-2-carbonyl)pyrrolidin-2-yl)-N-((5-chloro-1H-indazol-3-yl)methyl)thiazole-4-carboxamide (58);

2-((2S,4R)-4-amino-1-(6-chloroimidazo[1,2-a]pyridine-2-carbonyl)pyrrolidin-2-yl)-N-((6-chloro-1H-indazol-3-yl)methyl)thiazole-4-carboxamide (59);

2-((2S,4R)-4-amino-1-(6-chloroimidazo[1,2-a]pyridine-2-carbonyl)pyrrolidin-2-yl)-N-((1-amino-5,7-dimethylisoquinolin-6-yl)methyl)thiazole-4-carboxamide (60);

2-((2S,4R)-4-amino-1-(5,6-dichlorobenzo[b]thiophene-2-carbonyl)pyrrolidin-2-yl)-N—((S)-6-guanidino-1-(methylamino)-1-oxohexan-2-yl)thiazole-4-carboxamide (61);

2-((2S,4R)-4-amino-1-(6-chlorobenzo[b]thiophene-2-carbonyl)pyrrolidin-2-yl)-N—((S)-6-guanidino-1-(methylamino)-1-oxohexan-2-yl)thiazole-4-carboxamide (62);

2-((2S,4R)-4-amino-1-(4-chlorobenzo[b]thiophene-2-carbonyl)pyrrolidin-2-yl)-N—((S)-6-guanidino-1-(methylamino)-1-oxohexan-2-yl)thiazole-4-carboxamide (63);

2-((2S,4R)-4-amino-1-(5-(trifluoromethyl)benzo[b]thiophene-2-carbonyl)pyrrolidin-2-yl)-N—((S)-6-guanidino-1-(methylamino)-1-oxohexan-2-yl)thiazole-4-carboxamide (64);

2-((2S,4R)-4-amino-1-(6-methylbenzo[b]thiophene-2-carbonyl)pyrrolidin-2-yl)-N—((S)-6-guanidino-1-(methylamino)-1-oxohexan-2-yl)thiazole-4-carboxamide (65);

2-((2S,4R)-4-amino-1-(6-chloroquinoline-3-carbonyl)pyrrolidin-2-yl)-N—((S)-6-guanidino-1-(methylamino)-1-oxohexan-2-yl)thiazole-4-carboxamide (66);

2-((2S,4R)-4-amino-1-(2-chloroquinoline-6-carbonyl)pyrrolidin-2-yl)-N—((S)-6-guanidino-1-(methylamino)-1-oxohexan-2-yl)thiazole-4-carboxamide (67);

or a pharmaceutically acceptable salt thereof.

15. A pharmaceutical composition comprising a compound of claim 1, or a pharmaceutically acceptable salt thereof, and a pharmaceutically acceptable carrier.

16. A method of treating a plasma kallikrein (pKal)-mediated disease or condition in a subject in need thereof, the method comprising administering an effective amount of a compound of claim 1, or a pharmaceutically acceptable salt thereof.

17. The method of claim 16, wherein the pKal-mediated disease or condition is edema, an ocular disorder, or an ischemia reperfusion injury.

18. The method of claim 17, wherein the pKal-mediated disease is edema, which is hereditary angioedema or diabetic macular edema.

19. The method of claim 17, wherein the pKal-mediated disease is an ocular disorder, which is selected from the group consisting of age-related macular degeneration (AMD), diabetic macular edema (DME), and diabetic retinopathy.

20. A compound of formula:

2-((R)-1-(6-Chloroimidazo[1,2-a]pyridine-2-carbonyl)pyrrolidin-2-yl)-N—((S)-6-guanidino-1-(methylamino)-1-oxohexan-2-yl)thiazole-4-carboxamide (3);

2-((R)-1-(6-Chloroimidazo[1,2-a]pyridine-2-carbonyl)pyrrolidin-2-yl)-N—((R)-6-guanidino-1-(methylamino)-1-oxohexan-2-yl)thiazole-4-carboxamide (4);

2-((2R,4S)-1-(6-Chloroimidazo[1,2-a]pyridine-2-carbonyl)-4-hydroxy pyrrolidin-2-yl)-N—((S)-6-guanidino-1-(methylamino)-1-oxohexan-2-yl)thiazole-4-carboxamide (7);

2-((2R,4S)-1-(6-Chloroimidazo[1,2-a]pyridine-2-carbonyl)-4-hydroxypyrrolidin-2-yl)-N—((R)-6-guanidino-1-(methylamino)-1-oxohexan-2-yl)thiazole-4-carboxamide (8);

2-((2R,4R)-1-(6-Chloroimidazo[1,2-a]pyridine-2-carbonyl)-4-hydroxy pyrrolidin-2-yl)-N—((S)-6-guanidino-1-(methylamino)-1-oxohexan-2-yl)thiazole-4-carboxamide (9);

2-((2R,4R)-1-(6-Chloroimidazo[1,2-a]pyridine-2-carbonyl)-4-hydroxy pyrrolidin-2-yl)-N—((R)-6-guanidino-1-(methylamino)-1-oxohexan-2-yl)thiazole-4-carboxamide (10);

2-((2S,4R)-4-amino-1-(cyclohexanecarbonyl)pyrrolidin-2-yl)-N—((S)-6-guanidino-1-(methylamino)-1-oxohexan-2-yl)thiazole-4-carboxamide (17);

2-((S)-1-(6-Chloroimidazo[1,2-a]pyridine-2-carbonyl)pyrrolidin-2-yl)-N—((S)-6-guanidino-1-(methylamino)-1-oxohexan-2-yl)thiazole-4-carboxamide (33);

2-((S)-1-(6-Chloroimidazo[1,2-a]pyridine-2-carbonyl)pyrrolidin-2-yl)-N—((R)-6-guanidino-1-(methylamino)-1-oxohexan-2-yl)thiazole-4-carboxamide (34);

2-((2S,4S)-1-(6-Chloroimidazo[1,2-a]pyridine-2-carbonyl)-4-hydroxypyrrolidin-2-yl)-N—((S)-6-guanidino-1-(methylamino)-1-oxohexan-2-yl)thiazole-4-carboxamide (37);

2-((2S,4R)-1-(6-Chloroimidazo[1,2-a]pyridine-2-carbonyl)-4-hydroxypyrrolidin-2-yl)-N—((S)-6-guanidino-1-(methylamino)-1-oxohexan-2-yl)thiazole-4-carboxamide (38);

2-((2S,4R)-1-(6-Chloroimidazo[1,2-a]pyridine-2-carbonyl)-4-hydroxypyrrolidin-2-yl)-N—((R)-6-guanidino-1-(methylamino)-1-oxohexan-2-yl)thiazole-4-carboxamide (39);

or a pharmaceutically acceptable salt thereof.

* * * * *